(12) United States Patent
Messina

(10) Patent No.: US 11,090,305 B2
(45) Date of Patent: Aug. 17, 2021

(54) METHODS AND COMPOSITIONS TO REDUCE OXIDATIVE STRESS

(71) Applicant: University of Massachusetts, Boston, MA (US)

(72) Inventor: Louis M. Messina, Westborough, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 16/374,369

(22) Filed: Apr. 3, 2019

(65) Prior Publication Data

US 2019/0275047 A1    Sep. 12, 2019

Related U.S. Application Data

(62) Division of application No. 15/438,244, filed on Feb. 21, 2017, now Pat. No. 10,251,887, which is a division of application No. 14/535,690, filed on Nov. 7, 2014, now Pat. No. 9,579,321, which is a division of application No. 13/386,462, filed as application No. PCT/US2010/002095 on Jul. 22, 2010, now Pat. No. 9,089,573.

(60) Provisional application No. 61/357,179, filed on Jun. 22, 2010, provisional application No. 61/227,768, filed on Jul. 22, 2009.

(51) Int. Cl.

| | |
|---|---|
| *A61K 31/00* | (2006.01) |
| *A61K 31/34* | (2006.01) |
| *A61K 31/495* | (2006.01) |
| *C12P 13/10* | (2006.01) |
| *A61K 31/519* | (2006.01) |
| *A61K 31/198* | (2006.01) |
| *A61K 31/375* | (2006.01) |
| *A61K 45/06* | (2006.01) |
| *A61K 48/00* | (2006.01) |
| *A61K 35/13* | (2015.01) |

(52) U.S. Cl.
CPC .......... *A61K 31/519* (2013.01); *A61K 31/198* (2013.01); *A61K 31/375* (2013.01); *A61K 45/06* (2013.01); *A61K 48/005* (2013.01); *A61K 31/495* (2013.01); *A61K 35/13* (2013.01); *A61K 2300/00* (2013.01); *C12N 2799/022* (2013.01); *C12P 13/10* (2013.01)

(58) Field of Classification Search
CPC .. A61K 31/198; A61K 31/395; A61K 31/495; A61K 31/519; A61K 2300/00; C12P 13/10
USPC .............. 514/1, 249, 474; 435/114
See application file for complete search history.

(56) References Cited

U.S. PATENT DOCUMENTS

| | | |
|---|---|---|
| 7,060,295 B2 | 6/2006 | Richardson et al. |
| 2003/0077335 A1 | 4/2003 | Richardson et al. |
| 2003/0216400 A1 | 11/2003 | Rabelink et al. |
| 2004/0034030 A1 | 2/2004 | Richardson et al. |
| 2004/0198738 A1 | 10/2004 | Kawashima et al. |
| 2006/0009458 A1 | 1/2006 | Ishihara et al. |
| 2008/0139668 A1 | 6/2008 | Kwon et al. |
| 2008/0268066 A1 | 10/2008 | Yie et al. |
| 2009/0076014 A1 | 3/2009 | Oppenheimer et al. |

FOREIGN PATENT DOCUMENTS

| | | |
|---|---|---|
| EP | 0908182 | 4/1999 |
| WO | WO 02/17898 | 3/2002 |
| WO | WO 2004/017955 | 3/2004 |
| WO | WO 2006/050581 | 5/2006 |

OTHER PUBLICATIONS

Yan et al., 2012, Molecular Medicine, vol. 18, p. 1221-1230.*
Tomkin et al., 2014, Expert Opinion on Investigational Drugs, vol. 23, No. 10, pp. 1411-1421.*
Ito et al., 2015, Drugs, vol. 75, p. 1715-1724.*
Aguirre R. et al., Inflammation in the vascular bed: importance of vitamin C, Pharmacol. Ther., 119:96-103 (2008).
Assmus et al., "Transplantation of progenitor cells and regeneration enhancement in acute myocardial infarction (TOPCARE-AMI)," Circulation, Dec. 2002, 106: 3009-3017.
Bevers L. et al., "Tetrahydrobiopterin, but not L-arginine, decreases NO synthase uncoupling in cells expressing high levels of endothelial NO synthase," Hypertension, 47:87-94 (2006).
Böger R. et al., "L-arginine improves vascular function by overcoming the deleterious effects of ADMA, a novel cardiovascular risk factor," Alt. Med. Rev., 10:14-8 (2005).
Böger R. et al., "Restoring vascular nitric oxide formation by L-arginine improves the symptoms of intermittent claudication in patients with peripheral arterial occlusive disease", J. Am. Coll. Card., 32:1336-44 (1998).
Donnan P. et al., "Diet as a risk factor for peripheral arterial disease in the general population: the Edinburgh Artery Study," Am. J. Clin. Nutr., 57:917-21 (1993).
Endres M. et al., "Targeting eNOS for stroke protection," Trends in Neuroscience, 27:283-289 (2004).

(Continued)

*Primary Examiner* — Shin Lin Chen

(74) *Attorney, Agent, or Firm* — Fish & Richardson P.C.

(57) ABSTRACT

The invention relates to therapeutic applications for compositions that reduce the level of oxidative stress on cells in vivo or in vitro. The invention describes methods for improving the therapeutic properties of stem cells. The invention also provides combination therapies that are useful to balance the oxidative microenvironment of cells in vivo or in vitro.

7 Claims, 62 Drawing Sheets

(56) References Cited

OTHER PUBLICATIONS

European Office Action in Application No. 10738057.8, dated Jun. 8, 2017, 7 pages.
Heitzer T. et al., "Tetrahydrobiopterin improves endothelium-dependent vasodilation by increasing nitric oxide activity in patients with type II diabetes mellitus," Diabetologia, 43:1435-8. (2000).
Heller R. et al., "L-ascorbic acid potentiates endothelial nitric oxide synthesis via a chemical stabilization of tetrahydrobiopterin," J. Biol. Chem., 276:40-7 (2001).
Huang A. et al., Ascorbic acid enhances endothelial nitric-oxide synthase activity by increasing intracellular tetrahydrobiopterin, J. Biol. Chem., 275:17399-406 (2000).
International Search Report issued in Int. Appln. No. PCT/US2010/002095, dated Dec. 17, 2010, 7 pages.
Joshi M. et al., "Receptor-mediated activation of nitric oxide synthesis by arginine in endothelial cells," Proc. Natl. Acad. Sci. U.S. A., 104:9982-7 (2007).
Klipstein-Grobusch K. et al. Dietary antioxidants and peripheral arterial disease: the Rotterdam Study, Am. J. Epidemiol., 154:145-9 (2001).
Kohil R., "Dietary L-arginine supplementation enhances endothelial nitric oxide synthesis in streptozotocin-induced diabetic rats," J. Nutr., 134:600-8 (2004).
Kurowska E., "Nitric oxide therapies in vascular diseases," Current Pharmaceutical Design, 8:155-166 (2002).
Kuzkaya N. et al., "Interactions of peroxynitrite, tetrahydrobiopterin, ascorbic acid, and thiols," J. Biol. Chem., 278:22546-54 (2003).
Langlois M. et al., "Serum vitamin C concentration is low in peripheral arterial disease and is associated with inflammation and severity of atherosclerosis," Circulation, 103:1863-8 (2001).
Marietta M., :Nitric oxide synthase structure and mechanism, J Biol. Chem., 268:12231-12234 (1993).
Maxwell A. et al., "Nutritional therapy for peripheral arterial disease: a double-blind, placebo-controlled, randomized trial of HeartBar," Vasc. Med., 5:11-9 (2000).
Mias et al., "Ex Vivo Pretreatment with Melatonin Improves Survival, Proangiogenic/Mitogenic Activity, and Efficiency of Mesenchymal Stem Cells Injected into lschemic Kidney," Stem Cells, Jul. 2008, 26: 1749-1757.
Office Action in European Application No. 10738057.8, dated Nov. 15, 2018, 6 pages.
Osiecki et al., 2004, Alternative Medicine review, vol. 9, No. 1, p. 32-53.
Pacher P. et al., "Nitric oxide and peroxynitrite in health and disease," Physiol. Rev., 87:315-424 (2007).
Peterson T. et al., "Opposing effects of reactive oxygen species and cholesterol on endothelial nitric oxide synthase and endothelial cell caveolae," Circ. Res., 85:29-37 (1999).
Sawabe K. et al., "Tetrahydrobiopterin uptake in supplemental administration: elevation of tissue tetrahydrobiopterin in mice following uptake of the exogenously oxidized product 7,8-dihydrobiopterin and subsequent reduction by an anti-folate sensitive process," J. Pharmacol. Sci., 96:124-33 (2004).
Schmidt T. et al., "Mechanisms for the role of tetrahydrobiopterin in endothelial function and disease," Clin. Sci., 113:47-63 (2007).
Silvestro A. et al., "Intermittent claudication and endothelial dysfunction," Eur. Heart J., 4:B35-40 (2002).
Silvestro A. et al., "Vitamin C prevents endothelial dysfunction induced by acute exercise in patients with intermittent claudication," Atherosclerosis, 165:277-83 (2002).
Spieker L. et al., "Current strategies and perspectives for correcting endothelial dysfunction in atherosclerosis," Journal of Cardiovascular Pharmacology, 38:S35-41 (2001).
Tarpey, Margaret, 2002, Arterioscler Thronnb Vas Biol., 22: 1519-1521.
Tentolouris et al., 2000, International Journal of Cardiology, vol. 75, p. 123-128.
Ueda S. et al., "Tetrahydrobiopterin restores endothelial function in long-term smokers,". J. Am. Coll. Card., 35:71-5 (1999).
Undurti N. D., 2007, Application No. 1200/CHE/2004 A, India, publication date Jul. 27, 2007.
Wijnen M. et al. "Antioxidants reduce oxidative stress in claudicants," J. Surg. Res., 96:183-7 (2001).
Wilson A. et al., "L-arginine supplementation in peripheral arterial disease: no benefit and possible harm," Circulation, 116:188-95 (2007).
Yamamizu K. et al., "Oral administration of both tetrahydrobiopterin and L-arginine prevents endothelial dysfunction in rats with chronic renal failure," J. Cardiovasc. Pharmacol., 49:131-9 (2007).
Yan J. et al., "Oral tetrahydrobiopterin improves the beneficial effect of adenoviral-mediated eNOS gene transfer after induction of hindlimb ischemia," Mol. Ther., 18:1482-9 (2010).
Yan J. et al., "Tetrahydrobiopterin, L-Arginine and Vitamin C Act Synergistically to Decrease Oxidative Stress, Increase Nitric Oxide and Improve Blood Flow after Induction of Hindlimb Ischemia in the Rat," Mol. Med., 18:676-684 (2012).
Yao et al., "Oxidative Stress on Progenitor and Stem Cells in Cardiovascular Diseases," Current Pharmaceutical Biotechnology, Apr. 2006, 7: 101-108.
Blum et al., "The effects of L-arginine on atherosclerosis and heart disease," International Journal of Cardiovascular Interventions, Jan. 1, 1999, 2(2):97-100.
EP Office Action in European Application No. 10738057.8, dated Apr. 6, 2020.
Gokce et al., "Long-term ascorbic acid administration reverses endothelial vasomotor dysfunction in patients with coronary artery disease," Circulation, Jun. 29, 1999, 99(25):3234-40.
Hattori et al., "Oral administration of tetrahydrobiopterin slows the progression of atherosclerosis in apolipoprotein E-knockout mice," Arteriosclerosis, Thrombosis, and Vascular Biology, Apr. 1, 2007, 27(4):865-70.
Kuzkaya et al., "Interactions of peroxynitrite, tetrahydrobiopterin, ascorbic acid, and thiols implications for uncoupling endothelial nitric-oxide synthase," Journal of Biological Chemistry, Jun. 20, 2003, 278(25):22546-54.
Landmesser et al., "Oxidation of tetrahydrobiopterin leads to uncoupling of endothelial cell nitric oxide synthase in hypertension," The Journal of Clinical Investigation, Apr. 15, 2003, 111(8):1201-9.
Moss et al., "Nutraceutical therapies for atherosclerosis," Nature Reviews Cardiology, Sep. 2016, 13(9):513.
Park et al., "Endothelial nitric oxide synthase affects both early and late collateral arterial adaptation and blood flow recovery after induction of hind limb ischemia in mice," Journal of Vascular Surgery, Jan. 1, 2010, 51(1):165-73.
Vásquez-Vivar et al., "Superoxide generation by endothelial nitric oxide synthase: the influence of cofactors," Proceedings of the National Academy of Sciences, Aug. 4. 1998, 95(16):9220-5.

* cited by examiner

* Indicates P<0.01 n=10 control
n= 5 BH4/L-arg/VitC p=0.039

P<0.05, indicates significant difference between two groups

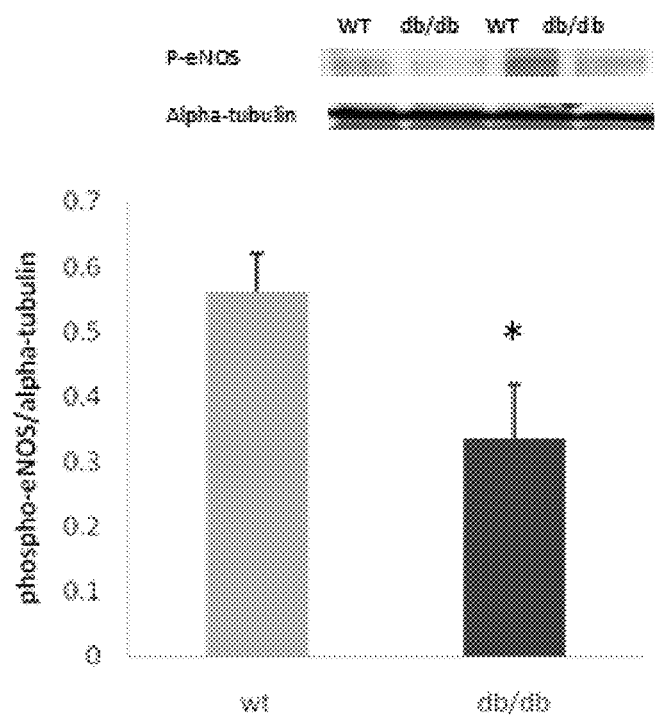
FIG. 34D
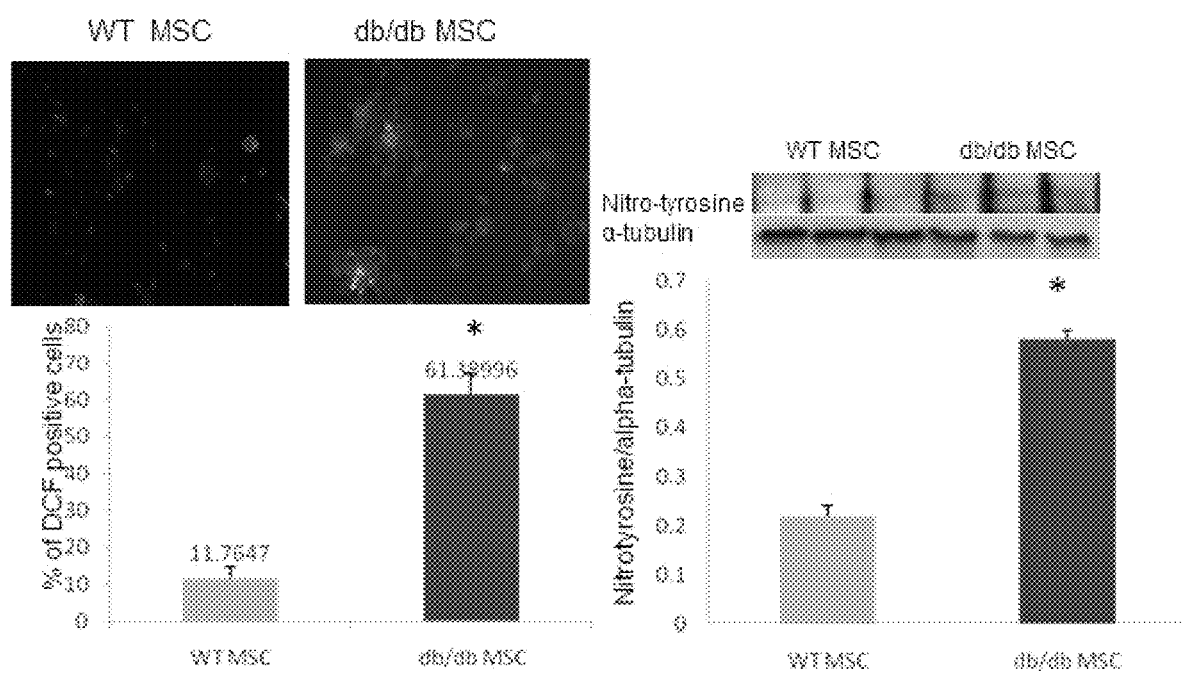
FIG. 35A
FIG. 35B

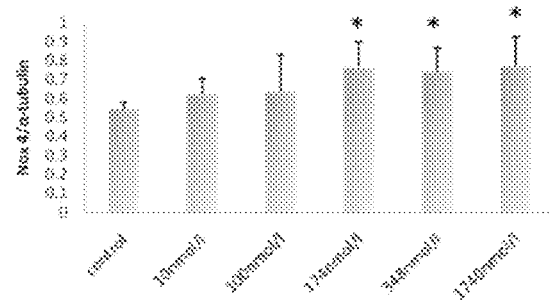 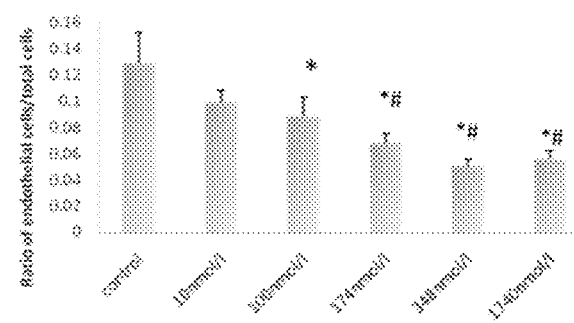
FIG. 41A            FIG. 41D
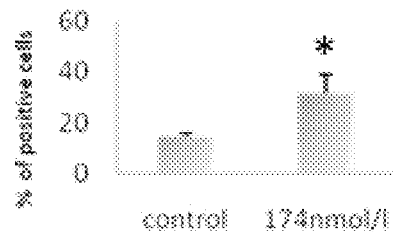 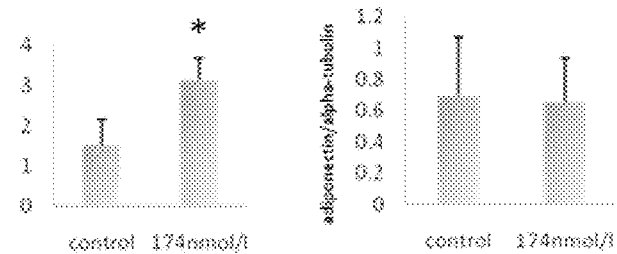
FIG. 41B            FIG. 41E
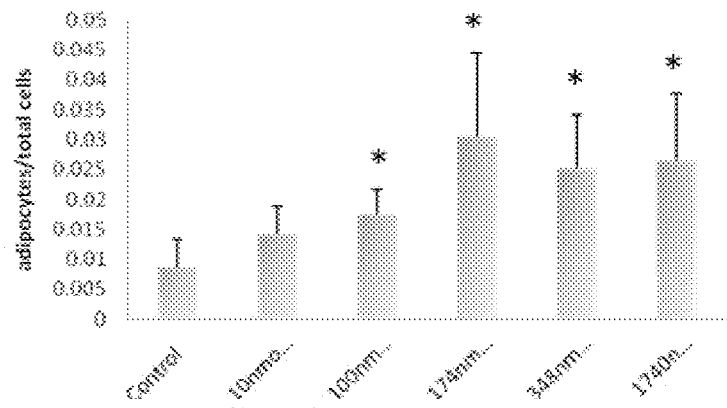
FIG. 41C

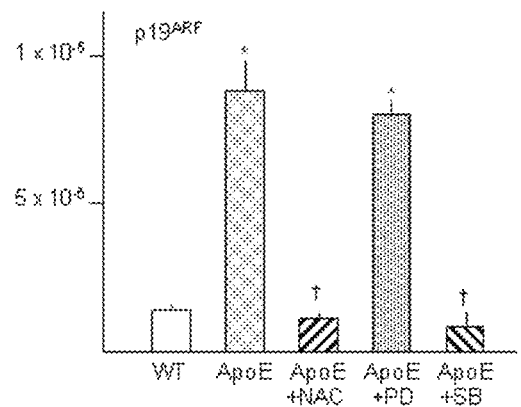
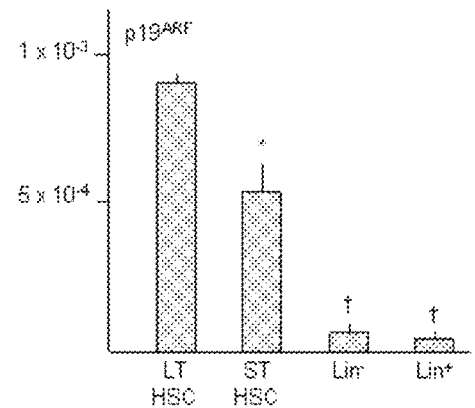
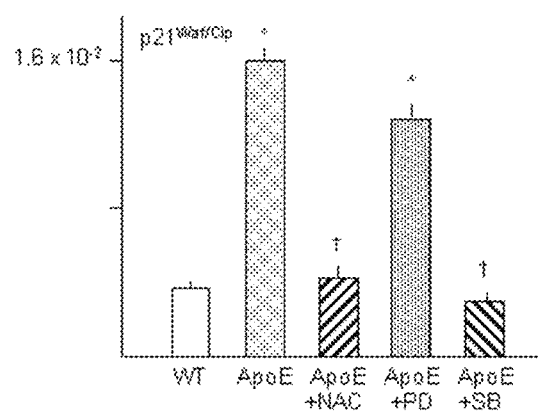
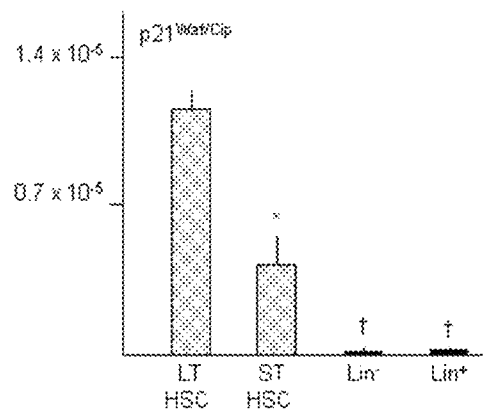
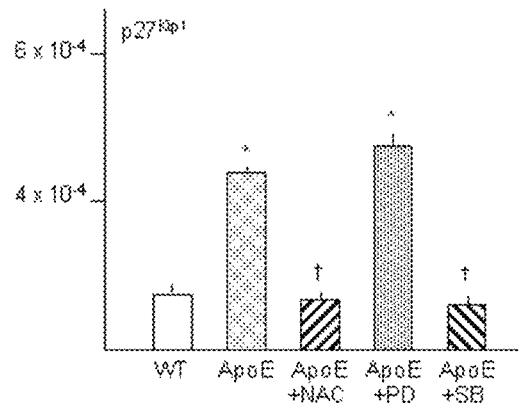
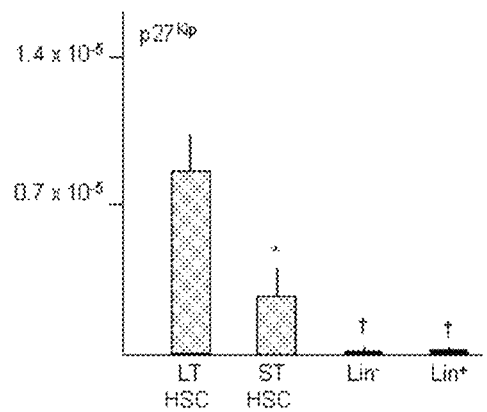
FIG. 45A                FIG. 45B

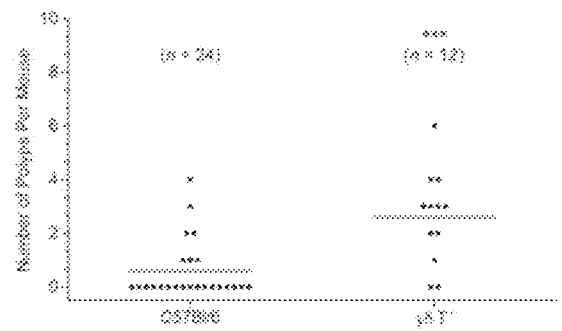
FIG. 52A
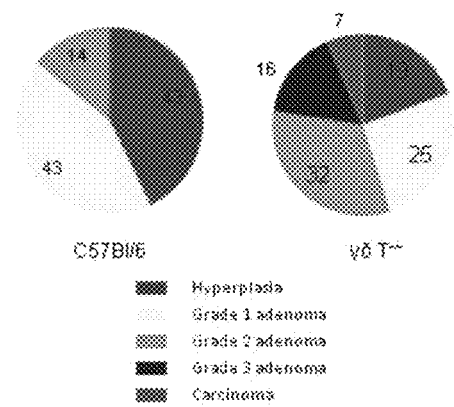
FIG. 52B
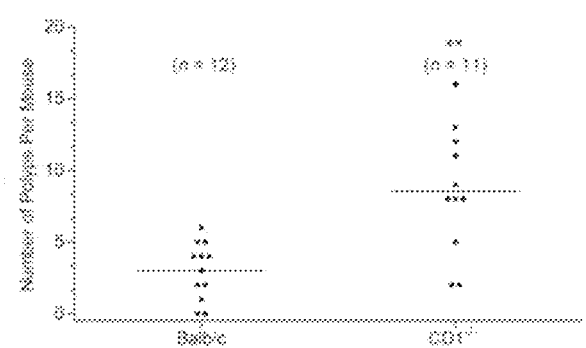
FIG. 52C
FIG. 52D
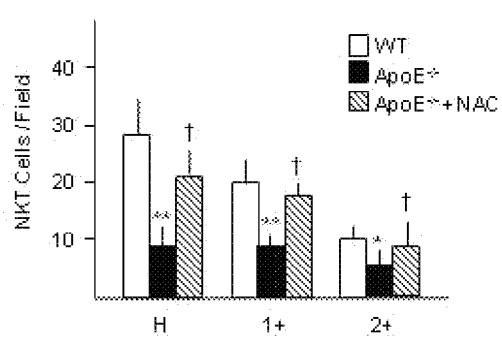
FIG. 52E
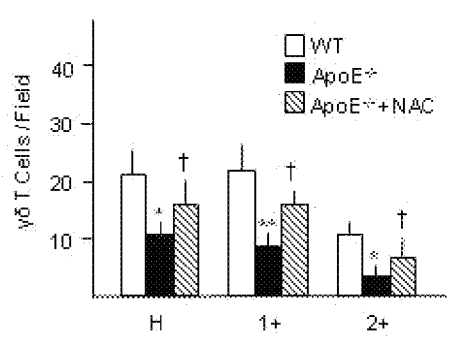
FIG. 52F

FIG. 52G            FIG. 52H

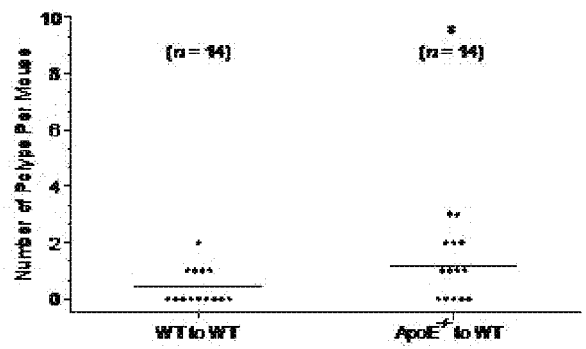
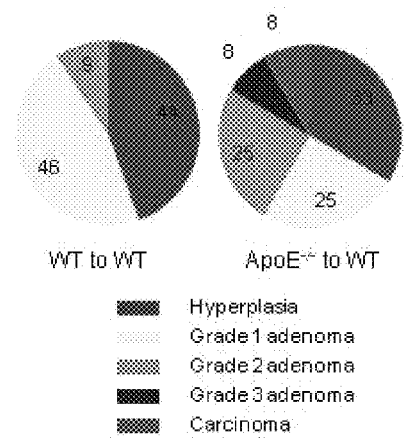
FIG. 54A
FIG. 54B
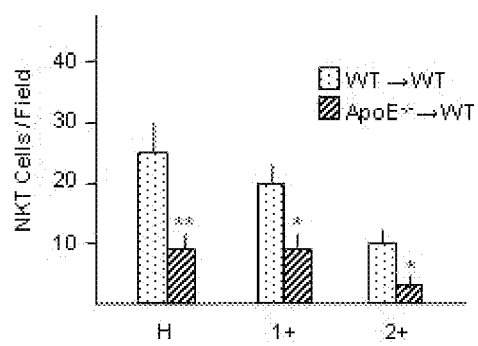
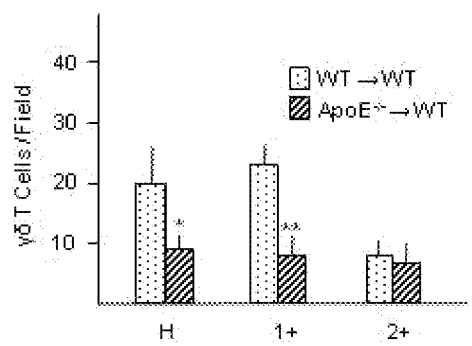
FIG. 54C
FIG. 54D B Lymphocyte concentration was increased in the bone marrow of Type 1 diabetic mice

*, p<0.05 vs Wild Type and Type 2

Monocytes concentration was significantly decreased in the bone marrow of Type 2 diabetic mice

*, P<0.05 vs Wild Type and Type 1

Red Cell concentration was significantly increased in the bone marrow of Type 2 diabetic mice

*, P<0.05 vs Wild Type and Type 1.

METHODS AND COMPOSITIONS TO REDUCE OXIDATIVE STRESS

RELATED APPLICATIONS

This application is a divisional application of and claims priority to U.S. patent application Ser. No. 15/438,244, filed on Feb. 21, 2017, which is a divisional application of and claims priority to U.S. patent application Ser. No. 14/535,690, filed Nov. 7, 2014 (now U.S. Pat. No. 9,579,321), which is a divisional application of U.S. patent application Ser. No. 13/386,462, filed Apr. 3, 2012 (now U.S. Pat. No. 9,089,573), which is the U.S. National Stage Of International Application No. PCT/US2010/002095, filed on Jul. 22, 2010 which claims the benefit under 35 U.S.C. § 119(e) of U.S. provisional application 61/227,768, filed Jul. 22, 2009, and U.S. provisional application 61/357,179, filed Jun. 22, 2010, the entire disclosures of each of which are incorporated herein by reference.

STATEMENT OF FEDERALLY SPONSORED RESEARCH

This invention was made with Government support under Grant number HL068042 and HL075353. The Government has certain rights in the invention.

BACKGROUND

Oxidative stress has been indicated to cause or contribute to certain diseases and disorders. A number of methods and compositions have been suggested to decrease, prevent, or ameliorate conditions associated with chronic or acute oxidative stress. However, many of the mechanisms are not fully understood, and there remains a need for further compositions and therapeutic methods.

SUMMARY OF THE INVENTION

Some aspects of this invention are based on the discoveries that (i) oxidative stress is a critical factor in numerous diseases and conditions not previously appreciated to be caused by/or associated with oxidative stress; (ii) oxidative stress plays a more prominent role in the outcome of numerous diseases and conditions than previously appreciated; and (iii) normalization of the redox state of a cell or tissue can be achieved by administering a composition or combination of agents as provided herein, resulting in reversal or reduction of oxidative cell or tissue injury.

Accordingly, some aspects of this invention provide new applications for clinical management of oxidative stress in cells, tissues, or microenvironments. Further, some aspects of this invention provide compositions, combinations, and methods for normalizing the redox state of a cell, tissue, or microenvironment in vitro, ex vivo, or in vivo.

Aspects of this invention relate to compositions and combinations of agents for prevention and/or reduction/treatment of oxidative stress. In some embodiments, compositions or combinations of agents are provided for prevention and/or reduction/treatment of oxidative stress in a subject. In some embodiments, compositions or combinations of agents are provided for prevention and/or reduction/treatment of oxidative stress in cells, tissues, or microenvironments in vivo, ex vivo, or in vitro.

In some embodiments, a composition and/or a combination for prevention and/or reduction/treatment of oxidative stress is provided that comprises (A) an agent or agents that reduce/s oxidative stress of an in vivo microenvironment or an activator of an anti-oxidative pathway, (B) a co-factor and/or activator that maintains and/or balances an oxidation/reduction pathway, and (C) an anti-oxidant and/or a free radical scavenger that maintains availability of the co-factor and/or activator.

In some embodiments, the agent provided under (A) is a substrate for an agonistic enzyme of an anti-oxidant pathway. In some embodiments, the agent provided under (A) is an essential amino acid. In some embodiments, the agent provided under (A) is L-Arginine, N-acetyl-cysteine (NAC), or L-Cysteine, or a combination thereof. In some embodiments, the agent provided under (A) is L-Arginine.

In some embodiments, the agent reducing oxidative stress provided under (A) is a nucleic acid construct. In some embodiments, the construct is an adenoviral construct.

In some embodiments, the agent provided under (B) is a co-factor of an agonistic enzyme of an anti-oxidant pathway. In some embodiments, the agent provided under (B) is an essential co-factor of an agonistic enzyme of an anti-oxidant pathway. In some embodiments, the agent provided under (B) is a pteridine. In some embodiments, the agent provided under (B) is tetrahydrobiopterin (BH4), 6R-BH4, trihydrobiopterin (BH3), dihydrobiopterin (BH2), sapropterin, sepiapterin, or a BH4-derivative, or a combination thereof. In some embodiments, the oxidation/reduction pathway is the nitric oxide pathway. In some embodiments, the agonistic enzyme is nitric oxide synthase. In some embodiments, the enzyme is endothelial NOS (eNOS). In some embodiments, the enzyme is neuronal NOS (nNOS). In some embodiments, the enzyme is inducible NOS (iNOS).

In some embodiments, the agent provided under (C) is an agent with reducing properties. In some embodiments, the agent provided under (C) is an agent able to sequester oxidative radicals. In some embodiments, the agent under (C) is ascorbic acid, ascorbate, Glutathione, Lipoic acid, a carotene, for example beta-carotene, α-Tocopherol, or Ubiquinol, or a combination thereof.

In some embodiments a composition comprises a single agent under (A), (B), and/or (C). In some embodiments, a composition as provided herein comprises 2, 3 or more agents under (A), (B), and/or (C). To illustrate with some non-limiting examples: in some embodiments, a composition provided herein may comprise 1 agent under (A), 1 agent under (B), and 1 agent under (C), whereas another composition may comprise 2 agents under (A), 1 agent under (B) and 3 agents under (C), and yet another composition may comprise 2 agents under (A), 2 agents under (B) and 5 agents under (C) and so forth.

In some embodiments, composition for the reduction of oxidative stress in stem or progenitor cells comprises agents under (A), (B), and (C) in a balanced ratio as described elsewhere herein.

In some embodiments, the agent provided under (A) is L-Arginine, the agent provided under (B) is BH4, and the agent provided under (C) is ascorbic acid. In some embodiments, (A) L-arginine, (B) tetrahydrobiopterin, sepiapterin and/or dihydrobiopterin are administered in a ratio of about 10(A):1(B), e.g., in a ratio of 8.85(A):1(B). In some embodiments, (A) L-arginine and (C) ascorbic acid and/or ascorbate are administered in a ratio of about 1(A):1(C).

In some embodiments, aspects of the invention relate to a composition consisting essentially of active ingredients being: (A) an agent reducing oxidative stress of an in vivo microenvironment, (B) a co-factor and/or activator that maintains and/or balances the oxidation/reduction pathways, and (C) an anti-oxidant and/or a free radical scavenger that maintains availability of the co-factor and/or activator. In some embodiments, a composition is provided that essentially consists of (A) an essential amino acid, for example, L-arginine, (B) a pteridine, for example, BH4, 6R-BH4, BH3, BH2, sapropterin, sepiapterin, or a BH4-derivative, and (C) ascorbic acid or ascorbate, Glutathione, Lipoic acid, a carotene, for example beta-carotene, α-Tocopherol, or Ubiquinol, or a combination thereof.

In some embodiments, a composition is provided that essentially consists of the active ingredients (A) L-Arginine, (B) BH4, and (C) is ascorbic acid. In some embodiments, a composition is provided consisting essentially of the active ingredients (A) L-arginine, (B) BH4, and (C) ascorbic acid or ascorbate in a ratio of A:B:C of 1-30:1:0.1-15. In some embodiments, the ratio of A:B is about 10:1, for example 8.85:1. In some embodiments, the ratio of B:C is about 1:10, for example, 1:8.85. In some embodiments, the ratio of A:C is about 1:1.

In some embodiments, aspects of the invention relate to a kit comprising the following compounds: (A) an agent reducing oxidative stress of an in vivo microenvironment, (B) a co-factor and/or activator that maintains and/or balances the oxidation/reduction pathways, and (C) an anti-oxidant and/or a free radical scavenger that maintains availability of the co-factor and/or activator. In some embodiments, the compounds provided under (A), (B), and (C) in the kit are comprised in a pharmaceutical formulation appropriate for enteral administration. In some embodiments, the compounds provided in the kit are comprised in a pharmaceutical formulation appropriate for oral administration. In some embodiments, the compounds are formulated in a pharmaceutical formulation appropriate for parenteral administration. In some embodiments, a first compound is comprised in a pharmaceutical formulation appropriate for enteral administration and a second compound is comprised in a formulation appropriate for parenteral administration. In some embodiments, the second compound is said agent reducing oxidative stress of an in vivo microenvironment provided under (A). In some embodiments, the agent reducing oxidative stress of an in vivo microenvironment provided under (A) is L-arginine. In some embodiments, the agent reducing oxidative stress of an in vivo microenvironment provided under (A) is a nucleic acid construct. In some embodiments, the construct is an adenoviral construct. In some embodiments, the co-factor and/or activator provided under (B) is BH4, 6R-BH4, BH3, BH2, sapropterin, sepiapterin, or a BH4-derivative. In some embodiments, the anti-oxidant and/or free radical scavenger provided under (C) is ascorbic acid or ascorbate, Glutathione, Lipoic acid, a carotene, for example beta-carotene, α-Tocopherol, or Ubiquinol, or a combination thereof.

It will be understood by those of skill in the art that the agents described herein may be used in the form of pharmaceutically acceptable salts. In some embodiments, a composition provided herein is mixed with or dissolved in a pharmaceutically acceptable carrier.

In some embodiments, aspects of this invention relate to the discovery that oxidative injury can cause impairment of stem and progenitor cell function. Some aspects of this invention relate to the discovery that this impairment can be ameliorated or reversed by compositions and/or combinations of agents as provided herein.

In some embodiments, a composition for the reduction of oxidative stress in stem or progenitor cells is provided. In some embodiments, the stem or progenitor cells are embryonic stem cells, induced pluripotent stem cells, hematopoietic stem or progenitor cells, mesenchymal stem or progenitor cells, neuronal or neural stem or progenitor cells, or glial stem or progenitor cells. In some embodiments, a composition for the reduction of oxidative stress as provided herein is useful for reducing oxidative stress in stem or progenitor cells in vivo, in vitro, or ex vivo. In some embodiments, a composition for the reduction of oxidative stress as provided herein is useful for the reduction of oxidative stress in endothelial stem or progenitor cells or bone marrow-derived stem or progenitor cells. In some embodiments, a composition for the reduction of oxidative stress in stem or progenitor cells comprises an agent or agents provided under (A), (B), and (C), as described herein. In some embodiments, composition for the reduction of oxidative stress in stem or progenitor cells comprises agents under (A), (B), and (C) in a balanced ratio as described elsewhere herein.

In some embodiments, a composition for the prevention and/or reduction/treatment of oxidative stress in stem or progenitor cells is provided that comprises (A) an agent reducing oxidative stress of an in vivo microenvironment. In some embodiments, the agent provided under (A) is NAC.

In some embodiments, aspects of the invention relate to the use of therapeutic compositions and/or combinations to prevent or treat conditions caused by oxidative stress in a subject. Aspects of the invention relate to the use of certain compositions and/or combinations to treat a subject in need thereof. In some embodiments, methods are provided for the reduction of oxidative stress in a subject by administering a composition or combination provided herein to the subject.

In some embodiments, a method is provided comprising administering to a subject having or being indicated to have an imbalanced oxidant/antioxidant in vivo microenvironment, diagnosed of being exposed to oxidative stress, and/or showing a symptom of oxidative stress, a balanced ratio of (A) an agent or agents that reduces oxidative stress of an in vivo microenvironment or an activator of an anti-oxidative pathway, and (B) a co-factor and/or activator that maintains and/or balances the oxidation/reduction pathways, and (C) an anti-oxidant and/or a free radical scavenger that maintains availability of the co-factor and/or activator. In some embodiments, administration of a composition or a combination of agents as provided under (A), (B), and (C) herein, is referred to as a triple therapy.

In some embodiments, a method is provided comprising administering to a subject having or being indicated to have an imbalanced oxidant/antioxidant in vivo microenvironment, diagnosed of being exposed to oxidative stress, and/or showing a symptom of oxidative stress, a balanced ratio of agents that reduce oxidative stress of an in vivo microenvironment comprising (A) an essential amino acid and an activator of an anti-oxidative pathway, (B) a co-factor and/or activator that maintains and/or balances an oxidation/reduction pathway, and (C) an anti-oxidant and/or a free radical scavenger that maintains availability of the co-factor and/or activator.

In some embodiments, a useful method comprises administering to a subject (A) an agent reducing oxidative stress of an in vivo microenvironment, (B) a co-factor and/or activator that maintains and/or balances an oxidation/reduction pathway, and (C) an anti-oxidant and/or a free radical scavenger that maintains availability of the co-factor and/or activator, wherein the compounds are administered in an amount sufficient to promote a beneficial therapeutic effect (e.g., reduce oxidative stress in a tissue of said subject, promote healthy function, differentiation, proliferation, survival, and/or maintenance of stem and/or progenitor cells in said subject).

In some embodiments, method for improving and/or optimizing a reduction/oxidation state of a biochemical microenvironment in a subject comprises administering to a subject a composition consisting essentially of (A) an agent reducing oxidative stress of an in vivo microenvironment, (B) a co-factor and/or activator that maintains and/or balances an oxidation/reduction pathway, and (C) an anti-oxidant and/or a free radical scavenger that maintains availability of the co-factor and/or activator.

In some embodiments, aspects of the invention provide a method for providing and/or maintaining a balanced equilibrium of (A) an agent reducing oxidative stress of an in vivo microenvironment, and (B) a co-factor and/or activator that maintains and/or balances the oxidation/reduction pathways, and (C) an anti-oxidant and/or a free radical scavenger that maintains availability of the co-factor and/or activator in a subject, said providing and/or maintaining comprising administering (A) the agent, (B) the co-factor and/or activator and (C) the anti-oxidant and/or free radical scavenger in a balanced ratio to a subject, and monitoring availability and/or biological activity of (A) the agent, (B) the co-factor and/or activator and (C) the anti-oxidant and/or free radical scavenger in a target cell, tissue, or microenvironment in said subject, and, optionally, repeating the administration of the agent, the co-factor and/or activator and the anti-oxidant and/or free radical scavenger, if the availability or biological activity is found to be below a threshold or control level. In some embodiments, the threshold or control level is an average level found in healthy individuals. In some embodiments, the threshold or control level of at least 2-fold, at least 3-fold, at least 4-fold, at least 5-fold, at least 7.5-fold, or at least 10-fold the level observed in the subject before a composition as provided herein was administered.

In some embodiments, the administration of a composition or combination as described herein is an adjunct therapy to a clinical intervention targeted to revascularize a tissue.

In some embodiments, a triple therapy as described herein is administered to a donor of a cell population, for example a stem cell population, before said cell population is isolated from the donor. In some embodiments, triple therapy as described herein is administered to the recipient of a cell population, for example a stem cell population, before, during or after receiving said stem cell population, in order to balance redox state of the engraftment microenvironment. For example, a donor, from which a hematopoietic stem cell population is isolated for transplantation to a recipient, may receive triple therapy in advance of the isolation, in order to balance the redox state of the HSC microenvironment. The recipient of the HSC transplant may receive triple therapy before transplantation, during transplantation, and/or after transplantation of the HSC population.

In some embodiments, triple therapy may be administered to a subject, for example a recipient of a cell transplant, to prevent or minimize oxidant injury to stem cells of the subject. In some embodiments, transient triple therapy may be administered to a subject until a certain clinical purpose has been achieved, for example, in the case of a stem cell recipient, this may include, for example, successful engraftment of the transplanted stem cells or their differentiated progeny, or regression or reversal of a disease or condition.

In some embodiments, a method for use of a composition for the reduction of oxidative stress in stem or progenitor cells is provided. In some embodiments, a method to reduce oxidative stress in cell or progenitor cells is provided. In some embodiments, such a method comprises contacting a composition for the reduction of oxidative stress as provided herein with a stem or progenitor cell or cell population in vivo. In some embodiments, such a method comprises contacting a composition for the reduction of oxidative stress as provided herein with a stem or progenitor cell or cell population in vitro. In some embodiments, such a method comprises contacting a composition for the reduction of oxidative stress as provided herein with a stem or progenitor cell or cell population ex vivo. In some embodiments, a method for the reduction of oxidative stress is provided herein that is useful for the reduction of oxidative stress in endothelial stem or progenitor cells or bone marrow-derived stem or progenitor cells. In some embodiments, a method for the reduction of oxidative stress in stem or progenitor cells is provided that comprises contacting the cells with an agent or agents provided under (A), (B), and (C), as described herein. In some embodiments, a method for the reduction of oxidative stress in stem or progenitor cells is provided that comprises contacting the cells with a composition or a combination of the agents provided under (A), (B), and (C) herein in a balanced ratio. Suitable balanced ratios for such methods are described elsewhere herein, for example, in Table 1. In some embodiments, a method for the reduction of oxidative stress in stem or progenitor cells as provided herein comprises contacting the cells with a single agent, for example, NAC. In some embodiments, a method for the reduction of oxidative stress in stem or progenitor cells as provided herein comprises contacting the stem or progenitor cells in vivo, ex vivo, or in vitro. In some embodiments, the stem and/or progenitor cells are endothelial cells, and/or bone marrow cells.

In some embodiments, a method is provided comprising administering an agent, composition, or a combination as provided herein via an enteral route. In other embodiments, the administering is via a parenteral route. In some embodiments involving the administration of a multi-agent composition or combination, for example, in some triple therapy embodiments, a first compound and/or agent is administered via an enteral route and a second compound and/or agent is administered via a parenteral route. In some embodiments, the second compound and/or agent is an adenoviral construct reducing oxidative stress.

In some embodiments, a method for reducing oxidative stress in a subject, cell, tissue, or microenvironment as provided herein further comprises diagnosing a disorder caused or associated with oxidative stress of an in vivo biochemical microenvironment, a deficiency in stem and/or progenitor cell differentiation, proliferation, survival and/or maintenance, or a state of oxidative stress or associated with oxidative stress in the subject, cell, tissue, or microenvironment, and administering the compounds and/or agents to the subject, cell, tissue, or microenvironment based on the result of said diagnosing or determining.

In some embodiments, the disorder associated with oxidative stress of an in vivo biochemical microenvironment, a deficiency in stem and/or progenitor cell differentiation, proliferation, survival and/or maintenance is claudication, myocardial infarction, atherosclerosis and/or ischemia, peripheral vascular disease, specific cancer types/scenarios (e.g., treatment/prevention of oxidative risk factors, treatment/prevention of oxidative stress that impairs immune surveillance for cancer, adjunct therapy to conventional cancer therapy), cardiovascular disease, inflammatory disease, stem cell dysfunction (e.g., due to imbalanced differentiation as a result of oxidative stress), and/or a cell aging-related disease.

In some embodiments, the subject is further monitored for symptoms of a disorder associated with oxidative stress of an in vivo biochemical microenvironment, a deficiency in stem and/or progenitor cell differentiation, proliferation, survival and/or maintenance before, during, and/or after administering said compounds and/or agents. In some embodiments, the monitoring comprises assessing a biomarker associated with oxidative stress, a deficiency in stem and/or progenitor cell differentiation, proliferation, survival and/or maintenance, and/or oxidative stress before, during, and/or after administering said compounds and/or agents.

It should be appreciated that methods for detecting and/or monitoring the redox status or the level of oxidative stress in a subject (or in a sample such as a cellular or tissue sample) and/or comparing the measurements to one or more reference amounts or levels may be performed on a computer. In some embodiments, a database (e.g., stored in a computer and/or on a computer-readable medium) may include patient and/or reference values useful according to aspects of the invention (e.g., including historical and/or treatment values for a subject).

In some embodiments, aspects of the invention relate to the use of certain compositions and/or combinations to reduce oxidative stress in a population of cells, for example a population of stem and/or progenitor cells in vivo, ex vivo, or in vitro. In some embodiments, methods are provided to reduce oxidative stress in a cell or a cell population, for example, a stem or progenitor cell or population, by contacting the cell or cell population with a composition or combination provided herein.

Aspects of the invention relate to the use of certain compositions and/or combinations to normalize or restore stem cell or progenitor cell maintenance, population homeostasis, repopulation capacity, proliferation rate, differentiation potential, and/or differentiation pattern. For example, aspects of the invention relate to the use of certain compositions and/or combinations to normalize or restore stem cell or progenitor cell maintenance, population homeostasis, repopulation capacity, proliferation rate, differentiation potential, and/or differentiation pattern in stem or progenitor cells in or obtained from a subject diagnosed with a disease associated with or caused by oxidative stress, diagnosed to be or have been exposed to oxidative stress, or showing a symptom of oxidative stress. Aspects of the invention also may be used to stimulate the growth, survival, and/or development of stem and/or progenitor cells in vivo or ex vivo.

These and other aspects of the invention are illustrated by the following non-limiting drawings, description, examples and claims.

BRIEF DESCRIPTION OF THE DRAWINGS

FIGS. 34A-34D. Effect of endogenic (endothelial cell) medium on the differentiation of WT and db/db MSC.

FIGS. 35A-35B. DCF-DA staining for intracellular reactive oxygen species in WT and db/db MSC.

FIGS. 41A-41E. Expression of Nox 4 in wt MSC after insulin treatment (Western blot).

FIGS. 45A-45B. Expressions of $p19^{Arf}$, $p21^{Waf1}$, and $p27^{Kip1}$ are increased in HSCs from ApoE$^{-/-}$ mice.

FIGS. 52A-52H. NKT and γδT cells participate in immunosurveillance of AOM-induced colorectal neoplasia and are reduced in polyps from hypercholesterolemic mice.

FIGS. 54A-54D. Chimeric WT mice transplanted with ApoE$^{-/-}$ HSCs show increased susceptibility to AOM-induced colorectal neoplasia.

DETAILED DESCRIPTION

It has been discovered that oxidative stress is associated with numerous diseases and conditions, including diseases and conditions not previously associated with oxidative stress. It has further been discovered that oxidative stress is a critical factor in clinical outcome of numerous diseases and conditions and that a reduction or reversal of oxidative stress is a key factor in achieving positive clinical outcome. Methods and compositions for the reduction of oxidative stress have been developed and are disclosed herein.

Aspects of the invention relate to compositions and methods for reducing oxidative stress in cells and/or tissue of a subject. Accordingly, aspects of the invention can be useful to prevent and/or treat conditions associated with oxidative stress. Some aspects of the invention relate to the discovery that oxidative stress can cause oxidative injury to stem and progenitor cells, which can result in impairment of stem cell function. Methods, compositions and combinations provided herein are useful to prevent or reverse/ameliorate oxidative injury to stem or progenitor cells, and to balance stem cell maintenance, proliferation and differentiation. Accordingly, compositions, combinations, and methods provided by the invention are useful to prevent and/or treat conditions caused by or associated with stem cell damage, dysregulation of stem cell proliferation and/or an inadequate stem cell differentiation pattern.

According to some aspects of this invention, the use of an anti-oxidative agent alone is not sufficient to reduce oxidative stress in some clinical scenarios, and might, in some cases, even result in detrimental effects. Some aspects of this invention relate to the surprising discovery that sustained balancing of the redox state of a target cell, tissue, or biochemical microenvironment is necessary to achieve a reduction of oxidative stress and/or a related therapeutic effect, and that anti-oxidative agents alone cannot always effect this balance and may even cause harm to certain patient populations. Specifically, some single-therapy approaches have been shown to be of limited success or even detrimental to certain patient populations (see, for example, Circulation 2007, 116:188-195; JAMA 2006, 295, 1:58-64, JAMA. 2007; 297(8):842-857 Eur. Heart J. 24:1287-1295, 2003). Accordingly, compositions and methods to balance reduction/oxidation pathways in a more reliable manner than single anti-oxidative agents are highly desirable and some aspects of this invention provide methods and compositions useful for the reduction of oxidative stress by effecting a suitable balance of the redox state of a target cell, tissue, or microenvironment.

Figure 1:
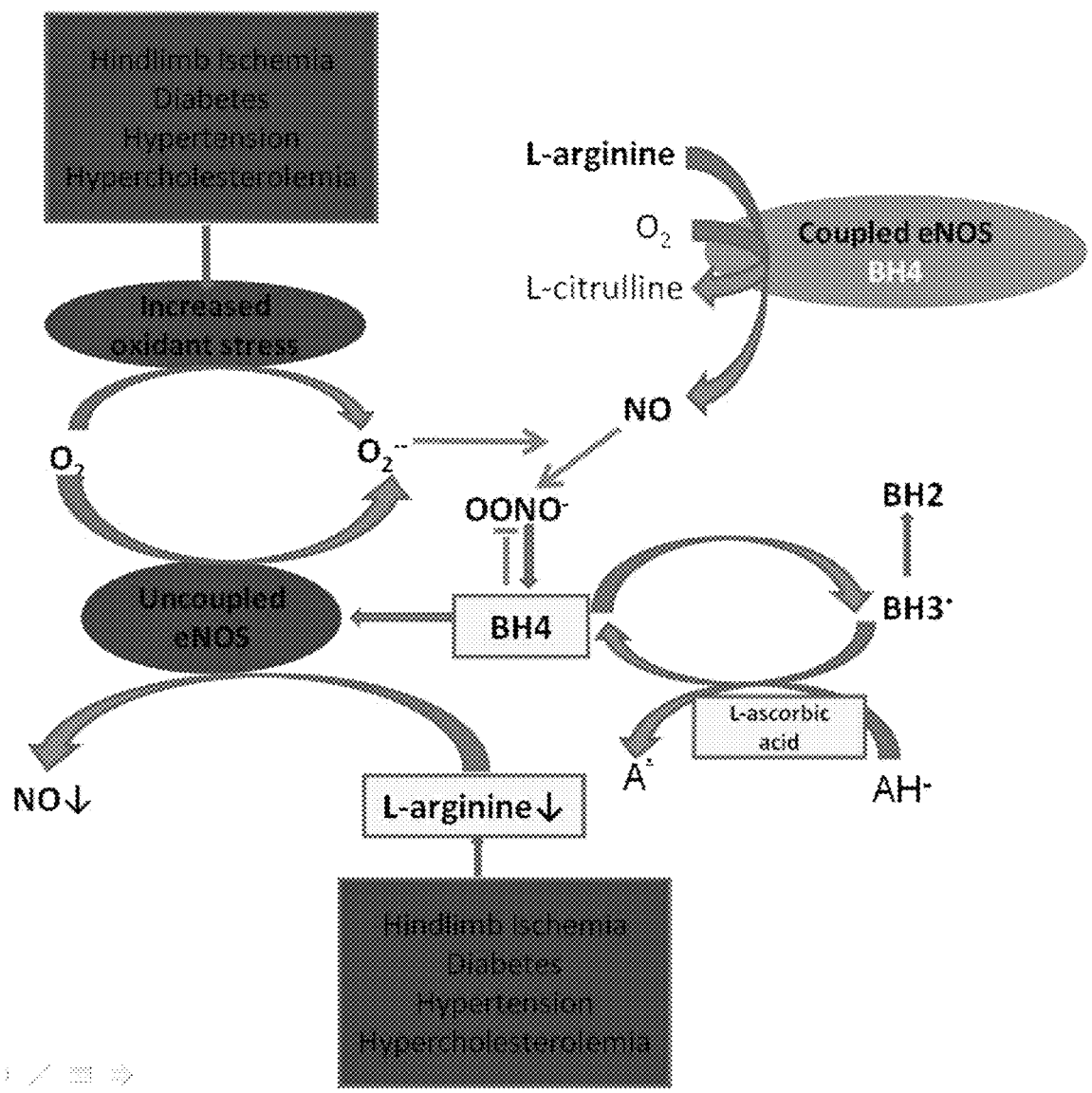
FIG. 1. Overview of molecular pathways related to oxidative stress.

In some embodiments, compositions, combinations, and methods are provided that balance the redox pathway shown in FIG. 1. FIG. 1 shows a non-limiting overview of molecular pathways related to oxidative stress. As illustrated, eNOS generates NO during the oxidation L-arginine to L-citrulline. An essential co-factor in this reaction is tetrahydrobiopterin (BH4) which maintains eNOS in the dimeric configuration wherein electron transfer from the flavin of the reductase domain of one monomer to the heme group within the oxidase domain of the other monomer occurs, ultimately resulting in oxidation of L-arginine. In the absence of BH4, or under conditions of systemic oxidative stress such as hypercholesterolemia, diabetes, smoking or obesity, eNOS becomes uncoupled, e.g., there is a loosening of the attachment between monomers; consequently, electron transfer between monomers fails to occur and the electron flux results in oxidation of molecular oxygen to form superoxide anion ($O2-$), a highly toxic free radical. Importantly, BH4 can itself undergo oxidation to form 7,8-dihydrobiopterin, which is functionally inactive. This circumstance can potentiate a vicious cycle in which uncoupled (BH4-deficient and/or systemic oxidative stress) eNOS generates $O2-$ which in turn oxidizes available BH4, causing further uncoupling of eNOS. Vitamin C, or L-ascorbic acid, is a potent antioxidant and has been shown to preserve BH4 levels and enhance endothelial NO production in vitro. For example, $ONOO-$ reacts with BH4 6-10 times faster when in the presence of ascorbate. The intermediate product of the reaction between $ONOO-$ and BH4 is the trihydrobiopterin radical ($BH3-$), which is reduced back to BH4 by ascorbate. Thus, ascorbate does not protect BH4 from oxidation but rather recycles BH3 radical back to BH4.

In some embodiments, compositions, combinations, and methods are provided that reduce or prevent oxidative stress by providing a substrate for a nitric oxide synthase, and, at the same time, providing a co-factor that maintains the synthase in a coupled state. In some embodiments an antioxidant or free radical scavenger also is provided.

In some embodiments, oxidative stress is defined as a state where a cell, tissue, or microenvironment is imbalanced with respect to reactive oxygen molecular pathways leading to cell or tissue damage, for example, due to a preponderance of superoxide, nitrites, nitrates or free radicals.

In some embodiments, a state of oxidative stress is determined or determinable by assessing a biomarker associated with oxidative stress, for example, as provided herein, in the cell, tissue, microenvironment, or subject in question, and comparing the results with a control or reference result, for example, the average result found in healthy cells, tissues, microenvironments, or subjects.

In some embodiments, a disease associated with oxidative stress or a symptom of oxidative stress is, e.g., claudication, myocardial infarction, atherosclerosis and/or ischemia, peripheral vascular disease, specific cancer types/scenarios (e.g., treatment/prevention of oxidative stress that impairs immune surveillance for cancer, adjunct therapy to conventional cancer therapy), cardiovascular disease, inflammatory disease, stem cell dysfunction (e.g., due to imbalanced differentiation as a result of oxidative stress), and/or a cell aging-related disease, a disorder associated with a deficiency in nitric oxide bioavailability, a deficiency in stem and/or progenitor cell differentiation capacity, proliferation, survival and/or maintenance, including, but not limited to, a deficiency in wound healing.

In some embodiments, oxidative stress in a subject is determined if the subject is diagnosed with an oxidative stress-related disease as provided herein. In some embodiments, oxidative stress in a subject is determined if a biomarker indicating an oxidative state, for example, a biomarker indicating a level of superoxide, nitrites, nitrates or free radicals, or a biomarker indicating the activity of an oxidative biochemical pathway, for example, a pathway leading to the production of such oxidative moieties, is elevated as compared to a healthy subject or healthy subjects. In some embodiments, oxidative stress in a subject is determined if a biomarker indicating a reductive state, for example, a biomarker indicating a level of an antioxidant, or a biomarker indicating the activity of reducing biochemical pathways, is reduced as compared to a healthy subject or healthy subjects. In some embodiments, oxidative stress is determine in a subject if the results from the biomarker or biomarkers assessed are statistically significantly different from those observed in a healthy subject or healthy subjects. It should be appreciated that the level of oxidative stress in a subject may be measured and/or estimated systemically (e.g., by evaluating exhaled and/or circulatory marker levels) or for particular tissues or cellular samples (e.g., by performing one or more suitable assays on a biopsy such as a tissue biopsy, or by analyzing specific cells, for example from a particular region or tissue or by isolating or enriching a sample for one or more particular cell types, for example based on cell surface markers that can be used for FACS-based cell sorting or other enrichment method).

In some embodiments, a subject that is identified as having abnormal (e.g., above normal) levels of oxidative stress may be treated with one or more compositions described herein in order to prevent, or reduce the risk of or development of, a disease or condition associated with oxidative stress. However, in some embodiments, a subject that is at risk of developing a disease associated with oxidative stress may be treated with one or more compositions as described herein regardless of whether the level of oxidative stress in that subject is determined. For example, a subject that has diabetes, hypercholesterolemia, an inflammatory disease (e.g., inflammatory bowel disease or syndrome, ulcerative colitis, Crohn's disease, etc.), cancer, or other disease, may be treated with one or more compositions described herein. However, it should be appreciated that in some embodiments a subject receiving a treatment described herein may be evaluated before, during, and/or after treatment to determine whether the dosages used are sufficient to balance the oxidative environment (e.g., restore normal levels of oxidative stress) of the subject (e.g., as a whole, or for particular tissue or cell types).

Many human diseases and disorders are caused, at least in part, by chronic or acute oxidative stress. Oxidative stress is a general term referring to an imbalance in the reduction-oxidation (redox) state of a cell, tissue, or microenvironment. Redox imbalances related to oxidative stress are characterized by a disability of the affected cell, tissue, or microenvironment to readily sequester or detoxify reactive oxygen species or easily repair damage caused by oxidation. For example, all of the major risk factors for the development of cardiovascular disease (e.g., development of atherosclerosis) injure artery walls by oxidative stress: e.g., hypercholesterolemia, diabetes, hypertension, obesity, and smoking. For example, oxidation of LDL in the vascular endothelium is a well-established precursor to vascular plaque formation.

Non-limiting examples of specific diseases or disorders caused by or related to oxidative stress include Cardiovascular disease (atherosclerosis), Myocardial Infarction (MI), Stroke due to carotid artery disease, Atherosclerosis, Heart Failure, Peripheral Arterial Disease (PAD), Intermittent Claudication, Critical Limb Ischemia, chronic fatigue syndrome, and insulin resistance. Some neurodegenerative diseases, for example Parkinson's Disease, ALS, and Alzheimer's Disease are also suspected to be related to oxidative stress. Other diseases that are suspected to be related to oxidative stress include, for example, autoimmune diseases, ataxia telangiectasia. Oxidative stress has further been linked to play a role in the onset, the progression, and the therapeutic outcome of clinical intervention in various types of cancer and inflammatory diseases. Further, according to aspects of the invention, oxidative stress can perturb tissue homeostasis by damaging stem and/or progenitor cells, which in turn can lead to aberrant cell proliferation and/or anomalous differentiation patterns in the affected tissue. In some embodiments, oxidative damage to stem and/or progenitor cells may be irreversible, and may, by itself, lead to the manifestation of a disease or disorder, or worsen an existing condition related to oxidative stress. However, in some embodiments, damage associated with oxidative stress may be reversed, at least in part, using one or more compositions described herein.

In some embodiments, aspects of this invention relate to the discovery that oxidative injury in stem or progenitor cells leads to dysfunction of the affected cells the manifestation of which accounts for the clinical presentation of many diseases not previously linked to stem or progenitor cell dysfunction, e.g., impaired wound healing in diabetics. Without wishing to be bound by theory, some aspects of this invention provide that other clinical manifestations, for example, impaired resistance to infection in diabetics, also are linked to oxidative injury to stem or progenitor cells. Further, some aspects of this invention provide that it is likely that the pathogenesis of many common diseases is due to oxidative stress-induced stem cell dysfunction.

Accordingly, in some embodiments, aspects of the invention relate to compositions and their use for treating one or more diseases or conditions described herein.

Oxidative stress can cause injury to stem and progenitor cells, resulting in multiple clinical manifestations of stem cell dysfunction in human patients having a disease associated with oxidative stress. In some embodiments, it is provided that oxidative stress, for example, in subjects having an oxidative stress-associated disease, causes injury to a stem and/or a progenitor cell population resulting in impaired stem/progenitor cell function, impaired stem cell/progenitor cell proliferation and/or proliferation capacity, impaired stem cell/progenitor cell differentiation, differentiation capacity, and/or aberrant stem cell/progenitor cell differentiation patterns.

In some embodiments, it is provided that oxidative stress causes injury to somatic (adult) stem cells. In some embodiments, it is provided that oxidative stress causes injury to progenitor cells. Examples of cell types susceptible to oxidative stress injury, according to some aspects of this invention, include, but are not limited to hematopoietic stem cells (HSCs), mesenchymal stem cells (MSCs), endothelial stem cells, neural stem cells, intestinal stem cells, mammary stem cells, olfactory stem cells, neural crest stem cells, and testicular stem cells, as well as progenitor cells derived from any of these stem cell types.

In some embodiments, it is provided that oxidative stress causes injury to pluripotent stem cells, for example, to embryonic stem cells (ESCs) or induced pluripotent stem cells (iPS cells).

In some embodiments, stem or progenitor cell injury in a subject is caused by oxidative stress associated with a disease or condition, for example, a disease or condition as described elsewhere herein (e.g., cardiovascular disease, PAD, diabetes, ischemia, claudication, etc.). In some embodiments, stem or progenitor cell injury in a subject is caused by sporadic oxidative stress, for example, oxidative stress associated with a subject's environment or lifestyle (e.g., smoking).

Accordingly, in some embodiments, aspects of the invention relate to compositions and their use in combination with protecting stem or progenitor cell function and/or restoring stem or progenitor cell function. In some embodiments, methods involve administering therapeutically effective amounts of compositions described herein to a subject (e.g., a human subject). In certain embodiments, methods involve treating a donor subject prior to removing stem or progenitor cells in order to protect or restore the function of the donor cells. In certain embodiments, methods involve treating a recipient of stem or progenitor cells in order to promote optimal function of the donor cells in the recipient. In some embodiments, methods involve treating stem or progenitor cells ex vivo (e.g., after obtaining them from a donor, but before implanting them in a recipient), for example, with or without expanding the cells ex vivo. In some embodiments, combinations of two or three of these acts may be used. It should be appreciated that some of these embodiments may be particularly beneficial if the donor and/or the recipient have conditions associated with above-normal levels of oxidative stress (diabetes, obesity, hypercholesterolemia, etc.). However, methods of the invention may be used in conjunction with a donor, recipient, and/or cells that do not have any risk factors or high levels of oxidative stress in order to protect and/or promote optimal properties of the stem or progenitor cells.

Some aspects of this invention relate to the discovery that conditions such as hypercholesterolemia (e.g., caused either by genetic deletion of ApoE or by a high fat diet) and experimental type 2 diabetes (db/db mouse/leptin receptor KO) cause oxidant injury to hematopoietic and mesenchymal stem cells that impairs their most fundamental functions. Without wishing to be bound by theory, it is believed that the observed injury of stem cells consists of an oxidant-specific injury that affects the disease phenotype. For example, hypercholesterolemia causes loss of quiescence and accelerated aging of HSCs and impairs T cell specification that alters immune surveillance for cancer such as colon cancer as described in more detail herein. Without wishing to be bound by theory, it is believed that the risk of experimentally induced colon cancer in mice is linearly related to the extent of oxidant stress of the hematopoietic stems cells (r value 0.92), as described elsewhere herein. Some aspects of this invention relate to the discover that oxidant injury and its consequences on HSC proliferation and lineage specification as well as the risk of cancer can be reduced or reversed by a composition or combination as provided herein, for example, by providing an agent or agents that reduce/s oxidative stress of an in vivo microenvironment or an activator of an anti-oxidative pathway, a co-factor and/or activator that maintains and/or balances an oxidation/reduction pathway, an anti-oxidant and/or a free radical scavenger that maintains availability of the co-factor and/or activator and/or a combination thereof. In some embodiments, oxidant injury and its consequences on HSC proliferation and lineage specification as well as the risk of cancer can be reduced or reversed by N-acetylcysteine (NAC); ascorbic acid; a combination of L-Arg, and BH4; a combination of L-Arg, BH4, and ascorbic acid; or any other compound or composition described herein.

In some embodiments, aspects of this invention provide that injury to hematopoietic stem cells in diabetic subjects is associated with suboptimal clinical outcome in HSC transplantation involving a diabetic subject as either donor or recipient. Further, injury to mesenchymal stem cells in oxidative stress environments results in impaired MSC function, manifest, for example, in impaired wound healing observed in subjects with oxidative stress-associated disease, for example, diabetes. Oxidative stress can further cause injury to endothelial progenitor cells, resulting in impaired revascularization capacity observed in subjects with oxidative stress-associated disease.

Oxidative stress-induced injury to stem and progenitor cell populations, as well as the manifestations of the resulting impairment in stem and progenitor cell function can be observed in various animal models of oxidative stress-associated disease. For example, diabetic mice, e.g., db/db mice, exhibit multiple impairments associated with oxidative stress. Hematopoietic stem cells derived from diabetic db/db mice exhibit impaired repopulation capacity and aberrant differentiation patterns as described in more detail elsewhere herein. Accordingly, hematopoietic stem cells from diabetic subjects are associated with suboptimal clinical outcome, resulting in HSCs from diabetics generally being avoided for transplantation.

Further, according to some aspects of this invention, other stem and progenitor cell types, e.g., endothelial progenitor cells and mesenchymal stem cells are affected in db/db mice, as manifested in impaired neovascularization and wound healing capacity in db/db mice.

It is further described herein that experimental type 2 diabetes impairs HSC lineage specification of monocytes and accounts for the impairment in wound healing phenotype in this mouse model of type 2 diabetes. Without wishing to be bound by theory, it is further believed that the other key disease phenotype of diabetics, impaired resistance to infection is also dependent on the consequences of oxidant injury to stem cells.

Some aspects of this invention relate to the development of biological therapies for various disease including, for example, cancer, particularly those sensitive to immune modulation, diabetes, and atherosclerosis. Some aspects of this invention relate to the discovery that systemic conditions that are known to cause oxidant stress such as hypercholesterolemia, smoking, diabetes, hypertension, and obesity, induce oxidant stress in stem cells whereby the nature of the impairment of HSC function is specific to the change in oxidant-antioxidant systems within stem cells. The changes include those downstream from redox systems such as nitrosylation of tyrosine residues by peroxynitrates.

Some aspects of this invention relate to the discovery that the presence of conditions causing oxidative stress in either the donor or recipient of a stem or progenitor cell transplant are of critical importance in the failure of cell therapy approaches. For example, the presence of systemic conditions causing oxidant stress in a subject that is a donor or stem or progenitor cells can impair the quality, the repopulation capacity, and the differentiation pattern of the donated stem cells, as described herein, while the presence of such conditions in the recipient of stem or progenitor cells can affect the recipient's likelihood of successful cell therapy. Accordingly, such conditions are potential targets for treatment to reduce the specific oxidant stress.

In the circumstance of mesenchymal stem cells (MSCs), type 2 diabetes-associated oxidative stress restricts their multipotency increasing their propensity to differentiate into adipocytes and restricting their capacity to differentiate into endothelial cells. This impairment of mesenchymal stems cells by type 2 diabetes also affects their ability to respond and therapeutically enhance neovascularization after the induction of hindlimb ischemia, as demonstrated herein. It is also provided herein that hypercholesterolemia restricts MSC capacity to differentiate into endothelial cells and thereby may impair various forms of neovascularization.

Some aspects of this invention provide that cancers that are sensitive to the body's immune surveillance system, for example, colon cancer, renal cell cancer, prostate cancer, and sarcoma, may be treated adjunctively in a way to normalize HSC function and thereby the effectiveness of their immune surveillance system to fight cancer. In some embodiments, compositions, combinations and methods are provided for the reversal of HSC oxidant stress and associated functional impairments (e.g., normalization of T gamma delta and natural killer T cell number and function) by administering a triple therapy and/or N-acetylcysteine composition or combination as provided herein, for example, by a method provided herein. In some embodiments, reversal of oxidant injury to stem or progenitor cells is effected by administering any system that normalizes redox state of stem cells as provided herein.

Some aspects of this invention relate to the discovery that oxidative injury to HSCs causes aberrant Notch expression, for example, aberrant Notch1 expression, resulting in impaired lineage differentiation, as described in more detail elsewhere herein. In some embodiments, compositions, combinations, or methods are provided to normalize HSC function by normalizing Notch expression, for example, by contacting affected HSCs with NAC or other composition described herein or by reducing Notch1 expression in HSCs via RNAi methodology, for example, by lentivirus-mediated si-RNA.

Some embodiments provide methods for reversing or ameliorating impaired wound healing in patients with type 2 diabetes. In some embodiments, a method is provided to reverse or ameliorate oxidative injury to mesenchymal stem cells in a diabetic subject by administering a composition or a combination as provided herein to the subject. In some embodiments, a method is provided for in vitro reversal of mesenchymal stem cell oxidant stress comprising contacting the cell with a composition or combination as provided herein, for example, with NAC, a triple therapy composition, or any substance or composition described herein that normalizes MSC redox state. In some embodiments, a method is provided for in vitro siRNA-mediated knockdown of Nox 4 in mesenchymal stem cells to specifically reverse oxidant stress of MSCs caused by type 2 diabetes.

In some embodiments, a method for stem cell therapy, for example, hematopoietic and mesenchymal stem cell therapy, in a subject (e.g., a human subject) having oxidative stress, for example, a subject having hypercholesterolemia or diabetes, is provided. In some embodiments, the method comprises in vitro restoration of stem cell function by NAC, or other composition described herein (e.g., a mono, double, or triple therapy described herein) or by any means that reverses stem cell oxidant stress. In some embodiments, the method comprises in vivo reversal of systemic oxidant stress in a subject that is a donor or a recipient of a stem or progenitor cell population by administering a composition or combination as provided herein, for example, a triple therapy composition or NAC to the subject.

Some aspects of this invention relate to the discovery of a specific molecular pathway by which hypercholesterolemia or diabetes causes accelerated aging of stem and progenitor cells. Without wishing to be bound by theory, it is believed that HSCs and MSCs aging is central to tissue aging. Some aspects of this invention provide that healing after major tissue injury can be enhanced by compositions, combinations, and/or methods as provided herein, especially when conditions that cause systemic oxidant stress such as cardiovascular risk factors are present in the individual. Accordingly, compositions and methods described herein may be useful to promote wound healing in a subject (e.g., a human) that has suffered a traumatic injury. In some embodiments, compositions and methods described herein may be used to help promote wound healing in a subject (e.g., a human subject) recovering from a surgical intervention.

Some aspects of this invention relate to compositions, combinations, and methods useful for the prevention, reduction, or treatment of oxidative stress in stem or progenitor cell transplantation scenarios, for example, in bone marrow transplantation. Without wishing to be bound by theory, it is believed that bone marrow, and HSC transplantation is an eNOS/nitric oxide dependent process. It is believed that systemic oxidant stress of a bone marrow cell donor or recipient effects the success of the bone marrow transplantation. In some embodiments, a method is provided comprising isolating HSCs, for example, as a bone-marrow-derived cell population, from a donor subject, and to perform FACS on the obtained cell population to isolate HSCs with no or only minor oxidant injury. Biomarkers for determining such HSCs with no or only minor oxidative injury are described in more detail elsewhere herein. In some embodiments, the method comprises isolating the HSCs with minor or no oxidative injury and administering the isolated HSCs to a recipient subject. In some embodiments, such transplantation strategies using HSC populations enriched for cells having no or minor oxidative injury have a higher rate of success for effective bone marrow rescue. In some embodiments, such methods increase the rate of bone marrow transplantation success for current conditions for which it is used. In some embodiments, such methods expand current indications of stem or progenitor cell transplantation, for example, by increasing the pool of potential donors.

In some embodiments, aspects of this invention relate to the prevention, amelioration, or reversal of stem and/or progenitor cell injury caused by oxidative stress. In some embodiments, compositions, combinations, and methods are provided for balancing the oxidative state of a stem and/or progenitor cell microenvironment in a subject, for example, in a subject having a disease associated with oxidative stress. In some embodiments, such methods involve administering to the subject (A) an agent reducing oxidative stress of an in vivo microenvironment, (B) a co-factor and/or activator that maintains and/or balances the oxidation/reduction pathways, and/or (C) an anti-oxidant and/or a free radical scavenger that maintains availability of the co-factor and/or activator, for example, in a balanced ratio, as described in more detail elsewhere herein. In some embodiments, compositions, combinations and methods are provided for balancing the oxidative state of a stem and/or progenitor cell microenvironment in vitro, for example, in a cell population in culture or in a cell population obtained from a cell donor for transplantation to a recipient subject. In particular, such compositions, combinations, and methods are useful for the reduction or prevention of oxidative stress or the reversal of oxidative injury in stem or progenitor cells obtained from a subject diagnosed with a disease or condition associated with oxidative stress, or for transplantation to a recipient diagnosed with such a disease or condition. In some embodiments, such methods involve administering to the subject (A) an agent reducing oxidative stress of an in vivo microenvironment, (B) a co-factor and/or activator that maintains and/or balances the oxidation/reduction pathways, and/or (C) an anti-oxidant and/or a free radical scavenger that maintains availability of the co-factor and/or activator, for example, in a balanced ratio, as described in more detail elsewhere herein.

In some embodiments, administering agents to a subject according to a therapeutic method provided herein results in reversal of oxidative stem or progenitor cell injury in the subject. In some embodiments, administering agents to a subject according to a therapeutic method provided herein results in an amelioration of oxidative stem or progenitor cell injury in the subject. In some embodiments, reversal and/or amelioration of oxidative injury results in an improvement of a clinical manifestation of oxidative stem or progenitor cell injury. For example, in some embodiments, reversal and/or amelioration of oxidative injury results in improvement or normalization of stem/progenitor cell function, stem cell/progenitor cell proliferation and/or proliferation capacity, stem cell/progenitor cell differentiation, differentiation capacity, and/or stem cell/progenitor cell differentiation patterns.

For example, administering a therapeutic composition as provided herein to a diabetic subject (e.g., a human patient, an experimental animal, for example, a db/db mouse) results, in some embodiments, in improvement of EPC revascularization capacity, HSC repopulation capacity, MSC wound healing capacity, and other beneficial clinical outcomes as described in more detail elsewhere herein. Further, in some embodiments, an agent provided herein, for example N-acetyl cysteine, may be used to reverse oxidative stress caused by ox-LDL induced oxidant stress of hematopoietic stem cells.

In some embodiments, methods for replenishing stem or progenitor cell populations damaged by oxidative stress in a subject (e.g., a human patient) are provided. In some embodiments, these methods comprise identification of a damaged (e.g., an irreversibly damaged) subpopulation of stem or progenitor cells and removal of cells belonging to such a subpopulation from the subject. In some embodiments, these methods comprise identification of a non-damaged subpopulation of stem or progenitor cells, isolation and amplification of cells belonging to such a subpopulation from a donor subject under conditions decreasing oxidative stress and administration of such non-damaged stem or progenitor cells to a recipient subject. In some embodiments, the identification of non-damaged cells comprises labeling the cells based on the expression of a biomarker indicating non-damaged status and isolating them from a population of cells. One example of such a labeling strategy is the use of 2',7'-dichlorodihydrofluoroscein diacetate (H2DCFDA), which is converted to the fluorescent 2',7'-dichlorofluoroscein (DCF) after oxidation. In some embodiments, isolating is performed by cell sorting using methods well known in the art, for example fluorescent or magnetic cell sorting technologies (FACS or MACS). In some embodiments, the donor and recipient are the same subject. In some embodiments, the donor and the recipient are not the same subject. In some embodiments, the donor and the recipient are genetically matched subjects. In some embodiments, the recipient undergoes whole-body irradiation before non-damaged stem cells are administered. In some embodiments, the stem or progenitor cells are hematopoietic stem or progenitor cells.

In some embodiments, FACS analysis is used for sorting cells. Stem cells are exposed to a fluorescent label for oxidant stress, e.g., DCF, and separated by FACS. However, alternative methods also may be used.

Some aspects of this invention relate to the discovery that oxidative stress, for example oxidative stress associated with a disease or condition as described herein (e.g., diabetes, cardiovascular disease, etc.), can be a detrimental factor in transplantation outcome. For example, some aspects of this invention provide that stem or progenitor cells exhibit diminished repopulation capacity if they are isolated from and/or transplanted into a subject having a disease or condition associated with oxidative stress. Some aspects of this invention provide methods for improving the performance of cells or tissues isolated from and/or transplanted into a subject having a disease or condition associated with oxidative stress (e.g., diabetes, cardiovascular disease, atherosclerosis, etc.).

In some embodiments, methods are provided to ameliorate oxidative stress in cells, for example, in stem or progenitor cells that are used in a transplantation. A non-limiting example for the use of stem and/or progenitor cells in transplantation is hematopoietic stem cell transplantation, for example, bone marrow transplantation. However, it will be appreciated by those of skill in the art that methods and compositions provided herein can be used for transplantations or other types of stem and/or progenitor cells, e.g., neural stem cells, mesenchymal stem cells, and myocardial progenitor cells. In some embodiments, methods are provided to ameliorate oxidative stress in cells that are part of a tissue used in a transplantation, for example, liver, kidney, or heart tissue.

In some embodiments, methods and compositions for administration to a stem or progenitor cell donor are provided that ameliorate or reverse oxidative injury to stem and/or progenitor cells in the donor. In some embodiments, the donor is a subject having a disease or condition associated with oxidative stress, for example, a cardiovascular disease, diabetes, or any other disease or condition provided herein. In some embodiments, a method is provided comprising administering a therapeutic composition as provided herein to a donor having a disease or condition associated with oxidative stress, for example, diabetes or a cardiovascular disease. In some embodiments, the donor is a subject disqualified from donating stem and/or progenitor cells because of having a disease or condition associated with oxidative stress and/or oxidative stem/progenitor cell injury.

In some embodiments, a method is provided for administering a therapeutic composition as provided herein, for example, a triple therapy composition, to the donor prior to obtaining a cell or cell population, for example, a stem and/or progenitor cell population, from the donor. In some embodiments, a method provided herein comprises monitoring the oxidative status of the donor, for example, the oxidative status of a cell, tissue or microenvironment of the donor, prior to obtaining a cell population from the donor. In some embodiments, a method provided herein comprises determining the oxidative state of a cell or cell population obtained from the donor. Methods for determining an oxidative state of a cell, tissue, or microenvironment are provided and described in more detail elsewhere herein and additional methods are well known to those in the art.

In some embodiments, a method is provided comprising contacting a cell population, for example, a stem or progenitor cell population obtained from a subject having a disease or condition associated with oxidative stress or a cell population having experienced or susceptible to oxidative injury, with a therapeutic composition provided herein. In some embodiments, a method provided herein comprises monitoring the oxidative state of a cell or population of cells before and/or after contacting the cell or cell population with a composition as provided herein. In some embodiments, a method provided herein comprises using the cell or cell population in a transplantation to a subject after contacting the cell with a composition provided herein and/or after the oxidative state of the cell or cell population has been determined to be normalized.

In some embodiments, a method is provided for administering a therapeutic composition as provided herein to a recipient of a cell transplant, for example, a stem or progenitor cell transplant or a tissue transplant. In some embodiments, a method provided herein comprises administering a therapeutic composition as provided herein to a recipient of a cell or tissue transplant, wherein the recipient has a disease or condition associated with oxidative stress. In some embodiments, a therapeutic composition as provided herein is administered to the subject prior, during and/or after transplantation of the cell or the cell population. In some embodiments, the oxidative state of the recipient is monitored prior, during and/or after transplantation. In some embodiments, administration of a composition as provided herein is commenced until a positive clinical outcome is achieved (e.g., repopulation of a cell niche, e.g., a hematopoietic stem cell niche, or restoration of a cellular function), or until an oxidative state (e.g., a normal or close to normal state) of a cell, cell population, tissue, or microenvironment in the recipient is determined.

In some embodiments, a method is provided comprising administering a composition or combination as described herein to a subject that is a donor of a stem or progenitor cell population prior to obtaining the stem or progenitor cells from the subject. For example, in some embodiments, a method is provided that comprises administering a triple therapy composition or combination or NAC or other composition described herein to a donor subject prior to bone marrow aspiration to reduce HSC oxidant stress. In some embodiments, the method further comprises FACS sorting of the obtained stem or progenitor cells, for example, HSCs, to identify the cells with low or no oxidant injury, isolating the identified cells, and/or administering the identified cells to a recipient subject.

In some embodiments, a method is provided comprising contacting stem or progenitor cells obtained from a donor subject with a composition of combination as provided herein. For example, in some embodiments, the method comprises contacting bone marrow cells with a triple therapy combination or NAC or other composition described herein prior to administering the cells to a recipient. In some embodiments, the method further comprises assessing a biomarker of oxidative stress in the stem or progenitor cells before administering them to a recipient subject. In some embodiments, the method comprises administering the stem or progenitor cells to a recipient based on the biomarker assessment indicating low or no oxidative injury to the stem or progenitor cells. In some embodiments, the method comprises administering the stem or progenitor cells after contacting them with the composition or combination as provided herein to a recipient and administering a composition or combination as provided herein to the recipient for a period of time in temporal proximity to the administration of the stem cells to the recipient. For example, in some embodiments, the method comprises administering a composition or combination as provided herein prior to the administration, during the administration, and/or after the administration of the stem cells to the recipient. In some embodiments, a combination or composition as provided herein is administered to a recipient subject for about 1, about 2, about 3, about 4, about 5, about 6, about 7, about 8, about 9 or about 10 weeks after administration of the stem or progenitor cells to the recipient.

In some embodiments, compositions, combinations and methods for prophylactic use are provided, for example, for prevention or reduction of the risk of oxidative stress or injury in a cell, tissue, microenvironment or subject. Many subjects have risk factors, for example, atherosclerosis, diabetes, ischemia, claudication, or cardiovascular disease, that predispose them to oxidative stress. These risk factors, for example, as described herein, are easily identified and arise from genetic as well as environmental factors. In some embodiments, the compositions, combinations, and methods are used in such subjects as preventative measures to halt or slow the development of oxidative stress. In some embodiments, such preventative applications of the compositions and combinations as provided herein have long term benefits on the health of the subjects.

Molecular Basis of Oxidative Stress

Oxidative stress involves the generation of reactive oxygen species, for example superoxide, peroxides, for example hydrogen peroxide or organic hydroperoxides, oxygen radicals, for example hydroxyl radicals, alkoxy radicals, and peroxy radicals, hypochlorous acid, and peroxynitrite. Some of the less reactive species, for example superoxide can be converted into more aggressive oxygen species that are capable of inflicting extensive cellular damage. Oxidative stress can irreversibly damage DNA and may, thus, impose long-term effects on the affected cells, tissues, or microenvironments.

A number of molecular pathways have been identified that regulate and balance the redox state of cells, tissues and microenvironments. The best studied cellular antioxidants are the enzymes superoxide dismutase, catalase, glutathione peroxidase, peroxiredoxins, and sulfiredoxin. Other examples of enzymes with antioxidant properties include paraoxonase, glutathione-S transferase, and aldehyde dehydrogenase. Other molecular pathways have also been implied for playing a role in regulating the redox state of cells, tissues and microenvironments. FIG. 1 outlines some of the interacting pathways that affect the redox state of cells, tissues, and microenvironments.

Methods and Biomarkers to Determine Oxidative Stress in Cells and Tissues

In some embodiments, methods and biomarkers for monitoring oxidative stress in cells, tissues, or microenvironments are provided. In some embodiments, methods for monitoring the effect of a therapeutic method or composition on oxidant stress is provided. In some embodiments, the method comprises a direct assessment of cell, tissue, or microenvironment redox state, for example, using an assay as described herein.

In some embodiments, the method comprises assessment of a systemic plasma biomarker, for example, serum nitrotyrosine levels or a scan of body that assesses systemic oxidant stress and stem cell redox state. Other methods and biomarkers for the assessment of the oxidative state of a cell, tissue, or microenvironment are well known to those of skill in the art.

For example, the oxidative state of a cell, tissue, or microenvironment can be determined by using one or more in vitro, ex vivo and/or in vivo assays well known to those of skill in the art, including, but not limited to, free radical assays (e.g., assays for superoxide radicals, oxygen radicals, hydrogen peroxide, hypochlorite radicals, hydroxyl, 2,2-diphenyl-1picryhydrazyl (DPPH) radicals, peroxyl radicals (e.g., peroxylnitrite radicals, such as N,N-dimethyl-p-phenyleneamine radicals, and alkylperoxyl radicals)), coupled cytochrome c reduction assays, haematoxylin oxidation assays, lipid peroxidation assays, aconitase assays, catalase assays, glutathione assays, glutathione peroxidase assays, glutathione reductase assays, lipid hyperoxide assays, malondialdehyde (MDA) assays, monoamine oxidase assays, protein oxidation assays, protein nitrosylation assays, SSAO (semicarbazide-sensitive amine oxidase) assays, and superoxide dismutase (SOD) assays. Accordingly, the effect of any agent as provided herein under (A), (B), or (C), alone, or in any combination of 2 or 3 thereof, on the oxidative state of a cell, tissue, or microenvironment can be determined and quantified.

In some embodiments, the oxidative state of a cell, tissue, or microenvironment is determined by assaying an RSNO biomarker, e.g., S-nitrosoglutathione (GSNO), Cys-NO, Hemoglobin-NO, or albumin-NO; or nitrite, nitrate, or ADMA (asymmetric dimethlyarginine) levels in the cell, tissue, or microenvironment, for example, as described in Warwick et al., *Biomarkers in pulmonary hypertension*. Eur Respir J. 2008 August; 32(2):503-12; and Kaneko et al., *Biochemical reaction products of nitric oxide as quantitative markers of primary pulmonary hypertension*. Am J Respir Crit Care Med. 1998 September; 158(3):917-23; all references incorporated herein by reference.

In some embodiments, the systemic oxidative state of a subject is determined by assaying exhaled NO, for example, as described in Marshall et al., *Exhaled Nitric Oxide During Exercise in Primary Pulmonary Hypertension and Pulmonary Fibrosis*. M Chest. 1997 January; 111(1):44-50, incorporated herein in its entirety by reference for disclosure of methods relevant to measuring exhaled NO.

In some embodiment, the oxidative state of a cell, tissue, or microenvironment is determined by assaying nitric oxide synthase (e.g., eNOS) activity. Nitric oxide synthase (e.g., eNOS) activity can be determined and/or quantified by in vitro, ex vivo, and/or in vivo assays well known to those of skill in the art, including, but not limited to, arginine to citrulline conversion assays, nitric oxide and/or nitrite assays, (e.g., determination of nitrite concentration in a biological sample, e.g., a body fluid, cell, tissue, or tissue culture sample, by assays known in the art, e.g., Griess method) and nitrotyrosine assays. Accordingly, the effect of an agent under (A) or under (B) on eNOS activity can be determined and quantified. An amount of such an agent appropriate for generating a balanced ratio of the agents provided under (A) or (B) can then be determined as an amount resulting in the same effect on eNOS activity as any of the ratios given for the combinations of agents herein.

Similarly, antioxidant properties of an agent provided under (C) can be determined and/or quantified by in vitro, ex vivo, and/or in vivo assays known to those of skill in the art, including, but not limited to, by ORAC (oxygen radical absorbance capacity). FRAP (ferric reducing/antioxidant power), TAC (total antioxidant capacity) assays. Those of skill in the art will recognize other assays suitable for determining and/or quantifying antioxidant properties of agents provided under (C). In some embodiments, an equivalent of an agent under (C) to a specified amount of a given agent, for example, 88.5 mg/kg/day vitamin C, is represented by the amount of agent having an essentially identical antioxidant capacity.

In some embodiments an assay involves using 2',7'-dichlorodihydrofluoroscein diacetate (H2DCFDA), which is converted to the fluorescent 2',7'-dichlorofluoroscein (DCF) after oxidation, as described herein.

It should be appreciated that one or more of these markers (or other markers described herein, for example, in the Examples or elsewhere herein, or other markers useful for measuring or assessing the redox state of a cell, tissue, or microenvironment) may be assayed and evaluated in conjunction with any of the applications described herein. Accordingly, markers described in the examples can be used in other applications described herein and are not limited to the details of the examples. In some embodiments, a reference redox level for a subject may be obtained prior to any treatment described herein and the redox level for the subject may be monitored during treatment and/or after treatment. In some embodiments, the redox level for the subject (prior to, during, and/or after treatment) may be compared to a reference level that may be the subject's reference level (e.g., the subject's level immediately prior to treatment or the subject's level taken at an earlier time, for example, at a time when the subject was healthy or did not have any signs of oxidative stress), or a third party reference level (e.g., a general standard indicative of a normal redox environment, or a standard or threshold indicative of abnormal oxidative stress). In some embodiments, the dosage of a composition (e.g., the dosage or a compound or the relative dosage of two, three, or more compounds in a combination therapy) may be adjusted during treatment (e.g., if a treatment is administered chronically, the dosage may be adjusted between administrations in response to redox information from the subject).

It should be appreciated that the assays described herein may be performed on any suitable sample (e.g., any suitable tissue, cellular, or other patient sample). In some embodiments, individual cell types or groups of cell types may be isolated or enriched prior to evaluating their redox status (e.g., by cell sorting using methods well known in the art, for example fluorescent or magnetic cell sorting technologies, for example FACS or MACS or other technique).

The Role of Nitric Oxide

Nitric oxide (NO) metabolism plays a key role in balancing the redox state of cells, tissues and microenvironments. Aberrant NO bioactivity can result in direct tissue toxicity and can contribute to vascular collapse. Growing evidence indicates that impaired endothelium-derived NO bioactivity is due, in part, to excess vascular oxidative stress. Decreased levels of NO can lead to impaired vascular homeostasis, vascular damage, endothelial dysfunction and vascular inflammation. Abnormal NO levels have further been associated with various carcinomas and inflammatory conditions. In addition, S-nitrosylation of protein residues is a common way in which proteins undergo post-translational modification under both normal and abnormal conditions. Therefore nitric oxide bioavailability has many direct and indirect mechanisms by which it exerts control of cell function and these mechanisms are highly sensitive to the redox state of the microenvironment. In some embodiments, abnormal NO levels result in abnormal patterns of S-nitrosylation on one or more proteins. It should be appreciated that these abnormal patterns can be used to evaluated the NO levels and/or the effectiveness of a composition described herein.

NO is synthesized by NO synthases (NOSs), of which three isoforms are known: endothelial (eNOS), neuronal (nNOS), and inducible (iNOS)—each with separate functions. NOSs oxidize the guanidine group of L-Arginine in a process that consumes five electrons and results in the formation of NO with stoichiometric formation of L-citrulline. NO synthesis involves the oxidation of NADPH and the reduction of molecular oxygen.

Single Therapy Approaches

In some embodiments, a single agent therapy approach is provided. In some embodiments, a single therapy approach comprises administering a composition provided herein to a cell, tissue, microenvironment or subject. In some embodiments, a single therapy approach comprises administering an agent that reduce/s oxidative stress of an in vivo microenvironment or an activator of an anti-oxidative pathway, a co-factor or activator that maintains and/or balances an oxidation/reduction pathway, or an anti-oxidant/free radical scavenger to a cell, tissue, microenvironment, or subject. In some embodiments, a single therapy approach comprises administering NAC to a cell, tissue, microenvironment, or subject. In some embodiments, a single therapy approach comprises administering ascorbic acid or ascorbate to a cell, tissue, microenvironment, or subject.

In some embodiments, a single therapy approach yields no beneficial effect on a targeted redox state and, sometimes, even increases oxidative stress and its clinical manifestation. For example, conventional approaches to boost vascular NO bioactivity to reduce oxidative stress have focused on administering agents stimulating eNOS activity, for example L-Arginine. Such single-therapy approaches have been shown to be of limited success or even detrimental to certain patient populations (see, for example, Circulation 2007, 116:188-195; JAMA 2006, 295, 1:58-64, JAMA. 2007; 297(8):842-857 Eur. Heart J. 24:1287-1295, 2003). However, according to some aspects of this invention, in situations where single therapy approaches are of very limited success, or, in some instances, even result in detrimental effects on redox state balance in target cells or tissues, a double or triple therapy approach may achieve the desired normalization of the redox state of a cell, tissue, or microenvironment.

Double Therapy Approaches

In some embodiments, a double agent therapy approach is provided. In some embodiments, a double therapy approach comprises administering a composition provided herein to a cell, tissue, microenvironment or subject. In some embodiments, a double therapy approach comprises administering two compounds selected from the group consisting of agent(s) that reduce/s oxidative stress of an in vivo microenvironment, activator(s) of an anti-oxidative pathway, co-factor(s) or activator(s) that maintains and/or balance an oxidation/reduction pathway, anti-oxidants and free radical scavenger(s) to a cell, tissue, microenvironment, or subject. In some embodiments, a double therapy approach comprises administering Arginine and BH4 to a cell, tissue, microenvironment, or subject.

Triple Therapy Approaches

In some embodiments, some aspects of this invention relate to the unexpected finding that, while some activators of molecular pathways that optimize or balance the redox state of a cell, tissue, or microenvironment often have no effect or even a detrimental effect when administered alone or in unbalanced compositions, the administration of such agents in a balanced ratio with other agents, such as co-factors and anti-oxidants, can significantly increase the beneficial effects on the redox state of a target cell, tissue, or microenvironment, and/or avoid the detrimental effects of the agent administered alone.

Accordingly, some aspects of this invention relate to methods and compositions that optimize or balance the redox state of a cell, tissue, or microenvironment by administering a balanced ratio of agents activating molecular pathways reducing oxidative stress to a subject, thus preventing, reducing, or ameliorating acute or chronic oxidative stress. Methods and balanced compositions useful to optimize or balance the redox state of a cell, tissue, or microenvironment are described herein.

In some embodiments, the method comprises administering to a subject a balanced ratio of (A) an agent reducing oxidative stress, (B) a co-factor and/or activator of a molecular pathway involved in the regulation of a cellular redox state, and (C) an antioxidant and/or free radical scavenger.

This administration of a balanced ratio of agents with three functions given under a, b, and c, is referred to herein as "triple therapy". In some embodiments, the antioxidant and/or free radical scavenger provided under (C) maintains availability of the co-factor and/or activator provided under (B), for example by inhibiting the oxidation of the co-factor and/or activator by free oxygen radicals. In some embodiments, the agent reducing oxidative stress provided under (A) is L-Arginine, N-acetyl-cysteine, and/or L-Cysteine. In some embodiments, the co-factor and/or activator of a molecular pathway involved in the regulation of a cellular redox state provided under (B) is BH4, 6R-BH4, BH3, BH2, sapropterin, sepiapterin, a BH4-derivative, or other pteridine. In some embodiments, the antioxidant and/or free radical scavenger provided under (C) is ascorbic acid, ascorbate, Glutathione, Lipoic acid, a carotene, for example beta-carotene, α-Tocopherol, and/or Ubiquinol. However, in some embodiments, other compounds may be used as aspects of the invention are not limited in this respect.

Balanced Ratios

The term "balanced ratio", as used herein, refers to a ratio of the agents provided herein that allows the agent reducing oxidative stress provided under (A) to reduce oxidative stress in a target cell, tissue, or microenvironment, the co-factor and/or activator provided under (B) to activate and/or maintain activity of a molecular pathway involved in the regulation of a cellular redox state and the antioxidant and/or free radical scavenger provided under (C) to maintain availability of the co-factor and/or free radical scavenger provided under (B). Some aspects of this invention relate to the discovery that, in some embodiments, while administered by itself or in an imbalanced ratio, an agent provided by some aspects of this invention may have no effect or even detrimental effects (see, for example, Circulation 2007, 116:188-195; JAMA 2006, 295, 1:58-64, JAMA. 2007; 297(8):842-857 Eur. Heart J. 24:1287-1295, 2003), administration of the agents in a balanced ratio is beneficial.

In some embodiments, the agents provided under (A), (B), and (C), as provided herein, are administered in doses as provided elsewhere herein or known to the skilled artisan to be clinically effective doses or doses below the compounds toxicity dosage. In some embodiments, a balanced ratio of agents given under (A), (B), and (C), as provided herein, is a ratio of (A):(B):(C) as given in Table 1 below:

TABLE 1

Exemplary balanced ratios of agents provided under (A), (B), and (C). The skilled artisan will understand that each given ratio between two agents (e.g., A and B) provided can be combined with each given ratio for any of these agents with the third agent (e.g., A:C or B:C) to result in a balanced ratio of the three agents within the scope of some embodiments of this invention.

| | Agent | | |
|---|---|---|---|
| | (A) | (B) | (C) |
| 1 | 1-20 | 1 | 1-20 |
| 2 | ~2.5 | 1 | 1-20 |
| 3 | ~5 | 1 | 1-20 |
| 4 | ~7.5 | 1 | 1-20 |
| 5 | ~8 | 1 | 1-20 |
| 6 | ~9 | 1 | 1-20 |
| 7 | ~10 | 1 | 1-20 |
| 8 | ~12 | 1 | 1-20 |
| 9 | ~20 | 1 | 1-20 |
| 10 | ~10 | 1 | ~10 |
| 11 | 1-30 | 1 | 0.1-15 |
| 12 | 2.5-30 | 1 | 0.1-15 |
| 13 | 5-30 | 1 | 0.1-15 |

TABLE 1-continued

Exemplary balanced ratios of agents provided under (A), (B), and (C). The skilled artisan will understand that each given ratio between two agents (e.g., A and B) provided can be combined with each given ratio for any of these agents with the third agent (e.g., A:C or B:C) to result in a balanced ratio of the three agents within the scope of some embodiments of this invention.

| | Agent | | |
|---|---|---|---|
| | (A) | (B) | (C) |
| 14 | 7.5-30 | 1 | 0.1-15 |
| 15 | 10-30 | 1 | 0.1-15 |
| 16 | 12-30 | 1 | 0.1-15 |
| 17 | 20-30 | 1 | 0.1-15 |
| 18 | 1-30 | 1 | 0.1-0.2 |
| 19 | 1-30 | 1 | 2-15 |
| 20 | 10-30 | 1 | 2-15 |
| 21 | 2.5-50 | 1 | 2-50 |
| 22 | 2.5-50 | 1 | ~2.5 |
| 23 | 2.5-50 | 1 | ~5 |
| 24 | 2.5-50 | 1 | ~7.5 |
| 25 | 8.85 | 1 | 8.85 |
| 26 | 2.5-50 | 1 | 5-100 |
| 27 | 5-50 | 1 | 10-100 |
| 28 | 10-20 | 1 | 10-1000 |
| 29 | 2.5-100 | 1 | 10-10000 |
| 30 | 10-100 | 1 | 100-10000 |
| 31 | 10-300 | 1 | 1-150 |
| 32 | 2-6 | 1 | 0.02-30 |

In some embodiments, the agent provided under (A) is L-Arginine or N-acetyl-cysteine (NAC). In some embodiments, the agent provided under (B) is tetrahydrobiopterin (BH4), trihydrobiopterin (BH3), dihydrobiopterin (BH2), sapropterin (6R-BH4, e.g., as sapropterin hydrochloride), or sepiapterin.

In some embodiments, the agent provided under (A), e.g., L-Arginine or NAC, is administered to a subject at a dosage between about 1 mg/kg/day and about 50 mg/kg/day. In some embodiments, the agent provided under (A), e.g., L-Arginine or NAC, is administered to a subject at a dosage between about 1 mg/kg/day and about 300 mg/kg/day. In some embodiments, the agent provided under (A), e.g., L-Arginine or NAC, is administered to a subject at a dosage between about 10 mg/kg/day and about 300 mg/kg/day. In some embodiments, the agent provided under (A), e.g., L-Arginine or NAC, is administered to a subject at a dosage of at least about 1, at least about 2, at least about 2.5, at least about 5, at least about 7.5, at least about 8, at least about 8.5, at least about 9, at least about 10, at least about 11, at least about 12, at least about 13, at least about 14, at least about 15, at least about 16, at least about 17, at least about 18, at least about 19, at least about 20, at least about 21, at least about 22.5, at least about 25, at least about 27.5, at least about 30, at least about 35, at least about 40, at least about 50, at least about 60, at least about 70, at least about 80, at least about 90, at least about 100, at least about 150, at least about 200, at least about 250, or at least about 300 mg/kg/day. In some embodiments, a cell or population of cells is contacted with the agent provided under (A), e.g., L-Arginine or NAC, for example, a cell obtained from a subject, for example, a cell donor, or a cell in culture. In some such embodiments, the cell is contacted in a solution, and the concentration of the agent provided under (A) is between about 0.01 micromol/l to about 1 millimol/l.

In some embodiments, the agent provided under (B), e.g., BH4 or sapropterin, is administered to a subject at a dosage between about 1 mg/kg/day and about 50 mg/kg/day. In some embodiments, the agent provided under (B), e.g., BH4 or sapropterin, is administered to a subject at a dosage of at least about 1, at least about 2, at least about 2.5, at least about 5, at least about 7.5, at least about 8, at least about 8.5, at least about 9, at least about 10, at least about 11, at least about 12, at least about 13, at least about 14, at least about 15, at least about 16, at least about 17, at least about 18, at least about 19, at least about 20, at least about 21, at least about 22.5, at least about 25, at least about 27.5, at least about 30, at least about 35, or at least about 40 mg/kg/day. In some embodiments, a cell or population of cells is contacted with the agent provided under (B), e.g., BH4 or sapropterin, for example, a cell obtained from a subject, for example, a cell donor, or a cell in culture. In some such embodiments, the cell is contacted in a solution, and the concentration of the agent provided under (B) is between about 0.01 micromol/l to about 1 millimol/l.

In some embodiments, the agent provided under (C) is ascorbic acid or ascorbate (e.g., vitamin C). In some embodiments, the agent provided under (C), e.g., ascorbic acid or ascorbate, is administered to a subject at a dosage between about 1 mg/kg/day and about 150 mg/kg/day. In some embodiments, the agent provided under (C), e.g., ascorbic acid or ascorbate, is administered to a subject at a dosage of at least about 1, at least about 2, at least about 2.5, at least about 5, at least about 7.5, at least about 8, at least about 8.5, at least about 9, at least about 10, at least about 11, at least about 12, at least about 13, at least about 14, at least about 15, at least about 16, at least about 17, at least about 18, at least about 19, at least about 20, at least about 21, at least about 22.5, at least about 25, at least about 27.5, at least about 30, at least about 35, at least about 40, at least about 50, at least about 60, at least about 70, at least about 80, at least about 90, at least about 100, at least about 110, at least about 125, at least about 130, at least about 140, or at least about 150 mg/kg/day. In some embodiments, a cell or population of cells is contacted with the agent provided under (C), e.g., ascorbic acid or ascorbate, for example, a cell obtained from a subject, for example, a cell donor, or a cell in culture. In some such embodiments, the cell is contacted in a solution, and the concentration of the agent provided under (A) is between about 0.01 micromol/l to about 1 millimol/l.

In some embodiments, each numeral provided for an agent under (A), (B), or (C) in Table 1 represents an equivalent of the respective agent. In some embodiments, an equivalent of an agent is the weight of the agent or the dosage of the agent (e.g., in mg/kg/day) administered to a subject. For example, a balanced ratio is, in some embodiments, a ratio of 88.5 mg/kg/day L-Arginine (A), 10 mg/kg/day BH4 (B), and 88.5 mg/kg/day Vitamin C (C) (A:B:C=8.85:1:8.85).

In some embodiments, the agent provided under (A) is L-Arginine, the agent provided under (B) is BH4 or 6R-BH4, and the agent provided under (C) is vitamin C. In some embodiments, agents are combined and/or administered to a subject in a ratio matching a functional effect of any of the agent combinations provided above. Functional effects of agents provided herein under (A), (B), and (C), for example, of L-Arginine, BH4, or a BH4 derivative, and Vitamin C, can be measured by methods and assays well known to those of skill in the art.

For example, the oxidative state of a cell, tissue, or microenvironment can be determined by using one or more in vitro, ex vivo and/or in vivo assays well known to those of skill in the art, including, but not limited to, free radical assays (e.g., assays for superoxide radicals, oxygen radicals, hydrogen peroxide, hypochlorite radicals, hydroxyl, 2,2-diphenyl-1picryhydrazyl (DPPH) radicals, peroxyl radicals (e.g., peroxylnitrite radicals, such as N,N-dimethyl-p-phenyleneamine radicals, and alkylperoxyl radicals)), coupled cytochrome c reduction assays, haematoxylin oxidation assays, lipid peroxidation assays, aconitase assays, catalase assays, glutathione assays, glutathione peroxidase assays, glutathione reductase assays, lipid hyperoxide assays, malondialdehyde (MDA) assays, monoamine oxidase assays, protein oxidation assays, protein nitrosylation assays, SSAO (semicarbazide-sensitive amine oxidase) assays, and superoxide dismutase (SOD) assays. Accordingly, the effect of any agent as provided herein under (A), (B), or (C), alone, or in any combination of 2 or 3 thereof, on the oxidative state of a cell, tissue, or microenvironment can be determined and quantified.

In some embodiments, a balanced combination of agents as provided herein is a combination that effects a normalization of the oxidative state of a cell, tissue, or microenvironment. In some embodiments, normalization of an oxidative state is a change from an oxidative state observed or associated with a disease or condition, for example, with oxidative stress, towards an oxidative state observed in or associated with a healthy or normal state.

For example, nitric oxide synthase (e.g., eNOS) activity can be determined and/or quantified by in vitro, ex vivo, and/or in vivo assays well known to those of skill in the art, including, but not limited to, arginine to citrulline conversion assays, nitric oxide and/or nitrite assays, (e.g., determination of nitrite concentration in a biological sample, e.g., a body fluid, cell, tissue, or tissue culture sample, by assays known in the art, e.g., Griess method) and nitrotyrosine assays. Accordingly, the effect of an agent under (A) or under (B) on eNOS activity can be determined and quantified. An amount of such an agent appropriate for generating a balanced ratio of the agents provided under (A) or (B) can then be determined as an amount resulting in the same effect on eNOS activity as any of the ratios given for the combinations of agents herein.

Similarly, antioxidant properties of an agent provided under (C) can be determined and/or quantified by in vitro, ex vivo, and/or in vivo assays known to those of skill in the art, including, but not limited to, by ORAC (oxygen radical absorbance capacity). FRAP (ferric reducing/antioxidant power), TAC (total antioxidant capacity) assays. Those of skill in the art will recognize other assays suitable for determining and/or quantifying antioxidant properties of agents provided under (C). In some embodiments, an equivalent of an agent under (C) to a specified amount of a given agent, for example, 88.5 mg/kg/day vitamin C, is represented by the amount of agent having an essentially identical antioxidant capacity.

In some embodiments, a balanced ratio comprises a ratio of A:B of ≥2.5:1, ≥3:1, ≥4:1, ≥5:1, ≥6:1, ≥7:1, ≥8:1, ≥9:1, ≥10:1, ≥12.5:1, ≥15:1, or ≥20:1. In some embodiments, a balanced ratio comprises a ratio of C:B of ≥1:1, >1:1, ≥2:1, ≥2.5:1, ≥3:1, ≥4:1, ≥5:1, ≥6:1, ≥7:1, ≥8:1, ≥9:1, ≥10:1, ≥12.5:1, ≥15:1, or ≥20:1.

It should be appreciated that any of the dosages and or relative ratios described herein also may be used in the context of single or double therapy as described herein.

It should be appreciated that any of the agents, compounds, or compositions described herein may be provided in appropriate salt forms, or in other forms that are physiologically acceptable (including precursors, for example substrates that generate the compound(s) of interest after administration or application). It also should be appreciated that in some embodiments the dosages and or ratios described herein may be approximate (e.g., +/−0-5%, +/−5-10%, or +/−10-15%, for example).

Patient Populations

In some embodiments, a therapeutic composition as provided herein is administered to a subject. In some embodiments, the subject is a human subject. In some embodiments, the subject is a non-human mammal. In some embodiments, the subject is a non-human primate. In some embodiments, the subject is a rodent. In some embodiments, the subject is a mouse, a rat, a cat, a dog, a cow, a sheep, a horse, a goat, or a pig. In some embodiments, the subject is a non-mammalian vertebrate.

In some embodiments, suitable subjects include subjects with increased levels of oxidated LDL as compared to average levels observed in healthy individuals. In some embodiments, suitable subjects include subjects with metabolic syndrome. In some embodiments, suitable subjects include subjects with diabetes. In some embodiments, suitable subjects include subjects with hypercholesterolemia. In some embodiments, suitable subjects include subjects exhibiting vascular plaque formation. In some embodiments, suitable subjects include subjects with cardiovascular disease. In some embodiments, suitable subjects include subjects with myocardial infarction (MI). In some embodiments, suitable subjects include subjects having or having had a stroke. In some embodiments, suitable subjects include subjects with carotid artery disease. In some embodiments, suitable subjects include subjects with atherosclerosis. In some embodiments, suitable subjects include subjects with heart failure. In some embodiments, suitable subjects include subjects with peripheral arterial disease (PAD). In some embodiments, suitable subjects include subjects with intermittent claudication. In some embodiments, suitable subjects include subjects with critical limb ischemia. In some embodiments, suitable subjects include subjects with chronic fatigue syndrome. In some embodiments, suitable subjects include subjects with insulin resistance.

In some embodiments, suitable subjects include subjects with hypertension. In some embodiments, suitable subjects include obese subjects. In some embodiments, suitable subjects include smokers.

In some embodiments, suitable subjects include subjects without increased levels of oxidated LDL as compared to average levels observed in healthy individuals. In some embodiments, suitable subjects include subjects without metabolic syndrome. In some embodiments, suitable subjects include subjects without diabetes. In some embodiments, suitable subjects include subjects without hypercholesterolemia. In some embodiments, suitable subjects include subjects exhibiting vascular plaque formation. In some embodiments, suitable subjects include subjects without cardiovascular disease. In some embodiments, suitable subjects include subjects without myocardial infarction (MI). In some embodiments, suitable subjects include subjects not having or not having had a stroke. In some embodiments, suitable subjects include subjects without carotid artery disease. In some embodiments, suitable subjects include subjects without atherosclerosis. In some embodiments, suitable subjects include subjects without heart failure. In some embodiments, suitable subjects include subjects without peripheral arterial disease (PAD). In some embodiments, suitable subjects include subjects without intermittent claudication. In some embodiments, suitable subjects include subjects without critical limb ischemia. In some embodiments, suitable subjects include subjects without chronic fatigue syndrome. In some embodiments, suitable subjects include subjects without insulin resistance. In some embodiments, suitable subjects include subjects that do not have vascular disease.

In some embodiments, suitable subjects include subjects with a neurodegenerative disease, for example, with Parkinson's Disease, ALS, or Alzheimer's Disease. In some embodiments, suitable subjects include subjects with autoimmune diseases. In some embodiments, suitable subjects include subjects with ataxia telangiectasia. In some embodiments, suitable subjects include subjects with cancer. In some embodiments, suitable subjects include subjects with an inflammatory disease.

In some embodiments, suitable subjects include subjects having a disease associated with oxidative stress that are also a donor and/or a recipient of a transplant, for example, a cell, cell population, or tissue transplant.

In some embodiments, suitable subjects include subjects receiving a drug inducing oxidative stress, for example, patients receiving an anti-cancer drug (e.g., 5-fluorouracil, NSC-741909, STA-4783, DL-buthionine-(SR)-sulfoximine, 2',7'-dichlorofluorescein diacetate, dihydroethidium).

In some embodiments, suitable subjects include subjects that are at risk for cancer. In some embodiments, suitable subjects include subjects that are genetically at risk for cancer. In some embodiments, suitable subjects include subjects that have been diagnosed with polyps, tissue dysplasia, or other similar condition. In some embodiments, suitable subjects include subjects that have an inflammatory condition (e.g., IBD, IBS, ulcerative colites, Crohn's disease, or other inflammatory condition). In some embodiments, suitable subjects include subjects that have cancer or have been treated for cancer (e.g., breast cancer, melanoma, any cancer described elsewhere herein, or any other cancer).

However, in some embodiments, certain compositions of the invention (e.g., double or triple therapies described herein) may be administered to any subject (e.g., a subject that is apparently healthy and has no or low risk factors for any diseases or conditions described herein) in order to provide a protective effect against diseases or conditions described herein. In some embodiments, compositions of the invention may be provided in a form suitable for oral administration (e.g., ingestion). However, one or more other forms, or combinations thereof, may be provided and/or administered in some embodiments.

It should be appreciated that compositions described herein may be administered in any suitable form. In some embodiments, a composition comprising two or more agents or compounds described herein (e.g., a double or triple therapy) may be formulated as a combination of all agents or compounds (e.g., in the form of a solid, liquid, powder, gel, or other form described herein). However, in some embodiments, a double or triple therapy may comprise administering the individual agents or compounds separately (e.g., to allow the relative dosages of each component to be adjusted as described herein). It should be appreciated that the agents may be administered at the same time, contemporaneously, or during a course of treatment. Accordingly, in some embodiments, a combined preparation of two or more components described herein may be provided for simultaneous, separate, or sequential use in therapy as described herein.

Dosage

The dosages of agents and compositions described herein depend on the specific clinical situation. Factors influencing actual dosage are, for example, the clinical scenario, for example the disease type and disease stage diagnosed in a subject, the age, weight, sex and overall health condition of a subject etc. As a general guideline, the agent reducing oxidative stress provided under (A) may be administered within the range of 0.1-1000 mg (agent)/kg (body weight of subject)/day. In some embodiments, the agent reducing oxidative stress provided under (A) may be administered within the range of 1-300 mg/kg/day. In some embodiments, the agent reducing oxidative stress provided under (A) may be administered within the range of 5-20 mg/kg/day. In some embodiments, the agent reducing oxidative stress provided under (A) may be administered at a dosage of about 5 mg/kg/day. In some embodiments, the agent reducing oxidative stress provided under (a) may be administered at a dosage of about 10 mg/kg/day. In some embodiments, the agent reducing oxidative stress provided under (A) may be administered at a dosage of about 20 mg/kg/day.

In some embodiments, fixed ratios of the agents provided under (A), (B) and (C), are administered, for example in a solid or liquid formulation containing all agents at a specific ratio or by combining individual agents or compositions containing one or more agents to result in a certain ratio. Ratios can be based, for example, on weight, volume, and/or biologic activity or a combination thereof.

In some embodiments, the methods or compositions provided herein are administered to a subject experiencing or suspected to experience oxidative stress or having or suspected to have a disease or disorder caused by or related to oxidative stress. In some embodiments, the active agents, compounds, compositions, or factors provided herein are administrated in an amount sufficient to prevent, reduce, or ameliorate oxidative stress in a target cell, tissue, or microenvironment of the subject.

Administration Routes, Schedules and Formulations

In some embodiments, the compounds and agents related to by some aspects of this invention are administered to a subject via an enteral or a parenteral route. In some embodiments, a composition of agents, for example a composition comprising agents described herein in a balanced ratio, are administered to a subject, wherein one or more agents are administered via an enteral route and one or more agents of the composition are administered via a parenteral route.

Aspects of this invention relate to compositions comprising an agent according to this invention. Pharmaceutical compositions of the present invention comprise an effective amount of an agent according to this invention, dissolved or dispersed in a pharmaceutically acceptable carrier. The phrases "pharmaceutical or pharmacologically acceptable" refers to molecular entities and compositions that do not generally produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated.

A composition may comprise different types of carriers depending on whether it is to be administered in solid, liquid or aerosol form, and whether it need to be sterile for such routes of administration as injection. The present invention can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference). In a particular embodiment, intraperitoneal injection is contemplated.

In certain embodiments, pharmaceutical compositions may comprise, for example, at least about 0.1% of an active compound. In other embodiments, the an active compound may comprise between about 2% to about 75% of the weight of the unit, or between about 25% to about 60%, or up to 99% of the composition, for example, and any range derivable therein.

The absolute amount administered of an agent will depend upon a variety of factors including the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Multiple doses of the agents of the invention are also contemplated. In some instances, when a agent of the invention is administered with another medicament, a sub-therapeutic dosage of either the agent or the another medicament, or a sub-therapeutic dosage of both, is used in the treatment of a subject having, or at risk of developing a disease or disorder related to oxidative stress. When a plurality of compounds are used together, either one, some or all of them may be administered in a sub-therapeutic dose to produce a desirable therapeutic result. A "sub-therapeutic dose" as used herein refers to a dosage, which is less than that dosage which would produce a therapeutic result in the subject if administered in the absence of the other agent or agents. Thus, the sub-therapeutic dose of an agent is one which would not produce the desired therapeutic result in the subject in the absence of the administration of the agents of the invention. Therapeutic doses of agents that are in clinical use are well known in the field of medicine. These dosages have been extensively described in references such as Remington's Pharmaceutical Sciences, 18th ed., 1990; as well as many other medical references relied upon by the medical profession as guidance for the treatment of diseases and disorders.

In some embodiments, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The agents of the invention may be derivatized in various ways. As used herein "derivatives" of the agents provided herein include salts (e.g., pharmaceutically acceptable salts), any complexes (e.g., inclusion complexes or clathrates with compounds such as cyclodextrins, or coordination complexes with metal ions such as Mn.sup.2+ and Zn.sup.2+), esters such as in vivo hydrolysable esters, free acids or bases, polymorphic forms of the compounds, solvates (e.g., hydrates), prodrugs or lipids, coupling partners and protecting groups. By "prodrugs" is meant for example any compound that is converted in vivo into a biologically active compound.

As set out herein, certain embodiments of the present invention may contain a basic functional group, such as amino or alkylamino, and are, thus, capable of forming pharmaceutically-acceptable salts with pharmaceutically-acceptable acids. The term "pharmaceutically-acceptable salts" in this respect refers to the relatively non-toxic, inorganic or organic acid addition salts of agents of the present invention. These salts can be prepared in situ in the administration vehicle or the dosage form manufacturing process, or by separately reacting a purified agent of the invention with a suitable organic or inorganic acid, and isolating the salt thus formed during subsequent purification. Representative salts include the bromide, chloride, sulfate, bisulfate, phosphate, phosphonate, nitrate, acetate, valerate, oleate, palmitate, stearate, laurate, benzoate, lactate, tosylate, citrate, maleate, fumarate, succinate, tartrate, napthylate, mesylate, glucoheptonate, lactobionate, and laurylsulphonate salts and the like. See, for example, Berge et al. (1977) J. Pharm. Sci. 66:1-19.

The pharmaceutically acceptable salts of the subject agents include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the agents of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. See, for example, Berge et al. (1977) J. Pharm. Sci. 66:1-19.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be advisable to include isotonic agents, such as, for example, sugars, sodium chloride or combinations thereof.

A variety of administration routes are available. The particular mode selected will depend, of course, upon the particular compound selected, the particular condition being treated and the dosage required for therapeutic efficacy. The methods of this invention, generally speaking, may be practiced using any mode of administration that is medically acceptable, meaning any mode that produces effective levels of protection without causing clinically unacceptable adverse effects. Examples of modes of administration are parenteral routes. The term "parenteral" includes subcutaneous, intravenous, intramuscular, intraperitoneal, and intrasternal injection, or infusion techniques. Other routes include but are not limited to oral, nasal, dermal, sublingual, and local.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The agents of the invention can be administered by any ordinary route for administering medications. Depending upon the type of cancer to be treated, compounds of the invention may be inhaled, ingested or administered by systemic routes. Systemic routes include oral and parenteral. Inhaled medications are employed in some embodiments because of the direct delivery to the lung, particularly in lung cancer patients. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. Examples of routes of administration include but are not limited to oral, parenteral, intramuscular, intranasal, intratracheal, intrathecal, intravenous, inhalation, ocular, vaginal, and rectal. For use in therapy, an effective amount of the compounds of the invention can be administered to a subject by any mode that delivers the nucleic acid to the affected organ or tissue. "Administering" the pharmaceutical composition of the present invention may be accomplished by any means known to the skilled artisan.

According to the methods of the invention, an agent may be administered in a pharmaceutical composition. In general, a pharmaceutical composition comprises an agent of the invention and a pharmaceutically-acceptable carrier. Pharmaceutically-acceptable carriers for agents of the invention are well-known to those of ordinary skill in the art. As used herein, a pharmaceutically-acceptable carrier means a non-toxic material that does not interfere with the effectiveness of the biological activity of the active ingredients.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents.

When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The agents of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of an active agent. Other compositions include suspensions in aqueous liquids or non-aqueous liquids such as a syrup, elixir or an emulsion.

When an agent provided herein is used therapeutically, in certain embodiments, a desirable route of administration may be by pulmonary aerosol. Techniques for preparing aerosol delivery systems containing compounds are well known to those of skill in the art. Generally, such systems should utilize components which will not significantly impair the biological properties of the agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

An agent of the invention may be administered directly to a tissue. Direct tissue administration may be achieved by direct injection. An agent may be administered once, or, alternatively, may be administered in a plurality of administrations. If administered multiple times, an agent may be administered via different routes. For example, the first (or the first few) administrations may be made directly into the affected tissue while later administrations may be systemic.

For oral administration, an agent can be formulated readily by combining with pharmaceutically acceptable carriers well known in the art. Such carriers enable an agent of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, an agent for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

An agent, when it is desirable to deliver it systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

Sustained release strategies may also be employed in the methods described herein. Some such method use polymers to effect a sustained release of an agent from a composition. Both non-biodegradable and biodegradable polymeric matrices can be used to deliver an agent of the invention to the subject. Such polymers may be natural or synthetic polymers. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, an agent of the invention may be delivered using the bioerodible implant by way of diffusion, and/or by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of an agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic diseases. Long-term release, as used herein, means that the implant is constructed and arranged to deliver therapeutic levels of the active ingredient for at least 30 days, and/or at least 60 days. Long-term sustained release implants are well-known to those of ordinary skill in the art and include some of the release systems described above.

Therapeutic formulations useful in the invention may be prepared for storage by mixing an agent having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Some compounds described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include a compound as described herein, along with instructions describing the intended therapeutic application and the proper administration. In certain embodiments a compound in a kit may be in a pharmaceutical formulation and dosage suitable for a particular application and for a method of administration.

Several methods are disclosed herein of administering a subject with a compound for the treatment of a particular condition. It is to be understood that in each such aspect of the invention, the invention specifically includes, also, the compound for use in the treatment or prevention of that particular condition, as well as use of the compound for the manufacture of a medicament for the treatment or prevention of that particular condition, disease or disorder.

The route, frequency, dosage, and time frame of administration may vary depending on the condition identified in the subject. For example, a single administration of the agents and compositions described herein may be sufficient to reduce, prevent, or ameliorate acute oxidative stress, whereas multiple doses, stretched out over a period of time, may be indicated in a subject experiencing chronic oxidative stress or one of its manifestations. It should further be appreciated that the biological stability of some of the agents provided herein may vary and that, in some embodiments, repeated administration of one or more agents of a balanced composition may be necessary in order to maintain a balanced ratio in the target cell, tissue, or microenvironment.

In some embodiments, bioavailability of an agent of the present invention, for example BH4, L-Arg or ascorbic acid, may be monitored prior to or after administration of an agent of the invention, and the appropriate dosage of the next administration of the agent be determined based on the measured bioavailability. In some embodiments, a level of an agent in a body fluid of the subject may be measured to monitor its bioavailability. In some embodiments, a biomarker indicating the level of bioavailability may be measured to monitor the agents bioavailability. In some embodiments, the redox state or oxidative state of a body fluid or tissue may be monitored and the appropriate dosage of an agent be determined based on the measured redox state. In some embodiments, oxidative stress may be directly measured, for example in a body fluid or tissue using methods of determining the redox state that are well known in the art. In some embodiments, a biomarker indicative of a certain redox state, for example of a state of oxidative stress, may be assessed in order to determine the redox state of a body fluid or tissue of the subject. Biomarkers indicative of oxidative stress are well known in the art and include, for example, measuring the levels of enzymatic and non-enzymatic antioxidants in a tissue or body fluid, for example alpha- and beta-carotene level, beta-cryptoxanthin level, lycopene level, tocopherol level, ubiquinone level, reduced and/or oxidized glutathione level and/or the ratio of these levels, superoxide dismutase expression level, glutathione peroxidase expression level, catalase expression level, and fatty acid patterns of phospholipids, measuring 5-hydroxymethyl-2-deoxyuridine level, 8-iso-prostaglandin F(2alpha) level, determining the peroxidizability index, level of a prooxidant, for example ceruloplasmin and copper, and/or other indicators well known in the art. Additional non-limiting examples of methods and assays to determine the oxidative state or redox state are described elsewhere herein.

In some embodiments, administration may continue until a desired endpoint, e.g., collateral artery enlargement to a certain diameter, reversal or regression of claudication or critical limb ischemia, regression of atherosclerosis, reversal of oxidant stress to HSCs, etc., has been reached.

In some embodiments, a single pill comprising the agents of the invention for triple therapy is administered. Such a pill may comprise a daily dosage of the agents of the invention. In other embodiments, the components are administered individually to the subject.

Compositions to Reduce Oxidative Stress

In some embodiments, the methods and compositions useful to reduce oxidative stress and/or to balance the oxidation-reduction state of a cell, tissue, or microenvironment increase the bioavailability of nitric oxide NO in the target cell, tissue, or microenvironment. In some embodiments, the method to increase the bioavailability of NO comprises administering to a subject a balanced ratio of the agent provided under (A) (e.g., L-Arginine), (B) (e.g., BH4), and (C) (e.g., ascorbic acid) or a pharmaceutically acceptable salt thereof. In some embodiments, the ratio of A:B:C (e.g., L-Arginine:BH4:ascorbic acid) is in the range of about 1-30:1:0.1-15. In some embodiments, the range of the ratio of A:C (e.g., L-Arginine:ascorbic acid) is within the range of 10:1 to 1:10. In some embodiments, the ratio of A:C is 1:1. In some embodiments, the ratio of L-Arginine:BH4: ascorbic acid is 8.85:1:8.85. In some embodiments, the dosage is within the range of: (A) (e.g., L-Arginine): 0.1-1000 mg/kg/day; (B) (e.g., BH4): 1-50 mg/kg/day; and (C) (e.g., ascorbic acid): 1-1000 mg/kg/day. In some embodiments, the dosage is within the range of: (A) (e.g., L-Arginine): 1-300 mg/kg/day; (B) (e.g., BH4): 1-50 mg/kg/day; and (C) (e.g., ascorbic acid): 0.1-150 mg/kg/day.

Combined Gene Therapy

In some embodiments, experiments used adenoviral vectors. Adenoviral vectors induce an immune response that can diminish eNOS expression or an immune response if administered a second time. To address these issues, alternative constructs (e.g., constructs based on Adeno-associated vectors, AAV) may be used. These vectors do not induce immune response, have prolonged expression, and are being tested in humans.

In some embodiments, gene therapy may be used for "Critical Limb ischemia," e.g., ischemic ulceration, rest pain, or dry gangrene all of which result in amputation unless blood flow via collateral arteries is increased rapidly and not for non-limb threatening conditions, claudication.

These and other aspects of the invention are illustrated by the following non-limiting examples and claims.

EXAMPLES

Example 1

Oral Tetrahydrobiopterin Improves the Beneficial Effect of Adenoviral-Mediated eNOS Gene Transfer on Perfusion and Muscle Histology after Induction of Hindlimb Ischemia.

In the absence of the co-factor tetrahydrobiopterin (BH4), endothelial nitric oxide synthase (eNOS) exists in an uncoupled form wherein eNOS activity generates superoxide anion ($O_2^-$) rather than nitric oxide (NO). In this context, administration of BH4 prior to gene transfer therapy with eNOS might maximize generation of eNOS-derived NO. Accordingly, in some embodiments dietary supplementation with BH4 may synergistically increase eNOS activity following AdeNOS gene transfer in the setting of hindlimb ischemia, leading to improved blood flow recovery and better preservation of muscle integrity.

Dietary supplementation with BH4 was initiated 1 week before unilateral femoral artery excision was performed in rats. Ten days later recombinant adenovirus containing bovine eNOS cDNA (AdeNOS) or PBS was infused intra-arterially into the ischemic hindlimb. Rats given co-treatment with BH4 and AdeNOS demonstrated greater $Ca^{2+}$-dependent NOS activity and blood flow recovery, and reduced nitrotyrosine accumulation and muscle necrosis in the ischemic hindlimb than rats given AdeNOS alone. Rats given BH4 alone showed less nitrotyrosine accumulation in the ischemic limb than rats on standard chow, although BH4 alone had no effect on NOS activity, flow recovery, or extent of muscle necrosis.

Accordingly, in some aspects co-treatment with BH4 and AdeNOS significantly improves the outcome of severe hindlimb ischemia, an effect mediated by reduced oxidant stress, increased NOS activity, and more effective blood flow recovery. The combination of eNOS gene transfer and oral BH4 supplementation may be an effective molecular therapy for patients who suffer complications of critical limb ischemia.

In some embodiments, generation of novel therapeutic modalities for the clinical problem of critical limb ischemia is clearly warranted by the substantial impact this condition has on morbidity and mortality, as well as on the paucity of existing effective treatment options [1]. In this context, the potential utility of intra-arterial gene transfer of eNOS into an ischemic limb has been evaluated as a therapeutic intervention designed to improve perfusion and minimize tissue loss. This treatment is based on evidence that nitric oxide (NO) derived from endothelial nitric oxide synthase (eNOS) is a potent vasodilator and signaling molecule that plays a essential role in vascular remodeling and perfusion recovery in response to acute hindlimb ischemia [7-9]. eNOS generates NO during the oxidation L-arginine to L-citrulline [10]. An essential co-factor in this reaction is tetrahydrobiopterin (BH4) which maintains eNOS in the dimeric configuration wherein electron transfer from the flavin of the reductase domain of one monomer to the heme group within the oxidase domain of the other monomer occurs, ultimately resulting in oxidation of L-arginine. In the absence of BH4, eNOS becomes uncoupled, e.g., there is a loosening of the attachment between monomers; consequently, electron transfer between monomers fails to occur and the electron flux results in oxidation of molecular oxygen to form superoxide anion ($O_2^-$), a highly toxic free radical [11,12]. Importantly, BH4 can itself undergo oxidation to form 7,8-dihydrobiopterin, which is functionally inactive. This circumstance can potentiate a vicious cycle in which uncoupled (BH4-deficient) eNOS generates $O_2^-$ which in turn oxidizes available BH4, causing further uncoupling of eNOS [13]. See, for example, FIG. 1.

The capacity of eNOS to generate either NO or $O_2^-$ raises an important question regarding the potential therapeutic efficacy of eNOS administration in the setting of critical limb ischemia. It might be logically anticipated that administration of exogenous eNOS, e.g., delivered by a transgene directly into the limb vasculature, would result in increased generation of eNOS-derived NO, with a subsequent enhancement in NO-mediated collateral artery vasodilation and remodeling, and hence restoration downstream perfusion. However, if eNOS is administered into an environment deficient in BH4 it is conceivable that this exogenous eNOS would remain uncoupled, thus generating $O_2^-$ in lieu of NO resulting in tissue injury. This putative scenario might be of particular relevance in the setting of critical limb ischemia, a circumstance in which increased tissue oxidative stress and hence reduced BH4 availability might be expected according to some aspects of the invention.

This investigation tested the hypothesis that dietary supplementation with BH4 enhances the beneficial effects of intra-arterial gene transfer of eNOS in the setting of severe hindlimb ischemia in rats. Dependent variables included hindlimb perfusion, collateral artery size, $Ca^{2+}$-dependent NOS activity, peroxynitrite formation, and determination of muscle necrosis by nitroblue tetrazolium and muscle histology.

Methods

Experimental Animals:

The study was approved by the Institutional Animal Care and Use Committee at the University of California, San Francisco. Adult male Sprague-Dawley rats (265-285 g; Charles River Laboratories, Wilmington, Mass.) were used in all experiments. All rats underwent induction of severe hindlimb ischemia as previously described [3]. Briefly, the left common femoral artery and its branches were excised under 2% isoflurane, while the right hindlimb served as an internal control.

Treatment Groups:

The [PBS, –BH4] group was maintained on standard rat chow and received intra-arterial PBS infusion 10 days after induction of hindlimb ischemia. The [PBS, +BH4] group was given dietary BH4 supplementation, described below, and received intra-arterial PBS infusion 10 days after induction of hindlimb ischemia. The [eNOS, –BH4] group was maintained on standard chow and received intra-arterial AdeNOS infusion, described below, 10 days after induction of hindlimb ischemia. The [eNOS, +BH4] group was given dietary BH4 supplementation and received intra-arterial AdeNOS infusion 10 days after induction of hindlimb ischemia.

Dietary BH4 Supplementation:

Powdered standard rat chow was obtained from Research Diets (New Brunswick, N.J.). The chow was supplemented with BH4, 0.04 g/20 g chow (Schircks Laboratories, Jonas, Switzerland). This supplementation was designed to provide 10 mg/Kg/day of BH4 based on the average amount of chow ingested per rat per day. Assigned rats were begun on the supplemented diet 1 week before induction of hindlimb ischemia and were continued on the diet until the end of study. Food supply within each cage was changed every other day.

Recombinant Adenovirus Preparation and In Vivo Gene Transfer:

Recombinant adenovirus containing bovine eNOS cDNA driven by the Rous sarcoma virus promoter (AdeNOS; a generous gift from Dr. Beverly Davidson at the University of Iowa College Medicine) was propagated and titrated in 293 cells as described previously [3]. Adenovirus stocks were stored at –80° C., then thawed immediately before use and diluted in PBS to achieve a final concentration of $1 \times 10^{10}$ plaque forming units per milliliter (pfu/ml). AdeNOS was administered via intra-arterial injection under temporary venous occlusion. The left common femoral vein was occluded with a microvascular clamp; thereafter, the saphenous artery was cannulated in a retrograde manner and AdeNOS ($10^{10}$ pfu/ml; 0.7 ml) or saline (0.7 ml) was infused. The venous clamp was removed 30 minutes later. Previous work has demonstrated optimal eNOS gene transfer to the hindlimb vasculature using this technique [3].

Laser Doppler Perfusion Imagining:

Hindlimb blood flow was determined by means of laser Doppler imaging (Moor Instruments, Ltd., Devon, United Kingdom). Flow was measured preoperatively, immediately after arterial excision, immediately before AdeNOS or saline administration, and on days 4, 7, 21, and 30 thereafter. Scans were obtained during inhalation of 1% isoflurane while core body temperature was maintained between 36.8-37.2° C. by means of a heating element driven by a rectal temperature probe. Scans were repeated three times and the average for each rat determined. Data were expressed as the ratio of ischemic:non-ischemic hindlimb.

Angiograms:

Angiograms were performed on day 30 after AdeNOS or saline injection (40 days after induction of ischemia). Barium sulfate (2.5 ml; EZPaqe, Merry X-Ray, South San Francisco, Calif.) was infused into the infra-renal aorta after ligation of the proximal aorta and inferior vena cava during inhalation of 2% isoflurane. A grid was superimposed over the film between the greater trochanter of the femur to the patella. The number of intersections between contrast-filled vessels and gridlines was determined independently by 3 blinded observers. The angioscore was calculated as the average ratio of intersections to the total number of gridlines.

Immunohistological Staining:

Analysis of eNOS expression by immunostaining was carried out 4 days after AdeNOS or saline administration (14 days after induction of ischemia) insofar as previous work has demonstrated maximal vascular AdeNOS expression at this time point [3]. Cryosections (10 µm) of gastrocnemius and tibialis anterior muscle were stained with monoclonal antibody specifically targeting the bovine eNOS expressed by the transgene (1:50 dilution; BD Biosciences, San Diego, Calif.) or monoclonal antibody directed against nitrotyrosine (1:50 dilution; Cayman Chemical, Ann Arbor, Mich.). Biotinylated secondary antibody was applied (1:250 dilution) and staining was detected using the Vectastain DAB kit (both Vector Laboratories, Burlingame, Calif.). Sections were counterstained with eosin. Negative controls were created by substituting blocking buffer for primary antibody.

Western Blotting:

eNOS and nitrotyrosine expression were assessed by western blotting. A portion of the gastrocnemius muscle harvested on day 4 after AdeNOS or saline administration (14 days after induction of ischemia) was snap frozen in liquid $N_2$. 100 µg of protein was separated on a 12% SDS-polyacrylamide gel for nitrotyrosine or 7.5% SDS-polyacrylamide gel for eNOS and transferred to nitrocellulose membranes (BioRad Laboratories, Hercules, Calif.). Membranes were incubated overnight (4° C.) with monoclonal antibodies directed against eNOS (BD Biosciences, San Diego, Calif.) or nitrotyrosine (Cayman Chemical, Ann Arbor, Mich.), then horseradish peroxidase-conjugated secondary antibody was applied for 2 hours. Immunoreactive bands were visualized using the enhanced chemiluminescence system (Amersham, Arlington Heights, Ill.). Band intensity was determined by densitometry. Data were expressed as a ratio of the band of interest to the α-tubulin band.

$Ca^{2+}$-Dependent NOS Activity:

A portion of the gastrocnemius muscle harvested on day 4 after AdeNOS or saline administration (14 days after induction of ischemia) was snap frozen in liquid $N_2$ for subsequent analysis of $Ca^{2+}$-dependent NOS activity (EMD Chemicals, Gibbstown, N.J.). 50 µg of muscle protein homogenate was incubated in 10 mM NADPH, 1 µCi/µl $^{14}C$-arginine, 6 mM $CaCl_2$, 50 mM Tris.HCl (pH 7.4), 6 µM BH4, 2 µM FAD, and 2 µM FMN for 30 minutes at 37° C. The reaction was stopped with 400 µl of 50 mM Hepes (pH 5.5) and 5 mM EDTA. Identical samples were prepared without $CaCl_2$ and all reactions were performed in duplicate. The radioactivity of the sample eluate was measured in a liquid scintillation counter. Enzyme activity was expressed as counts per million per minute per microgram protein (CPM/min/ug). The $Ca^{2+}$-NOS activity was calculated by subtracting the NOS activity measured without calcium from the total activity measured in the presence of calcium.

Evaluation of Muscle Necrosis:

Muscle necrosis was assessed on day 7 after AdeNOS or saline administration (17 days after induction ischemia) as previous work demonstrated maximal evidence of necrosis within this time frame after induction of hindlimb ischemia in the rat [3]. Muscle necrosis was determined using cut sections of tibialis anterior and gastrocnemius muscle. Muscle samples were cut transversely into 3 pieces (cuts made in 2 mm increment); two sections were stained with nitroblue tetrazolium (NBT). These sections were incubated in phosphate buffered saline (pH 7.4) containing 0.033% NBT (Fischer Biotech, Austin, Tex.) and 0.133% NADH (Roche Diagnostics, Indianapolis, Ind.) for 10 min, and then fixed in 4% paraformaldehyde for 24 hours. The areas of viable (stained) and non-viable (unstained) tissue were quantified using Image Pro software (Media Cybernetics, Bethesda, Md.) and the average taken for each rat. The third cut muscle section was used for H&E staining.

Statistical Analysis:

Analysis was performed using analysis of variance (ANOVA). Post-hoc Student-Newman-Keuls tests were carried out if the ANOVA f-statistic was significant to determine sites of difference. Probability values less <0.05 was accepted as significant.

Results

Figure 2A:
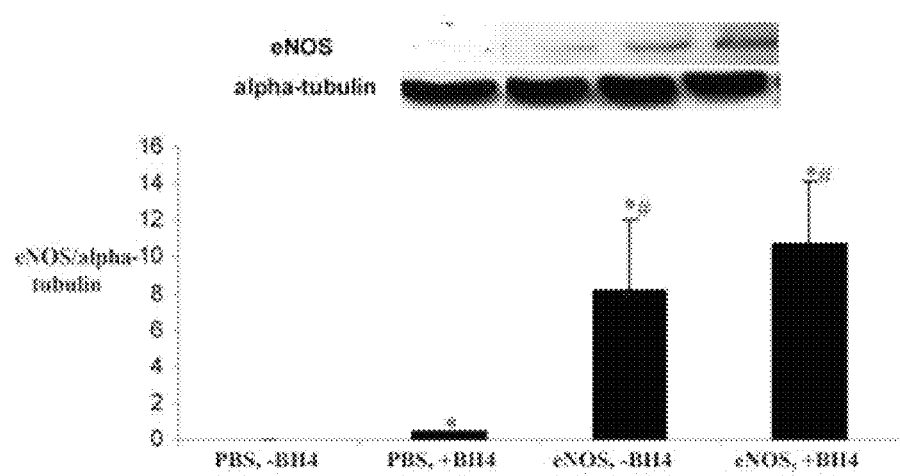
FIGS. 2A-2C. Effect of treatments on NOS expression and activity in gastrocnemius muscle.
Figure 2B:
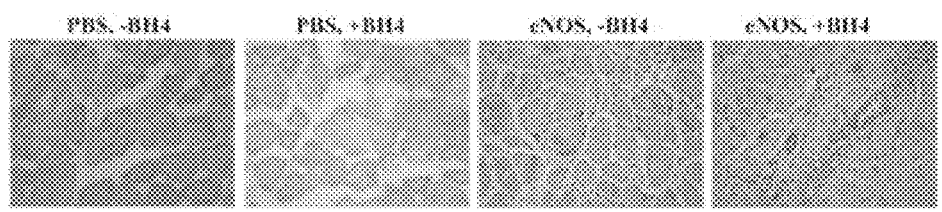
Figure 2C:
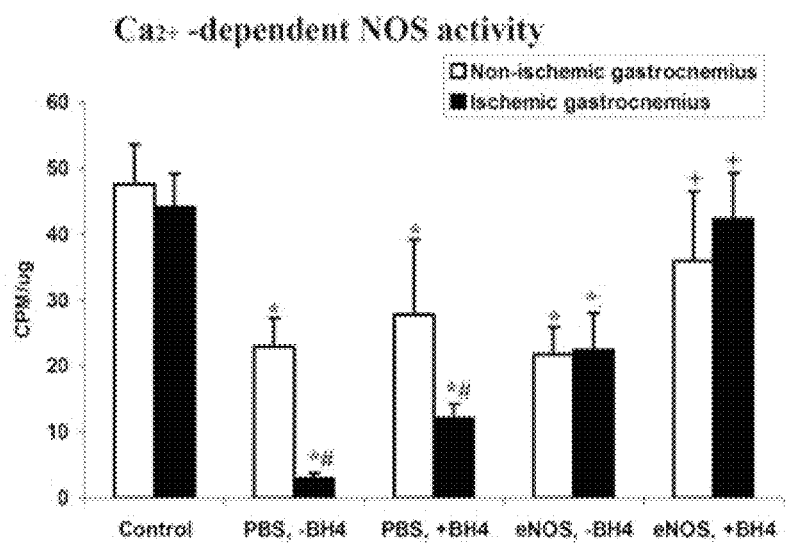

Oral $BH_4$ had No Effect on Bovine eNOS Expression Following AdeNOS Gene Transfer:

As expected, neither the [PBS, −BH4] nor [PBS, +BH4] groups demonstrated evidence of bovine eNOS, whereas bovine eNOS was present in the [eNOS, −BH4] and [eNOS, +BH] groups (FIGS. 2A-2B). FIGS. 2A-2C show the effect of treatments on NOS expression and activity in gastrocnemius muscle. Gastrocnemius muscle was harvested 4 days after AdeNOS infusion (14 days after induction of ischemia). (A) Expression of bovine eNOS. Data are expressed as the ratio of bovine eNOS to α-tubulin band intensities (both expressed in arbitrary densitometry units). m±sd; n=4; * $P<0.05$ vs. [PBS, −BH4] group; #$P<0.05$ vs. [PBS, +GH4 group]. Insert is a representative blot; lanes, from left to right: [PBS, −BH4]; [PBS, +BH4]; [eNOS, −BH4]; [eNOS, +BH4]. (B) Representative photomicrographs of bovine eNOS immunostaining from each group. Bovine eNOS is stained brown; the slide was counter-stained with eosin; 200×. (C) $Ca^{2+}$-dependent NOS activity. Data are expressed as CPM/µg muscle tissue. An additional group, labeled control, was studied in this experiment. This control group underwent sham femoral artery excision, were on a standard diet throughout the study, and received neither PBS nor AdeNOS. m±sd; n=5; * $P<0.05$ vs. control group; #$P<0.05$ ischemic vs. non-ischemic hindlimb; +$p<0.05$ for [eNOS, +BH4] vs. [PBS, −BH4], [PBS, +BH4], or [eNOS, −BH4]. Dietary supplementation with BH4 had no effect on bovine eNOS expression within ischemic muscle, e.g., expression was similar in the [eNOS, −BH4] and [eNOS, +BH] groups.

Oral BH4 Enhanced the Effect of AdeNOS on $Ca^{2+}$-dependent NOS Activity in Ischemic Muscle:

An additional group of rats was evaluated in the study of eNOS activity. This group, designated the control group, underwent a sham femoral artery excision under isoflurane anesthesia, was fed normal chow throughout the study, and received neither PBS nor AdeNOS infusion. $Ca^{2+}$-dependent NOS activity, e.g., the combination of endothelial NOS and neural NOS activities, was significantly greater in the gastrocnemius muscles from these control rats than in all other groups, except the [eNOS, +BH4] group, which demonstrated a similar level of $Ca^{2+}$-dependent NOS activity (FIG. 2C). $Ca^{2+}$-dependent NOS activity was significantly lower in the ischemic than non-ischemic gastrocnemius muscles in the [PBS, −BH4] and [PBS, +BH4] groups. In contrast, NOS activity was similar in the ischemic and non-ischemic gastrocnemius muscles in the [eNOS, −BH4] and [eNOS, +BH4] groups. Most importantly, $Ca^{2+}$-dependent NOS activity was significantly greater in the [eNOS, +BH4] group than in the [eNOS, −BH4] group, indicating that the addition of dietary BH4 enhanced NOS activity in the setting of hindlimb ischemia.

Figure 3A:
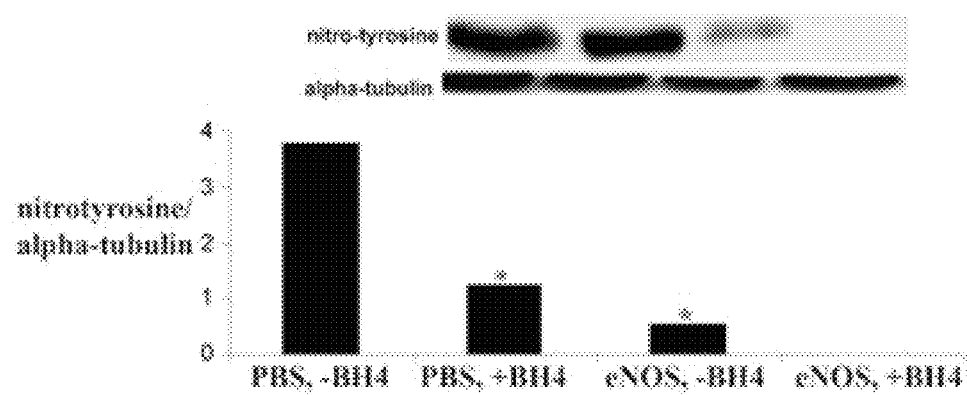
FIGS. 3A-3B. Effects of treatments on gastrocnemius nitrotyrosine accumulation.
Figure 3B:
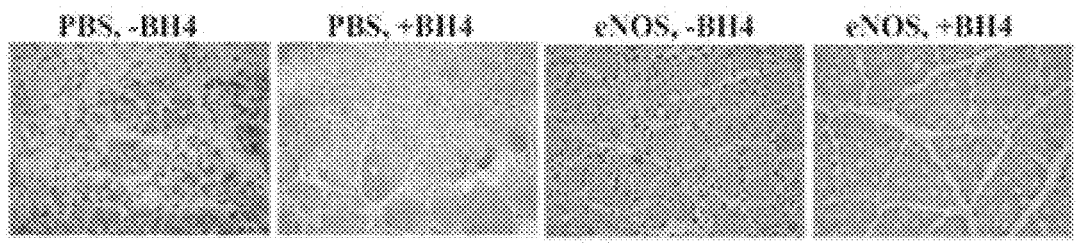

Oral BH4 Enhanced the Effect of AdeNOS on Reduction of Peroxynitrite after Hindlimb Ischemia:

Nitrotyrosine, a marker of peroxynitrite-induced protein nitrosylation, was present as in the ischemic gastrocnemius muscle in the [PBS, −BH4] group as evidenced by both western blotting and immunohistochemistry (FIGS. 3A-3B). FIGS. 3A-3B show effects of treatments on gastrocnemius nitrotyrosine accumulation. Gastrocnemius muscle was harvested 4 days after AdeNOS infusion (14 days after induction of ischemia). (A) Expression of nitrotyrosine. Data are expressed as the ratio nitrotyrosine to α-tubulin band intensities (both expressed in arbitrary densitometry units). Nitrotyrosine was not detected in any gastrocnemius muscle in the [eNOS, +BH4] group. m±sd; n=4; * P<0.05 vs. [PBS, −BH4]. Insert is representative blot; lanes, from left to right: [PBS, −BH4], [PBS, +BH4], [eNOS, −BH4], and [eNOS, +BH4]. (B) Representative photomicrograph of nitrotyrosine immunostaining from each group. Nitrotyrosine is stained brown; slide was counter-stained with eosin; 200×. The level of nitrotyrosine accumulation in the ischemic gastrocnemius muscle was significantly less in the [PBS, +BH4] and [eNOS, −BH4] groups than in the [PBS, −BH4] group, indicating that the singular additions of BH4 or AdeNOS were sufficient to reduce nitrotyrosine accumulation. Most striking, however, was the virtual absence of nitrotyrosine in the ischemic gastrocnemius muscle from the [eNOS, +BH4] group; hence, co-treatment with BH4 and AdeNOS exerted a synergistic effect in the reduction of nitrotyrosine accumulation.

Figure 4A:
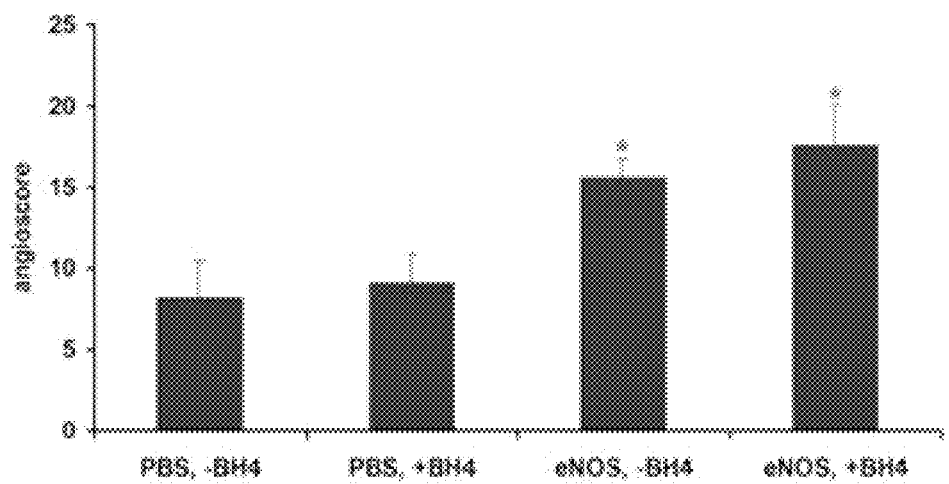
FIGS. 4A-4C. Effects of treatments on collateral artery enlargement.
Figure 4B:
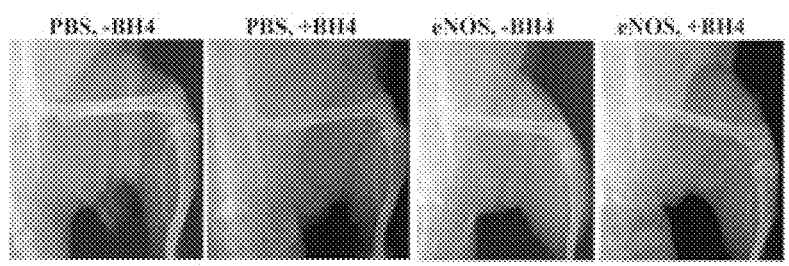
Figure 4C:
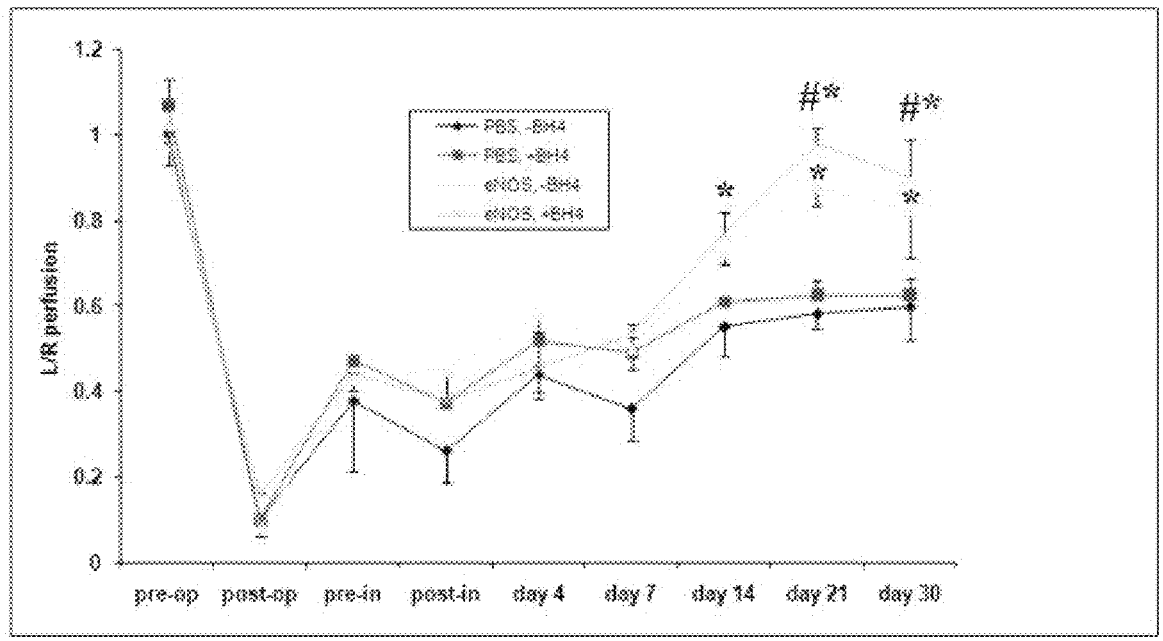

Oral BH4 Failed to Enhance the Effect of AdeNOS on Collateral Artery Enlargement after Hindlimb Ischemia:

The angioscore, a measure of collateral artery enlargement, was significantly greater in the [eNOS, −BH4] and [eNOS, +BH] groups than in the [PBS, −BH4] and [PBS, +BH4] groups (FIGS. 4A-4C). FIGS. 4A-4C show effects of treatments on collateral artery enlargement. Angiograms were performed 30 days after intra-arterial AdeNOS or PBS infusion (40 days after induction of ischemia). (A) Angioscores. Score was determined by counting the number of intersections between visible collateral arteries and a grid superimposed over the radiograph. m±sd, n=8; * P<0.05 vs. [PBS, −BH4] and [PBS, +BH4]. (B) Representative radiograph from each group. (C) Effects of treatments on hindlimb blood flow recovery. Laser-Doppler perfusion imaging was carried out prior to induction of hindlimb ischemia (pre-op); immediately after induction of hindlimb ischemia (post-op); immediately prior to AdeNOS infusion (pre-in); immediately after AdeNOS infusion (post-in), and they on days 4-30 after AdeNOS infusion. Note that AdeNOS was delivered 10 days after induction of ischemia. m±sd, n=8; * P<0.05 vs. [PBS, −BH4] and [PBS, +BH4]; #P<0.05 vs. [eNOS, −BH4]. The angioscore of the [eNOS, +BH4] group was similar to that of the [eNOS, −BH4] group, e.g., the addition of dietary BH4 to AdeNOS treatment did not improve the angioscore more than AdeNOS alone.

Oral BM Enhanced the Effect of AdeNOS on Restoration of Blood Flow Following Induction of Acute Ischemia:

Significant differences among groups were not evident until day 14 after intra-arterial AdeNOS or PBS administration (day 24 after induction of ischemia). At this time point, blood flows in the [eNOS, −BH4] group was greater than that in the [PBS, +BH4] group, indicating that singular treatment with AdeNOS, but not BH4, was sufficient to improve post-ischemia perfusion recovery at this time point (FIG. 4C). Flow recovery in the [eNOS, +BH4] group was significantly greater than the [eNOS, −BH4] group on day 21 and 28 after AdeNOS treatment (31 and 38 days after induction of ischemia), e.g., co-treatment with BH4 and AdeNOS put forth a synergistic effect in the improvement of flow recovery in the setting of hindlimb ischemia.

Figure 5A:
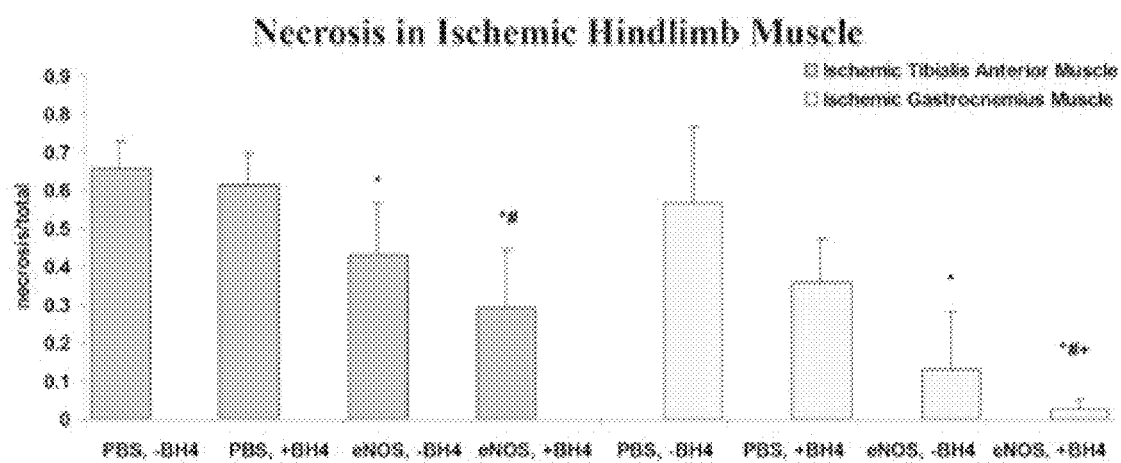
FIGS. 5A-5C. Effects of treatments on muscle necrosis in the ischemic hindlimb.
Figure 5B:
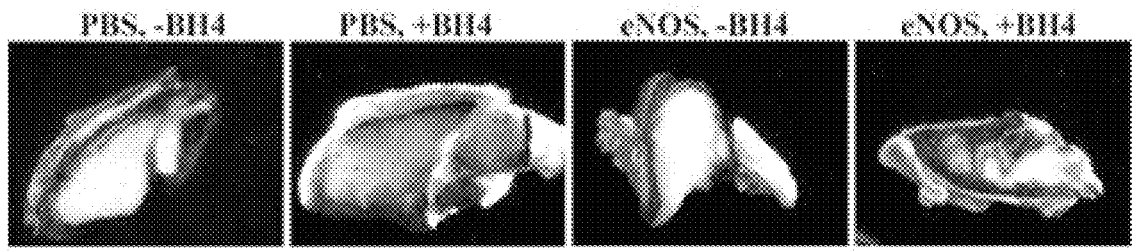
Figure 5C:
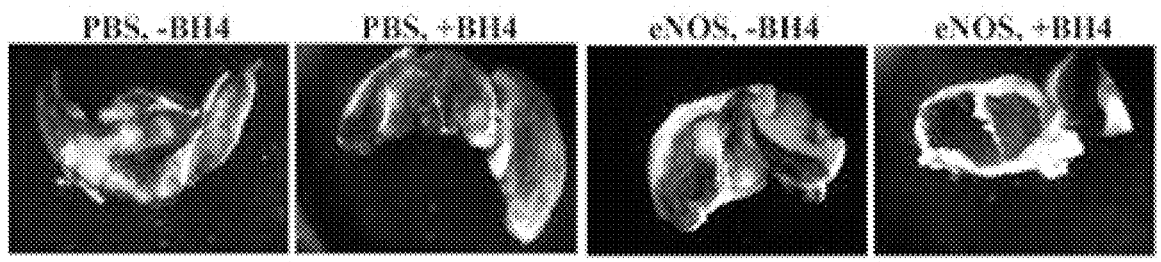
Figure 6A:
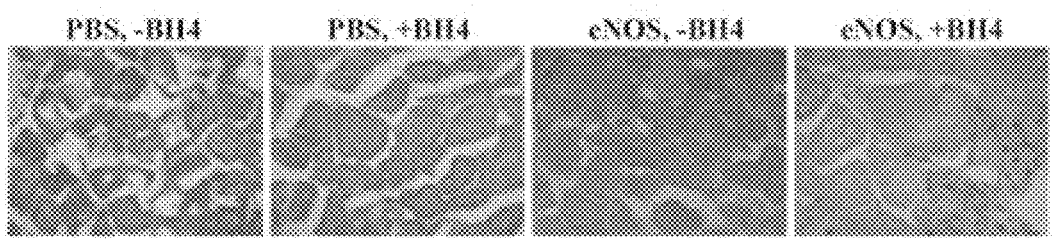
FIGS. 6A-6B. Effects of treatments on muscle histology in ischemic hindlimb.
Figure 6B:
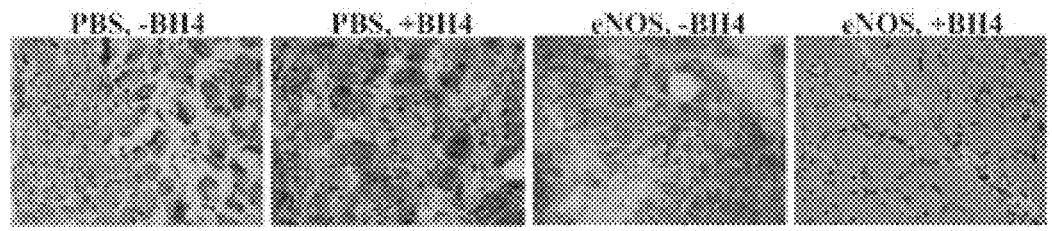

Oral BM Enhanced the Effect of AdeNOS on Reduction of Muscle Necrosis after Hindlimb Ischemia:

NBT staining demonstrated substantial muscle necrosis in the ischemic tibialis anterior and gastrocnemius muscles in the [PBS, −BH4] and [PBS, +BH4] groups 7 days after intra-arterial PBS administration (17 days after induction of ischemia) (FIGS. 5A-5C). FIGS. 5A-5C show effects of treatments on muscle necrosis in the ischemic hindlimb. Muscles were harvested 7 days after intra-arterial AdeNOS or PBS infusion (17 days after induction of ischemia). (A) Quantification of muscle necrosis. Tibialis anterior and gastrocnemius muscles from the ischemic hindlimb were cut in cross-section and the cut surface stained with nitroblue tetrazolium; viable tissue takes up the stain. The amount of non-viable (unstained) and total surface area was determined with Image Pro software and expressed as a ratio of necrotic to total surface area. m±sd, n=6; * P<0.05 vs. [PBS, −BH4]; #P<0.05 vs. [PBS, +BH4]; +P<0.05 vs. [eNOS, −BH4]. (B) Representative photos of tibialis anterior muscle from each group. Necrotic tissue appears yellow-white. (C) Representative photos of gastrocnemius muscle from each group. Necrotic tissue appears yellow-white. The level of muscle necrosis evident on NBT staining was less in the [eNOS, −BH4] or [eNOS, +BH4] groups than in groups receiving only intra-arterial PBS. Most importantly, however, the extent of muscle necrosis in the ischemic gastrocnemius muscle was significantly less in the [eNOS, +BH4] group than in the [eNOS, −BH4] group, e.g., co-treatment with AdeNOS and BH4 afforded a synergistic effect on the reduction of ischemic muscle necrosis. These differences were also qualitatively evident in H&E stained sections of anterior tibialis and gastrocnemius muscles from the four study groups (FIGS. 6A-6B). FIGS. 6A-6B show effects of treatments on muscle histology in ischemic hindlimb. Muscles were harvested 7 days after intra-arterial AdeNOS or PBS infusion (17 days after induction of ischemia). Cryosections (10 μm) stained with hematoxylin & eosin. 200×. Sections are representative samples from 6 separate experiments. (A) Tibialis anterior muscle from ischemic hindlimb from each group. (B) Gastrocnemius muscle from ischemic hindlimb from each group.

Figure 7:
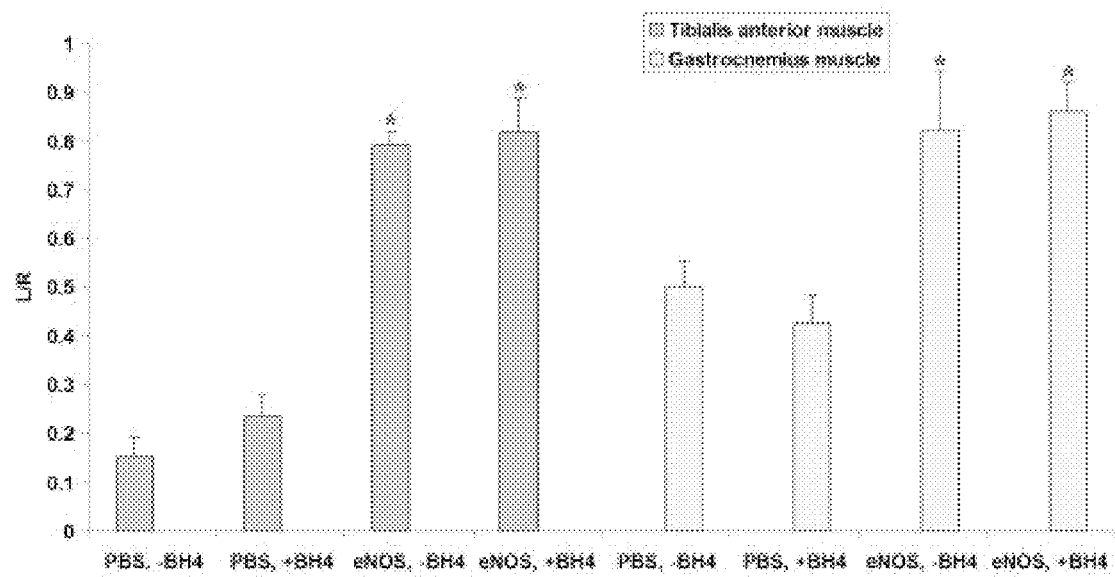
FIG. 7. Effects of treatments on muscle weights in ischemic hindlimb.

Indeed, the histology noted in the [eNOS, +BH4] was remarkably free of extensive necrosis or inflammation. In contrast, muscle histology in the [PBS, −BH4] and [PBS, +BH4] groups revealed heavy nuclear staining in the inter-myofibril connective tissue, as well as an inflammatory cell infiltrate. Finally, the weights of the ischemic tibialis anterior and gastrocnemius muscles, when expressed as a ratio to weight of the non-ischemic muscles, were significantly greater in the [eNOS, −BH4] and [eNOS, +BH4] groups than in the [PBS, −BH4] and [PBS, +BH4] groups (FIG. 7). FIG. 7 shows effects of treatments on muscle weights in ischemic hindlimb. Muscles were harvested 7 days after intra-arterial AdeNOS or PBS infusion (17 days after induction of ischemia). Data are expressed as the ratio of the weights of the ischemic hindlimb (left side) to the non-ischemic hindlimb (right side). m±sd, n=6; * P<0.05 vs. [PBS, −BH4] and [PBS, +BH4] groups.

Accordingly, in some aspects dietary supplementation with BH4 significantly augments the beneficial effect of intra-arterial AdeNOS gene transfer therapy in the recovery from acute hindlimb ischemia. Rats in the [eNOS, +BH4] group demonstrated a twofold greater $Ca^{2+}$-dependent NOS activity and better perfusion recovery within ischemic muscle than the [eNOS, −BH4] group. Moreover, co-treatment with dietary BH4 and intra-arterial AdeNOS eliminated gastrocnemius muscle nitrotyrosine accumulation and resulted in a 75% less muscle necrosis than rats given AdeNOS alone. These findings are the first evidence BH4 and AdeNOS co-treatment generates synergistic beneficial effects in the setting of hindlimb ischemia.

The present findings confirm the established importance of eNOS-derived NO in modulating the response to hindlimb ischemia [2-8]. NO serves to vasodilate collateral arteries immediately following induction of ischemia [14]. NO also participates in collateral artery remodeling, a process termed arteriogenesis, which permanently increases the net cross sectional area of the collateral artery system so that it approximates the level that was present prior to loss of the large conduit artery loss (e.g., loss of the femoral artery) [15]. Arteriogenesis includes NO-derived mobilization of vascular progenitor cells from marrow [16] and non-marrow [17] sources which then participate in vascular remodeling. The net outcome NO-based vasodilation and arteriogenesis is return of downstream perfusion and, in the context of hindlimb ischemia, restoration of $O_2$ transport to the distal hindlimb [18]. It might be argued that co-treatment with BH4 and AdeNOS had a limited effect on vascular recovery. The flow ratios in the [eNOS, +BH4] vs. [eNOS, −BH4] groups were 0.94±0.05 vs. 0.83±0.05, respectively, on day 30, and no difference in collateral artery enlargement, as evidenced by angioscore, was evident between these groups. It is important to note, however, that the relationship between vessel dimension, flow rate and tissue oxygen uptake (or $O_2$ sufficiency) is not linear in skeletal muscle and that substantial compromise of tissue oxygenation can occur even in the presence of minor differences in blood flow rate [18]. In this context, the most relevant dependent variable measured in this study was muscle integrity, which was much more effectively preserved in the gastrocnemius muscle of the [eNOS, +BH4] group, a finding that clearly indicates that net oxygen transport to the hindlimb was substantially improved by co-treatment with dietary BH4 and AdeNOS.

The synergy between BH4 and AdeNOS treatments were likely mediated by at least two established mechanisms. First, BH4 is itself a potent antioxidant that eliminates peroxynitrite, the free radical responsible for nitrotyrosine formation, 6-10 times faster than thiols (e.g., glutathione) and ascorbate [13]. This beneficial effect was evidenced by the reduction of nitrotyrosine accumulation in the ischemic gastrocnemius muscle in the [PBS, +BH4] group. Second, an intracellular eNOS:BH4 molar ratio >1 causes eNOS uncoupling wherein enzyme catalytic activity yields $O_2^-$, rather than L-citrulline and NO because the electron flow between eNOS monomers is diverted away from the L-arginine binding site, resulting in reduction of molecular oxygen rather than L-arginine [19]. Thus, supplementation with dietary BH4 should reduce the possibility of eNOS uncoupling, enhance NO production, and reduce eNOS-derived $O_2^-$ production in a manner that has been previously demonstrated both in vitro [19] and in vivo [20]. These events most certainly occurred in the ischemic gastrocnemius muscle of the [eNOS, +BH4] group, as evidenced by the significant increase in $Ca^{2+}$-dependent NOS activity. This assay measures the reduction of L-arginine to form L-citrulline and NO, and thus reflects the activity of coupled eNOS, e.g., a reaction in which NO, not $O_2^-$ is generated [10]. Moreover, neural NOS is minimally expressed in skeletal muscle, e.g., under the experimental conditions herein, measurement of $Ca^{2+}$-dependent NOS activity is a faithful quantitation of eNOS activity.

It might be argued that the present findings would be more compelling if BH4 at its oxidation product, 7,8-dihydrobiopterin (BH2) [11] had been measured. Most studies in which BH4 and eNOS are measured utilize cells (e.g., Crabtree et al.) [19] or aorta (e.g., Bendell et al.) [20]. Measurement of BH4/BH2 in skeletal muscle requires removal of arteries or arterioles from the muscle tissue, as using homogenates of whole muscle to measure BH4/BH2 generates an unacceptably high signal-to-noise ratio in the assay output [21]. This type of vascular dissection is virtually impossible in the presence of ischemic muscle damage, as was present in to some extent in 3 of the 4 study groups in this project. However, it should be appreciated that the absence of BH4 measurements neither minimizes nor invalidates the importance of the present findings. Significant, and physiological relevant differences were present between the [eNOS, −BH4] and [eNOS, +BH4] group and these findings clearly support the experimental hypothesis.

The therapeutic goal of the medical or surgical treatment of peripheral arterial disease or critical limb ischemia is preservation of muscle integrity and thus pain-free limb function [22]. The present findings demonstrate, for the first time, that co-treatment with dietary BH4 and intra-arterial AdeNOS significantly reduce the degree of gastrocnemius muscle necrosis in the setting of acute hindlimb ischemia, a commonly used and highly relevant pre-clinical model of peripheral arterial disease [23]. It is interesting to note that previous clinical trials designed to improve vascular outcome by increasing eNOS expression or function (e.g., the VIVA trial) [24] have met with limited success. Accordingly, in some embodiments supplementation with BH4 may be used to significantly improve the clinical therapeutic efficacy of treatments aimed to improve eNOS expression, particularly in circumstances wherein oxidation of endogenous BH4 might have occurred (e.g., in the setting of hindlimb ischemia).

References
1. Shammas N. (2007) Epidemiology, classification, and modifiable risk factors of peripheral arterial disease. *Vasc Health Risk Man* 3:229-234.
2. Brevetti L, Chang D, Tang G, Sarkar R, Messina L. (2003) Overexpression of nitric oxide synthase increases skeletal muscle blood flow and oxygenation in severe rat hindlimb ischemia. *J Vasc Surg* 38:820-826.

3. Yan J, Tang G, Wang R, Messina, L. (2005) Optimization of adenovirus-mediated endothelial nitric oxide synthase delivery in rat hindlimb ischemia. *Gene Therapy* 12:1640-1650.
4. Smith R, Lin K, Agata J, Chao L, Chao, J. (2002) Human endothelial nitric oxide synthase gene delivery promotes angiogenesis in a rat model of hindlimb ischemia. *Arterioscler Thromb Vasc Biol* 22:1279-1285.
5. Tsutsui M, Chen A, O'Brien T, Crotty T, and Katusic, Z. (1998) Adventitial expression of recombinant eNOS gene restores NO production in arteries without endothelium. *Arterioscler Thromb Vasc Biol* 18:1231-1241.
6. Katusic Z. (2002) Therapeutic angiogenesis: new indication for endothelial NO synthase gene transfer. *Arterioscler Thromb Vasc Biol* 22:1254-1255.
7. Murohara T, Asahara T, Silver M, Bauters C, Masuda H, Kalka C, Kearny M, Chen D, Symes J F, Fishman M C, Huang P L, Isner J M. (1998) Nitric oxide synthase modulates angiogenesis in response to tissue ischemia. *J Clin Invest* 101:2567-2578.
8. Buckwalter J, Curtis V, Valic Z, Ruble S, Clifford P. (2003) Endogenous vascular remodeling in ischemic skeletal muscle: a role for nitric oxide. *J Appl Physiol* 94:935-940.
9. Lloyd P, Yang H, Terjung R. (2001) Arteriogenesis and angiogenesis in rat ischemic hindlimb: role of nitric oxide. *Am J Physiol* 281:H2528-2538.
10. Marietta M. (1993) Nitric oxide synthase structure and mechanism. *J Biol Chem* 268:12231-12234.
11. Alp N, Schmidt T. (2007) Mechanisms for the role of tetrahydrobiopterin in endothelial function and disease. *Clin Sci* 113:47-63.
12. Vasquez-Vivar J, Kalyanaraman B, Martasek P, Hogg N, Masters B, Karoui H, Tordo P, Pritchard K. (1998) Superoxide generation by endothelial nitric oxide synthase: the influence of cofactors. *Proc Natl Acad Sci* 95:9220-9225.
13. Kuzkaya N, Weismann N, Harrison D, Dikalov S. (2003) Interaction of peroxynitrite, tetrahydrobiopterin, ascorbic acid, and thiols. *J Biol Chem* 278:22546-22554.
14. Mees B, Wagner S, Ninci E, Tribulova S, Martin S, van Haperen R, Kostin S, Heil M, de Crom R, Schaper W. (2007) Endothelial nitric oxide synthase activity is essential for vasodilation during blood flow recovery but not for arteriogenesis. *Arterioscler Thromb Vasc Biol* 27:1-8.
15. Helisch A, Schaper W. (2003) Arteriogenesis: the development and growth of collateral arteries. *Microcirculation* 10:83-97.
16. Aicher A, Heeschen C, Mildner-Rihm C, Urbich C, Ihling C, Technau-Ihling K, Zeiher A, and Dimmeler S. (2003) Essential role of endothelial nitric oxide synthase for mobilization of stem and progenitor cells. *Nat Med* 9:1370-1376.
17. Aicher A, Rentsch M, Saski, K-I, Ellwart J, Fandrich F, Siebert R, Cooke J, Dimmeler S, Heeschen C. (2007) Nonbone marrow-derived circulating progenitor cells contribute to postnatal neovascularization following tissue ischemia. *Circ Res* 100:581-589.
18. Granger H J, Goodman A, Granger D N. (1976) Role of resistance and exchange vessels in the local microvascular control of skeletal muscle oxygenation in the dog. *Circ Res* 38:379-385.
19. Crabtree M, Tatham A, Al-Wakeel Y, Warrick N, Hale A, Cai S, Channon K, Alp N. (2009) Quantitative regulation of intracellular endothelial nitric-oxide synthase (eNOS) coupling by both tetrahydrobiopterin-eNOS stoichiometry and biopterin redox status. *J Biol Chem* 284:1136-1144.
20. Bendell J, Alp N, Warrick N, Cai S, Adlam D, Rockett K, Yokoyama M, Kawashima S, Channon K. (2005) Stoichiometric relationships between endothelial tetrahydrobiopterin, endothelial NO synthase (eNOS) activity, and eNOS coupling in vivo. Insights from transgenic mice with endothelial-targeted GTP cyclohydrolase 1 and eNOS overexpression. *Circ Res* 97:864-871.
21. Delp M, Behnke B, Spier S, Wu G, Mueller-Delp J. (2008) Ageing diminishes endothelium-dependent vasodilation and tetrahydrobiopterin content in rat skeletal muscle arterioles. *J Physiol* 586:1161-1168.
22. Raegensteiner J, Hiatt W. (2002) Current medical therapies for patients with peripheral arterial disease: A critical review. *Am J Med* 112:49-57.
23. Waters R, Terjung R, Peters K, Annex B. (2004) Preclinical models of human peripheral arterial occlusive disease: implications for investigating therapeutic agents. *Am J Physiol* 97:773-780.
24. Henry T, Annex B, McKendall G, Azarin M, Lopex J, Giordano F, Shah P, Willerson J, Benza R, Berman D, Gibson M, Bajamonde A, Rundle A, Fine J, McCluskey E. (2003) The VIVA trial: Vascular endothelial growth factor in ischemia for vascular angiogenesis. *Circulation* 107:1359-1365.

Example 2

Dietary Supplementation with Tetrahydrobiopterin, L-Arginine Ketoglutarate, and L-Ascorbic Acid Restores Blood Flow Recovery and Increases Nitric Oxide Bioavailability after Hindlimb Ischemia in Rat.

This study tested the hypothesis that dietary co-supplementation with tetrahydrobiopterin (BH4), L-arginine, and L-ascorbic acid acts synergistically to improve perfusion and tissue recovery in response to acute hindlimb ischemia more than supplementation with a single agent.

Rats were fed normal chow, chow supplemented with BH4 or L-arginine, alone or in combination, or chow supplemented with BH4+L-arginine+L-ascorbic acid for one week prior to induction of unilateral hindlimb ischemia, induced by excision of a segment of the left common femoral artery. Co-supplementation with BH4+L-arginine resulted in greater eNOS expression and $Ca^{2+}$-dependent eNOS activity in gastrocnemius from the ischemic hindlimb, as well as greater recovery of foot perfusion and more collateral artery enlargement than did rats receiving either agent separately. The addition of L-ascorbic acid to the BH4+L-arginine regimen did not further improve these dependent variables. However, rats given all three supplements demonstrated less $Ca^{2+}$-independent activity, less nitrotyrosine accumulation, and less gastrocnemius muscle necrosis, on both macroscopic and microscopic levels.

Accordingly, co-supplementation with BH4+L-arginine significantly improved vascular recovery from hindlimb ischemia by normalizing eNOS activity. The addition of L-ascorbic acid to this regimen provided the additional benefit of reduced nitrotyrosine accumulation and tissue injury following hindlimb ischemia. Oral co-supplementation of L-arginine, BH4, and L-ascorbic acid holds promise as a means to induce collateral artery enlargement.

Endothelial dysfunction is a hallmark of peripheral artery disease (PAD) [1]. Central to the development of endothelial dysfunction, regardless of its cause, is a reduction in the bioavailability of nitric oxide (NO) derived from endothelial nitric oxide synthase (eNOS). Three fundamental mechanisms can compromise NO bioavailability: loss of eNOS expression, loss of eNOS-derived NO production, e.g., functional inactivation of eNOS, and inactivation of NO by superoxide anion ($O_2^-$) to form peroxynitrite ($OONO^-$) [2,3]. In some embodiments, it is likely that all three mechanisms contribute to the endothelial dysfunction characteristic of PAD because increased oxidative stress is a common antecedent in the pathogenesis of this disease and can reduce NO bioavailability.

At least two characteristics of eNOS render it susceptible to oxidative stress. First, eNOS transcription, post-translational modification, and trafficking to the caveolae are attenuated by the accumulation of reactive oxygen species (ROS) within the endothelial cell [4]. Second, the eNOS co-factor tetrahydrobiopterin (BH4) is highly susceptible to oxidation [5]. BH4 maintains eNOS in its functional dimeric form; in the absence of BH4, eNOS becomes uncoupled so that the electron flux is diverted away from the L-arginine binding site and instead reduces molecular oxygen, generating $O_2^-$ [6]. This circumstance initiates a vicious cycle, wherein eNOS catalytic activity produces $O_2^-$, not NO, worsening existent oxidative stress.

These molecular characteristics of eNOS predict that several therapeutic options might prove effective for the treatment of PAD, namely dietary supplementation with an antioxidant, or with the eNOS substrate L-arginine, or with the eNOS cofactor BH4. Vitamin C, or L-ascorbic acid, is a potent antioxidant and has been shown to preserve BH4 levels and enhance endothelial NO production in vitro [7]. ONOO– reacts with BH4 6-10 times faster when in the presence of ascorbate. The intermediate product of the reaction between ONOO– and BH4 is the trihydrobiopterin radical (BH3), which is reduced back to BH4 by ascorbate. Thus, ascorbate does not protect BH4 from oxidation but rather recycles BH3 radical back to BH4 [8]. Vitamin C levels are low in PAD patients, [9] and acute [10] or short term [11] vitamin C supplementation reduce PAD symptoms. However, cross sectional epidemiological surveys have failed to find a clear link between long term vitamin C intake and PAD symptoms or disease progression [12,13]. L-arginine supplementation showed exciting promise in short term studies of PAD [14,15] but this effect was not observed in a subsequent long term study by the same group [16]. BH4 improves eNOS-dependent vasodilation in long term smokers and patients with type II diabetes, conditions associated with increased oxidative stress [17,18]. BH4 has not been specifically evaluated as a therapeutic modality in PAD.

In some embodiments, the potential synergistic effect of combined therapy (e.g., of BH4, L-arginine, and L-ascorbic acid) may be used in the prevention and treatment of PAD. For example, supplementation with L-arginine alone might prove deleterious in the face of endothelial oxidative stress inasmuch as the resultant increase in eNOS catalytic activity might generate $O_2^-$, not NO, if BH4 levels were reduced by oxidation. Thus, in some embodiments co-supplementation of L-arginine with L-ascorbic acid and BH4 may be used to enhance the therapeutic outcome by reducing oxidant stress and preserving eNOS in its functional dimeric form, respectively. This action would enhance eNOS-derived NO production and, by quenching existent $O_2^-$, reduce NO inactivation by its reaction with $O_2^-$.

One goal of this study was to evaluate the effect of combined dietary supplementation with BH4, L-arginine, and L-ascorbic acid and its ability to improve hindlimb perfusion recovery and preservation of tissue integrity in response to severe hindlimb ischemia. To this end, severe hindlimb ischemia was generated in the rat by means of femoral artery excision. Measured dependent variables included gastrocnemius muscle eNOS expression and activity, hindlimb laser Doppler perfusion and collateral artery enlargement, and gastrocnemius nitrotyrosine accumulation and tissue necrosis.

Methods and Materials

Supplements:

Dietary supplements included: BH4 (10 mg/Kg/day; Schircks Laboratories, Jonas, Switzerland); L-arginine, provided as L-arginine α-ketoglutarate (hereafter: L-arginine; 88.5 mg/Kg/day; Body Tech, North Bergen, N.J.); and L-ascorbic acid (88.5 mg/Kg/day, Aldrich Sigma, St. Louis, Mo.).

Animals:

All protocols were approved by the Institutional Animal Care and Use Committee at the University of California, San Francisco. Adult male Sprague-Dawley rats weighing 265-285 g (Charles River Laboratories, Wilmington, Mass.) were maintained in a clean housing facility on a 12 hour light/dark cycle.

Preparation:

Severe ischemia was induced in the left hindlimb. The femoral artery was ligated between the inguinal ligament and popliteal fossa, and the ligated section and its branches were excised. This procedure was carried out under anesthesia with 2% isofluorane. The untreated right hindlimb served as an internal control for each rat. An additional group of sham-operated rats were also used for selected assays. These rats underwent isolation of the femoral artery in the left hindlimb under 2% isofluorane anesthesia, but the artery was left intact.

Study Design:

All rats were fed standard chow in powder form and water ad libitum (Deans Feeds, Redwood City, Calif.). Animals were randomly selected to receive normal chow, chow with a single added supplement (BH4 or L-arginine), chow supplemented with BH4+L-arginine, or chow supplemented with BH4+L-arginine+L-ascorbic acid. Dietary supplementation was commenced 7 days prior to the induction of hindlimb ischemia and was continued until sacrifice of the animal. Chow was replaced every 2 days. The time of sacrifice varied with the measured endpoint under consideration, as described below. Rats in the sham-operated group received normal chow throughout the course of study.

Methods of Endpoint Measurement:

Western Blotting:

Rats were sacrificed 14 days after induction of ischemia for measurement of gastrocnemius muscle eNOS and nitrotyrosine expression. The timing of sacrifice was selected based on previous work that demonstrated maximal post-ischemic change in these variables at this time [19]. Samples were homogenized in liquid nitrogen and transferred to NP-40 lysis buffer, comprised of 50 mM HEPES (pH 7.5), 150 mM NaCl, 10% glycerol, 1.5 mM $MgCl_2$, 1 mM EDTA, 100 mM NaF, 1% NP 40, 1 mM PMSF, and 1 g/ml aprotinin. The lysates were centrifuged, the supernatant recovered, and the protein concentration determined (Pierce Biotechnology, Rockford, Ill.). 100 μg of protein per sample was separated on a 7.5% or 12% SDS-polyacrylamide gel for determination of eNOS or nitrotyrosine, respectively, and then electroblotted on nitrocellulose membranes (Bio-Rad, Hercules, Calif.). Membranes were incubated overnight at 4° C. with mouse monoclonal anti-nitrotyrosine (Cayman Chemical Co., Ann Arbor, Mich., 1:1000) or mouse monoclonal anti-eNOS (BD Transduction Laboratories, San Diego, Calif., 1:1000) and then incubated for 2 h with horseradish peroxidase-conjugated anti-mouse IgG antibody (Pierce Biotechnology, 1:5000). Immunoreactive bands were visualized using the enhanced chemiluminescence system (Amersham, Arlington Heights, Ill.). Band density was quantitated by standard densitometry and the intensity of the band of interest expressed as a function of the α-tubulin band.

eNOS Activity:

Rats were sacrificed 14 days after induction of ischemia for determination of gastrocnemius muscle NOS activity. The timing of sacrifice was selected based on previous work that demonstrated maximal post-ischemic change in this variable at this time [19]. Muscles were homogenized in ice-cold buffer (250 mM Tris-HCl, pH 7.4, 10 mM EDTA, 10 mM EGTA), centrifuged, and the protein in the supernatant adjusted to 5 µg/ml. Samples were incubated in 10 mM NADPH, 1 µCi/µl $^{14}$C-Arg, 6 mM $CaCl_2$, 50 mM Tris.HCl (pH 7.4), 6 µM BH4, 2 uM FAD, and 2 µM FMN for 30 minutes at 37° C. The reaction was stopped with 400 µl of 50 mM Hepes, pH 5.5, 5 mM EDTA. Identical samples were prepared without $CaCl_2$ and all reactions were performed in duplicate. The radioactivity of the sample eluate was measured and expressed as CPM/µg protein. The $Ca^{2+}$-dependent NOS activity, which corresponds to the sum of the endothelial and neural NOS isoforms, was calculated by subtracting the NOS activity measured in the absence of $CaCl_2$) from the NOS activity measured in the presence of $CaCl_2$). The $Ca^{2+}$-independent NOS activity corresponds to inflammatory isoform of NOS, or iNOS.

Hindlimb Perfusion:

Hindlimb blood flow was determined by means of laser Doppler imaging (Moor Instruments, Ltd., Devon, United Kingdom). Flow was measured preoperatively, immediately after arterial excision, and then 3, 7, 14, 21, 28, 35, and 42 days after induction of ischemia. Scans were obtained during inhalation of 1% isofluorane while core body temperature was maintained between 36.8-37.2° C. Scans were repeated three times and the average for each rat determined. Data were expressed as the ratio of ischemic:non-ischemic hindlimb.

Angiograms:

Angiograms were performed 42 days after induction of ischemia. Barium sulfate (2.5 ml; EZPaqe, Merry X-Ray, South San Francisco, Calif.) was infused into the infrarenal aorta after ligation of the proximal aorta and inferior vena cava during inhalation of 2% isofluorane. A grid was superimposed over the film between the greater trochanter of the femur to the patella. The number of intersections between contrast-filled vessels and gridlines was determined independently by 3 blinded observers. The angioscore was calculated as the average ratio of intersections to the total number of gridlines. Within the experimental setting of this study, the angioscore is a marker of collateral artery enlargement; thus, as collateral arteries dilate and remodel in response to femoral artery excision their diameters increase, enhancing their visibility on the x-ray film and thus increasing the angioscore [19].

Nitroblue Tetrazolium (NBT) Staining to Detect Muscle Necrosis:

The left gastrocnemius muscle was removed 7 days after induction of ischemia. The timing of sacrifice was selected based on previous work that demonstrated maximal post-ischemic muscle necrosis at this time [19]. The muscle was cut transversely into three 2 mm sections. Two sections were used for NBT staining while the third was frozen (−80° C.) in OCT embedding compound. Sections for NBT staining were incubated in PBS containing 0.033% NBT (Fisher Biotech, Austin, Tex.) and 0.133% NADH (Roche Diagnostics, Indianapolis, Ind.) at 21° C. for 10 min. The samples were then fixed in 4% paraformaldehyde for 24 hours. The areas of viable tissue, indicated by dark blue color, and non-viable tissue, indicated by white color, were measured by quantitative image analysis (ImagePro, Media Cybernetics, Bethesda, Md.). Data were expressed as the ratio of non-viable tissue to total tissue area. Measurements were made on the four exposed cut surfaces and the average taken, and used as a single data point for each animal. The frozen section was used to prepare cryosections (10 µm) for H&E staining to evaluate histological integrity of the muscle, as well as detect the presence of an inflammatory infiltrate.

Statistical Analysis:

Analyses were carried out by means of analysis of variance (ANOVA). Post-hoc Student-Newman-Keuls tests were carried out if the ANOVA f-statistic was significant to determine sites of difference within the ANOVA format. Probability values less <0.05 was accepted as significant for all statistical calculations.

Results

Figure 8:
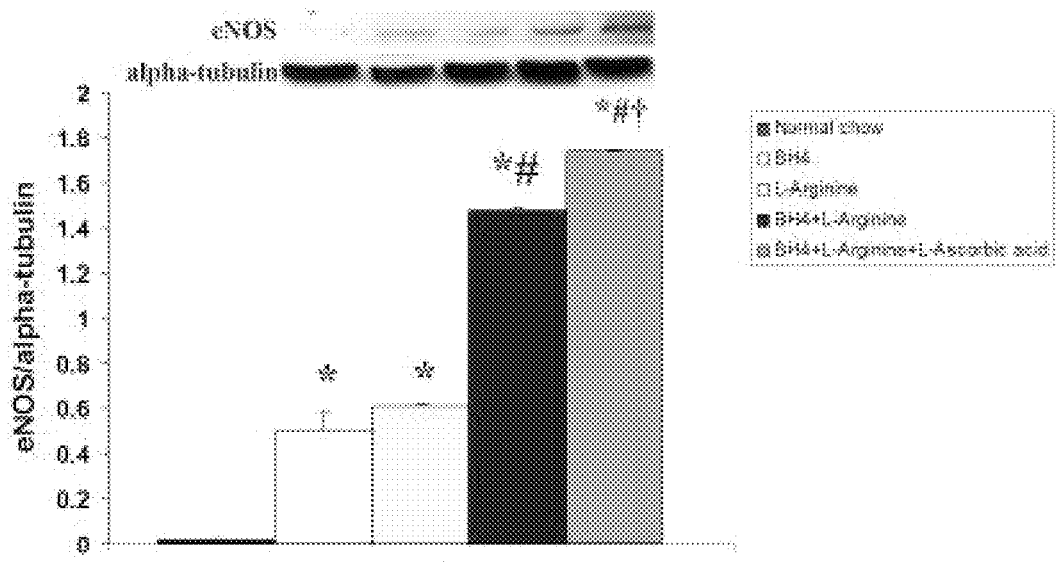
FIG. 8. Effects of oral administration of BH4, L-arginine, and L-ascorbic acid on eNOS expression in the gastrocnemius muscle from the ischemic hindlimb.

Effects of Oral BH4, L-Arginine, and L-Ascorbic Acid on Gastrocnemius eNOS Expression:

Dietary supplementation of BH4, L-arginine, and L-ascorbic acid significantly affected eNOS expression in the ischemic gastrocnemius muscle (FIG. 8). FIG. 8 shows effects of oral administration of BH4, L-arginine, and L-ascorbic acid on eNOS expression in the gastrocnemius muscle from the ischemic hindlimb. Muscle was harvested 14 days after induction of ischemia for evaluation of eNOS expression. m±sd; n=3; * p<0.05 vs. normal chow group; #p<0.05 vs. BH4 or L-arginine groups; † p<0.05 vs. BH4+L-arginine group. The inset shows a representative blot. From left-to-right, these bands represent the following groups: normal chow, chow supplemented with BH4, chow supplemented with L-arginine, chow supplemented with BH4+L-arginine, and chow supplemented with BH4+L-arginine+L-ascorbic acid.

Rats given single supplementation with BH4 or L-arginine demonstrated similar levels of eNOS expression and these levels were significantly greater than that of rats fed normal chow. Rats given two (BH4+L-arginine) or three (BH4+L-arginine+L-ascorbic acid) supplements also had similar levels of eNOS expression and these levels were greater than those in mice given single supplements. Hence, the combination of BH4 and L-arginine had an additive effect on eNOS expression, whereas the addition of L-ascorbic acid failed to provide any additional beneficial effect.

Figure 9A:
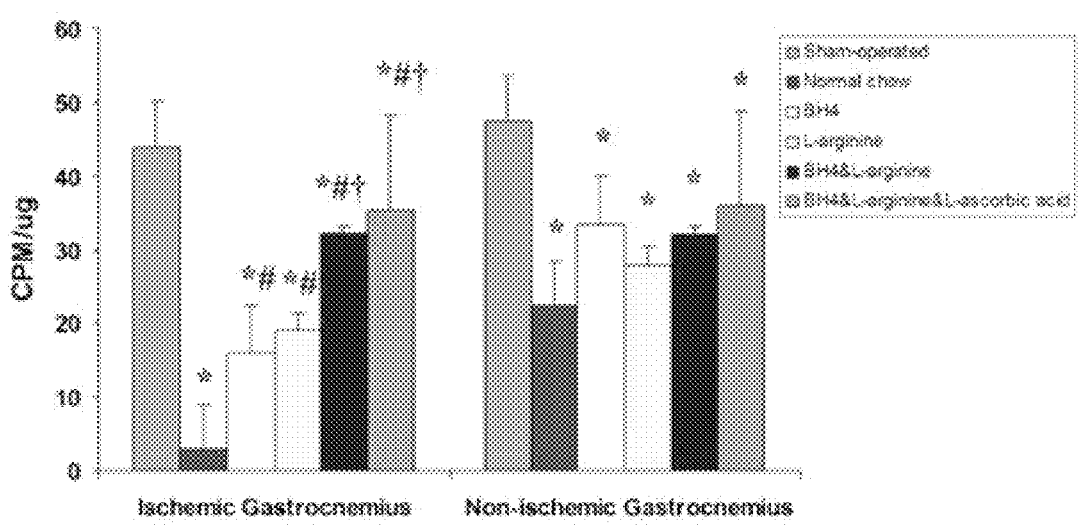
FIGS. 9A-9B. Effects of oral administration of BH4, L-arginine, and L-ascorbic acid on calcium dependent- and independent-NOS activity in the gastrocnemius muscles from the ischemic and nonischemic hindlimbs.
Figure 9B:
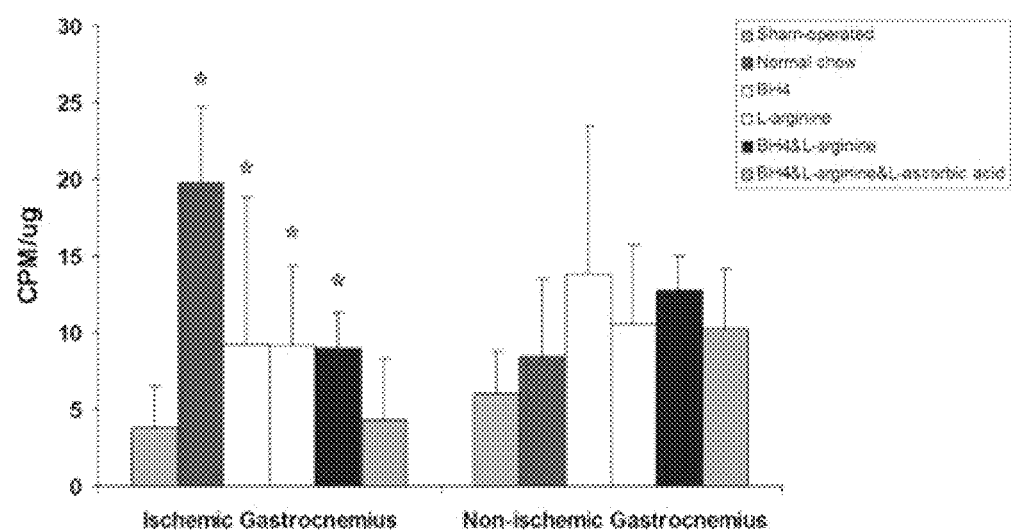

Effects of Oral BH4, L-Arginine, and L-Ascorbic Acid on Gastrocnemius $Ca^{2+}$-Dependent NOS Activity:

Dietary supplements affected $Ca^{2+}$-dependent NOS activity in the ischemic gastrocnemius muscle and the pattern of change mirrored that noted for eNOS expression (FIGS. 9A-9B). FIGS. 9A-9B show effects of oral administration of BH4, L-arginine, and L-ascorbic acid on calcium dependent- and independent-NOS activity in the gastrocnemius muscles from the ischemic and nonischemic hindlimbs. Muscle was harvested 14 days after induction of ischemia for evaluation of NOS activity. m±sd; n=6, * p<0.05 vs. sham-operated group; #p<0.05 vs. normal chow group; † p<0.05 vs. BH4 or L-arginine groups.

Thus, rats given a single dietary supplement (BH4 or L-arginine) demonstrated $Ca^{2+}$-dependent NOS activities that were similar to each other, and greater than that of rats fed normal chow. Rats given two (BH4+L-arginine) or three (BH4+L-arginine+L-ascorbic acid) supplements also displayed similar levels of $Ca^{2+}$-dependent NOS activity and these levels were significantly greater than those of rats given single dietary supplements. The combination of BH4 and L-arginine generated an additive effect, whereas the addition of L-ascorbic acid did not result in a significant additional effect on $Ca^{2+}$-dependent NOS activity. Although the use of multiple dietary supplements had the greatest positive effect on $Ca^{2+}$-dependent NOS activity, the levels noted in these two groups were still significantly less than that noted in the left hindlimb of sham-operated rats. Moreover, $Ca^{2+}$-dependent NOS activity in the right hindlimb of sham-operated animals was significantly greater than the activity level in the non-ischemic (right) hindlimb in control rats. Dietary supplementation did not significantly affect $Ca^{2+}$-dependent activity in the non-ischemic hindlimb.

Effects of Oral BH4, L-Arginine, and L-Ascorbic Acid on Gastrocnemius $Ca^{2+}$-Independent NOS Activity:

$Ca^{2+}$-independent NOS activity was significantly greater in the ischemic gastrocnemius from rats fed normal chow than in the left gastrocnemius of sham-operated rats (FIG. 9). Rats fed a single supplement (BH4 or L-arginine), or the combination of these two agents demonstrated $Ca^{2+}$-independent NOS activity statistically similar to the normal chow group, e.g., there was no beneficial effect noted in these dietary intervention groups. However, rats provided with three dietary supplements (BH4+L-arginine+L-ascorbic acid) demonstrated $Ca^{2+}$-independent NOS activity levels in the ischemic gastrocnemius muscle that were lower than the other dietary intervention groups, but were similar to the level noted in the left gastrocnemius muscle from sham-operated rats. The $Ca^{2+}$-independent activity level in the gastrocnemius muscle from the non-ischemic (right) hindlimb from control rats was similar to that in the right hindlimb from sham-operated animals. None of the dietary supplementation regimens had an effect on the $Ca^{2+}$-independent activity level in the non-ischemic hindlimb.

Figure 10:
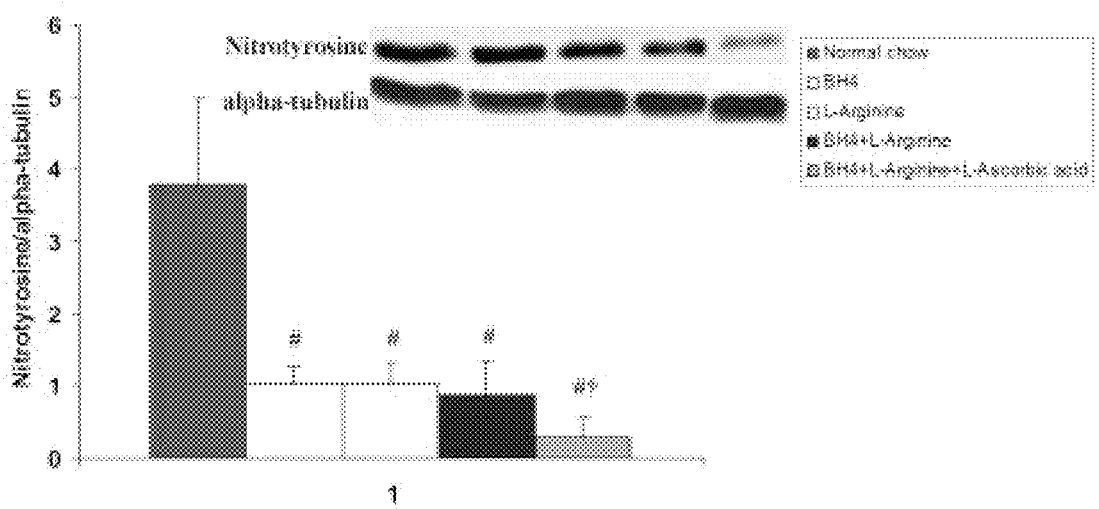
FIG. 10. Effects of oral administration of BH4, L-arginine, and L-ascorbic acid on peroxynitrate formation in gastrocnemius muscle from the ischemic hindlimb.

Effects of Oral BH4, L-Arginine, and L-Ascorbic Acid on Gastrocnemius Nitrotyrosine Accumulation:

Dietary supplementation affected nitrotyrosine accumulation in the ischemic gastrocnemius muscle (FIG. 10). FIG. 10 shows effects of oral administration of BH4, L-arginine, and L-ascorbic acid on peroxynitrate formation in gastrocnemius muscle from the ischemic hindlimb. Muscle was harvested 14 days after induction of hindlimb ischemia. m±sd; n=3; #$p<0.05$ vs. normal chow group; † $p<0.05$ vs. BH4 group, L-arginine group, or BH4+L-arginine group. The inset shows a representative blot. From left-to-right, these bands represent the following groups: normal chow, chow supplemented with BH4, chow supplemented with L-arginine, chow supplemented with BH4+L-arginine, sham-operated left gastrocnemius, and chow supplemented with BH4+L-arginine+L-ascorbic acid.

Rats given a single dietary supplement (BH4 or L-arginine), or the combination of these dietary agents displayed similar nitrotyrosine levels. These levels were significantly less than the level noted in rats fed normal chow, but significantly greater than that noted in the left gastrocnemius of sham-operated rats. Rats provided with all three dietary supplements (BH4+L-arginine+L-ascorbic acid) exhibited a nitrotyrosine level significantly less than mice given a single supplement (BH4 or L-arginine) or the combination of these two agents. It is noteworthy that nitrotyrosine accumulation in the gastrocnemius of sham-operated mice was virtually undetectable (data not shown).

Figure 11A:
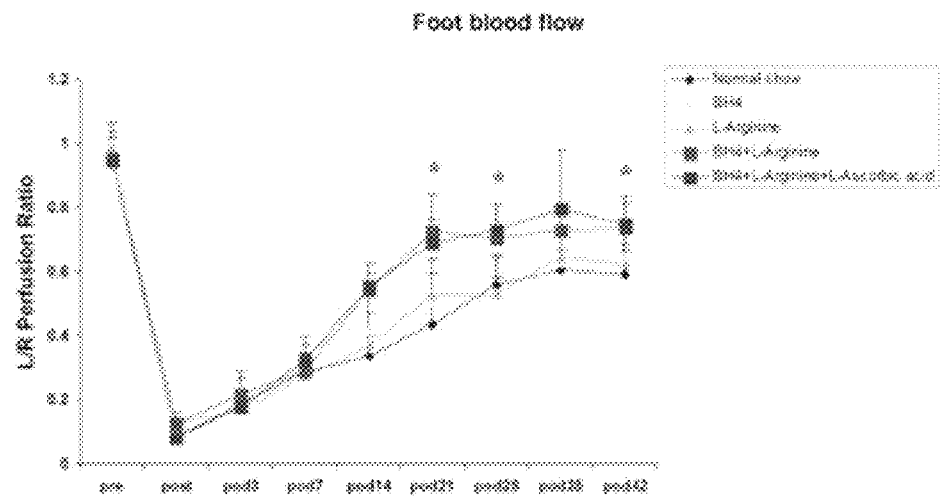
FIGS. 11A-11C. Effects of oral administration of BH4, L-arginine, and L-ascorbic acid on hindlimb circulation.
Figure 11B:
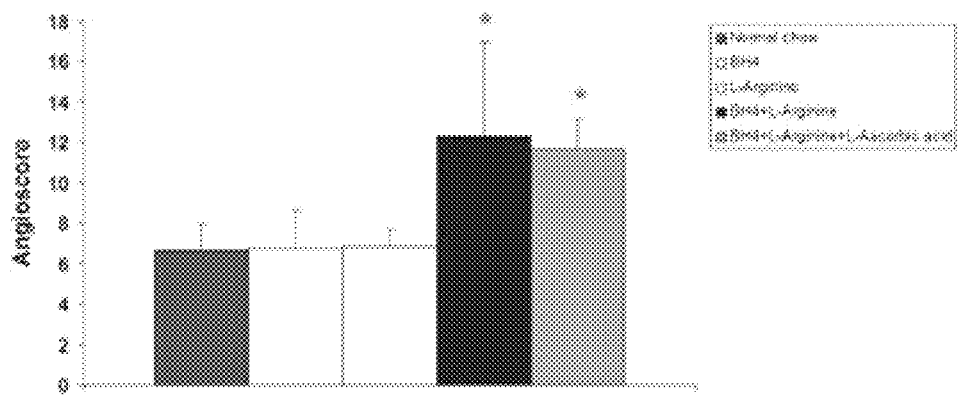
Figure 11C:
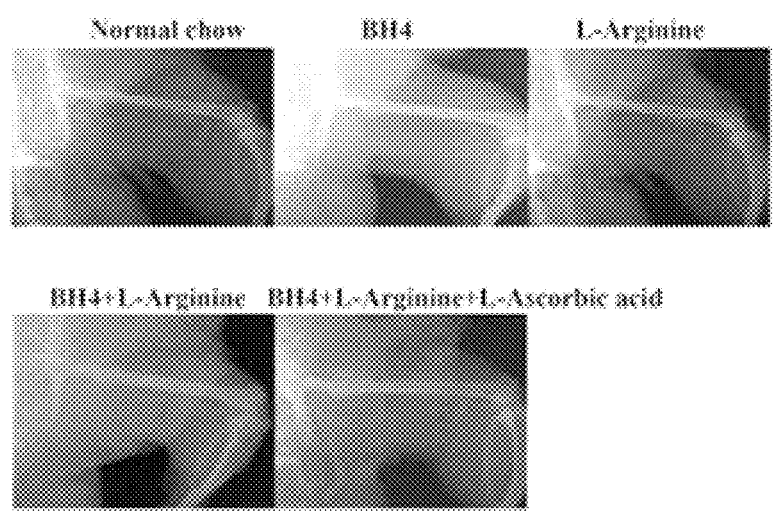

Effects of BH4, L-Arginine, and L-Ascorbic Acid on Hindlimb Perfusion:

Dietary supplementation significantly affected recovery of hindlimb perfusion after induction of severe ischemia and this effect was regimen and time-dependent (FIG. 11A). FIGS. 11A-11C show effects of oral administration of BH4, L-arginine, and L-ascorbic acid on hindlimb circulation. (A) Perfusion recovery. Blood flow was determined by laser Doppler perfusion imaging prior to femoral artery excision (Pre), immediately after femoral artery excision (Post), and on post-operative days (POD) 3-42. Data are expressed as the ratio of perfusion in the ischemic to non-ischemic hindlimbs. m±sd; n=6 for all groups; * $p<0.05$ for BH4+L-arginine group or BH4+L-arginine+L-ascorbic acid group vs. normal chow, BH4, or L-arginine groups. (B) Quantitation of angioscores. The angioscore was determined by counting the intersections between contrast-filled collateral arteries and gridlines superimposed upon the film. The angioscore for each rat was determined by three blinded observers and the average taken as a single data point. m±sd; n=6; * $p<0.05$ for BH4+L-arginine group or BH4+L-arginine+L-ascorbic acid group vs. normal chow, BH4, or L-arginine groups. (C) Representative angiogram from each study group. Rats given a single supplement (BH4 or L-arginine) demonstrated similar degree of perfusion recovery in the foot and this level was also similar to that noted in rats fed normal chow. Rats provided with two (BH4+L-arginine) or three (BH4+L-arginine+L-ascorbic acid) supplements showed significantly greater recovery of foot perfusion than rats fed normal chow or rats given a single dietary supplement. This difference was evident at the later phase of recovery, on days 21, 28, or 42 after induction of ischemia. A similar pattern was noted for collateral artery angioscores determined on day 42 after induction of ischemia. Hence, the angioscore was significantly greater in rats given 2 (BH4+L-arginine) or 3 (BH4+L-arginine+L-ascorbic acid) supplements than in rats fed normal chow or in rats given a single supplement (FIGS. 11B and 11C).

Figure 12A:
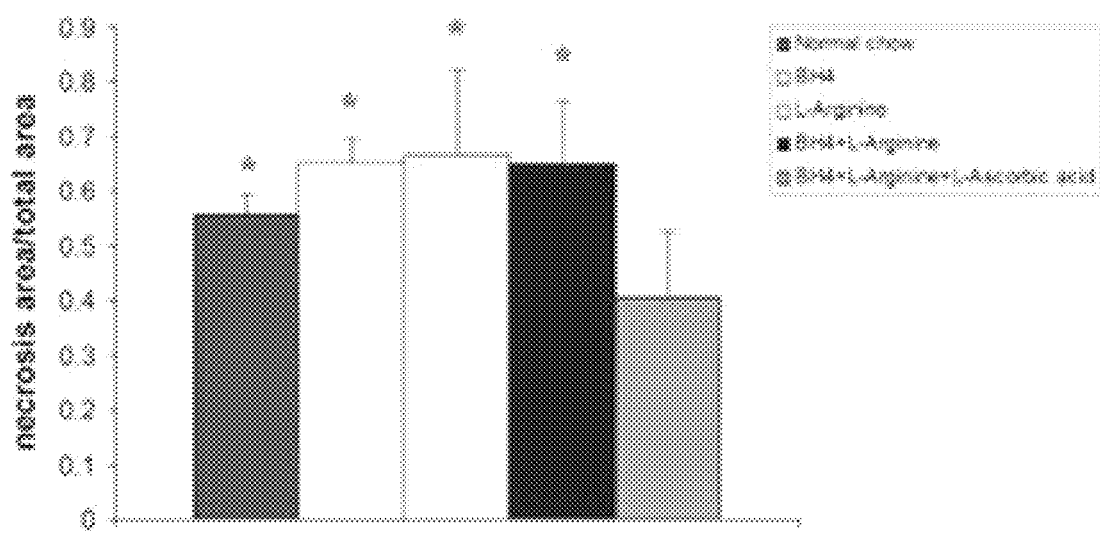
FIGS. 12A-12B. Gross appearance of the cut surface of the gastrocnemius muscle from the ischemic hindlimb.
Figure 12B:
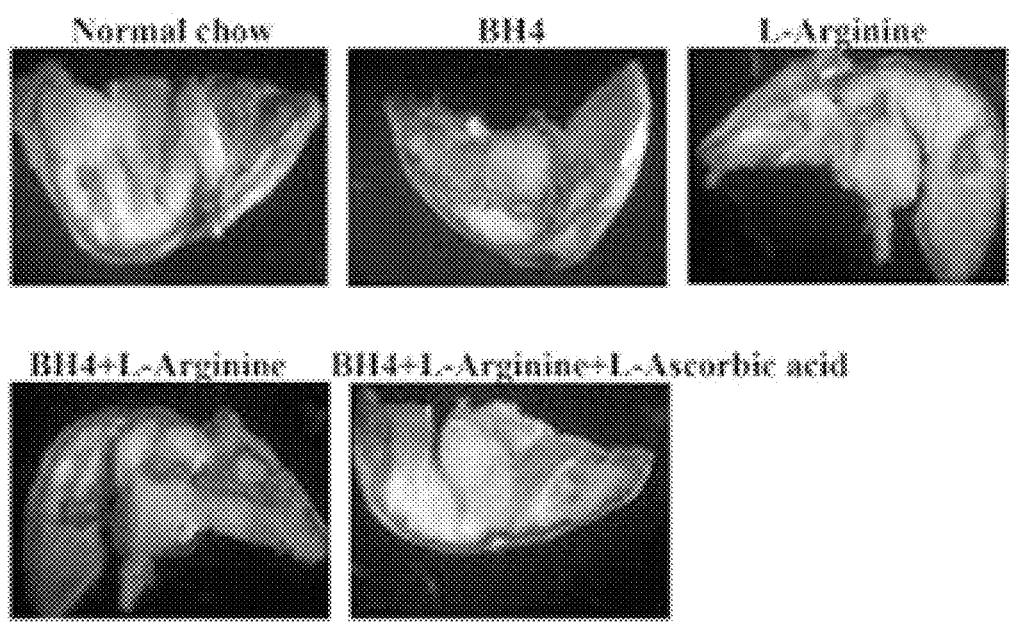
Figure 13:
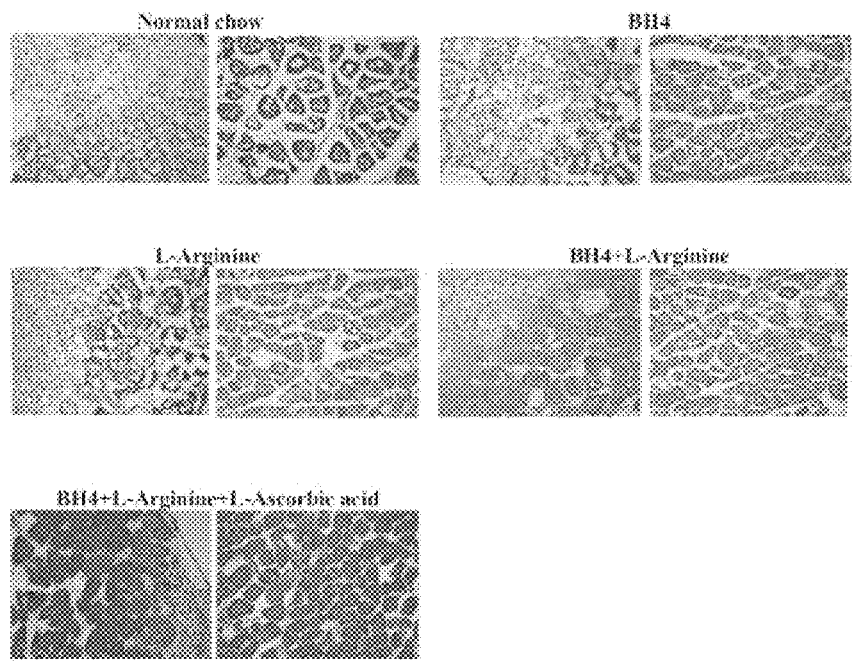
FIG. 13. Histological appearance of the gastrocnemius muscle from the ischemic hindlimb.

Effects of Oral BH4, L-Arginine, and L-Ascorbic Acid on Gastrocnemius Muscle Necrosis:

The extent of gastrocnemius necrosis was affected by the provision of dietary supplements. Rats given a single supplement (BH4 or L-arginine) or the combination of these agents manifest a similar degree of gastrocnemius muscle necrosis. Moreover, the extent of necrosis noted in these dietary intervention groups was similar to that noted in rats fed normal chow, e.g., these dietary regimens did not improve post-ischemic muscle integrity. However, rats provided with all three dietary supplements (BH4+L-arginine+L-ascorbic acid) had significantly less gastrocnemius necrosis than rats fed normal chow, rats provided with a single dietary supplement, or rats given the combination of BH4+L-arginine. This difference was evident on macroscopic and microscopic levels. The percentage of the cut surface of the ischemic gastrocnemius muscle that was necrotic, determined by NBT staining, was significantly less in the BH4+L-arginine+L-ascorbic acid group than in all other groups (FIGS. 12A-12B). FIGS. 12A-12B show gross appearance of the cut surface of the gastrocnemius muscle from the ischemic hindlimb. Muscle was harvested 7 days after the induction of hindlimb ischemia and stained with nitroblue tetrazolium to determine the presence of viable tissue. (A) Quantitation of viable tissue. The surfaces areas of non-viable tissue and the total cut surface were determined using ImagePro software. Four cut surfaces were evaluated per muscle and the average used as a single data point for each animal. Data are expressed as the ratio of the surface area of non-viable tissue to the total surface area of the cut tissue. m±sd; n=6; * $p<0.05$ vs. normal chow group. (B) Representative cut surface areas from each study group. Groups fed normal chow, or supplemented with BH4, or L-arginine, or both agents demonstrated similar histological evidence of severe necrosis: muscle nuclei were nearly absent, intramyofiber vacuolization was substantial, and the distance between myofibers was large (FIG. 13). FIG. 13 shows histological appearance of the gastrocnemius muscle from the ischemic hindlimb. Muscle was harvested 7 days after the induction of hindlimb ischemia. Two images are shown for each study group, both from the same animal in that group. The image on the left was taken from an area of representative maximal inflammation, whereas the image on the right was taken from an area of representative of muscle necrosis. These images were representative of a total of 6 animals studied in each treatment group. H&E staining, magnification 200×.

A pronounced inflammatory infiltrate was also present in these groups. In contrast, the BH4+L-arginine+L-ascorbic acid group demonstrated good preservation of muscle histology and only a limited inflammatory cell infiltrate.

Accordingly, in some aspects tetrahydrobiopterin (BH4), L-arginine, and L-ascorbic acid act synergistically and dietary co-supplementation with these compounds improves perfusion and tissue recovery in response to acute hindlimb ischemia more than supplementation with a single agent. Interestingly, two patterns of effect emerged. Co-supplementation with BH4+L-arginine improved the dependent variables eNOS expression, $Ca^{2+}$-dependent NOS activity, foot perfusion, and the collateral artery angioscore more than the addition of either component separately, whereas the addition of L-ascorbic acid did not provide further beneficial effect on these variables. In contrast, co-administration of all three dietary supplements had a significantly greater effect than BH4 or L-arginine, given individually or in combination, when the dependent variables of $Ca^{2+}$-independent NOS activity, nitrotyrosine accumulation, or muscle necrosis were measured.

eNOS expression, $Ca^{2+}$-dependent NOS activity, foot perfusion, and the collateral artery angioscore are linked by established cause-and-effect relationships. eNOS-derived NO is a potent vasodilator; [2] hence, the increased eNOS expression and activity present in the BH4+L-arginine group should result in an NO-dependent increase in foot perfusion and this expectation was realized by the experiments described herein. Moreover, eNOS-derived NO is a critical determinant in the response to hindlimb ischemia [20,21]. This effect is direct, based on the vasodilator effect of NO, [22] but also indirect, insofar as eNOS-derived NO is critical to collateral artery remodeling. These effects include mobilization of endothelial progenitor cells (EPC) from bone marrow and their subsequent homing to the ischemic hindlimb [23]. Once there, EPC participate in post-ischemic arteriogenesis, the process wherein existing collateral arteries undergo remodeling designed to restore vascular conductance [24]. This process was evidenced by the increased angioscore, a marker of collateral artery enlargement, in rats provided with L-arginine+BH4 dietary supplements.

Accordingly, in some embodiments the addition of L-ascorbic acid to the BH4+L-arginine regimen failed to further improve foot perfusion or the angioscore in the setting of hindlimb ischemia. Without wishing to be bound by theory, its capacity as an antioxidant enhances NO bioavailability by quenching $O_2^-$, thus limiting the inactivation of NO which occurs when $O_2^-$ and NO combine to produce $OONO^-$ [3].

L-ascorbic acid also stabilizes existing BH4 [8] and increases endothelial BH4 synthesis, [25] thus minimizing eNOS 'uncoupling' which, in turn, lessens generation of $O_2^-$ by eNOS and reduces vascular oxidative stress [7]. However, BH4 is itself a potent antioxidant [7] and administration of exogenous BH4 has been established to increase endothelial BH4 levels [26]. Moreover, L-arginine directly stimulates eNOS expression, [27] enhances eNOS activity by a receptor-dependent, G protein-linked process, [28] and limits the inhibitory effect of asymmetric dimethylarginine on eNOS-derived NO production [29]. Accordingly, in some embodiments under the experimental conditions imposed by hindlimb ischemia co-supplementation with BH4+L-arginine sufficiently restored endothelial BH4 levels and intracellular redox balance. Hence, the addition of L-ascorbic acid failed to provide an additional advantage with regards to eNOS expression or activity, and hence NO bioavailability. Consequently, the NO-dependent endpoints of foot perfusion and collateral artery angioscore were not significantly affected by the inclusion of L-ascorbic acid.

$Ca^{2+}$-independent NOS activity and tissue nitrotyrosine accumulation were significantly lower in rats receiving all three dietary supplements than in rats receiving BH4 or L-arginine, or the combination of the two. When measured by methods used herein, $Ca^{2+}$-independent NOS activity is an authentic reflection of iNOS activity, inasmuch as the assay was conducted in vitro, in the absence of shear stress which can activate eNOS in the absence of $Ca^{2+}$ via phosphorylation [30]. The marked elevation of iNOS activity in rats fed normal chow indicates the presence of post-ischemia inflammation, which is also evidenced by the cellular inflammatory infiltrate in this group. Nitrotyrosine accumulation is indicative of $OONO^-$ induced damage [31] and it is interesting the group which exhibited the least amount of tissue damage, e.g., rats provided with all three supplements, also had the least nitrotyrosine accumulation. Moreover, rats in the triple therapy group demonstrated a virtual absence of nitrotyrosine, a circumstance that paralleled the absence of nitrotyrosine in the gastrocnemius muscle from sham-operated rats. Accordingly, in some aspects the present findings indicate that muscle injury following ischemia is not entirely contingent upon loss of perfusion, inasmuch as co-supplementation with the antioxidant L-ascorbic acid clearly reduced tissue injury and eliminated nitrotyrosine accumulation, but did not affect perfusion or collateral artery enlargement. Instead, in some embodiments L-ascorbic acid may be used to provide an antioxidant effect that limits tissue injury generated by inflammatory cells whose action is dependent, in part, on oxidant production (e.g., neutrophils and macrophages). This effect could be direct, due to the antioxidant activity of L-ascorbic acid, or indirect, due to the beneficial effect of L-ascorbic acid on BH4 levels, [8,25] insofar as BH4 also exhibits potent antioxidant activity [7].

Although it is well established that endothelial dysfunctional related to vascular oxidative stress is a critical factor in PAD pathogenesis, dietary supplementation with L-arginine or antioxidants, such as L-ascorbic acid, have had equivocal effects on long term outcome [12,13,16]. Dietary supplementation with L-arginine alone has a beneficial effect when given acutely, e.g., via intravenous infusion [14] or for short duration (2 months), [15] and these clinical results are consistent with the positive effects observed in rats provided with dietary L-arginine. However, long term administration of L-arginine (6 months) not only failed to demonstrate a beneficial effect, but resulted in a degree of eNOS-dependent vascular reactivity significantly less than that of the placebo group [16]. The present findings demonstrated increased iNOS activity after induction of ischemia. If a similar circumstance is present in PAD, then the singular dietary supplementation with L-arginine, the substrate for all NOS isoforms, might serve to worsen vascular inflammation, a critical participant in the pathogenesis of PAD.[1] Vitamin C reduces vascular inflammation, [32] improves redox balance [11] and eNOS-dependent vascular reactivity, [10] but these effects have only been evaluated on a short term basis, whereas retrospective cross-sectional studies have failed to confirm that dietary supplementation with antioxidants improves PAD outcome [12,13]. Accordingly, in some embodiments the provision of BH4+L-arginine+L-ascorbic acid acting synergistically may be a useful therapeutic alternative in PAD treatment. To this end, the use of sapropterin dihydrochloride, a synthetic form of (6R)-L-erythro-5,6,7,8-tetrahydrobiopterin recently approved for the treatment of phenylalanine hydroxylase deficiency [33], might provide a practical means for the provision of BH4. However, other alternatives also may be used.

The aforementioned interpretation must be viewed within the context of the experimental model used in this work. Femoral artery excision generates an acute, severe degree of hindlimb ischemia in which tissue inflammation is the consequence of abrupt loss and then a slow recovery of perfusion. PAD is a progressive disease in which tissue ischemia evolves over years, and in which vascular inflammation, a critical component of underlying atherosclerosis, precedes loss of perfusion [1]. Moreover, the experimental design initiated dietary supplements prior to the initiation of ischemia, whereas treatment of PAD would commence only after symptoms, specifically claudication, were evident, a circumstance that occurs only after significant atherosclerosis is present. Even within light of these caveats, however, the clearly superior outcome of rats provided with BH4+L-arginine+L-ascorbic acid supports the use of a co-supplementation strategy as a therapeutic alternative in PAD.

References

1. Silvestro A, Oliva G, Brevetti G. Intermittent claudication and endothelial dysfunction. *Eur Heart J* 4:B35-B40, 2002.
2. Marietta M. Nitric oxide synthase structure and mechanism. *J Biol Chem* 268:12231-12234, 1993.
3. Pacher P, Beckman J, Liaudet L. Nitric oxide and peroxynitrite in health and disease. *Physiol Rev* 87:315-424, 2007.
4. Peterson T, Poppa V, Uba H, Wu A, Yan C, Berk B. Opposing effects of reactive oxygen species and cholesterol on endothelial nitric oxide synthase and endothelial cell caveolae. *Circ Res* 85:29-37, 1999.
5. Kuzkaya N, Weissman N, Harrison D, Dikalov S. Interactions of peroxynitrite, tetrahydrobiopterin, ascorbic acid, and thiols. *J Biol Chem* 278:22546-22554, 2003.
6. Bevers L, Braam B, Post J, van Zonneveld A, Rabelink T, Koomans H, Verhaar M, Joles J. Tetrahydrobiopterin, but not L-arginine, decreases NO synthase uncoupling in cells expressing high levels of endothelial NO synthase. *Hypertension* 47:87-94, 2006.
7. Schmidt T, Alp N. Mechanisms for the role of tetrahydrobiopterin in endothelial function and disease. Clin Sci 113:47-63, 2007.
8. Heller R, Unbehaun A, Schellenberg B, Mayer B, Werner-Felmayer G, Werner R. L-ascorbic acid potentiates endothelial nitric oxide synthesis via a chemical stabilization of tetrahydrobiopterin. *J Biol Chem* 276:40-47, 2001.
9. Langlois M, Duprez D, Delanghe J, De Buyzere M, Clement D. Serum vitamin C concentration is low in peripheral arterial disease and is associated with inflammation and severity of atherosclerosis. *Circulation* 103: 1863-1868, 2001.
10. Silvestro A, Scopacasa F, Oliva G, de Cristofaro T, Iuliano L, Brevetti G. Vitamin C prevents endothelial dysfunction induced by acute exercise in patients with intermittent claudication. *Atherosclerosis* 165:277-283, 2002.
11. Wijnen M, Coolen S, Vader H, Reijenga J, Huf F, Roumen R. Antioxidants reduce oxidative stress in claudicants. *J Surg Res* 96:183-187, 2001.
12. Donnan P, Thomson M, Fowkes F, Prescott R, Housley E. Diet as a risk factor for peripheral arterial disease in the general population: the Edinburgh Artery Study. *Am J Clin Nutr* 57:917-921, 1993.
13. Klipstein-Grobusch K, den Breeijen J, Grobbee D, Boeing H, Hofman A, Witteman J. Dietary antioxidants and peripheral arterial disease: the Rotterdam Study. *Am J Epidemiol* 154:145-149, 2001.
14. Boger R, Bode-Boger S, Thiele W, Creutzig A, Alexander K, Frolich J. Restoring vascular nitric oxide formation by L-arginine improves the symptoms of intermittent claudication in patients with peripheral arterial occlusive disease. *J Am Coll Card* 32:1336-1344, 1998.
15. Maxwell A, Anderson B, Cooke J. Nutritional therapy for peripheral arterial disease: a double-blind, placebo-controlled, randomized trial of HeartBar. *Vasc Med* 5:11-19, 2000.
16. Wilson A, Harada R, Nair N, Balasubramanian N, Cooke J. L-arginine supplementation in peripheral arterial disease: no benefit and possible harm. *Circulation* 116:188-195, 2007.
17. Ueda S, Matsuoka H, Miyazaki H, Usui M, Okuda S, Imaizumi T. Tetrahydrobiopterin restores endothelial function in long-term smokers. *J Am Coll Card* 35:71-75, 1999.
18. Heitzer T, Krohn, K, Albers S, Meinertz T. Tetrahydrobiopterin improves endothelium-dependent vasodilation by increasing nitric oxide activity in patients with Type II diabetes mellitus. Diabetologia 43:1435-1438, 2000.
19. Yan J-L, Tang G, Wang R, Messina, L. Optimization of adenovirus-mediated endothelial nitric oxide synthase delivery in rat hindlimb ischemia. *Gene Therapy* 12:1640-1650, 2005.
20. Yu J, Demuink E, Zhuang Z, Drinane M, Kauser K, Rubanyi G, Qian H, Murata T, Escalante B, Sessa W C. Endothelial nitric oxide synthase is critical for ischemic remodeling, mural cell recruitment, and blood flow reserve. *Proc Natl Acad Sci* 102:10999-11004, 2005.
21. Lloyd P, Yang H, Terjung R. Arteriogenesis and angiogenesis in rat ischemic hindlimb: role of nitric oxide. *Am J Physiol* 281:H2528-H2538, 2001.
22. Mees B, Wagner S, Ninci E, Tribulova S, Martin S, van Haperen R, Kostin S, Heil M, de Crom R, Schaper W. Endothelial nitric oxide synthase activity is essential for vasodilation during blood flow recovery but not for arteriogenesis. *Arterioscler Thromb Vasc Biol* 27:1-8, 2007.
23. Aicher A, Heeschen C, Mildner-Rihm C, Urbich C, Ihling C, Technau-Ihling K, Zeiher A, Dimmeler S. Essential role of endothelial nitric oxide synthase for mobilization of stem and progenitor cells. Nature Medicine 9:1370-1376, 2003.
24. Helisch A, Schaper W. Arteriogenesis: the development and growth of collateral arteries. Microcirculation 10:83-97, 2003.

25. Huang A, Vita J, Venema R, Keaney J Jr. Ascorbic acid enhances endothelial nitric-oxide synthase activity by increasing intracellular tetrahydrobiopterin. *J Biol Chem* 275:17399-17406, 2000.
26. Sawabe K, Wakasugi K, Hasegawa H. Tetrahydrobiopterin uptake in supplemental administration: elevation of tissue tetrahydrobiopterin in mice following uptake of the exogenously oxidized product 7,8-dihydrobiopterin and subsequent reduction by an anti-folate-sensitive process. *J Pharmacol Sci* 96:124-133, 2004.
27. Kohil R. Dietary L-arginine supplementation enhances endothelial nitric oxide synthesis in streptozotocin-induced diabetic rats. *J Nutr* 134:600-608, 2004.
28. Joshi M, Ferguson T, Johnson F, Johnson R, Parthasarathy S, Lancaster. J Jr. Receptor-mediated activation of nitric oxide synthesis by arginine in endothelial cells. *Proc Natl Acad Sci* 104:9982-9987, 2007.
29. Boger R, Ron E. L-arginine improves vascular function by overcoming the deleterious effects of ADMA, a novel cardiovascular risk factor. Alt Med Rev 10:14-18, 2005.
30. Ayajiki K, Kindermann M, Hecker M, Fleming I, Busse R. Intracellular pH and tyrosine phosphorylation but not calcium induce shear stress-induced nitric oxide production in native endothelial cells. *Circ Res* 78:750-758, 1996.
31. Beckman J, Koppenol W. Nitric oxide, superoxide, and peroxynitrite: the good, the bad, and ugly. *Am J Physiol* 1996; 271:C1424-C1437.
32. Aguirre R, May J. *Inflammation* in the vascular bed: Importance of vitamin C. *Pharmacol Ther* 119:96-103, 2008.
33. Levy H, Milanowski A, Chakrapani A, Cleary M, Lee P, Trefz F, Whitley C, Feillet F, Feigenbaum A, Bebchuk J, Christ-Schmidt H, Dorenbaum A. Efficacy of sapropterin dihydrochloride (tetrahydrobiopterin, 6R-BH4) for reduction of phenylalanine concentration in patients with phenylketonuria: a phase III randomised placebo-controlled study. *Lancet* 370:504-510, 2007.

Example 3

Triple Administration of BH4/L-Arginine/Vitamin C Feeding Reduces Plaque Formation in Apoe$^{h/h}$Ldlr$^{-/-}$ Mice.

Apoe$^{h/h}$Ldlr$^{-/-}$ mice with different oral supplementation in both male and female mice were studied.

Figure 14:
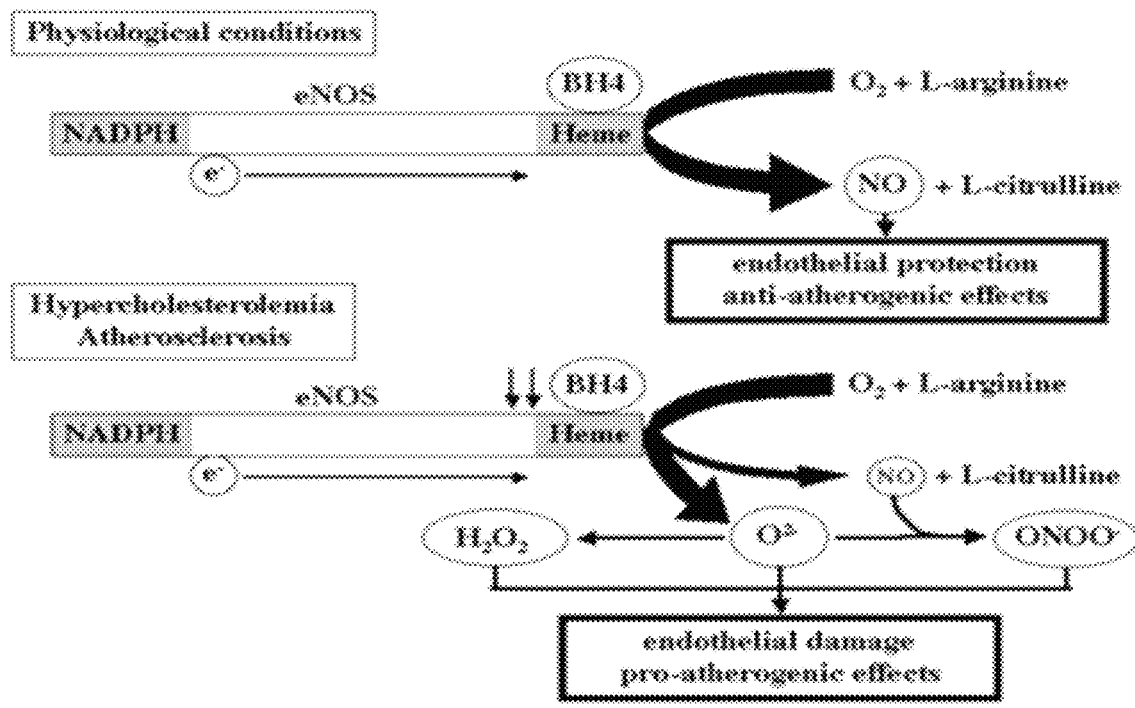
FIG. 14. Effect of eNOS function on plaque formation in arteriosclerosis.

Hypothesis:

Long term administration of BH4/L-arginine/Vitamin C may improve the eNOS function and reduce plaque formation in atherosclerotic Apoe$^{h/h}$Ldlr$^{-/-}$ mice. FIG. 14 shows the effect of eNOS function on plaque formation in arteriosclerosis.

Figure 15:
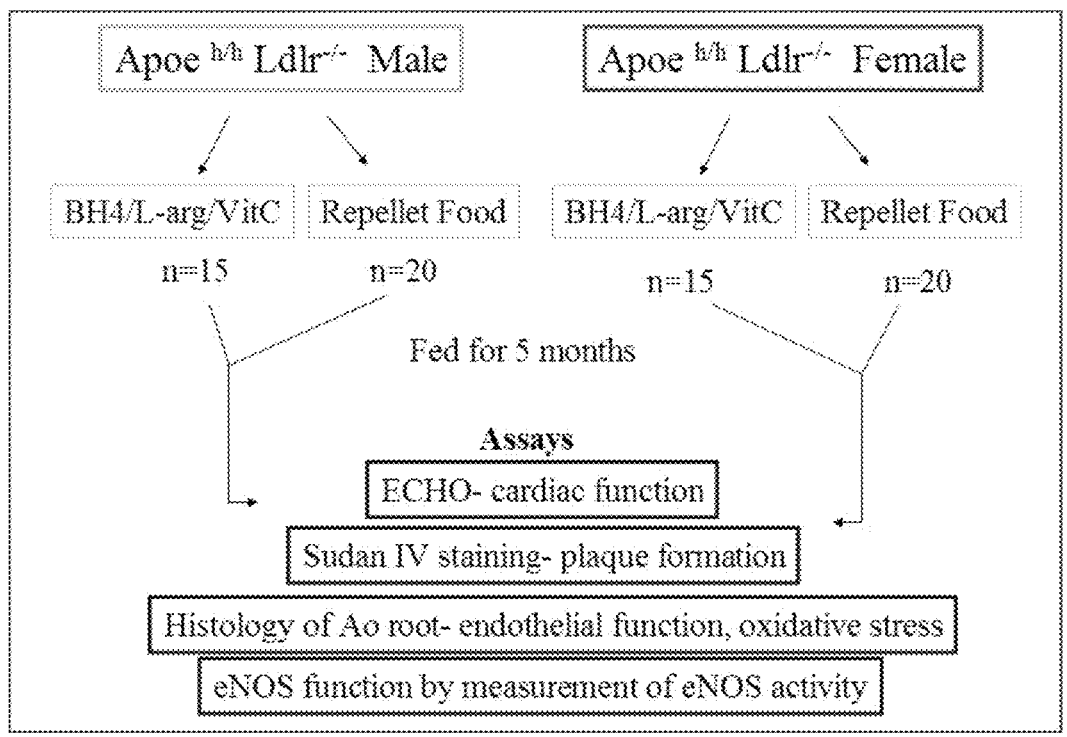
FIG. 15. Outline of cardiac study design.

Study I:

Oral supplementation of BH4/L-arginine/Vitamin C in male Apoe$^{h/h}$Ldlr$^{-/-}$ mice. The study design is outlined in FIG. 15.

Figure 16:
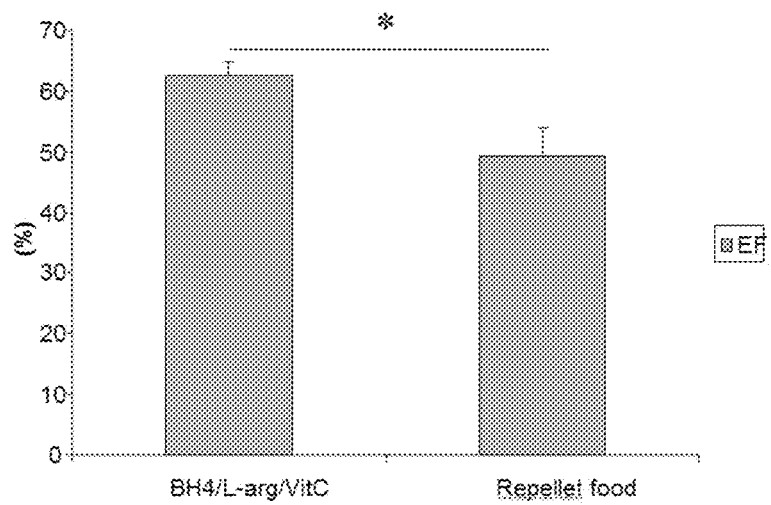
FIG. 16. Ejection fraction value of left ventricle in male of $Apoe^{h/h}Ldlr^{-/-}$ mice after different feedings.

Study I-I:

Detection of cardiac function and area of aortic root in both BH4/L-arginine/Vitamin C feeding and control groups. FIG. 16 shows the ejection fraction value of left ventricle in male of Apoe$^{h/h}$Ldlr$^{-/-}$ mice after different feedings. The Ejection Fraction (EF):

$$LVEDV = \frac{8}{3} \times \frac{Ad^2}{\pi Ld}$$

$$LVESV = \frac{8}{3} \times \frac{As^2}{\pi Ls}$$

$$LVEF=(LVEDV-LVESV)/LVEDV\times 100.$$

An analysis can include evaluating the M-mode, anterior wall thickness (systolic, diastolic), posterior wall thickness (systolic, diastolic), left ventricular end-diastolic dimension (LVDd), left ventricular end-systolic dimension (LVDs), and determining the FS (Fraction shorting)=(LVDd−LVDs)/LVDd*100(%). The aorta area measurement were obtained in different groups of Apoe$^{h/h}$Ldlr$^{-/-}$ male mice. The aorta area in BH4/L-arg/VitC feeding group significantly increased than that in control repellet food feeding group. * p<0.01.

Advanced echocardiogram was used to detect the cardiac output function, such as ejection fraction (EF) in mice from different groups, measure EF.

In addition the movies of aortic root were taken at the same plane in each mouse and the area of aortic root was measured in one of the regions where arteriosclerosis is most easily formed. (The area is from the aortic valve to its descending 2 cm square).

Figure 17:
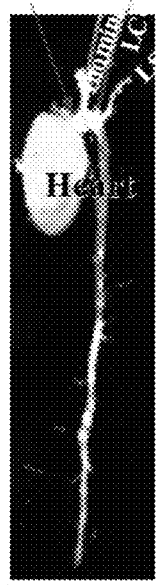
FIG. 17. Aorta area measurement in different groups of $Apoe^{h/h}Ldlr^{-/-}$ male mice.
Figure 17:
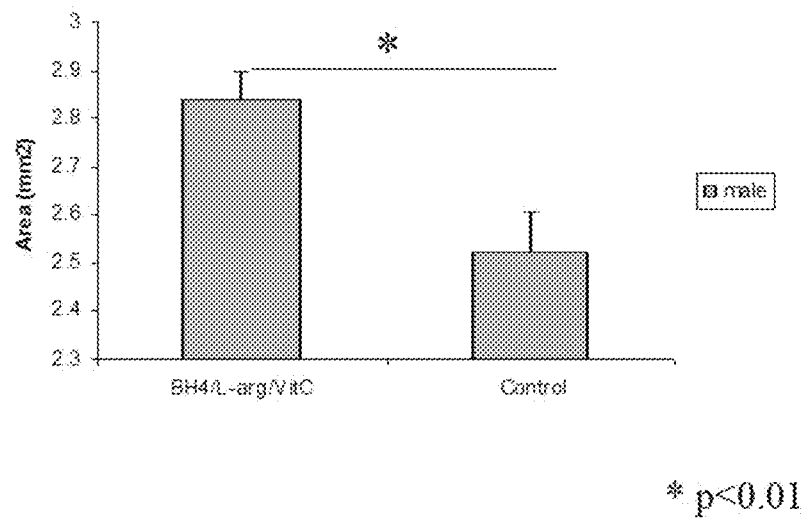

The aorta area in BH4/L-arg/VitC feeding group significantly increased relative to that in control repellet food feeding group as illustrated in FIG. 17.

Summary I-I:

Ejection fraction of left ventricle increased significantly in male Apoe$^{h/h}$Ldlr$^{-/-}$ mice after long term oral supplementation of BH4/L-arg/VitC than after repellet food feeding.

Aorta root area is significantly bigger in male Apoe$^{h/h}$Ldlr$^{-/-}$ mice after long term oral supplementation of BH4/L-arg/VitC than after repellet food feeding.

Study II-II:

Plaque formation was evaluated in the descending aorta after BH4/L-arginine/Vit C and control repellet food feeding in female Apoe$^{h/h}$Ldlr$^{-/-}$ mice.

Figure 18:
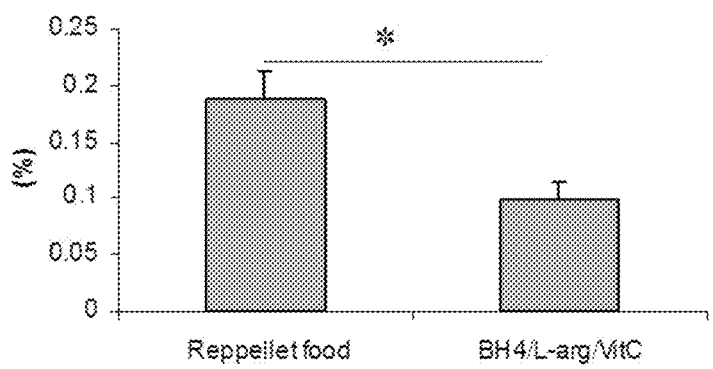
FIG. 18. Quantitative analysis of plaque area over descending aorta area in $Apoe^{h/h}Ldlr^{-/-}$ female mice with different feeding.

The same assays were used as described before. Results are illustrated in FIG. 18.

Summary II-II:

The percentage of plaque area in the descending aorta significantly decreased after long term BH4/L-arginine/Vitamin C feeding compared to repellet food feeding group in female Apoe$^{h/h}$Ldlr$^{-/-}$ mice.

Figure 19A:
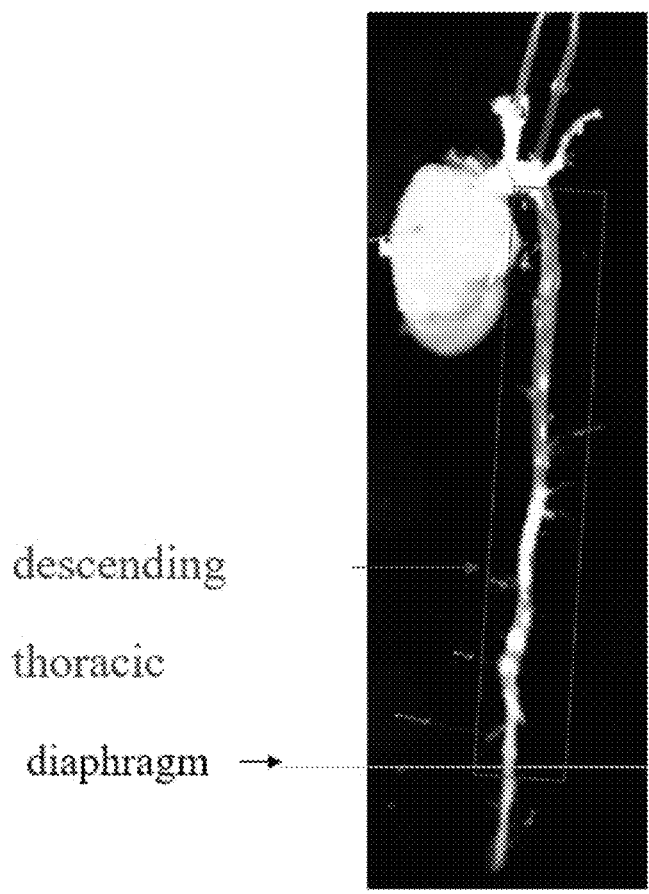
FIGS. 19A-19B. Illustration of descending aorta (A) and comparison of descending aorta in control and treatment group (B).
Figure 19B:
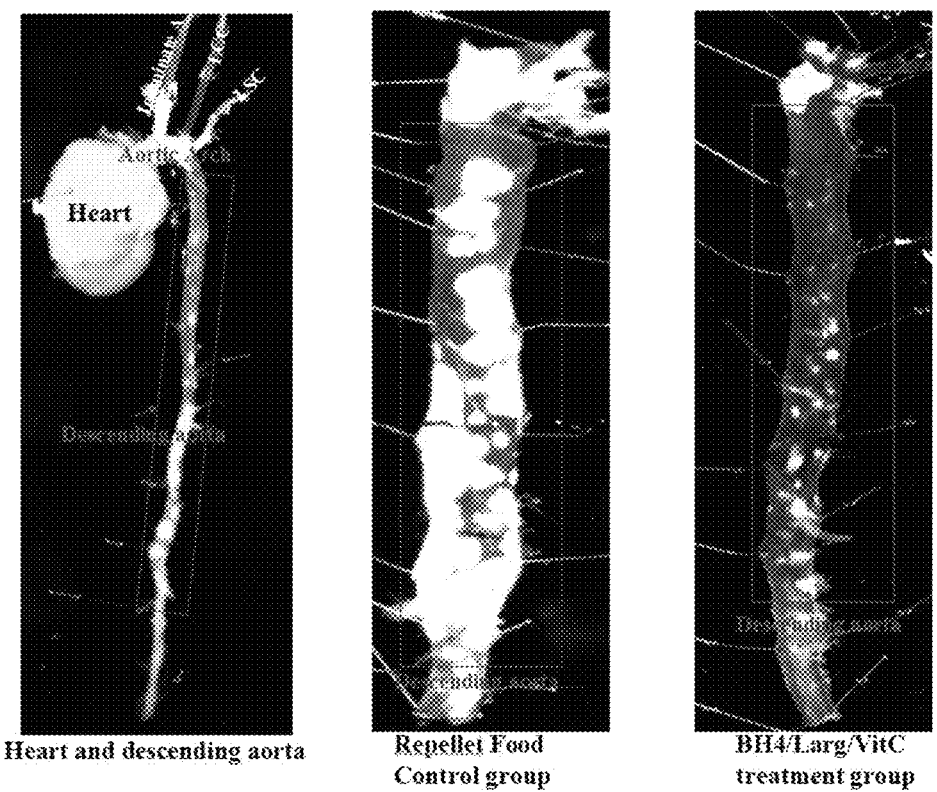

Study I-II:

Plaque formation in the descending aorta after BH4/L-arginine/Vit C and control repellet food feeding in male Apoe$^{h/h}$Ldlr$^{-/-}$ mice (FIG. 19). FIG. 19A shows an illustration of descending aorta. FIG. 19B shows comparison of descending aorta in control and treatment group. Left: Dissected heart and aorta. Middle and right: Pin out aorta before Sudan IV staining.

Sudan IV staining was used to detect plaques in descending aorta.

Descending aorta here used is starting from the end of aortic arch to the end of thoracic aorta, see photo on right side.

Summary I-II:

The percentage of plaque area in the descending aorta significantly decreased after long term BH4/L-arginine/Vitamin C feeding compared to repellet food feeding group in male Apoe$^{h/h}$Ldlr$^{-/-}$ mice.

Study III:

Comparison study of plaque formation between male and female after different feeding in Apoe$^{h/h}$Ldlr$^{-/-}$ mice (FIGS.

Figure 20:
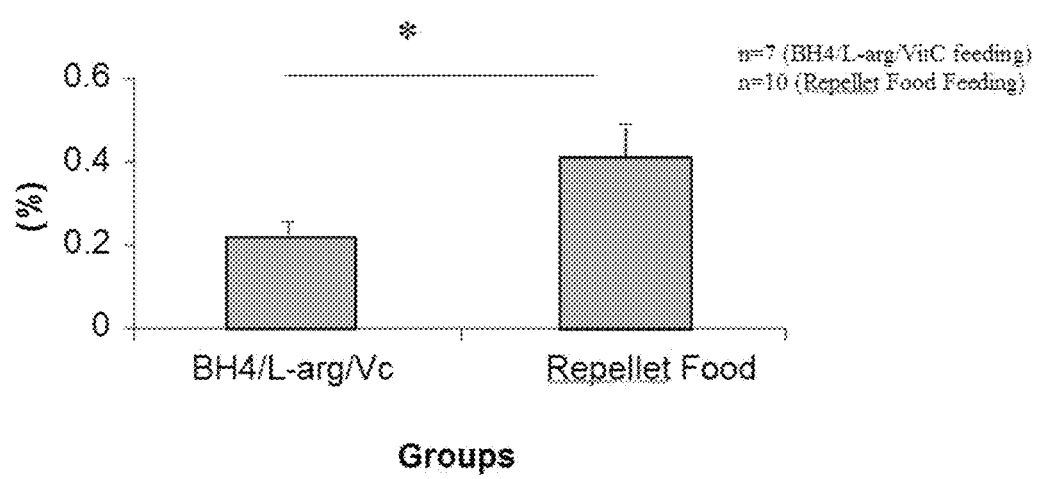
FIG. 20. Quantitative analysis of plaque area over descending aorta area in male $Apoe^{h/h}Ldlr^{-/-}$ mice with different feedings.
Figure 21:
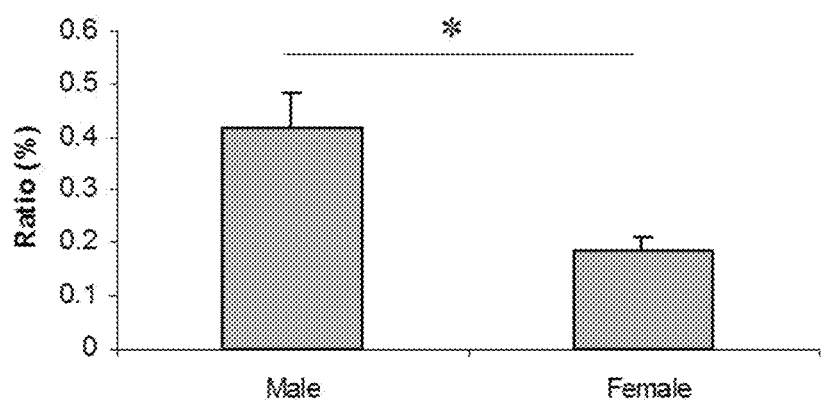
FIG. 21. Quantitative analysis of area ratio of plaque over descending aorta in both male and female $Apoe^{h/h}Ldlr^{-/-}$ mice with repellet food feeding (control groups).
Figure 22:
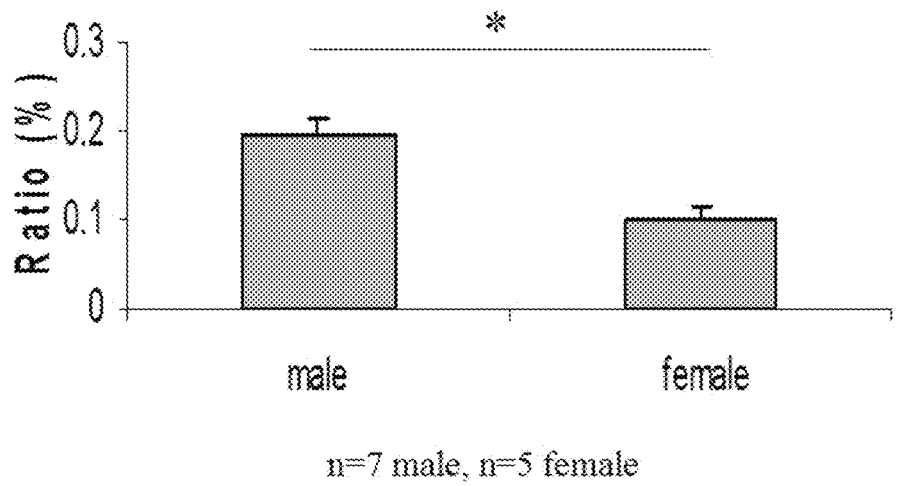
FIG. 22. Quantitative analysis of area ratio of plaque over descending aorta in both male and female $Apoe^{h/h}Ldlr^{-/-}$ mice with BH4/L-arg/VitC food feeding (treatment groups).
Figure 23:
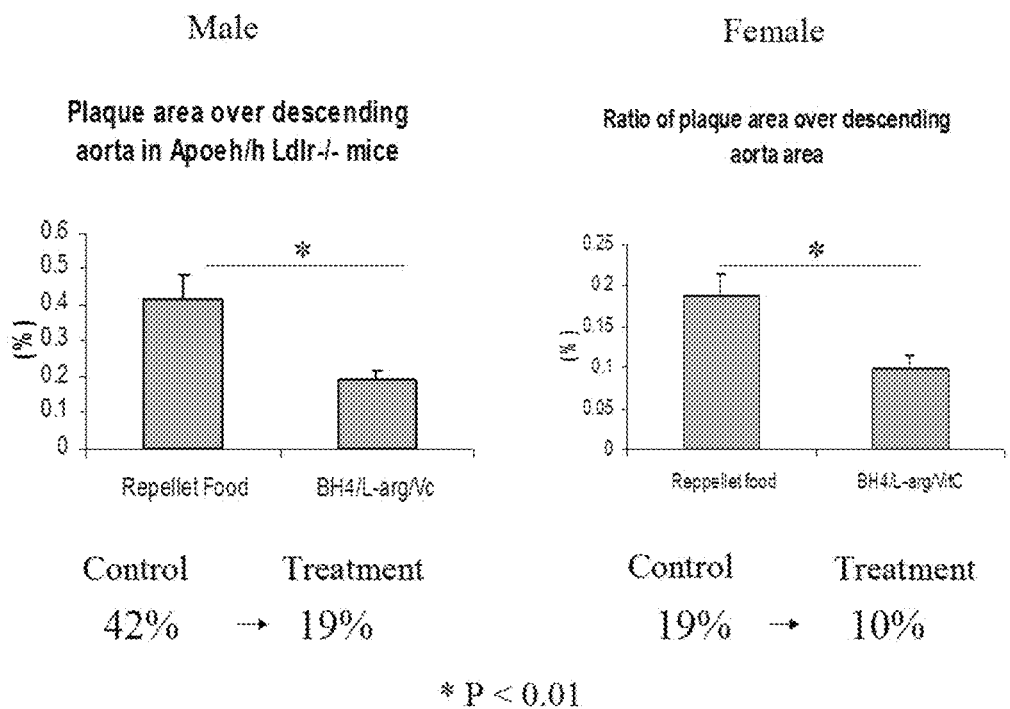
FIG. 23. Comparison of plaque ratio with different feeding between male and female mice.

20-23). FIG. 20 shows quantitative analysis of plaque area over descending aorta area in male Apoe$^{h/h}$Ldlr$^{-/-}$ mice with different feedings. n=7 (BH4/L-arg/VitC feeding), n=10 (Repellet Food Feeding), *: P<0.05, indicates significant difference between two groups. The area ratio of plaque over descending aorta between male and female Apoe$^{h/h}$Ldlr$^{-/-}$ mice after feeding with repellet food was compared. FIG. 21 shows a quantitative analysis of area ratio of plaque over descending aorta in both male and female Apoe$^{h/h}$Ldlr$^{-/-}$ mice with repellet food feeding (control groups). Comparison of plaque ratio between male and female Apoe$^{h/h}$Ldlr$^{-/-}$ mice with repellet food. n=10 in each group, *: p<0.01. FIG. 22 shows a quantitative analysis of area ratio of plaque over descending aorta in both male and female Apoe$^{h/h}$Ldlr$^{-/-}$ mice with BH4/L-arg/VitC food feeding (treatment groups). Comparison of plaque ratio in Apoe$^{h/h}$Ldlr$^{-/-}$ mice after feeding with BH4/L-arg/VitC. n=7 male, n=5 female. *: P<0.05. FIG. 23 shows a comparison of plaque ratio with different feeding between male and female mice.

Summary III

In Apoe$^{h/h}$Ldlr$^{-/-}$ mice, plaque formation is significantly more severe in males than in females under normal control repellet food.

After long term BH4/L-arginine/Vit C feeding, both male and female showed about 50% decrease of plaque than repellet food feeding group. However, still more plaques exist in male descending aorta than in female Apoe$^{h/h}$Ldlr$^{-/-}$ mice.

Example 4

Mesenchymal Stem Cell (MSC) Dysfunction During Neovascularization after Hindlimb Ischemia in Db/Db Mice.

Diabetes and Peripheral Artery Disease—Development of More Effective Therapies for PAD is a National Health Care Priority:

Diabetes is epidemic. It affects 170 million people world wide, including 21 million in USA. Further, the population over 70 years of age is increasing. Diabetes is an important risk factor for peripheral arterial disease. Diabetic foot ulcers are the leading cause of hospital admissions for people with diabetes in developed world. Diabetic foot ulcers, in concert with PAD and critical limb ischemia are a leading cause of lower limb amputation.

Post-Ischemic Neovascularization—Definition of Terms

Arteriogenesis is the expansion of pre-existing collateral arteries and can be quantitated, for example, by measuring limb blood flow, the number (e.g., by angiography) and diameter (e.g., by immunohistochemistry) of collateral arteries.

Angiogenesis is the de novo creation of capillaries within the ischemic muscle and can be measured, for example, by quantitating the ratio of CD31+ cells (endothelial cells) and myofibers.

The effects of the diabetic phenotype on the vascular response to hindlimb ischemia, particularly the effects of oxidant stress on eNOS, endothelial progenitor cells and mesenchymal stem cells were investigated in the following studies:

Study 1: Direct Comparison of the Effects of Type 1 and Type 2 Diabetes on the Response to the Induction of Hindlimb Ischemia.

The goal of this study was to determine if the responses of type 1 and type 2 diabetic mice to hindlimb ischemia were similar. It was hypothesized that type 2 diabetic mice would exhibit a less effective neovascularization response to hindlimb ischemia. The basis for this hypothesis was that the type 2 diabetic phenotype includes hyperglycemia and an atherogenic dyslipidemia, both factors that might independently compromise the capacity for neovascularization in the response to ischemia.

Choice of Animal Models:

C57BL/6 mice treated with streptozotocin (STZ) were used as a model of type 1 diabetes. STZ destroys 13 cells and induces profound hyperglycemia. This action is rapid (days) and highly reproducible.

The Lepr$^{db/db}$ (db/db) mouse was used as a model of type 2 diabetes. Db/db mice lack the Ob-Rb leptin receptor. Leptin, an adipokine, regulates hunger and hence food intake. db/db mice develop moderate hyperglycemia, insulin resistance, an atherogenic dyslipidemia, and obesity by 2 months of age. The db/db mouse has been used as a type 2 model in >2000 published studies.

Figure 24:
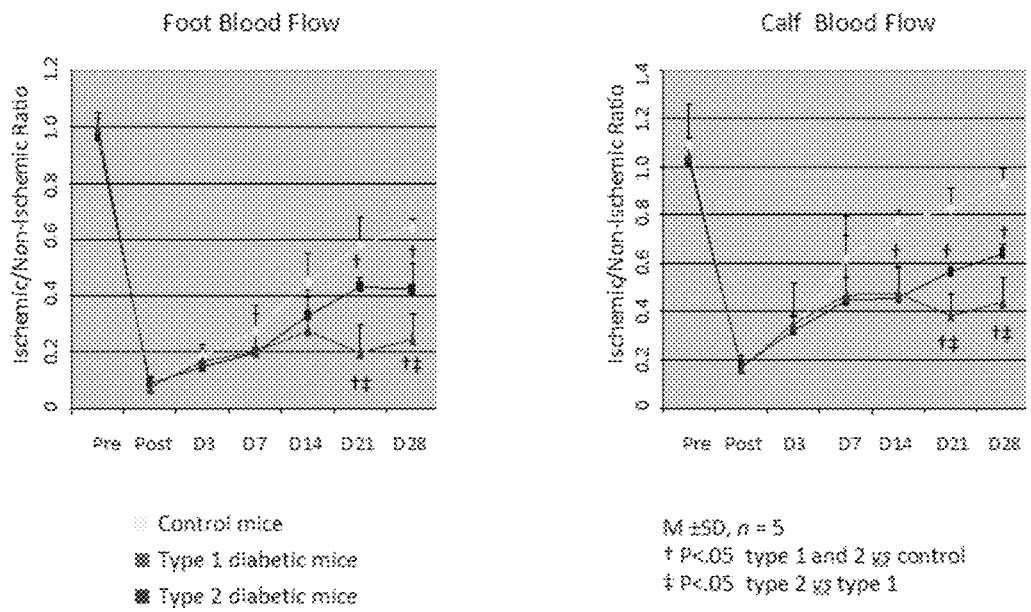
FIG. 24. Effects of type 1 and 2 diabetes on recovery of calf and foot blood flow following induction of hindlimb ischemia.
Figure 25:
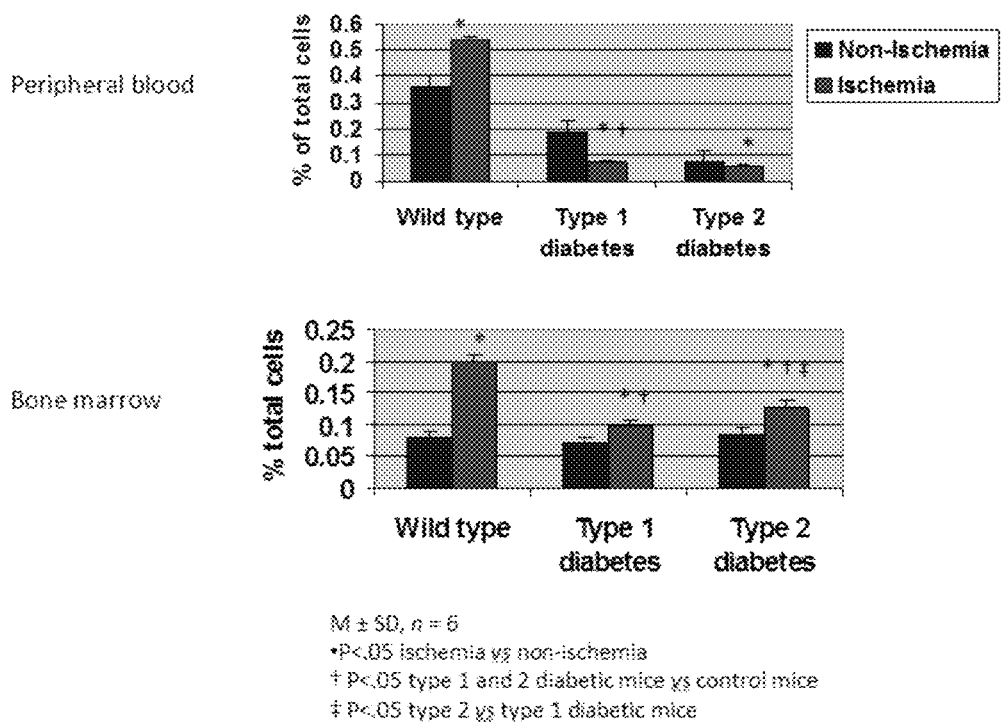
FIG. 25. Effects of type 1 and type 2 diabetes on EPC concentration in bone marrow and peripheral blood.
Figure 26:
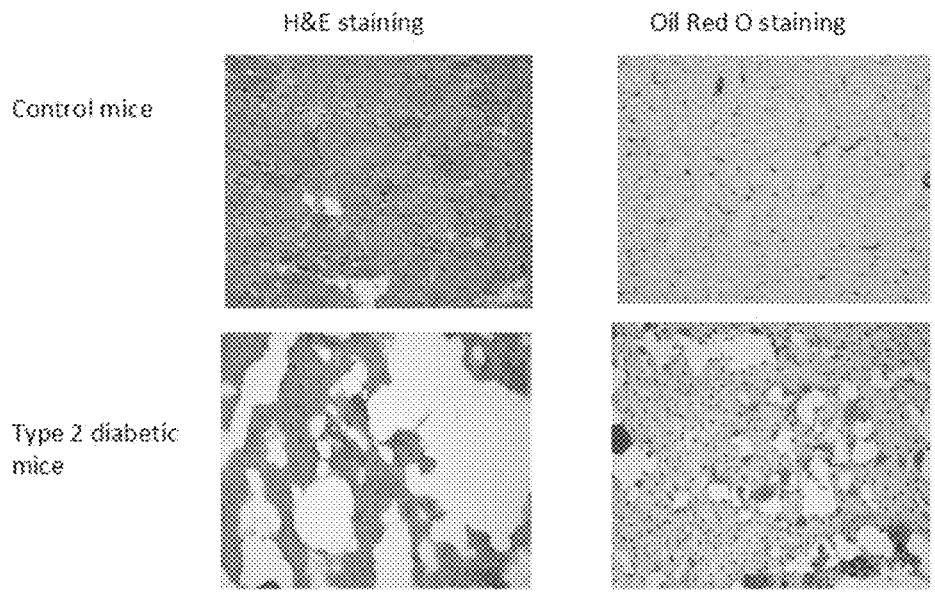
FIG. 26. Histology of the ischemic hindlimb in control and type 2 diabetic mice 28 days after induction of ischemia.

Effects of type 1 and 2 diabetes on recovery of calf and foot blood flow following induction of hindlimb ischemia are shown in FIG. 24. Effects of type 1 and type 2 diabetes on EPC concentration in bone marrow and peripheral blood are shown in FIG. 25. FIG. 26 shows histology of the ischemic hindlimb in control and type 2 diabetic mice 28 days after induction of ischemia.

In summary, the type 2 diabetic mouse (db/db) exhibits greater impairment in the vascular response to hindlimb ischemia: db/db mice exhibit less effective arteriogenesis (less flow recovery), less effective angiogenesis (capillary density), more impaired EPC function in vitro, and greater tissue injury.

A critical new observation from this study is the presence of substantial fatty infiltration in the ischemic (damaged) gastrocnemius muscle in type 2 diabetic mice, a finding that was not present in type 1 diabetic mice (see FIG. 26).

Study 2—a Novel Mechanism that Specifically Impairs the Vascular Response of Type 2 Diabetic Mice to Hindlimb Ischemia.

The goal of study 2 was to determine the cause of fatty infiltration in the ischemic gastrocnemius in type 2 diabetic mice. It was hypothesized that mesenchymal stem cells (MSC) that homed to the site of vascular injury differentiated into an adipocytic phenotype (see FIG. 27). The basis for this hypothesis is that db/db mice, which exhibit a type 2 diabetic phenotype, demonstrate significant fatty infiltration in damaged, ischemic muscle and that MSC differentiation into adipocytes might contribute to this process.

Mesenchymal Stem Cells (MSC):

MSC are pluripotent stem cells of bone marrow origin. Unlike other stem or progenitor cells, there is no cluster of surface phenotype markers that consistently and reproducibly characterize MSC. MSC are generally defined as bone marrow mononuclear cells that adhere to bare plastic (in culture) and demonstrate the ability to differentiate into multiple cell types, including chondrocytes, adipocytes, and endothelial cells. MSC mobilize from bone marrow and home to the sites of vascular injury where they participate in vascular repair. MSC have strong antiproliferative and anti-inflammatory properties.

Transplant Protocol:

In order to determine if MSCs were a source for the adipocyte infiltration into ischemic muscle, MSC were harvested and expanded ex vivo. Hindlimb ischemia was created and 24 hours later, 10$^7$ Ad-GFP transduced MSCs were transplanted via an intra-bone marrow injection route. Transplants of bone marrow-derived MSC were used to determine if the diabetic MSC or the diabetic environment participated in MSC differentiation towards adipocytes.

Transplant Paradigm (Donor→Recipient):
db/db MSC→WT (C57BL/6); db/db MSC→db/db; WT MSC→db/db; and WT MSC→WT.

Figure 28:
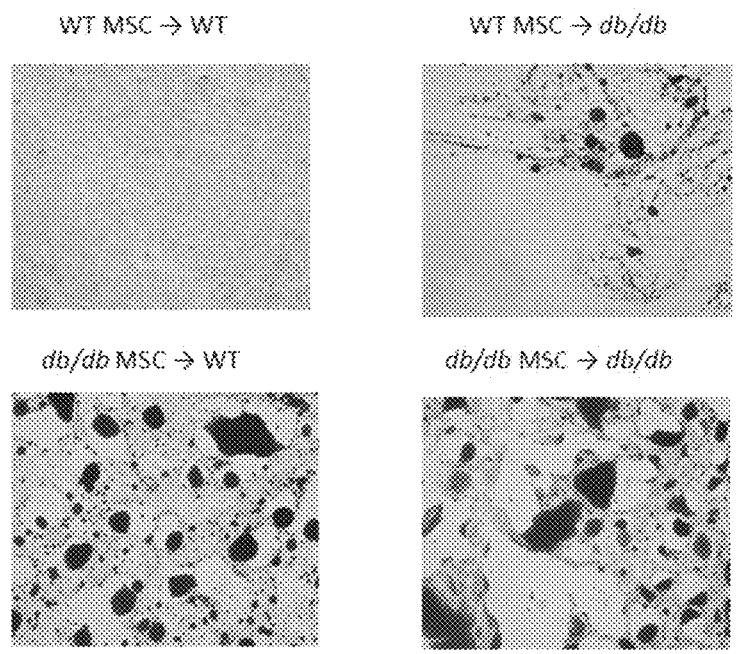
FIG. 28. Fate of transplanted mesenchymal stem cells within the ischemic hindlimb 14 days after induction of hindlimb ischemia.
Figure 29:
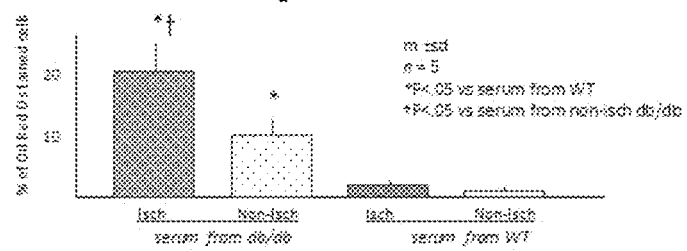
FIG. 29. Effects of different serums on generation of an adipocytic lineage in WT MSC.
Figure 29:
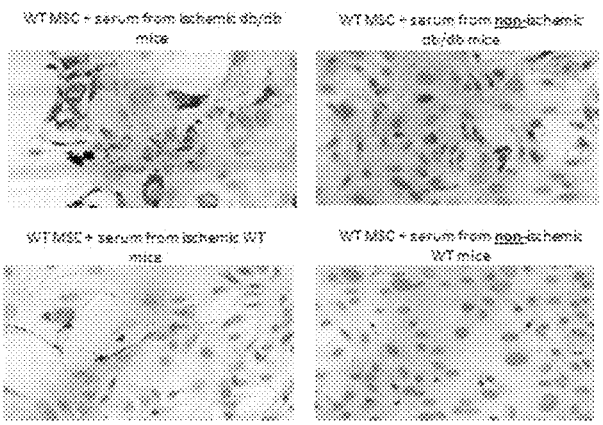

The fate of transplanted mesenchymal stem cells within the ischemic hindlimb was determined 14 days after induction of hindlimb ischemia (FIG. 28). Both the transplant of WT MSC into db/db and the transplant of db/db HSC into WT resulted in fatty infiltration (adipocytes) in ischemic muscle. These finding indicate that it is both the diabetic MSC and the diabetic environment that participate in directing differentiation of MSC towards an adipocyte phenotype. FIG. 29 shows effects of different serums on generation of an adipocytic lineage in WT MSC (upper panel), and representation photomicrographs of oil Red O staining of WT MSC cultures.

Figure 30:
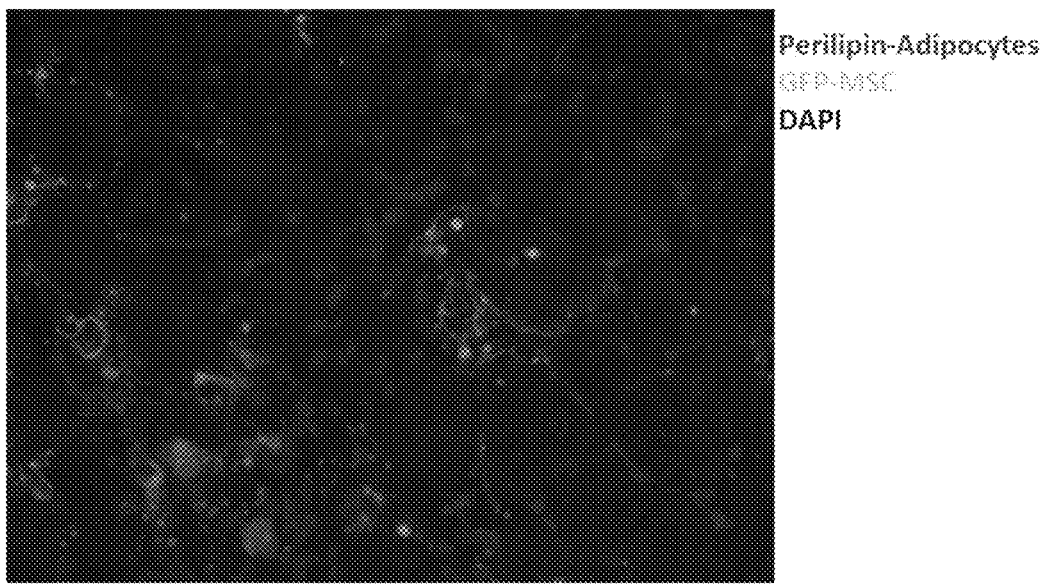
FIG. 30. Co-localization of bone marrow derived MSC and adipocytes.
Figure 31:
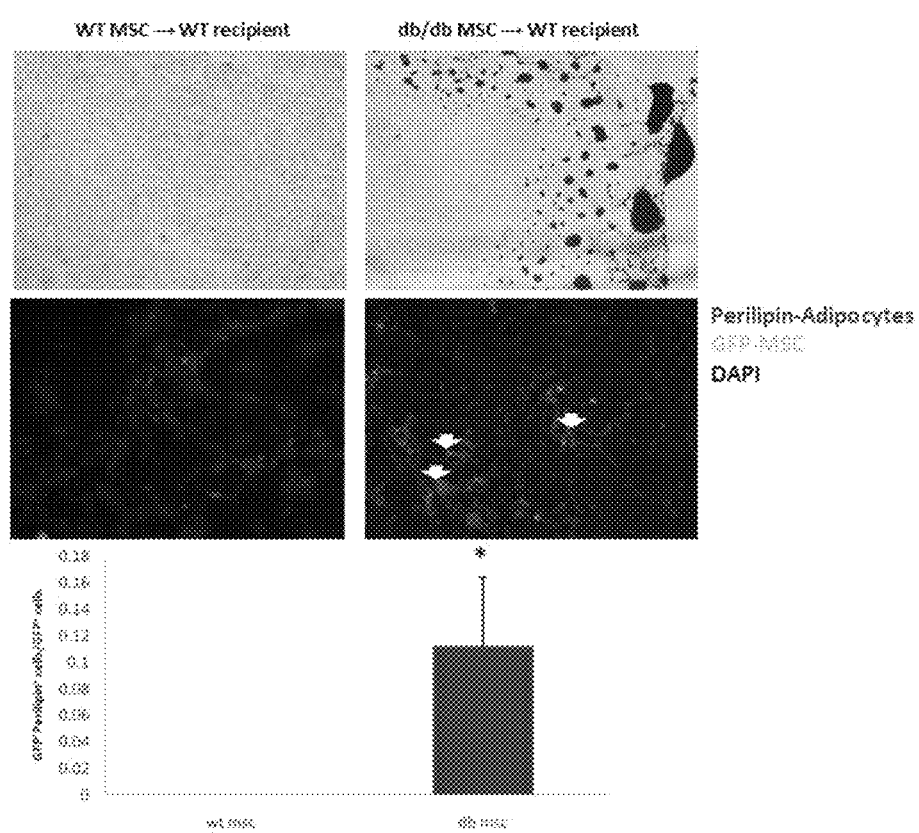
FIG. 31. Bone marrow derived MSCs differentiate into adipocytes.
Figure 32:
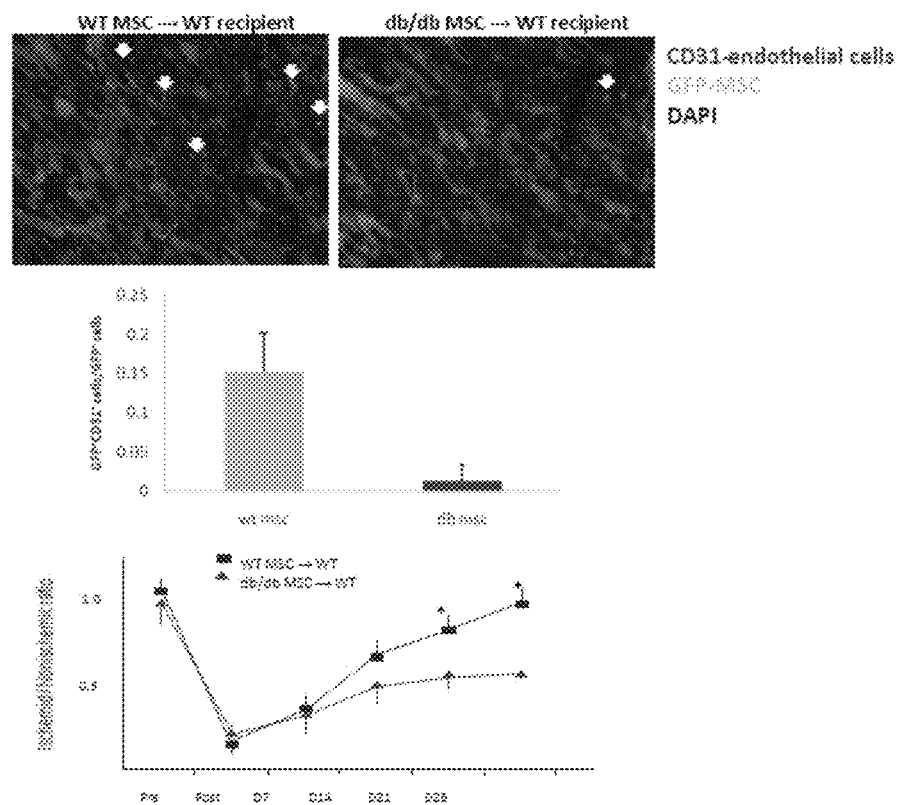
FIG. 32. Bone marrow derived MSCs differentiate into endothelial cells.

FIG. 30 shows co-localization of bone marrow derived MSC and adipocytes. FIG. 31 shows that bone marrow derived MSCs differentiate into adipocytes, and FIG. 32 shows that bone marrow derived MSCs differentiate into endothelial cells.

In summary, study 2 demonstrates that in the ischemic hindlimb of WT mice, bone marrow derived MSCs from db/db mice show higher differentiation capacity towards adipocytes and a lower differentiation capacity towards endothelial cells than do WT MSCs. Further, injection of bone marrow derived MSCs from db/db mice show lower blood flow recovery after transplantation into wt mice than do bone marrow derived MSCs from wt mice. Finally, blood flow recovery after injection of wt MSCs in wt mice was greater than wt without any MSC transplantation implying a substantial therapeutic benefit from MSC transplantation.

Study 3—Effect of Adipogenic and Endogenic Medium on eNOS, Phospho-eNOS, PPAR, and Adiponectin Expression and Differentiation Patterns of Wt and Db/Db MSCs.

Figure 27:
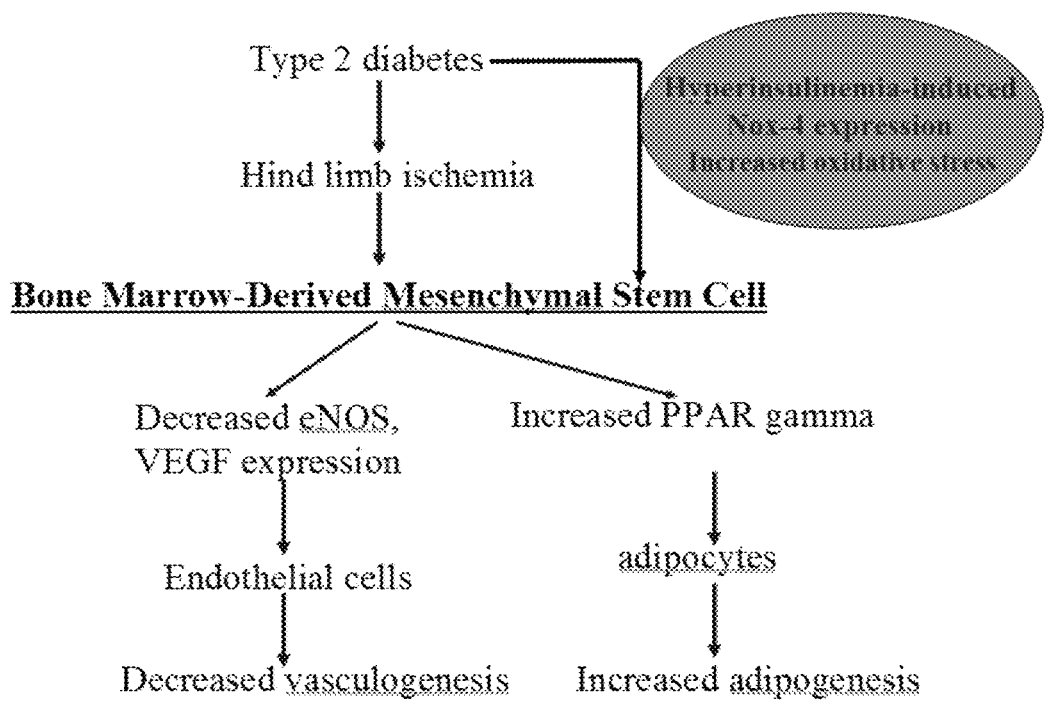
FIG. 27. Outline of possible responses to oxidative stress.
Figure 33A:
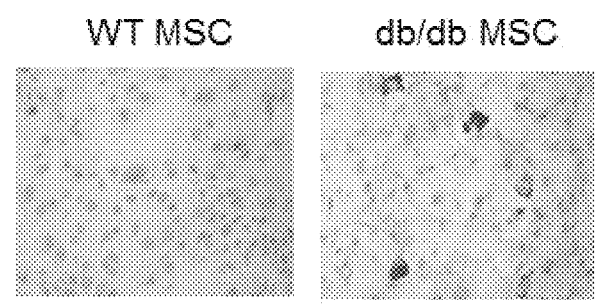
FIGS. 33A-33D. Effect of adipogenic medium on the differentiation of WT and db/db MSC.
Figure 33B:
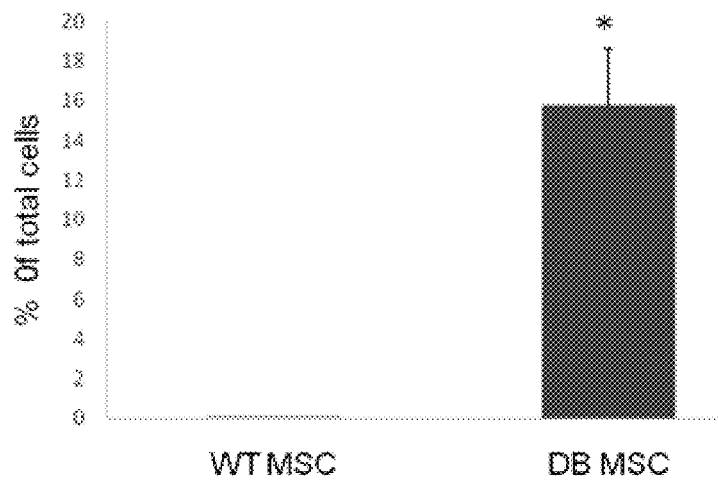

According to one embodiment, without wishing to be limited by theory, it was hypothesized that db/db MSCs would respond differently to differentiation stimuli than wt MSCs (see FIG. 27). FIGS. 33A and 33B show an effect of adipogenic medium on the differentiation of WT and db/db MSC. m±sd, n=5, *p<0.05. The % of db/db MSC that differentiated into adipocytes (as evidenced by Oil Red O staining) was significantly greater in db/db mice than WT. m±sd, n=5, *p<0.05. The % of db/db MSC that differentiated into adipocytes (as evidenced by Oil Red O staining) was significantly greater in db/db mice than WT.

Figure 33C:
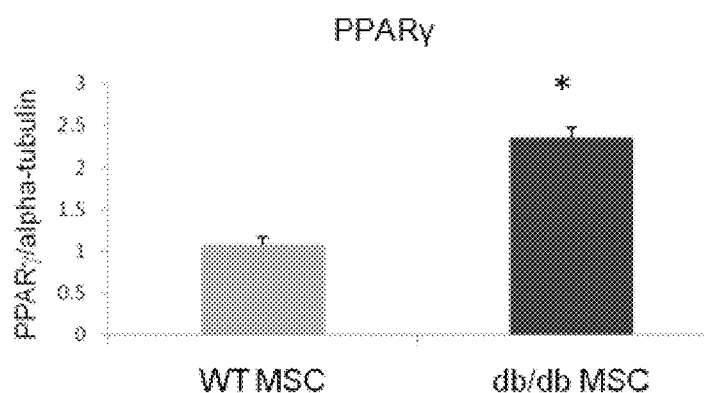
Figure 33D:
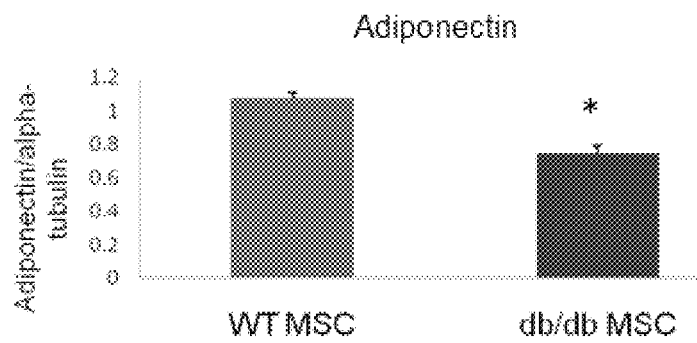

FIGS. 33C and 33D show PPARγ and adiponectin expression in WT and db/db MSC under basal conditions. m±sd, n=5, *p<0.05. The % of db/db MSC that differentiated to adipocytes (as evidenced by Oil Red O staining) was significantly greater than WT. PPARγ, a transcription factor requisite for adipocyte differentiation, was significantly greater in db/db MSC than WT.

Figure 34A:
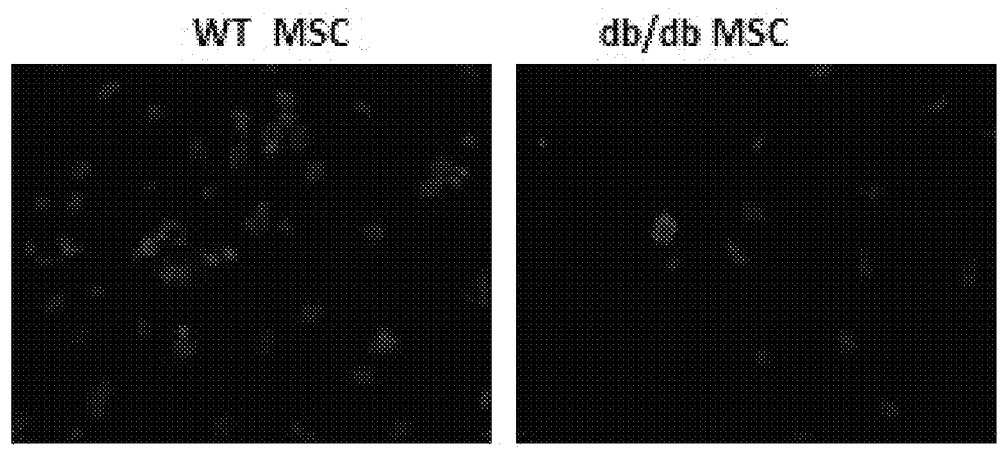
Figure 34B:
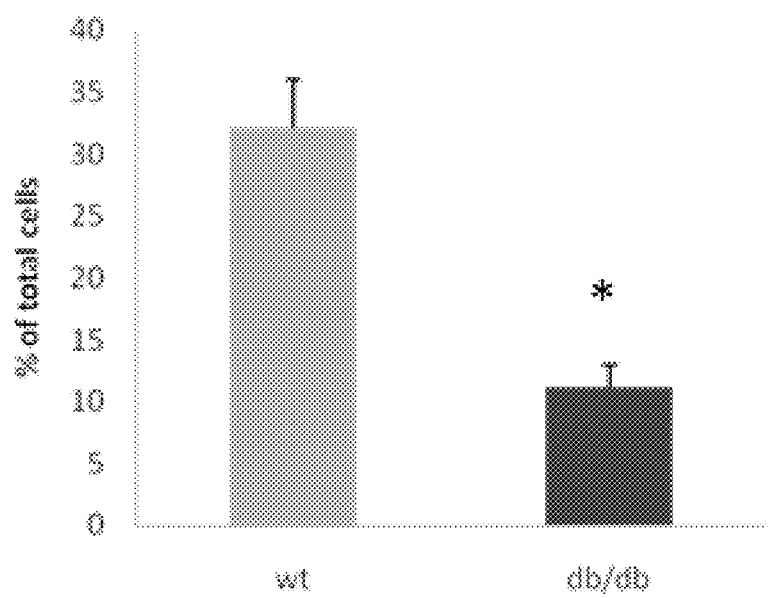
Figure 34C:
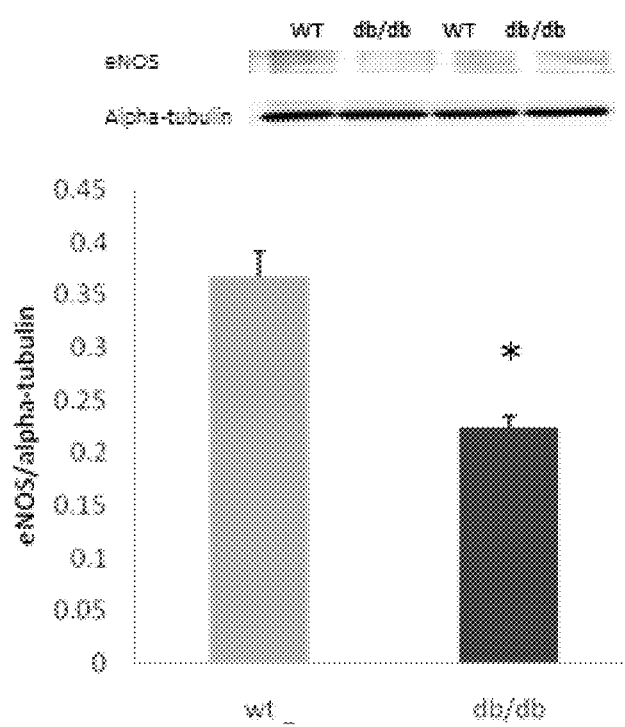

FIGS. 34A and 34B show an effect of endogenic (endothelial cell) medium on the differentiation of WT and db/db MSC. m±sd, n=5, *p<0.05. The % of db/db MSC that differentiated into endothelial cells (as evidenced by CD31 staining) was significantly lower in db/db mice than WT. FIGS. 34C and 34D show eNOS and phospho-eNOS expression in WT and db/db MSC under basal conditions. m±sd, n=4, *p<0.05. Decreased eNOS and phospho-eNOS expression was observed in db/db MSC.

In summary, in vitro, db/db MSCs show a greater rate of differentiation towards adipocytes and increased PPARγ, decreased adiponectin expression than WT MSCs. Further, db/db MSC show a decreased rate of differentiation towards endothelial cells and decreased eNOS and phospho-eNOS expression.

Study 4—Oxidative/Nitrative Stress in Db/Db MSCs and Effects of NAC.

Figure 36A:
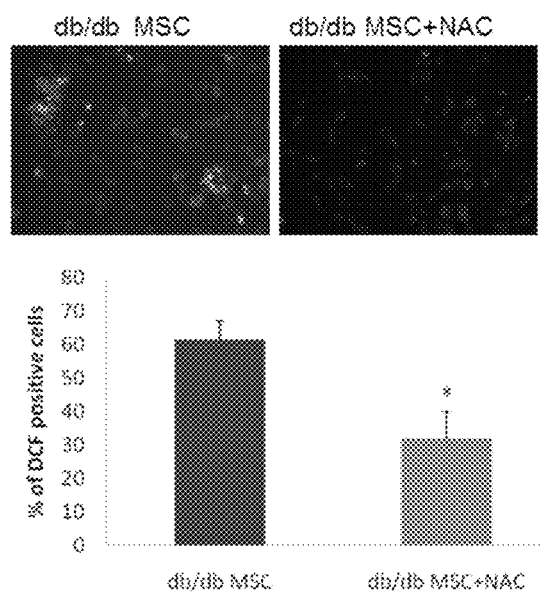
FIGS. 36A-36B. Effects of NAC on nitrotyrosine accumulation in db/db MSC.
Figure 36B:
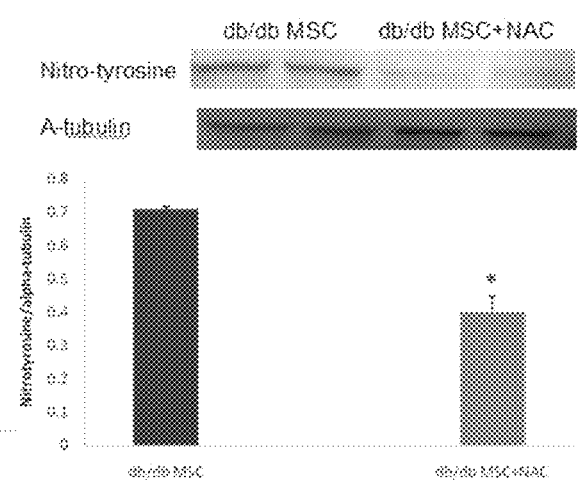

FIG. 35A shows DCF-DA staining for intracellular reactive oxygen species in WT and db/db MSC. Data are expressed as % positive DCF-DA cells/hpf. m±sd, n=5, *p<0.05. FIG. 35B shows nitrotyrosine expression in WT and db/db MSC. m±sd, n=5, *p<0.05. The db/db MSC expressed a greater oxidative/nitrative stress than WT MSC. FIG. 36A shows effects of NAC on DCF-DA staining in db/db MSC. m±sd, n=5, *p<0.05. FIG. 36B shows effects of NAC on nitrotyrosine accumulation in db/db MSC. m±sd, n=5, *p<0.05. Treatment of db/db MSC with NAC significantly reduced the presence of oxidative/nitrative stress. In summary, in vitro, db/db MSC show greater oxidative nitrostive stress than WT MSCs and this phenotype can be reversed by N-acetylcysteine (NAC).

Figure 37A:
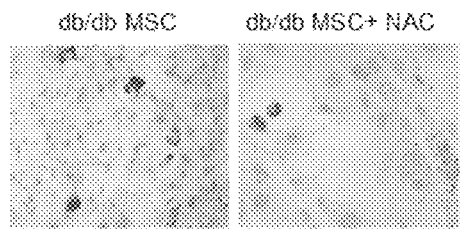
FIGS. 37A-37D. Effects of NAC on response of db/db MSC to adipogenic medium.
Figure 37C:
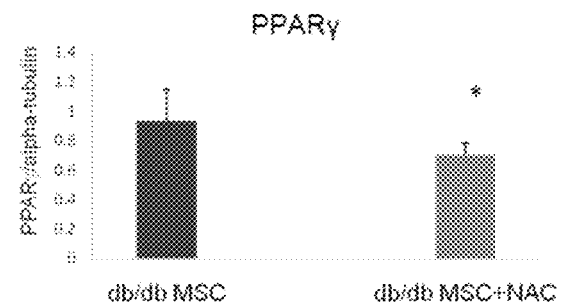
Figure 37B:
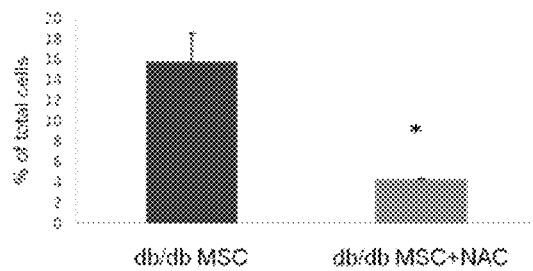
Figure 37D:
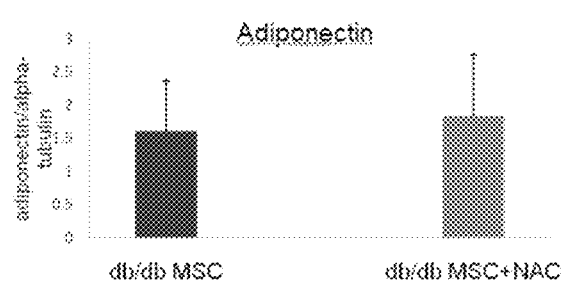

FIGS. 37A and 37B show effects of NAC on response of db/db MSC to adipogenic medium. Adipocytes were identified by Oil Red O staining. m±sd, n=5, *p<0.05. FIGS. 37C and 37D shows effects of NAC on basal PPARγ and adiponectin expression in db/db MSC. m±sd, n=5, *p<0.05. Correction of MSC oxidative stress with NAC reduced adipogenesis in db/db MSC, and also reduced basal PPARγ expression in these cells.

Figure 38A:
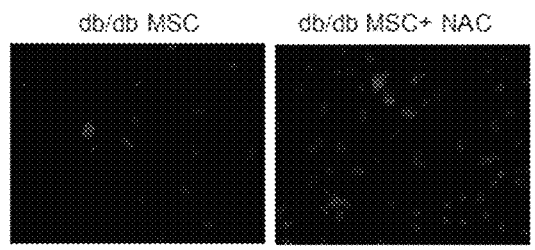
FIGS. 38A-38D. Effects of NAC on differentiation of db/db MSC towards endothelial cells.
Figure 38C:
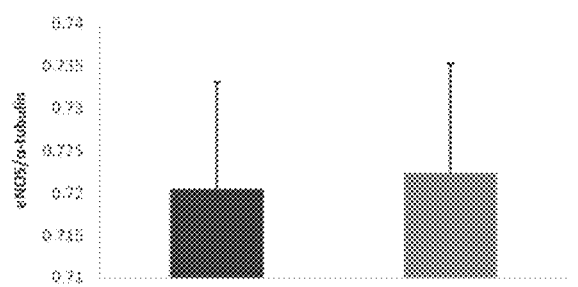
Figure 38B:
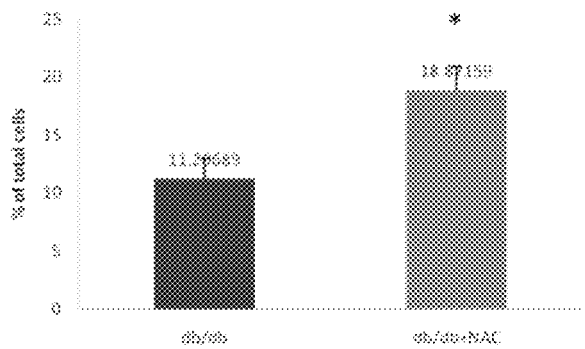
Figure 38D:
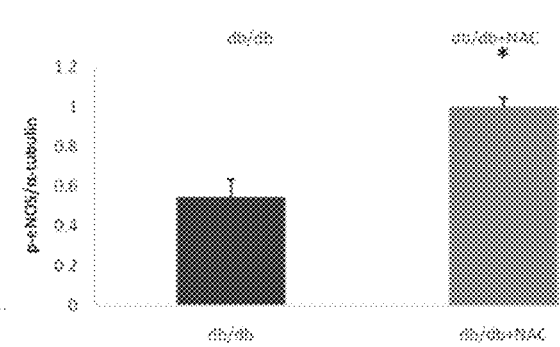

FIGS. 38A and 38B show effects of NAC on differentiation of db/db MSC towards endothelial cells. Endothelial cells were identified by CD31 staining. m±sd, n=4, *P<0.05. FIGS. 38C and 38D show effects of NAC on eNOS(G) and (H) p-eNOS expression in db/db MSC. m±sd, n=4, *P<0.05. In summary, NAC treated db/db MSC show decreased differentiation towards adipocytes and decreased PPARγ expression. Further, NAC treated db/db MSC show increased differentiation towards endothelial cells, decreased PPARγ expression, and increased phospho-eNOS expression but no change in eNOS expression.

Study 5—Nox Expression in Db/Db MSCs and Effect of Nox Knockdown on Oxidative Stress and Differentiation.

Figure 39A:
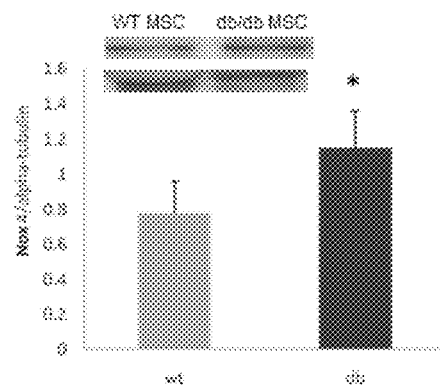
FIGS. 39A-39C. Nox 4 expression in wt and db/db MSC by western blot.
Figure 39B:
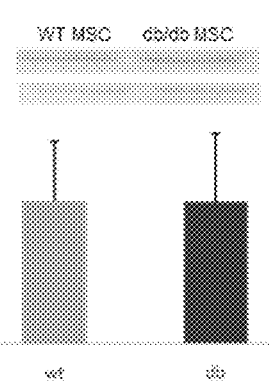
Figure 39C:
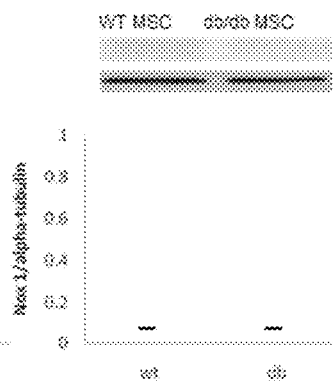

FIG. 39A shows Nox 4 expression in wt and db/db MSC by western blot. * p<0.05 vs WT, n=4. FIG. 39B shows Nox 2 expression in wt and db/db MSC by western blot. m±sd, n=4. FIG. 39C shows Nox 1 expression in wt and db/db MSC by western blot. m±sd, n=4. Increased Nox 4 expression was observed in db/db MSC as compared to wt. There was no difference in Nox 2 expression between db/db MSC and wt MSC. No detectable Nox 1 expression was observed in wt or db/db MSC. Nox 4 is an important source of oxidative stress in db/db MSC.

Figure 40A:
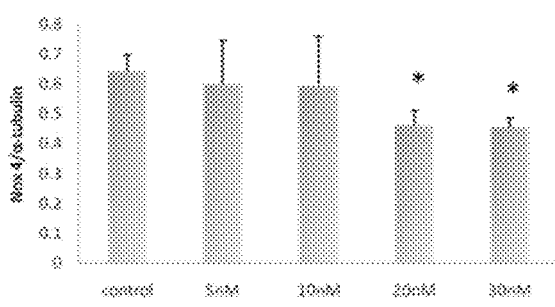
FIGS. 40A-40D. Knockdown of Nox 4 in db/db MSC by Si-RNA (Western blot).
Figure 40C:
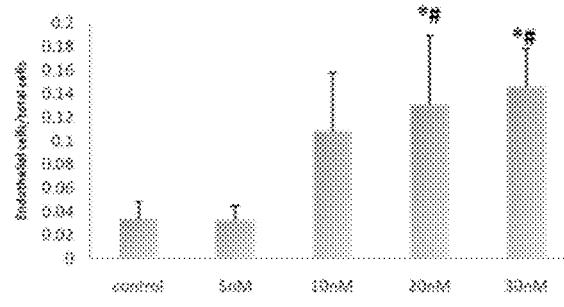
Figure 40B:
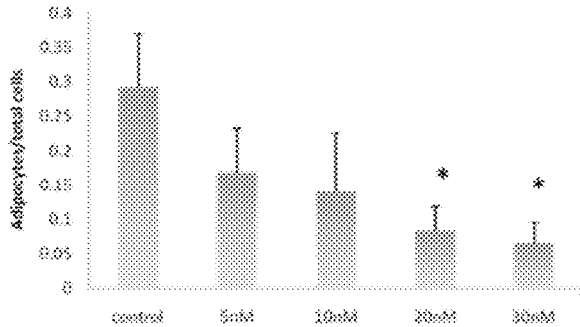
Figure 40D:
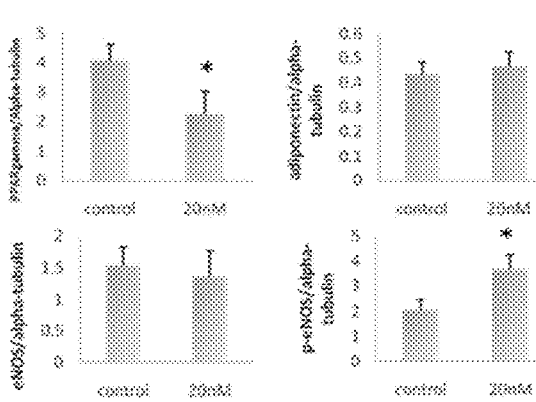

FIG. 40A shows knockdown of Nox 4 in db/db MSC by Si-RNA (Western blot). m±sd, n=4, *p<0.05 vs control. FIG. 40B shows effects of knockdown of Nox 4 by Si-RNA on response of db/db MSC to adipogenic medium. Adipocytes were identified by Oil Red O staining. m±sd, n=4, *p<0.05 vs control. FIG. 40C shows effects of knockdown of Nox 4 by Si-RNA on response of db/db MSC to endogenic medium. Endothelial cells were identified by CD31 staining. m±sd, n=4, *p<0.05 vs control, #p<0.05 vs 5 nM. FIG. 40D shows effects of knockdown of Nox 4 by si-RNA on basal PPARγ, adiponectin, eNOS and p-eNOS expression in db/db MSC. m±sd, n=3, *p<0.05.

In summary, inhibition of Nox 4 by Si-RNA decreased Nox 4 expression in db/db MSC. Further, db/db MSC showed decreased differentiation towards adipocytes and increased differentiation towards endothelial cells after knockdown of Nox 4 expression. Finally, db/db MSC showed increased p-eNOS and decreased PPARgamma expression after knockdown of Nox 4 expression.

Study 6—Insulin Induces Oxidative-Stress-Related Gene Expression Changes in MSCs.

FIG. 41A shows expression of Nox 4 in wt MSC after insulin treatment (Western blot). m±sd, n=4, *p<0.05 vs control. FIG. 41B shows quantification of DCF staining in wt MSC after insulin treatment. FIG. 41C shows effects of insulin on response of wt MSC to adipogenic medium. Adipocytes were identified by Oil Red O staining. m±sd, n=4, *p<0.05 vs control. FIG. 41D shows effects of insulin on response of wt MSC to endogenic medium. Endothelial cells were identified by CD31 staining. m±sd, n=4, *p<0.05 vs control, #p<0.05 vs 5 nM. FIG. 41E shows effects of insulin on basal PPARγ, adiponectin, eNOS and p-eNOS expression in wt MSC. m±sd, n=3, *p<0.05.

In summary, in WT MSCs, increased concentrations of insulin increased Nox 4 expression and oxidative stress. Further, in WT MSCs, increased concentrations of insulin increased PPARgamma and decreased p-eNOS expression. Finally, in WT MSCs, increased concentrations of insulin increased differentiation towards adipocytes and decreased differentiation towards endothelial cells.

Accordingly, bone marrow derived db/db MSCs differentiate into intermuscular adipocytes in response to hindlimb ischemia. WT mice transplanted with bone marrow derived db/db MSCs showed less blood flow recovery after induction of hindlimb ischemia than did Wt mice transplanted with bone marrow derived Wt MSCs. An important aspect of this difference is that bone marrow derived db/db MSC lose multipotency and show a propensity towards adipocyte differentiation rather than endothelial cell differentiation.

Increased oxidant stress secondary to hyperinsulinemia-induced Nox 4 expression is responsible for this impairment in db/db MSC functional capacity. This oxidant stress based restriction of MSC multipotency could account in part for the impaired capacity of diabetic patients to enlarge collateral arteries.

Example 5

Hypercholesterolemia Induces Oxidative Stress in Hematopoietic Stem Cells, Impairs Repopulation Capacity, and Causes Aberrant Lymphocyte Lineage Specification.

Hypercholesterolemia increases all-cause mortality [1,2]. Thus, while hypercholesterolemia is a critical determinant of atherosclerosis and its attendant cardiovascular morbidity and mortality [3], less than 40% of deaths in patients whose total serum cholesterol exceeds 240 mg/dl can be attributed to a cardiovascular etiology [4]. The remaining mortality is consequent to diseases that share an epidemiological link to hypercholesterolemia, but are not directly consequent to atherosclerosis. The mechanism, or mechanisms that underlie this linkage remain undetermined.

Hypercholesterolemia affects hematopoiesis. Patients with hypercholesterolemia manifest lymphocytosis, neutrophilia, and thrombocytosis [5]. Bone marrow CD34+ hematopoietic stem cells derived from hypercholesterolemic animals demonstrate enhanced myeloproliferative capacity and an increased rate of differentiation toward a CD11b monocyte lineage [6], while megakaryocyte ploidy is increased [7]. Increases in tissue SDF-1 production [5], progenitor cell $AT_1$ expression [6], and telomere shortening [8] have been identified as factors affecting hematopoietic function in hypercholesterolemia.

However, hypercholesterolemia can also induce oxidant stress [3,8]. If oxidant levels rise within hematopoietic stem cells (HSCs), then stem cell quiescence and function might be seriously compromised [9-11].

As described herein, HSCs from hypercholesterolemic mice demonstrate oxidant stress, a finding evident in both apolipoprotein E deficient mice and in mice fed a high cholesterol diet. Genomic analysis of these HSCs reveals downregulation of several genes responsible for intracellular antioxidant activity and upregulation of genes that contribute to premature HSC senescence. HSCs from hypercholesterolemic mice display reduced bone marrow repopulation capacity following competitive transplant, an effect reversed by in vivo treatment with the antioxidant N-acetylcysteine (NAC) or the p38 MAPK inhibitor SB203580. These HSCs also showed altered lymphocyte lineage specification, leading to reductions of peripheral blood B cell and NKT cell populations, and an increase in peripheral blood T cells. Collectively, these findings demonstrate a novel means by which hypercholesterolemia can affect hematopoietic function, e.g., by induction of intracellular oxidant stress.

Materials and Methods

Mice:

B6.129P2-Apoe$^{tmiUnc}$/J (ApoE$^{-/-}$) and C57Bl/6 mice were purchased from Jackson Laboratories, Bar Harbor, Me. The ApoE$^{-/-}$ group were fed standard chow. To create diet-induced hypercholesterolemia, some C57Bl/6 were fed the standard chow to which 1.25% cholesterol was added (by weight); this group was designated the high cholesterol diet (HCD) group. The wild type (WT) group consisted of C57BL/6 mice fed standard chow. Only male mice were used in all groups. Mice were housed in a barrier facility, in a 12 hr light/dark cycle. All animal care and use was approved by the Institutional Animal Care and Use Committee of the University of Massachusetts Medical School.

HSC Transplantation:

HSC were purified from freshly harvested bone marrow mononuclear cells as c-Kit$^+$Sca-1$^+$CD90.1$^{low}$Lin$^-$ by FACS sorting. Recipient mice were C57BL/6 (WT) on standard chow. Recipients underwent lethal irradiation (1100 Rads delivered in 2 doses 3 hr apart). Immediately after the 2$^{nd}$ irradiation, recipients were anesthetized (2% isoflurane) and 10$^6$ HSC/0.1 ml sterile PBS were transplanted via retro-orbital injection. Mice were followed for 12 weeks before study or administration of AOM.

Flow Cytometry:

Cells were stained with monoclonal antibodies conjugated to various fluoroprobes. These antibodies included: Notch1, cKit (2B8), Sca-1 (E13-161.7), CD4 (L3T4), CD8 (53-6.72), CD90.1, CD25, CD44, TCRβ, NK1.1, γδTCR, CD45.1, CD45.2. The lineage cocktail consisted of CD4, CD8, B220 (RA3-6B2), TER-119, Mac-1 (MI/70), and Gr-1 (RB6-8C5). All antibodies were purchased from BD Bioscience (San Diego, Calif.). FACS analysis was carried out on a FACS Diva.

Immunostaining:

The colon and rectum was removed en bloc from each mouse and the number of polyps was identified using a dissecting microscope. Each polyp was frozen in OCT at −80° C. and cryosections (10 μM) cut. H&E staining was used to identify the histological grade of each polyp, assigned by a pathologist blinded to study condition. Standard immunostaining protocol was used to identify γδT cells (monoclonal antibody to γδTCR, DAPI counterstaining) and NKT cells (monoclonal antibodies to TCR and NK1.1, DAPI counterstaining). Sections were viewed with a Zeiss immunofluorescent microscope and Axiovert software.

Quantitative Real Time PCR:

Thymocytes were sorted into DN1 (CD44$^+$CD25$^-$), DN2 (CD44$^+$CD25$^+$), DN3 (CD44$^-$CD25$^+$) and double positive (CD4$^+$CD8$^+$) subsets by FACS sorting. RNA was isolated from each cell fraction using Trizol Reagent (Invitrogen). Transcription to cDNA was performed using SuperScript III (Invitrogen). Mouse ribosomal 18S and mouse Notch1 primers were purchased from Operon. All PCRs were carried out in triplicate using an Eppendorf Mastercycler Realplex (Eppendorf, Hamburg, GR). The comparative Ct method was used to quantify transcripts that were normalized for murine 18S.

Results

HSCs from Hypercholesterolemic Mice Demonstrate Evidence of Oxidant Stress:

ApoE$^{-/-}$ mice had a higher serum total cholesterol than WT mice: 204±24 vs. 50±11 (m±sd, n=7, p<0.01). C57BL/6 mice fed a cholesterol-enriched diet (1.25 gm %) for 8 weeks, beginning at 2 months of age had a total serum cholesterol of 243±21 (n=7, p<0.05 vs. ApoE$^{-/-}$, p<0.01 vs. WT).

Figure 42A:
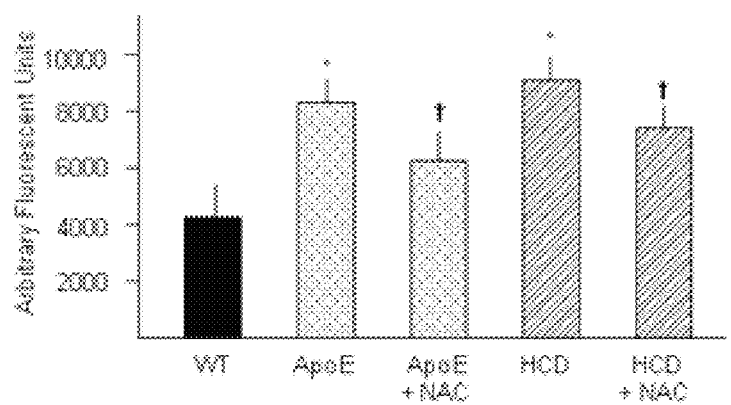
FIGS. 42A-42B. HSCs from hypercholesterolemic mice demonstrate evidence of oxidative stress.
Figure 42B:
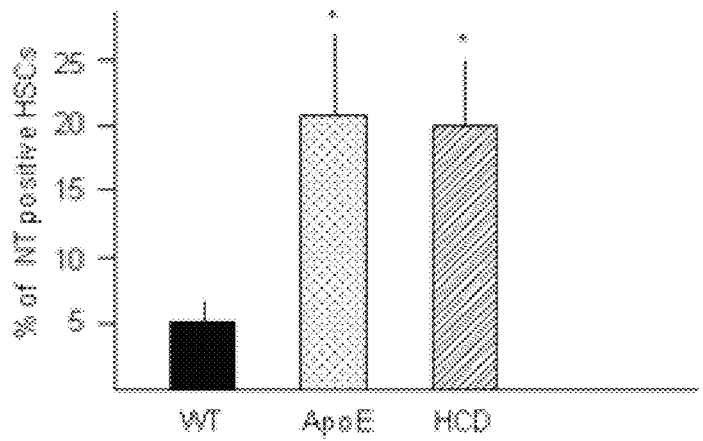

HSCs were purified from bone marrow mononuclear cells by multi-parameter FACS sorting using the surface phenotype cKit$^+$Sca-1$^+$CD90.1$^{low}$Lin$^-$. A greater percentage of HSCs from ApoE$^{-/-}$ and HCD mice stain with 2',7'-dichlorofluorescein diacetate than WT KSL cells, indicating a higher oxidant level in cells from hypercholesterolemic mice [12]. Two additional assays were carried out that confirmed this earlier finding: first, the level of $H_2O_2$ in HSC cell lysates, determined by spectrophotometry, was greater in ApoE$^{-/-}$ and HCD mice than in WT mice (FIG. 42A). FIGS. 42A-42B show HSCs from hypercholesterolemic mice demonstrate evidence of oxidative stress. (A) $H_2O_2$, determined by fluorescent spectroscopy in lysates from freshly harvested HSCs, was greater in ApoE and HCD mice than in WT mice, but was significantly decreased by in vivo NAC treatment. (B) The percentage of HSCs that demonstrated positive staining with nitrotyrosine antibodies was greater in ApoE and HCD mice than in WT mice. m±sd, n=5 mice per group, *p<0.05 vs. WT, † p<0.05 for NAC-treated groups vs. ApoE or HCD groups.

Second, a greater percentage of HSCs from ApoE$^{-/-}$ and HCD mice than WT mice stained for nitrotyrosine (FIG. 42B). Nitrotyrosine staining indicates peroxynitrite (OONO$^-$)-induced nitration of tyrosine residues and thus suggests that superoxide anion, necessary for OONO$^-$ generation, was present in greater quantity in HSCs from hypercholesterolemic than from WT, mice and that this reactive oxygen species (ROS) altered proteins in these cells [13,14].

One means by which hypercholesterolemia induces cellular oxidant stress is via oxidized low-density lipoproteins (oxLDL) [15] and immunofluorescent evidence of oxLDL in HSCs from ApoE$^{-/-}$ mice [12]. To gain further insight into the basis for increased oxidative stress in HSCs derived from hypercholesterolemic animals, the expression of more than 44,000 genes was examined using Agilent Mouse Whole Genome arrays. A significant attenuation in the expression of genes involved in the metabolism of reactive oxygen species was observed in ApoE$^{-/-}$ HSCs: expressions for several antioxidant systems, including SOD1 (superoxide dismutase), Gpx (glutathione peroxidase), and Prdx (peroxiredoxin) were less in HSCs from ApoE$^{-/-}$ than from WT mice (Table 2). The expression of ATM (ataxia telangiectasia mutated) was also less in ApoE$^{-/-}$ HSCs; in this context, it is known that ATM$^{-/-}$ mice demonstrate increased HSC oxidant stress and reduced HSC quiescence [9,10].

TABLE 2

ROS-related genes up- or down-regulated in HSCs from ApoE$^{-/-}$ mice.

| Gene symbol | Gene title |
|---|---|
| Downregulated genes | |
| Atm | Ataxia telangiectasia mutated |
| Atr | Ataxia telangiectasia and Rad3 related |
| FoxO3 | Forkhead box O 3 |
| Gpx1 | Glutathione peroxidase 1 |
| Gpx2 | Glutathione peroxidase 2 |
| Gpx6 | Glutathione peroxidase 6 |
| Nox4 | NADPH oxidase 4 |
| Prdx6 | Peroxiredoxin 6 |
| Sod1 | Superoxide dismutase 1 |
| Sod3 | Superoxide dismutase 3 |
| Txnrd2 | Thioredoxin reductase 2 |
| Upregulated genes | |
| Cdkn1 | Cyclin-dependent kinase inhibitor 1 |
| E2f1 | Transcription factor E2f1 |

Figure 43A:
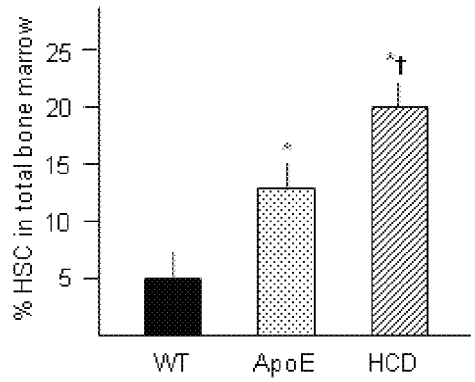
FIGS. 43A-43E. Fewer quiescent HSC are present in the bone marrow of hypercholesterolemic mice.

Fewer Quiescent HSC are Present in the Bone Marrow of Hypercholesterolemic Mice:

The number of bone marrow HSC, expressed as percentage of the total number of bone marrow mononuclear cells, was significantly greater in ApoE$^{-/-}$ and HCD mice than in WT mice (FIG. 43A). FIGS. 43A-43E show fewer quiescent HSC are present in the bone marrow of hypercholesterolemic mice. (A,B) The percentage of HSCs in the bone marrow mononuclear cell population was higher, while the percentage of long term-HSC (CD34$^-$HSCs) in the HSC population was less in ApoE and HCD than WT mice. (C) The percentage of side population cells (Hoechst$^{low}$ HSCs) in the HSC population was less in ApoE and HCD than WT groups. Representative FACS analyses are shown; numbers within each box are the m±sd for the group. (D) The percentage of CD45.2$^+$ mononuclear cells in peripheral blood was higher 8 and 12 weeks competitive transplantation with HSCs from WT than from ApoE mice. (E) The percentage of CD45.2$^+$ bone marrow mononuclear cells was less 12 weeks after competitive transplantation with HSCs from ApoE or HCD mice than from WT mice. However, in vivo treatment of ApoE donor mice with NAC prior to HSC harvest restored the capacity of ApoE HSCs to repopulate the recipient mouse bone marrow. m±sd, n=5 mice per group, *p<0.05 vs. WT, † p<0.05 vs. ApoE.

Figure 43B:
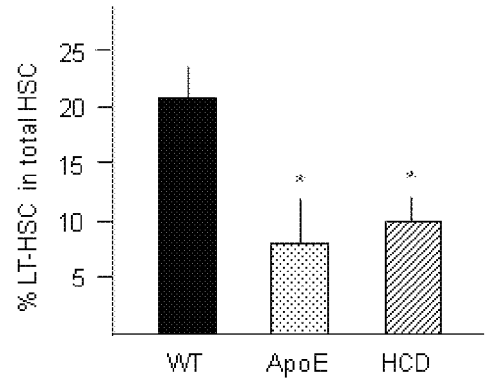
Figure 43C:
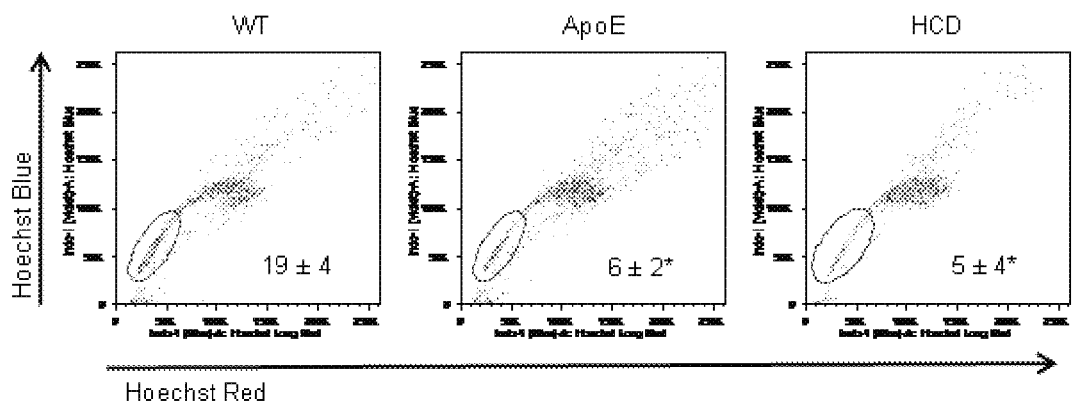

The percentage of long-term HSC (CD34$^-$cKit$^+$Sca-1$^+$CD90.1$^{low}$Lin$^-$) was also significantly reduced in the bone marrow of ApoE$^{-/-}$ and HCD mice (FIG. 43B). Furthermore, the percentages of HSC that demonstrated the side population phenotype, i.e., Hoechst", were significantly less in hypercholesterolemic mice than in WT mice (FIG. 43C). Long-term HSCs and side population cells are quiescent populations of HSCs and a reduction in the presence of these phenotypes is indicative of increased HSC turnover and loss of stem cell quiescence [16].

Figure 43D:
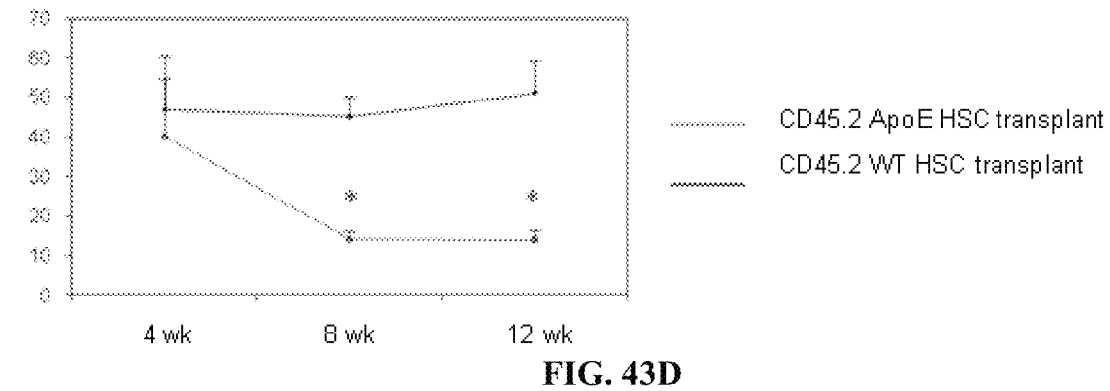
Figure 43E:
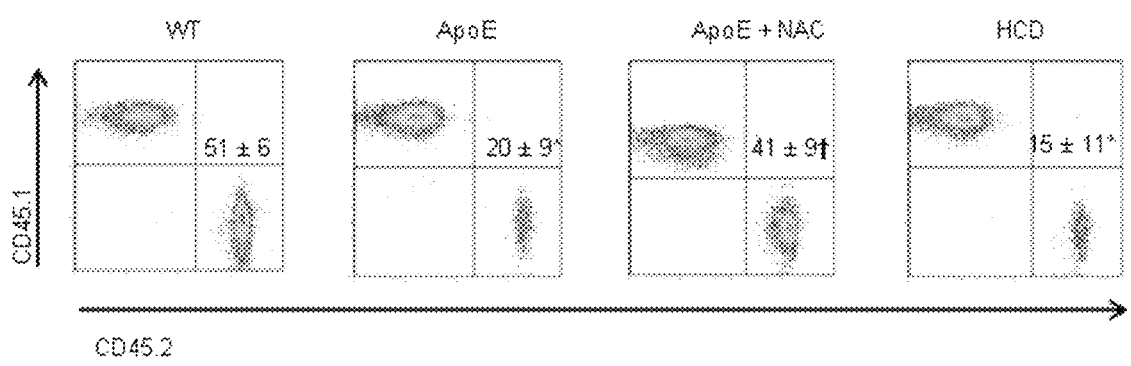
Figure 44A:
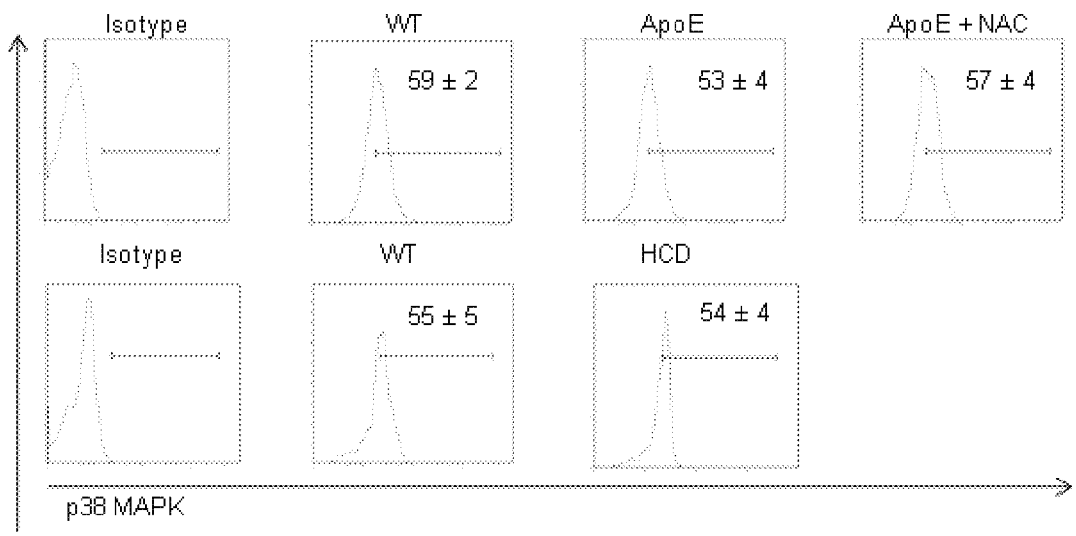
FIGS. 44A-44C. p38 MAPK activation is greater in HSC from hypercholesterolemic mice.
Figure 44B:
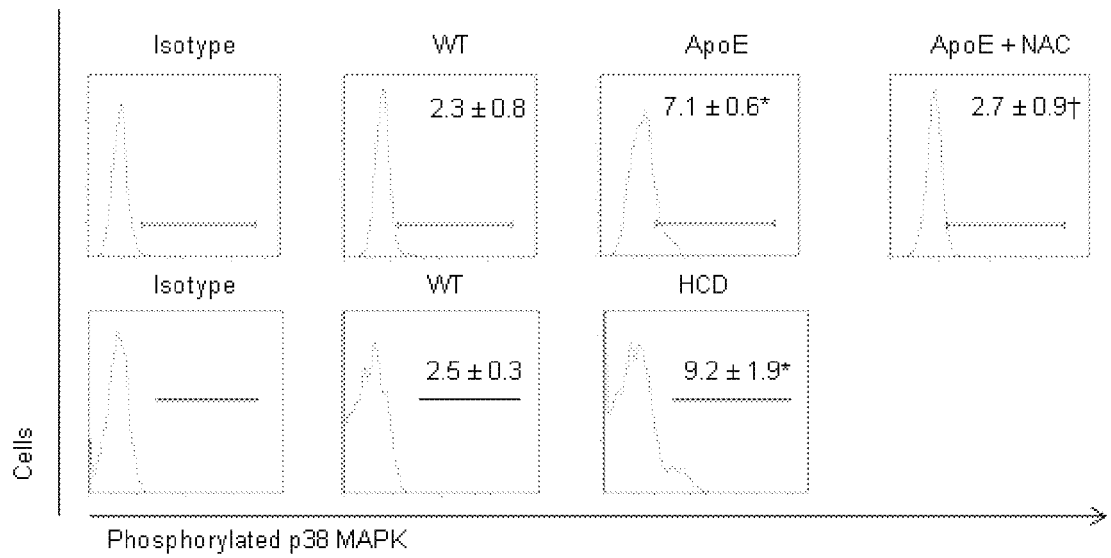
Figure 44C:
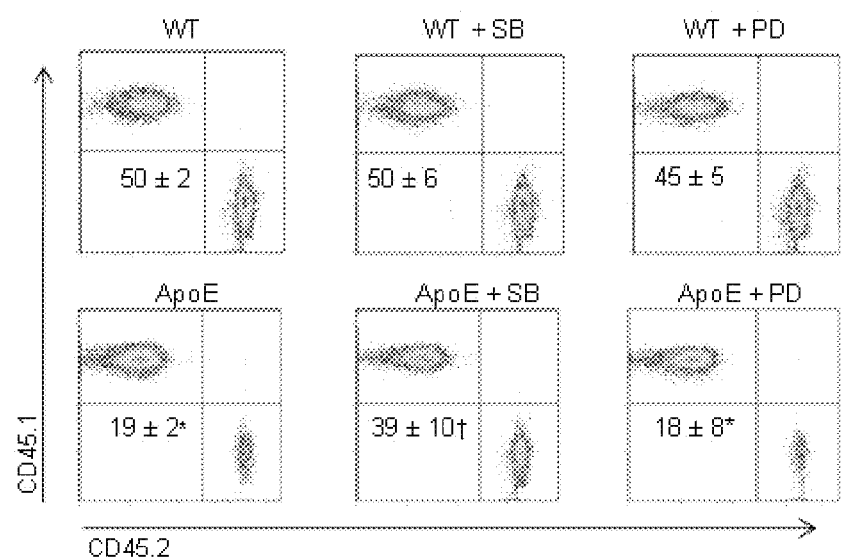

The functional consequence of this loss of quiescence by competitive transplantation was investigated next, insofar as the presence of quiescent HSC are critical for successful bone marrow reconstitution. HSCs from CD45.2 ApoE$^{-/-}$ or HCD mice were mixed 1:1 with CD45.1 WT HSCs and then transplanted into lethally irradiated CD45.1 WT recipients. The percentage of peripheral blood mononuclear cells expressing CD45.2 was significantly less 8 and 12 weeks after transplantation when HSCs from ApoE$^{-/-}$ mice were used than when the transplanted cells were entirely obtained from WT donors (FIG. 43D). Similarly, the percentage of bone marrow mononuclear cells expressing CD45.2 present 12 weeks after transplantation was significantly less when HSCs from ApoE$^{-/-}$ or HCD donor mice were used than when the transplanted cells were entirely obtained from WT donors (FIG. 43E). To confirm that the oxidant stress present in ApoE$^{-/-}$ HSC affected their efficacy during competitive transplantation, ApoE$^{-/-}$ mice were treated with NAC for 4 weeks prior to bone marrow harvest and HSC isolation. NAC treatment of ApoE$^{-/-}$ donor mice significantly increased the percentage of CD45.2$^+$ mononuclear cells in recipient bone marrow 12 weeks after competitive transplantation (FIG. 43E).

p38 MAPK Activation is Greater in HSCs from Hypercholesterolemic Mice:

Activation of p38 MAPK by ROS has been reported in Atm$^{-/-}$ mice and this event participates in ROS-induced loss of HSC quiescence [10,17]. Expression of p38 MAPK was similar in HSCs from ApoE$^{-/-}$, HCD, and WT mice. However, expression of activated (phosphorylated) p38 MAPK is greater in HSCs from hypercholesterolemic mice than from WT mice (FIGS. 44A and 44B). FIGS. 44A-44C show p38 MAPK activation is greater in HSC from hypercholesterolemic mice. FIG. 44A shows the percentage of HSCs expressing p38 MAPK was similar in ApoE, HCD, and WT mice. FIG. 44B shows the percentage of HSCs expressing phosphorylated (activated) p38 MAPK in HSC was higher in ApoE and HCD than in WT mice. However, in vivo treatment of ApoE mice with NAC significantly reduced this percentage. FIG. 44C shows that pretreatment of Apoe donor mice with the p38 inhibitor SB203580, but not the MEK 1 inhibitor PD98059 prior to harvest of HSC for transplant increased the percentage of CD45.2$^+$ bone marrow mononuclear cells 12 weeks after competitive transplant. Neither treatment affected the outcome of competitive transplant with WT HSCs. m±sd, n=5 mice per group, *p<0.05 vs. WT, † p<0.05 vs. ApoE.

In vivo treatment with the antioxidant NAC significantly reduced expression of activated p38 in ApoE$^{-/-}$ HSCs (FIG. 44A). NAC had no effect on activated p38 expression in WT HSCs (data not shown). These findings are consistent with ROS-induced activation of p38 MAPK.

Activation of p38 MAPK reduces HSC quiescence in Atm$^{-/-}$ mice [10]. To evaluate this phenomena in hypercholesterolemic mice, ApoE$^{-/-}$ and WT mice were treated with the selective p38 MAPK inhibitor SB203580 or the MEK 1 inhibitor PD98059 for 2 weeks prior to harvest of HSCs for transplant. CD45.2 ApoE$^{-/-}$ or WT HSCs with mixed 1:1 with CD45.1 WT HSCs and transplanted into lethally irradiated CD45.1 recipient mice. Treatment of ApoE$^{-/-}$ mice with SB203580, but not PD98059 significantly improved the efficacy of ApoE$^{-/-}$ HSCs in the competitive transplant paradigm (FIG. 44C). Neither drug affected the outcome of competitive transplant with CD45.2 WT HSCs (data not shown). Quiescent HSCs are the cells primarily responsible for bone marrow engraftment following transplant [17]; accordingly, these findings indicate that ROS-induced activation of p38 MAPK in HSCs from hypercholesterolemic mice impairs their quiescence, and hence functional efficacy.

Expressions of p19$^{ARF}$, p21$^{Waf1}$, and p27$^{Kip1}$ are Increased in HSCs from ApoE$^{-/-}$ Mice:

Screening of the genomic data using Ingenuity Pathways Analysis (Ingenuity® Systems, www.ingenuity.com) revealed that Cdkna1, a member of the CIP/KIP family of cyclin-dependent kinase inhibitors and central to the regulation of HSC quiescence [17-19], was consistently upregulated in the canonical pathways significantly differently between HSCs from ApoE$^{-/-}$ and WT mice. The expression of p15$^{Ink4b}$, p16$^{Ink4a}$, p18$^{Ink4c}$, p19$^{ARF}$, P21$^{Waf1}$, and p27$^{Kip1}$ was determined using RT-PCR, a more sensitive and quantitative assay, in ApoE$^{-/-}$ and WT HSCs. Expression of p15, p16, and p18 was not different between groups, whereas p19$^{Arf}$, p21$^{Waf1}$, and p27$^{Kip1}$ were significantly elevated in HSCs from ApoE$^{-/-}$ mice. In vivo treatment with the antioxidant NAC for 4 weeks reversed these increases in ApoE$^{-/-}$ HSCs (FIGS. 45A-45B). FIG. 45A shows expressions of p19$^{Arf}$, p21$^{Waf1}$, and p27$^{Kip1}$ are increased in HSCs from ApoE$^{-/-}$ mice. FIG. 45A illustrates that RT-PCR revealed more mRNA for p19$^{Arf}$, p21$^{Waf1}$, and p27$^{Kip1}$ in HSCs from ApoE$^{-/-}$ than from WT mice. Treatment of ApoE$^{-/-}$ mice with NAC or SB203580 fully reversed these increases, while treatment with PD98059 did not. m±sd, n=5, *p<0.001 vs. WT, † p<0.01 vs. ApoE. FIG. 45B shows that increased expressions of p19$^{Arf}$, p21$^{Waf1}$, and p27$^{Kip1}$ were greater in long-term than in short term-HSCs, and were fully absent in more mature cells. m±sd, n=5, *p<0.01 vs. long term-HSC, † p<0.01 vs. short term-HSC.

Moreover, the expressions of p19$^{Arf}$, p21$^{Waf1}$, and p27$^{Kip1}$ were higher in long term-HSCs than in short term-HSCs (CD34$^+$cKit$^+$Sca-1$^+$CD90.1$^{low}$Lin$^-$) from ApoE$^{-/-}$ mice, and expression of these factors was virtually undetectable in more mature cells (FIG. 45B).

Activated p38 MAPK upregulates the Ink4 family cyclin-dependent kinase inhibitors, including p16$^{Ink4a}$ and p19$^{Arf}$ in HSCs and this effect determines, in part, the effect of p38 MAPK on HSC quiescence in the presence of ROS [9,10]. In vivo treatment of ApoE$^{-/-}$ mice with the selective p38 MAPK inhibitor SB203580 significantly reduced HSC expression of p19$^{Arf}$, p21$^{Waf1}$, and p27$^{Kip1}$, whereas treatment with the MEK 1 inhibitor PD98059 had no effect (FIGS. 45A and 45B); neither drug affected expression of these proteins in WT HSCs (data not shown).

Figure 46A:
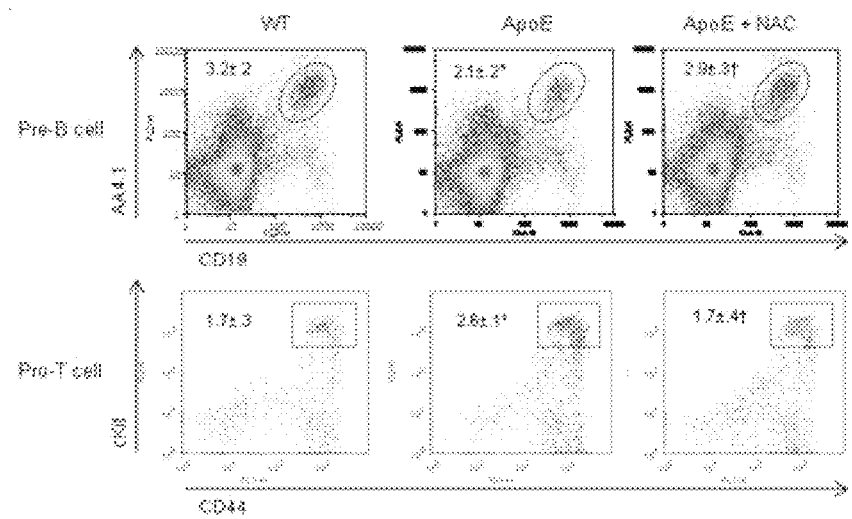
FIGS. 46A-46C. Lymphocyte lineage specification is altered in hypercholesterolemic mice.
Figure 46B:
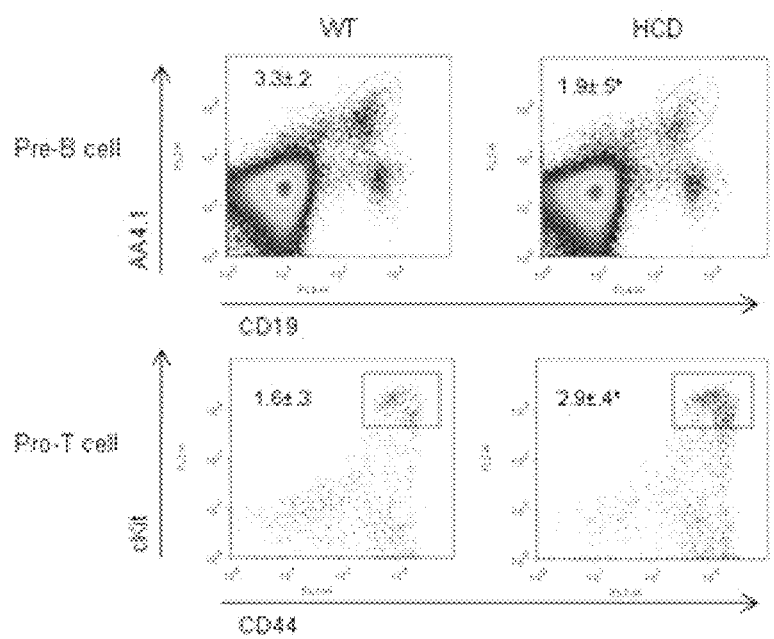
Figure 46C:
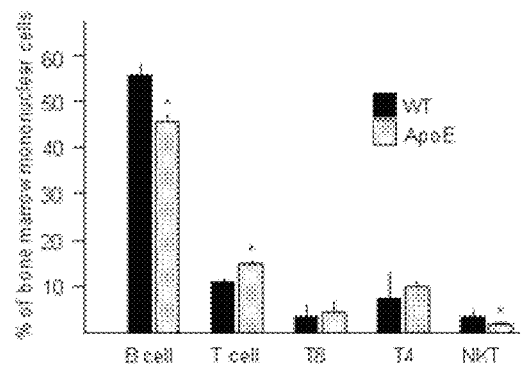

Lymphocyte Lineage Specification is Altered in Hypercholesterolemic Mice:

Hypercholesterolemia is associated with lymphocytosis [5], while induction of hypercholesterolemia in monkeys affects the rate of CD11b monocyte differentiation [6]. To determine if hypercholesterolemic mice demonstrate aberration in lymphocyte differentiation, the percentage of pre-B and pro-T cells was measured within the bone marrow. ApoE$^{-/-}$ and HCD mice demonstrated fewer pre-B cells (CD43$^+$CD19$^+$AA4.1$^+$) and more pro-T cells (Lin$^-$ILR7R$^{low/-}$cKit$^+$CD44$^+$) in the bone marrow than did WT mice (FIGS. 46A and 46B). FIGS. 46A-46C show lymphocyte lineage specification is altered in hypercholesterolemic mice. (A) The percentages of pre-B cells and pro-T cells in the bone marrow mononuclear cell population were lower and higher, respectively, in ApoE$^{-/-}$ than in WT mice. These changes were reversed by in vivo treatment of ApoE mice with NAC. (B) The percentages of pre-B cells and pro-T cells in the bone marrow mononuclear cell population were lower and higher, respectively, in HCD than in WT mice. (C) The percentage of mature B cells was lower and that of mature T cells higher in the peripheral blood mononuclear cell population from ApoE mice than from WT mice. The percentage of NKT cells was also less in ApoE mice.

Treatment of ApoE$^{-/-}$ mice with NAC reversed these effects, indicating that increased ROS was a determinant in causing these changes. The percentage of B220$^+$ B cells was higher and the percentage of CD3$^+$ T cells was lower in the peripheral blood mononuclear cell population of ApoE$^{-/-}$ than of WT mice, whereas the percentage of CD4 and CD8 T cells was not different between groups (FIG. 46C). The percentage of NK1.1$^+$ NKT cells was also lower in ApoE$^{-/-}$ than WT mice.

Figure 47A:
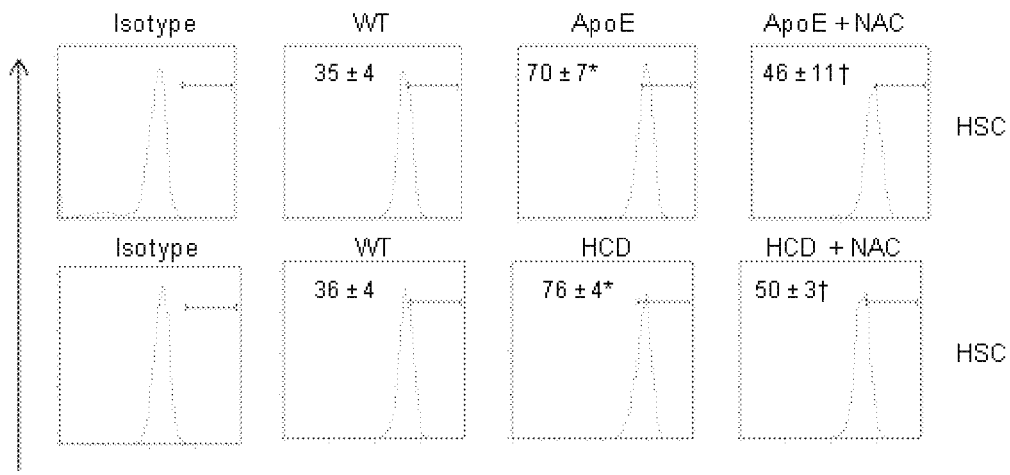
FIGS. 47A-47D. Notch 1 expression is greater in HSCs from hypercholesterolemic mice.

Notch1 Expression is Greater in HSCs from Hypercholesterolemic Mice:

The Notch family is an evolutionarily conserved system of receptors and ligands that play a fundamental role in regulating cell-fate decision in many types of stem and progenitor cells, including HSCs [20,21]. Notch1 plays a critical role in lymphocyte differentiation, wherein expression of Notch1 favors T cell differentiation [22-24]. To clarify the effects of hypercholesterolemia on the expression Notch family, the expression of Notch family was screened in HSCs isolated from WT and ApoE$^{-/-}$ mice. The percentage of HSCs expressing of Notch1 was higher in hypercholesterolemic than WT mice, whereas no differences in Notch2, Notch4, or Delta-like-1 were noted among groups (FIG. 47A). FIGS. 47A-47D show notch 1 expression is greater in HSCs from hypercholesterolemic mice. (A) The percentage of HSCs expressing Notch1 was twofold greater in ApoE$^{-/-}$ and HCD mice than from WT mice, and these effects were reversed by in vivo treatment with NAC. (B) Within the HSC population, a higher percentage of long term-HSCs expressed Notch1 than did short term-HSCs. This difference was evident in both WT and ApoE$^{-/-}$ mice, although the percentage of short term-HSCs expressing Notch1 was twofold higher in ApoE$^{-/-}$ than WT mice. (C) The percentages of pre-B cells and pro-T cells expressing Notch1 were greater in ApoE$^{-/-}$ than in WT mice, and these effects were reversed by in vivo treatment with NAC. (D) Treatment of ApoE$^{-/-}$, but not WT mice with SB203580 reduced the percentage of HSCs expressing Notch1. m±sd, n=5, *p<0.05 vs. WT, †p<0.05 vs. ApoE or HCD, p<0.05 vs. long-term HSCs.

Figure 47B:
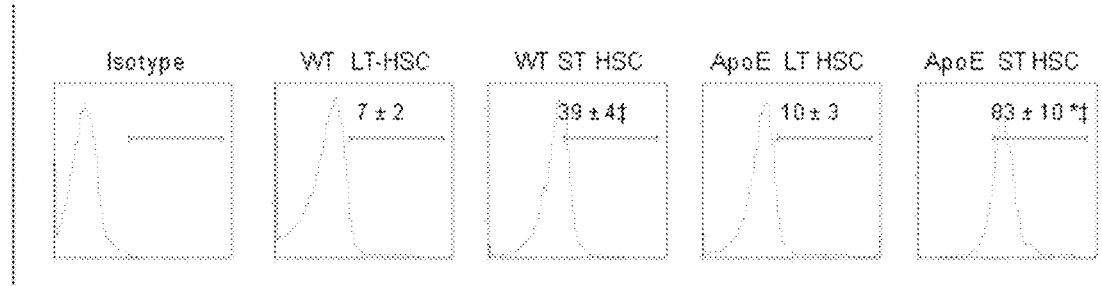
Figure 47C:
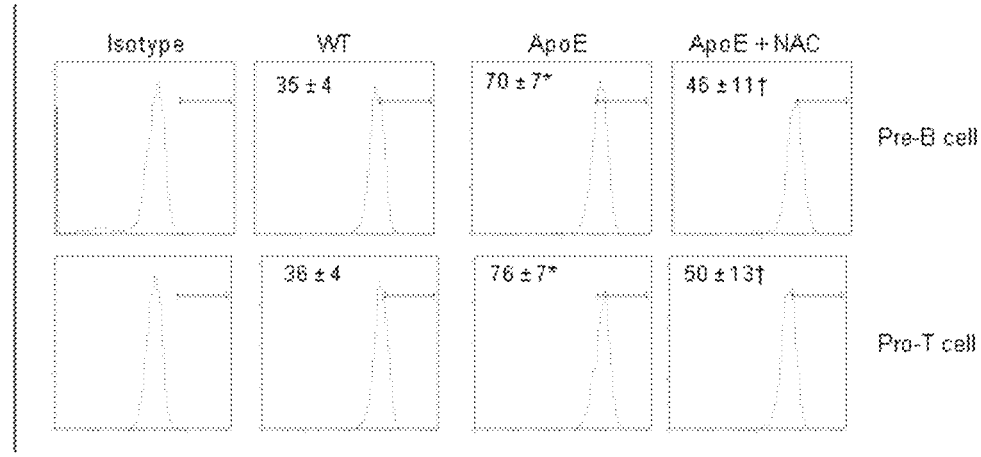
Figure 47D:
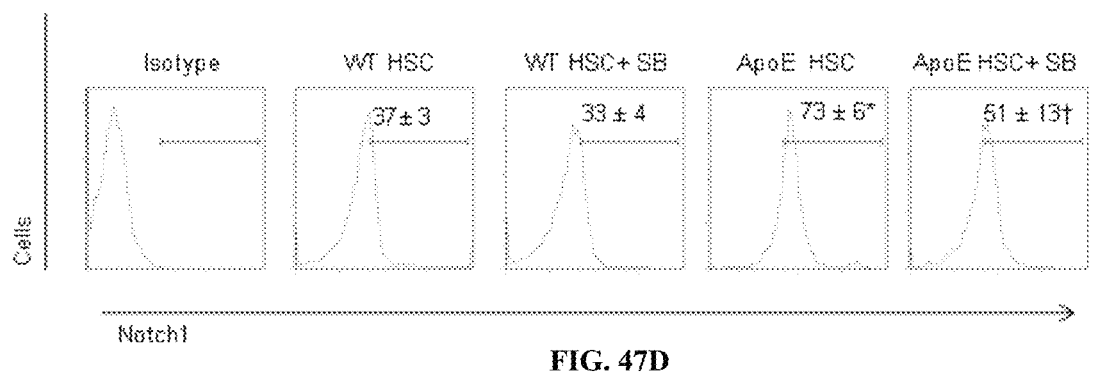

The percentage of short term-HSCs expressing Notch1 was higher than long term-HSCs in both ApoE$^{-/-}$ and WT mice. However, within the short term-HSC population, this percentage was higher in ApoE$^{-/-}$ than WT mice (FIG. 47B). Similarly, the percentage of the pre-B cell and pro-T cell populations expressing Notch1 was greater in ApoE$^{-/-}$ than WT mice (FIG. 47C).

Finally, to determine the potential roles of ROS and p38 MAPK on Notch expression in HSCs, these cells were purified from the bone marrow mononuclear cell populations from ApoE$^{-/-}$, HCD, and WT mice that had been treated with NAC or SB203580. Treatment with NAC significantly reduced the percentage of ApoE$^{-/-}$ and HCD HSCs expressing Notch1 (FIG. 47A); no effect was noted in WT mice (data not shown). Treatment with SB203580 significantly reduced the percentage of ApoE$^{-/-}$ HSCs expressing Notch1, whereas this treatment did not affect the WT group (FIG. 47C).

Accordingly, in some aspects HSCs from hypercholesterolemic mice demonstrated increased ROS that resulted in protein tyrosine nitration. The functional consequences of this hypercholesterolemia-induced oxidant stress included loss of HSC quiescence, which impaired bone marrow repopulation capacity, and altered lymphocyte lineage specification, as evidenced by changes in mature B and T cell populations in the peripheral blood of hypercholesterolemic mice. Restoration of HSC function, specifically repopulation capacity, was clearly evident following treatment of ApoE$^{-/-}$ mice with the antioxidant NAC, which acts to enhance glutathione peroxidase activity [28]. These findings are consistent with observations made in ATM' mice in vivo [9] and in HSCs treated with buthathione sulfoximide in vitro [10], wherein oxidant stress compromised HSC quiescence and function. The present findings demonstrate for the first time that hypercholesterolemia, a common clinical entity that significantly increases the risk of all-cause mortality [2], is associated with HSC dysfunction via generation of HSC oxidant stress.

It is clear that HSC from hypercholesterolemic mice manifest significant oxidant stress; however, the present findings are insufficient to draw firm conclusions regarding the mechanistic basis underlying this interaction. The uptake of oxidized low-density lipoprotein (oxLDL) in KSL cells from ApoE$^{-/-}$ mice was previously demonstrated [29]. OxLDL can increase intracellular oxidant production directly [30], or via induction of NADPH oxidase [31] or uncoupling of endothelial nitric oxide synthase [32]. The downregulation of Atm (ataxia telangiectasia mutated) in ApoE$^{-/-}$ KSL cells may be of particular relevance in HSC redox metabolism insofar as Atm$^{-/-}$ mice demonstrate significant oxidant stress, partly due to reduction of intracellular antioxidant systems [9]. Similarly, upregulation of Cdkn1a, the gene for p21$^{Waf1}$ may pertinent in loss of HSC redox balance based on its established capacity to increase intracellular ROS production [21]. The potential clinical relevance of hypercholesterolemia-induced HSC oxidant stress certainly warrants a more complete investigation into the mechanisms responsible for this cause-effect relationship. However, it should be appreciated that regardless of the precise mechanism, the data supports embodiments of the invention related to reducing hypercholesterolemia-induced oxidant stress and related therapeutic applications.

Several lines of evidence indicated a loss of HSC quiescence in hypercholesterolemic mice. First, both Apoe$^{-/-}$ and HCD groups demonstrated an increased number of KSL cells in the bone marrow mononuclear cell population, a finding consistent with increased turnover of HSCs within the osteoblastic bone marrow niche [16]. Second, the numbers of long-term HSCs and side population cells were significantly less in the KSL populations from ApoE$^{-/-}$ and HCD groups. These primitive cells are normally principal sites of HSC quiescence and their reduced numbers are consistent with increased HSC turnover [15,16]. Third, HSCs from hypercholesterolemic mice showed an impaired capacity to repopulate the bone marrow under conditions of competitive transplantation with HSCs from WT mice. Reconstitution of bone marrow requires transplantation of primitive HSCs, such as CD34$^-$ long term-HSC or side population cells [16,33]. These HSC were reduced in hypercholesterolemic mice and these reductions likely contributed to the impaired repopulation capacity of HSCs from these mice.

The Ink4/Arf and the Cip/Kip families of CDK inhibitors are critical in cell cycle regulation and participate in maintenance of HSC quiescence, i.e., the limitation of turnover of the most primitive HSC cell populations that is requisite to preserve the HSC pool from which all hematopoiesis is derived [9,16,24,34]. Ito et al. [9,10] demonstrated ROS-induced, p38-mediated upregulation in the Ink4/Arf family members p16$^{Ink4a}$ and p19$^{Arf}$ in Atm$^{-/-}$ mice that lead to loss of HSC quiescence, while genetic over-expression of p19$^{Arf}$ or p21$^{Waf1}$ generates premature HSC senescence and marrow failure [9,19]. The present findings indicate that a similar signaling paradigm occurs in HSCs from hypercholesterolemic ApoE$^{-/-}$ mice. Hence, oxidant stress, activation of p38 MAPK, and increased expression of p19$^{Arf}$, p21$^{Waf1}$, and p27$^{Kip1}$ were evident in ApoE$^{-/-}$ KSL, while the results of treatment with NAC or SB203580 indicated important roles for oxidant stress and p38 MAPK activation as mediators of the loss of repopulation capacity of ApoE$^{-/-}$ HSCs. Moreover, genomic data changes in canonical pathways relevant to cell cycle regulation that would favor loss of regulation and thus potential acceleration of HSC pool exhaustion. Collectively, these findings indicate that hypercholesterolemia induces HSC oxidant stress that leads to premature HSC senescence.

The Notch family of receptors and ligands plays a critical role in regulation of hematopoiesis [35]. Notch signaling induces stem cell self-renewal and progenitor cell expansion [36,37]. The present findings demonstrate an increase in the percentage of KSL cells expressing Notch1 in hypercholesterolemic mice, an effect most robust in short term-HSCs (CD34$^+$KSL), but also present in HSC progenitor cells. Notch1 expression in KSL cells from hypercholesterolemic mice was reduced by NAC and SB203580, a finding that supports a role for ROS and p38 MAPK in the elevation of Notch1 in these cells. Moreover, expansion of the bone marrow KSL population, which indicates loss stem cell quiescence and expansion of progenitor cells [16], is consistent with the increased expression of Notch1, particularly in short term-HSCs [36].

Notch signaling is also critical to the regulation of lymphocyte lineage specification.

Notch signaling targets early lymphoid-restricted progenitor cells, and is necessary and sufficient to induce T cell commitment in these cells [38-40]. In this context, the expansion of the pre-T cell population within the bone marrow and the concomitant increase in the percentage of CD3$^+$ cells in peripheral blood in ApoE$^{-/-}$ is fully consistent with the elevation of Notch1 expression in the HSCs from these mice. Moreover, the increased percentage of pre-B cells expressing Notch1 would predict a reduction in B cell lineage commitment [39], a circumstance evidenced by the reduced percentage of B220$^+$ cells in the peripheral blood of ApoE$^{-/-}$ mice. The reversal of these changes following NAC treatment indicates that HSC oxidant stress is a critical step in their induction.

In summary, the present findings indicate that hypercholesterolemia induces HSC oxidant stress, which leads to functional impairment of these cells, specifically loss of repopulation capacity and aberration of lymphocyte lineage specification. ApoE$^{-/-}$ KSL cells demonstrated changes in gene expression consistent with a loss of cell cycle regulation. This novel pathophysiological effect of hypercholesterolemia may underlie the established increase in all-cause mortality generated by hypercholesterolemia.

References

1. Goldbourt U, Holtzman E, Neufeld H N. Total and high density lipoprotein cholesterol in the serum and risk of mortality: evidence of a threshold effect. Br Med J 1985: 290, 1239-1243.
2. Chyou P H, Eaker E D. Serum cholesterol concentrations and all-cause mortality in older people. Age Ageing 2000; 29:69-74.
3. Wilkinson I B, Cockcroft J R. Cholesterol, endothelial function and cardiovascular disease. Curr Opin Lipidol 1998; 9:237-242.
4. Barter P, Gotto A M, LaRosa J C, et al. HDL cholesterol, very low levels of LDL cholesterol, and cardiovascular events. N Eng J Med 2007; 357:1301-1310.
5. Gomes A L, Carvalho T, Serpa J, et al. Hypercholesterolemia promotes bone marrow cell mobilization by perturbing the SDF-1:CXCR4 axis. Blood 2010; 115:3886-3894.
6. Strawn W B, Ferrario C M. Angiotensin II AT$_1$ receptor blockade normalizes CD11b$^+$ monocyte production in bone marrow of hypercholesterolemic monkeys. Atherosclerosis 2008; 196:624-632.
7. Pathansali R, Smith N, Bath P. Altered megakaryocyte-platelet haemostatic axis in hypercholesterolemia. Platelets 2001; 12:292-297.
8. Spyridopoulos I, Erben Y, Brummendorf T H, et al. Telomere gap between granulocytes and lymphocytes is a determinant for hematopoetic progenitor cell impairment in patients with previous myocardial infarction. Arterioscler Thromb Vasc Biol 2008; 28:968-974.
9. Ito K, Hirao A, Arai F, et al. Regulation of oxidative stress by ATM is required for self-renewal of haematopoietic stem cells. Nature 2004; 431:997-1002.
10. Ito K, Hirao A, Arai F, et al. Reactive oxygen species act through p38 MAPK to limit the lifespan of hematopoietic stem cells. Nat Med 2006; 12:446-451.
11. Tothova Z, Kollipara R, Huntly B J, et al. FoxOs are critical mediators of hematopoietic stem cell resistance to physiologic oxidative stress. Cell 2007; 128:325-339.
12. Tie G, Yan J, Deng A, et al. Hypercholesterolemia induces hematopoietic stem cell oxidant stress that increases azoxymethane-induced colorectal neoplasia in mice. *Under review*, J Clin Invest, 05/10.
13. Abello N, Kerstjens H A M, Postma D K, et al. Proteion nitration: Selectivity, physiochemical and biological consequences, denitration, and proteomic methods for the identification of tyrosine-nitrated proteins. J Proteome Res 2009; 8:3222-3238.
14. Rania A K, Perry G, Nunomura A, et al. Histochemical and immunocytochemical approaches to the study of oxidative stress. Clin Chem Lab Med 2000; 38:93-97.
15. Salvayre R, Auge N, Benoist H, et al. Oxidized low-density lipoprotein-induced apoptosis. Biochem Biophys Acta 2002; 202:213-221.
16. Arai F, Hirao A, Ohmura M, et al. Tie2/angiopoietin-1 signaling regulates hematopoietic stem cell quiescence in the bone marrow niche. Cell 2004; 118:149-162.
17. Arai F, Suda T. Maintenance of quiescent hematopoietic stem cells in the osteoblastic niche. Ann N Y Acad Sci 2007; 1106:41-53.19
18. Cheng T, Rodrigues N, Shen H, et al. Hematopoietic stem cell quiescence maintained by p21cip1/waf1. Science 2000; 287:1804-1808.
19. Inoue T, Kato K, Kato H, et al. Level of reactive oxygen species induced by p21$^{WAF(1)/CIP(1)}$ is critical for determination of cell fate. Cancer Sci 2009; 100:12756-1283.
20. Allman D, Punt J A, Izon D J, et al. An invitation to T and more: Notch signaling in lymphopoiesis. Cell 2002; 109:S1-S11.
21. Varnum-Finney B, Xu L, Brashem-Stein C, et al. Pluripotent, cytokine-dependent, hematopoietic stem cells are immortalzed by constitutive Notch signaling. Nature 2000; 6:1278-1281.
22. Kojika S, Griffin J D. Notch receptors and hematopoiesis. Exp Hematol 2001; 29:1041-1052.
23. Besseyrias V, Fiorini E, Strobl L J, et al. Hierachy of Notch-Delta interactions promoting T cell lineage commitment and maturation. J Exp Med 2007; 204:331-343.
24. Rothenberg E V, Moore J E, Yui M A. Launching the T cell-lineage developmental programme. Nat Rev Immunol 2008; 8:9-21.

Example 6

Hypercholesterolemia Induces Hematopoietic Stem Cell Oxidant Stress that Increases Azoxymethane-Induced Colorectal Neoplasia in Mice.

Hypercholesterolemia as been shown to increase the risk of all-cause mortality, including an increased risk of death from colon cancer. Here it is shown that hypercholesterolemia induces oxidant stress in hematopoietic stem cells (HSCs) that impairs development of NKT and γδT, cells and thereby increases azoxymethane (AOM)-induced colorectal neoplasia in mice. HSCs from hypercholesterolemic mice (apolipoprotein E null mice and C57BL/6 mice fed a high cholesterol diet) had higher oxidant levels than HSCs from C57BL/6 (WT) mice fed a standard diet, as well as a higher incidence and greater histological severity of AOM-induced colorectal neoplasia. Hypercholesterolemic mice had fewer γδT and NKT cells in the thymus, colon, or colorectal polyps. Each of these effects was reversed in vivo by treatment with N-acetylcysteine for 4 weeks. WT recipient mice transplanted with ApoE$^{-/-}$ HSCs demonstrated persistence of HSC oxidant stress 12 weeks post-transplant; they also demonstrated fewer NKT and γδT cells in the thymus, peripheral blood, and colonic mucosa, as well as a higher incidence and greater histological severity of AOM-induced polyps than WT recipient mice transplanted with WT HSCs. These findings reveal a novel mechanism whereby hypercholesterolemia causes oxidant-induced disruption of hematopoietic stem cell function that increases the risk of colorectal neoplasia.

Hypercholesterolemia is a well established and powerful risk factor for death from cardiovascular disease. Hypercholesterolemia has also been shown to increase the risk of all-cause mortality, including an increased risk of death from cancer [1]. Thus, epidemiological studies have linked hypercholesterolemia to an increased incidence of colorectal cancer in man [2-4] and hypercholesterolemia has been shown to increase the risk of colorectal cancer in mice [5-7]. One of the earliest and most compelling hypothesis to explain the mechanism by which hypercholesterolemia increases the risk of colorectal neoplasia proposed that hypercholesterolemia exerted a systemic, conditional influence that affected immunological mechanisms [8]. In support of this hypothesis, hypercholesterolemia has been shown to compromise both innate and acquired immunity causing an increased susceptibility to bacterial and fungal infections [9,10]. However the specific mechanism by which hypercholesterolemia might alter innate immunity has not been established, nor is it clear if such an effect alters the tumor immunosurveillance generated by the innate immune system. In some embodiments, hypercholesterolemia induces oxidant stress in hematopoietic stem cells, leading to impairment of HSC differentiation toward the cellular components critical to immunosurveillance against colorectal neoplasia.

It is reported herein that hypercholesterolemia, induced by genetic deficiency of apolipoprotein E (ApoE$^{-/-}$) or by a high cholesterol diet generates oxidant stress within hematopoietic stem cells (HSCs), reduces the differentiation of NKT and γδT cells in the thymus, and the resident populations of these cells in the healthy colon. Hypercholesterolemic mice demonstrate a higher incidence and histological severity of azoxy-methane (AOM)-induced colorectal neoplasia. Wild type (WT) recipient mice transplanted with ApoE$^{-/-}$-derived HSCs manifest continued HSC oxidant stress 12 weeks post-transplant, and demonstrate reduced NKT and γδT cell populations and an increased susceptibility to AOM-induced colorectal neoplasia. The paramount importance of HSC oxidant stress in each of these effects is evidenced by their reversal by in vivo treatment with the antioxidant N-acetylcysteine.

Methods

Mice:

All mice were purchased from Jackson Laboratories (Bar Harbor, Me.) and were maintained in the mouse barrier facility. Care of mice was in accordance with NIH guidelines and the Institutional Animal Care and Use Committee of the University of Massachusetts Medical School approved all protocols. Mice were kept on a 12 hr day/night schedule and were allowed free access to chow and water. ApoE$^{-/-}$ and WT mice were fed standard mouse chow (5.4 g fat/100 g diet, 0% cholesterol). HCD mice were fed a diet with 10 g fat/100 g diet, 11.25 g cholesterol/100 g diet (Research Diets, New Brunswick, N.J.). N-Acetylcysteine (NAC) was given by intraperitoneal injection (100 mg/Kg every other day for 4 weeks). Azoxymethane (AOM) was given by intraperitoneal injection (10 mg/Kg weekly for 3 weeks); 1% dextran sodium sulfate was added to the drinking water for the Pt week after AOM treatment.

HSC Transplantation:

HSC were purified from freshly harvested bone marrow mononuclear cells as c-Kit$^+$Sca-1$^+$CD90.1$^{low}$Lin$^-$ by FACS sorting. Recipient mice were C57BL/6 (WT) on standard chow. Recipients underwent lethal irradiation (1100 Rads delivered in 2 doses 3 hr apart). Immediately after the 2nd irradiation, recipients were anesthetized (2% isoflurane) and $10^6$ HSC/0.1 ml sterile PBS were transplanted via retro-orbital injection. Mice were followed for 12 weeks before study or administration of AOM.

Flow Cytometry:

Cells were stained with monoclonal antibodies conjugated to various fluoroprobes. These antibodies included: Notch1, cKit (2B8), Sca-1 (E13-161.7), CD4 (L3T4), CD8 (53-6.72), CD90.1, CD25, CD44, TCRβ, NK1.1, γδTCR, CD45.1, CD45.2. The lineage cocktail consisted of CD4, CD8, B220 (RA3-6B2), TER-119, Mac-1 (MI/70), and Gr-1 (RB6-8C5). All antibodies were purchased from BD Bioscience (San Diego, Calif.). FACS analysis was carried out on a FACS Diva.

Immunostaining:

The colon and rectum was removed en bloc from each mouse and the number of polyps was identified using a dissecting microscope. Each polyp was frozen in OCT at −80° C. and cryosections (10 μM) cut. H&E staining was used to identify the histological grade of each polyp, assigned by a pathologist blinded to study condition. Standard immunostaining protocol was used to identify γδT cells (monoclonal antibody to γδTCR, DAPI counterstaining) and NKT cells (monoclonal antibodies to TCR and NK1.1, DAPI counterstaining). Sections were viewed with a Zeiss immunofluorescent microscope and Axiovert software.

Quantitative Real Time PCR:

Thymocytes were sorted into DN1 (CD44$^+$CD25$^-$), DN2 (CD44$^+$CD25$^+$), DN3 (CD44$^-$CD25$^+$) and double positive (CD4$^+$CD8$^+$) subsets by FACS sorting. RNA was isolated from each cell fraction using Trizol Reagent (Invitrogen). Transcription to cDNA was performed using SuperScript III (Invitrogen). Mouse ribosomal 18S and mouse Notch1 primers were purchased from Operon. All PCRs were carried out in triplicate using an Eppendorf Mastercycler Realplex (Eppendorf, Hamburg, GR). The comparative Ct method was used to quantify transcripts that were normalized for murine 18S.

Results

Figure 48A:
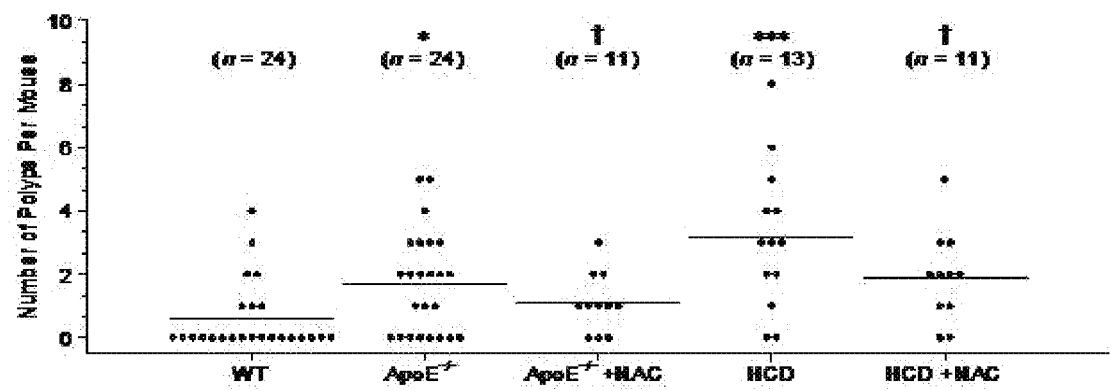
FIGS. 48A-48B. Hypercholesterolemic mice develop a higher incidence of polyps that exhibit greater histological severity in response to azoxymethane.
Figure 48B:
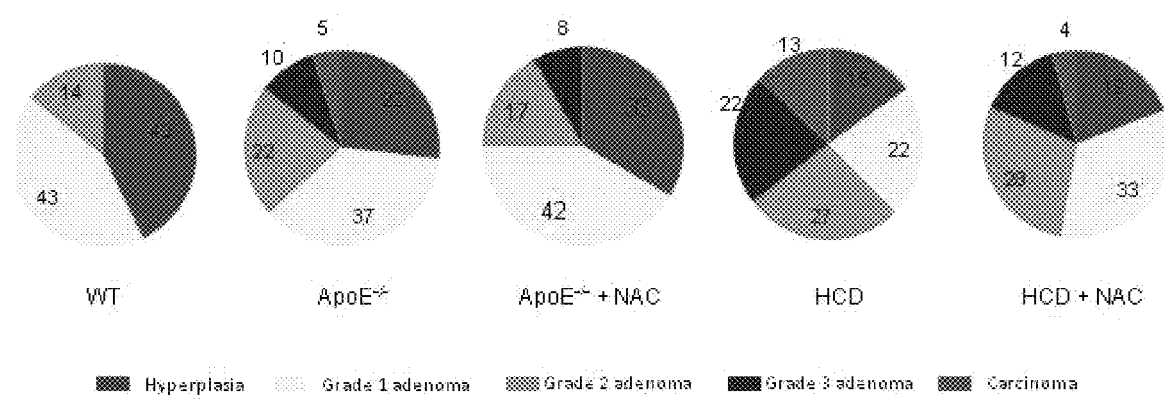
Figure 57A:
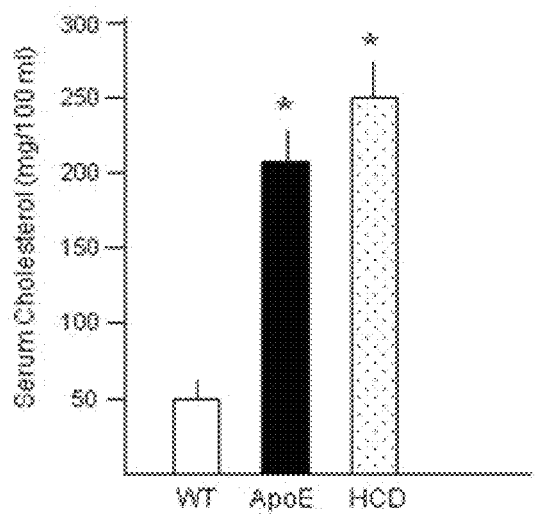
FIGS. 57A-57B. Serum cholesterol was greater in ApoE$^{-/-}$ and HCD mice, but was not affected by HSC transplant.
Figure 57B:
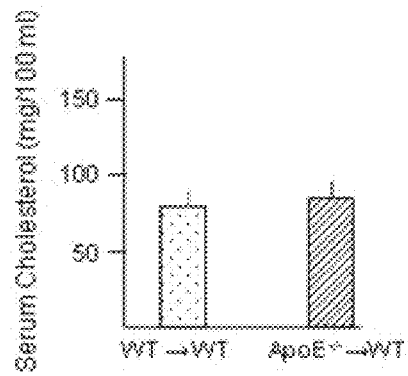

Hypercholesterolemic Mice Develop a Higher Incidence of Polyps that Exhibit Greater Histological Severity in Response to Azoxymethane:

To clarify the relationship between hypercholesterolemia and colorectal neoplasia studies were carried out in two established mouse models of hypercholesterolemia:

B6.129P2-Apoe$^{tm1Unc}$/J mice fed a normal diet (ApoE$^{-/-}$) and C57BL/6 mice fed a high cholesterol diet for 8 weeks (HCD); C57BL/6 mice fed a normal diet served as wild type (WT) controls. The fasting serum cholesterol levels were significantly greater in the ApoE$^{-/-}$ and HCD groups than in the WT group (FIG. 3A). FIGS. 57A-57B show serum cholesterol was greater in ApoE$^{-/-}$ and HCD mice, but was not affected by HSC transplant. (A) Total serum cholesterol measured under fasting conditions (16 hr) was greater in ApoE$^{-/-}$ and HCD groups than in the WT group. (B) Transplantation of HSCs from ApoE$^{-/-}$ mice to lethally irradiated WT recipients did not affect total serum cholesterol in the recipient. m±sd, p<0.01 vs. WT, n=6-8 mice per group. Azoxymethane (AOM), an established colorectal carcinogen that recapitulates tumor progression from hyperplasia through adenomatous polyp formation to adenocarcinoma [11], was given beginning at 3 months of age. Ten weeks later, the incidence and number of polyps were determined in the colon and rectum, and a pathologist blinded to study condition assigned each polyp a histological grade (hyperplasia, grade 1, 2, or 3 adenoma, or carcinoma). The percentage of mice who developed AOM-induced colorectal polyps was more than double in hypercholesterolemic mice than in WT mice: 67% in ApoE$^{-/-}$, and 84% in HCD, and 30% in WT. Similarly, the number of polyps per mouse was significantly greater in the ApoE$^{-/-}$ and HCD groups than in the WT group (FIG. 48A). FIGS. 48A-48B show hypercholesterolemic mice develop a higher incidence of polyps that exhibit greater histological severity in response to azoxymethane. (A) The total numbers of AOM-induced colorectal polyps per mouse were higher in ApoE$^{-/-}$ and HCD mice than WT mice. Horizontal bars in represent the means; *p<0.05 vs. WT; ***p<0.005 vs. WT; †p<0.05 for NAC-treated vs. ApoE$^{-/-}$ or HCD. (B) The histological severity of AOM-induced colorectal polyps was greater in ApoE$^{-/-}$ and HCD mice than in WT mice and these effects were reversed by in vivo pretreatment with NAC. The numbers provided represent the absolute number of polyps for each histological grade within each group.

The histological grades of the polyps were also dissimilar among groups. All the polyps in the WT group showed less advanced histological stages, e.g., hyperplasia, and grade 1 and grade 2 adenoma, and none demonstrated carcinoma. In sharp contrast, 15% of the polyps in the ApoE$^{-/-}$ mice and 36% of the polyps in the HCD mice showed the most advanced histological stages, e.g., grade 3 adenoma or carcinoma (FIG. 48B).

Figure 49A:
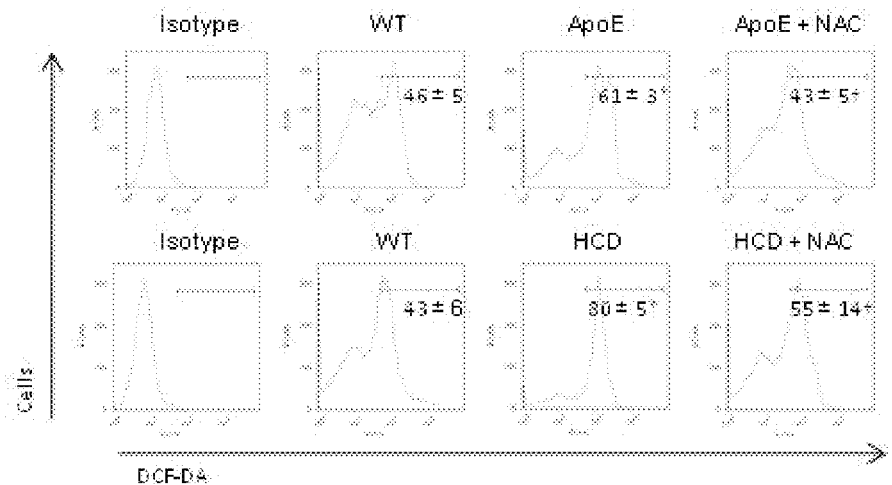
FIGS. 49A-49C. Hypercholesterolemia increases oxidant levels in hematopoietic stem cells.
Figure 49B:
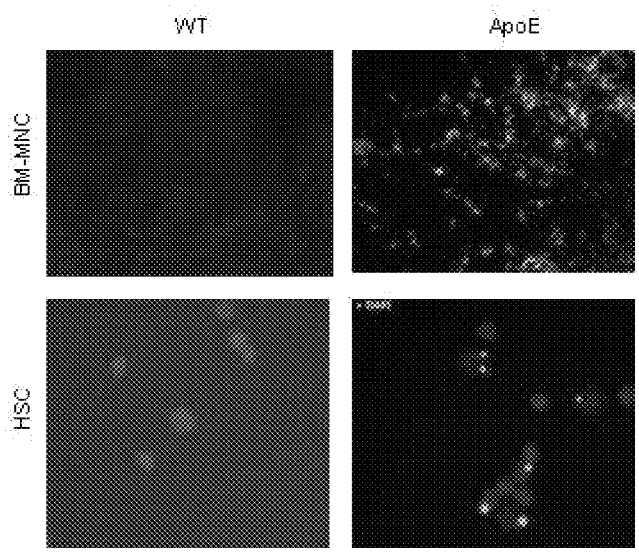
Figure 49C:
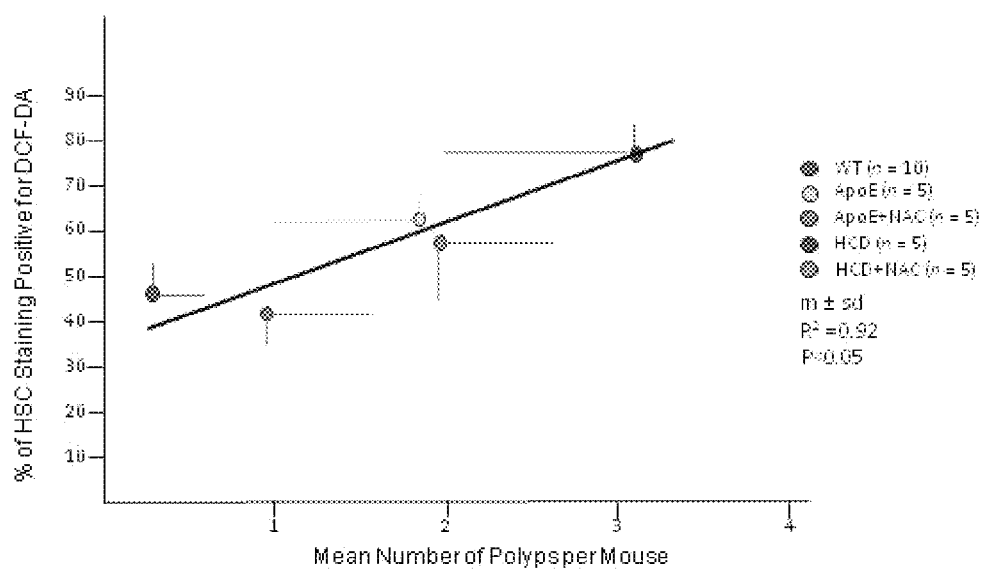

Hypercholesterolemia Increases Oxidant Levels in Hematopoietic Stem Cells:

It is known that hypercholesterolemia induces oxidant stress in many cell types [12,13]. To ascertain if hypercholesterolemia also induces oxidant stress in hematopoietic stem cells (HSCs), cKit$^+$Sca-1$^+$CD90.1$^{low}$Lin$^-$ cells were isolated from freshly harvested bone marrow cells and stained them for intracellular reactive oxygen species with 2',7'-dichlorofluorescein diacetate (DCF-DA). DCF-DA staining was significantly greater in HSCs harvested from ApoE$^{-/-}$ and HCD than in HSCs from WT mice (FIG. 49A). FIGS. 49A-49C show hypercholesterolemia increases oxidant levels in hematopoietic stem cells. (A) HSCs from ApoE$^{-/-}$ and HCD mice demonstrated significantly greater DCF-DA staining than HSCs than WT mice and these effects were reversed by in vivo treatment NAC. Numbers within each representative FACS analysis represent the m±sd of cells demonstrating DCF-DA staining >isotype antibody threshold. n=5; *p<0.05 vs. WT, †p<0.05 for NAC-treated vs. ApoE$^{-/-}$ or HCD. (B) Representative photomicrograph showing oxLDL-staining in HSC and BM-MNC from WT and ApoE$^{-/-}$ mice. (C) Regression of mean polyp number/mouse on the % of HSC staining for DCF-DA. These data represent the 30 mice shown in panel A; each data point represents the m±sd for a group (the WT groups were combined). Statistical analysis was carried out using the means for each group. This effect was significantly reversed by in vivo treatment of hypercholesterolemic mice for 4 weeks with the antioxidant N-acetylcysteine (NAC). One of the principal means by which hypercholesterolemia induces oxidant stress is via the generation of oxidized low density lipoprotein (oxLDL) [13]. Immunofluorescent staining demonstrated the presence of oxLDL in bone marrow mononuclear cells and HSCs freshly harvested from ApoE$^{-/-}$ mice, but not from WT mice (FIG. 49B).

It was next determined if the level of HSC oxidant stress affected the rate of development of AOM-induced colorectal polyps. Regression analysis between the percent of HSC demonstrating DCF-DA staining and the number of polyps/mouse revealed a highly significant correlation between these variables (FIG. 49C). Although correlation does not necessarily predict a cause-and-effect relationship between variables, this provides a strong correlation that supports a linkage between HSC oxidative stress and susceptibility to colorectal neoplasia in mice.

The Differentiation of NKTcells and γδT Cells is Reduced in Hypercholesterolemic Mice, as are the Resident Populations of these Cells in the Healthy Colon:

NKT and γδT cells display features of the innate immune system and, by interactions with antigen presenting cells, serve to bridge the innate and adaptive immune systems [14,15]. In this context, NKT cells [16-18] and γδT cells [14,19] participate in tumor immunosurveillance, e.g., the elimination of nascent transformed cells and restriction of tumor growth [20-22].

Accordingly, it was determined if the presence of NKT or γδT cells was affected by hypercholesterolemia. The percentages of DN1, DN2, DN3 cells in the thymus, as well as CD4, CD8, and double positive cells in peripheral blood were similar among the WT, ApoE$^{-/-}$, and HCD groups. The percentages of immature thymocyte stages and CD4 and CD8 T cells within peripheral blood were not affected by hypercholesterolemia. The percentages of DN1, DN2, and DN3 cells in the thymus, and of CD4 and CD8 T cells in peripheral blood were not different in WT and ApoE$^{-/-}$ mice, or was there an effect of in vivo NAC treatment on these variables. The percentages of DN1, DN2, and DN3 cells in the thymus, and of CD4 and CD8 T cells in peripheral blood were not different in WT and HCD mice, or was there an effect of in vivo NAC treatment on these variables. The percentages of DN1, DN2, and DN3 cells in the thymus, and of CD4 and CD8 T cells in peripheral blood were not different in WT recipient mice 12 weeks after a WT HSCs→WT transplant, an ApoE$^{-/-}$HSCs→WT transplant, or an ApoE$^{-/-}$+NAC HSCs→WT transplant mice. m±sd, n=5.

Figure 50A:
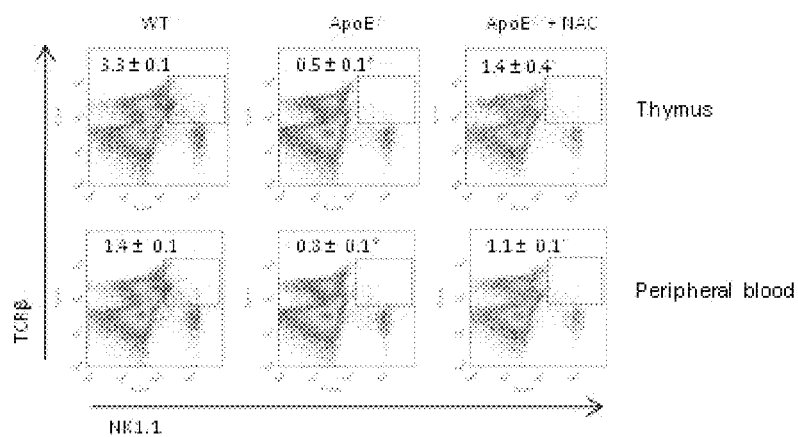
FIGS. 50A-50C. ApoE$^{-/-}$ mice have reduced differentiation of NKTcells and γδT cells, and reduced resident populations of these cells in the healthy colon.
Figure 50B:
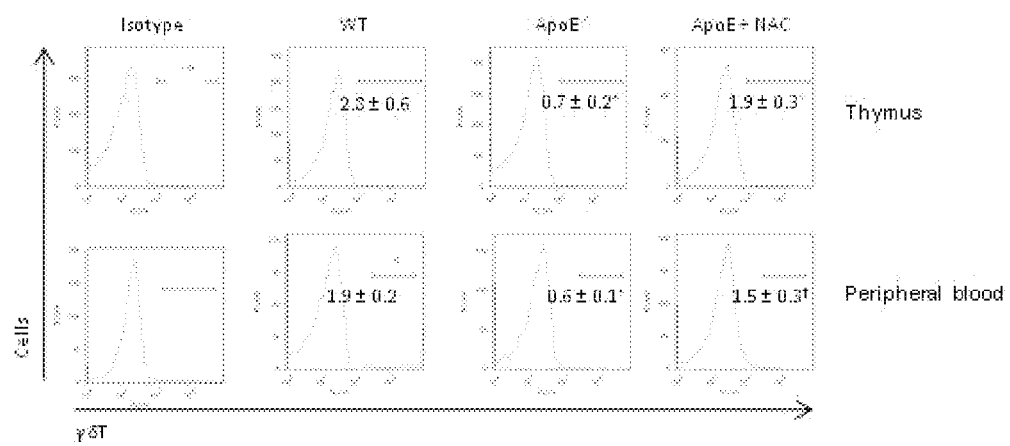
Figure 50C:
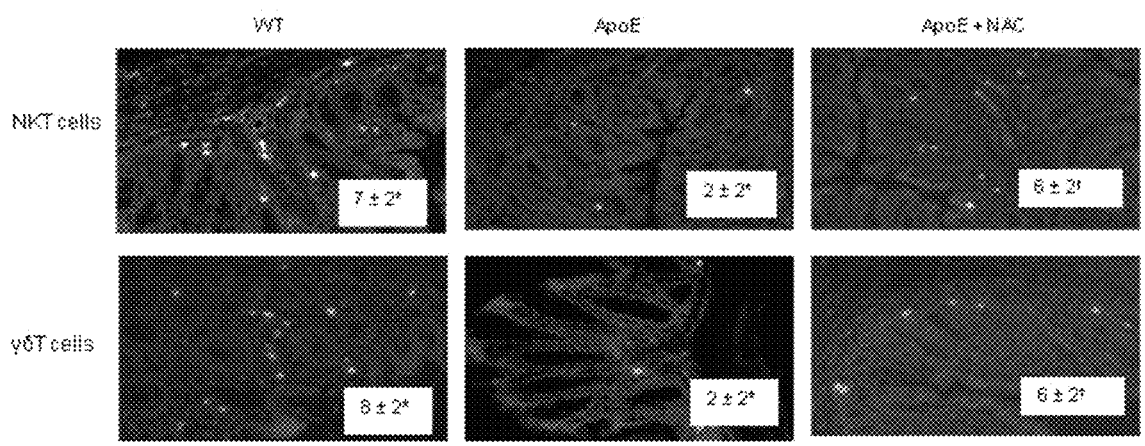
Figure 51A:
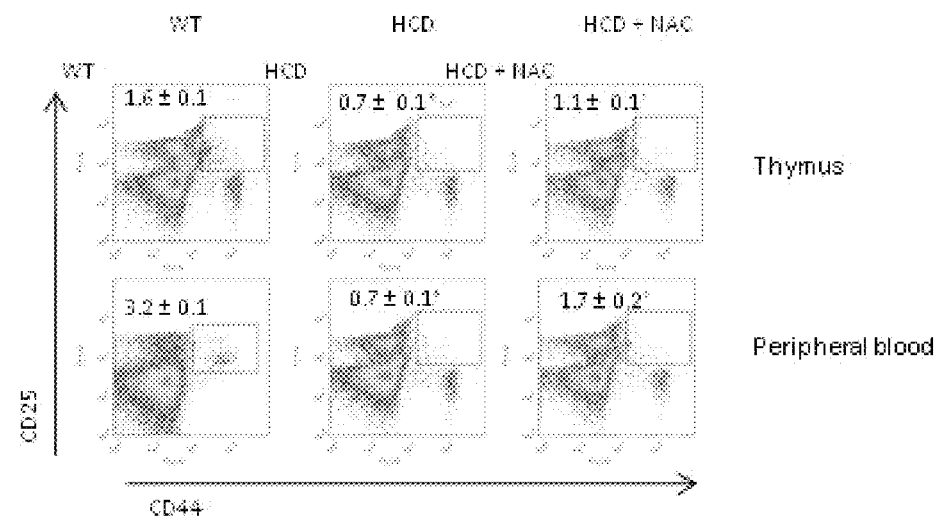
FIGS. 51A-51C. HCD have reduced differentiation of NKTcells and γδT cells, and reduced resident populations of these cells in the healthy colon.
Figure 51B:
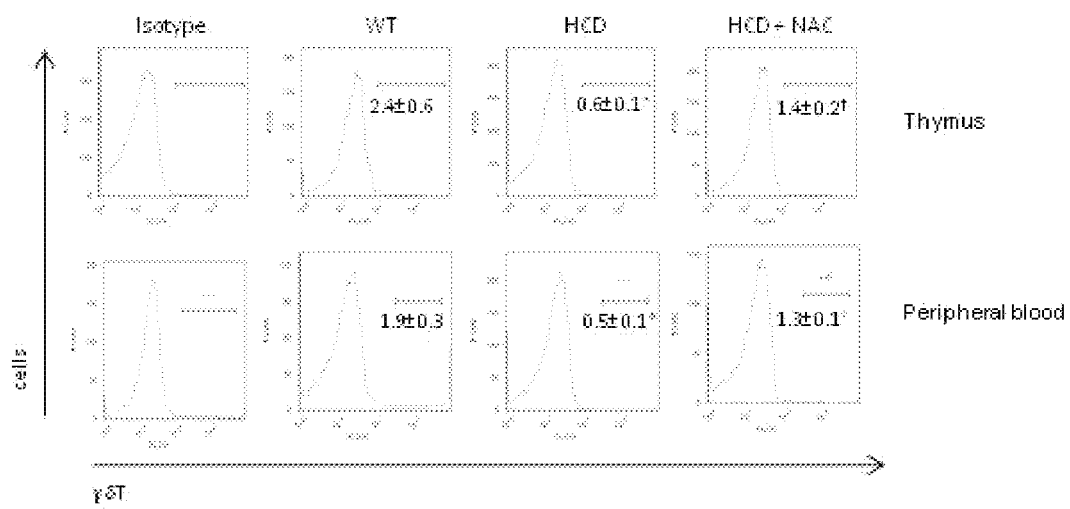
Figure 51C:
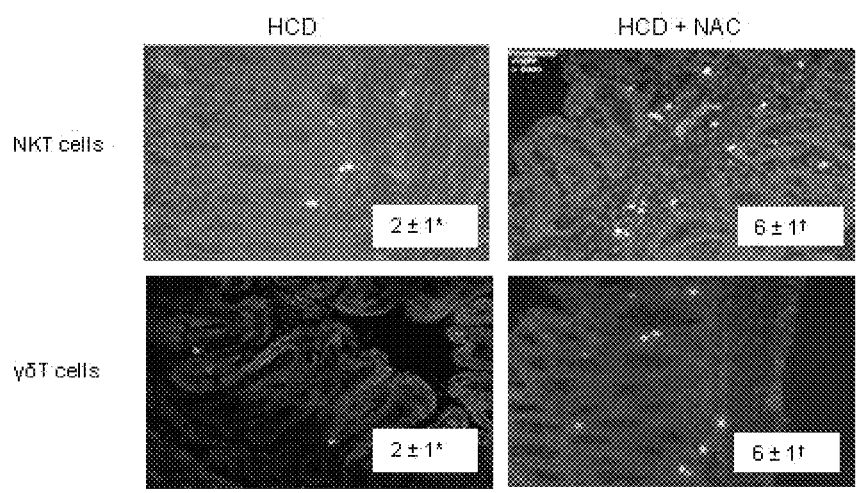

However, the percentages of γδT cells and NKT cells in the thymus and peripheral blood were significantly less in hypercholesterolemic mice than in WT mice. These effects were reversed by in vivo treatment with NAC for 4 weeks (FIGS. 50A and 50B, and FIGS. 51A and 51B). FIGS. 50A-50C show ApoE$^{-/-}$ mice have reduced differentiation of NKTcells and γδT cells, and reduced resident populations of these cells in the healthy colon. (A) The number of NKT cells in the thymus and peripheral blood were significantly lower in ApoE$^{-/-}$ mice than in WT mice and these effects were reversed by in vivo NAC treatment. (B) The number of γδT cells in the thymus and peripheral blood were significantly lower in ApoE$^{-/-}$ mice than in WT mice and these effects were reversed by in vivo NAC treatment. (C) The numbers of resident NKT and γδT cells within the healthy colon were significantly lower in ApoE$^{-/-}$ mice than in WT mice and these effects were reversed by in vivo treatment. Numbers with representative FACS and in photomicrograph inserts are the m±sd for each analysis. n=5; *p<0.05 vs. WT, †p<0.05 for NAC-treated vs. ApoE$^{-/-}$. FIGS. 51A-51C show HCD have reduced differentiation of NKTcells and γδT cells, and reduced resident populations of these cells in the healthy colon. (A) The number of NKT cells in the thymus and peripheral blood were significantly lower in HCD mice than in WT mice and these effects were reversed by in vivo NAC treatment. (B) The number of γδT cells in the thymus and peripheral blood were significantly lower in HCD mice than in WT mice and these effects were reversed by in vivo NAC treatment. (C) The numbers of resident NKT and γδT cells within the healthy colon were significantly lower in HCD mice than in WT mice and these effects were reversed by in vivo treatment. Numbers with representative FACS and in photomicrograph inserts are the m±sd for each analysis.

n=5; *p<0.05 vs. WT, †p<0.05 for NAC-treated vs. HCD.

NKT and γδT cells are also part of the gut-associated immune system, and a portion of these cells reside in the gut mucosa and submucosa. The status of these resident populations was evaluated by immunofluorescent staining of healthy colon and, in a pattern reminiscent of the changes in thymus and peripheral blood, found significantly fewer NKT and γδT cells in this tissue as well. Also as before, in vivo treatment of hypercholesterolemic mice with NAC for 4 weeks restored the colonic resident populations of NKT and γδT cells to WT levels (FIGS. 50C and 51C).

NKT and γδT Cells Participate in Immunosurveillance of AOM-Induced Colorectal Neoplasia and are Reduced in Polyps from Hypercholesterolemic Mice:

To confirm that NKT and γδT cells participate in tumor immunosurveillance specifically relevant to AOM-induced colorectal neoplasia, the effects of AOM was determined on mice genetically deficient in these cells types. γδTCR$^{-/-}$ mice, which lack γδT cells, and CD1$^{-/-}$ mice, which lack NKT cells were treated with AOM for 10 weeks. Both of these groups of mice displayed significantly greater incidence and histological severity of AOM-induced colorectal neoplasia than did the relevant control strain of mice (FIGS. 52A-52D). FIGS. 52A-52H show NKT and γδT cells participate in immunosurveillance of AOM-induced colorectal neoplasia and are reduced in polyps from hypercholesterolemic mice. FIGS. 52A-52D show that γδT$^{-/-}$ mice, who are genetically deficient in γδT cells, and CD1$^{-/-}$ mice, who are genetically deficient in NKT cells, had a higher incidence and a greater histological severity of AOM-induced colorectal neoplasia than their strain specific controls (C57Bl/6 and Balb/c, respectively). Horizontal bars in panels A and C represent the mean for each group; p<0.01 vs. WT; *p<0.005 vs. WT. The numbers provided in panels B and D represent the absolute number of polyps for each histological grade within each group. FIGS. 52E-52F show that there were fewer NKT and γδT cells in AOM-induced colorectal polyps histologically classified as hyperplasia, grade 1 adenoma (1+), or grade 2 adenoma (2+) in ApoE$^{-/-}$ and HCD mice than in WT mice. Pretreatment with NAC for 4 weeks prior to AOM administration reversed these effects. m±sd; n=5; *p<0.05 vs. WT; **p<0.01 vs. WT; †p<0.05 for NAC-treated vs. ApoE$^{-/-}$ or HCD.

It was next determined the numbers of NKT and γδT cells in AOM-induced colorectal polyps in hypercholesterolemic and WT mice. Polyps that displayed lower histological grades, e.g., hyperplasia, or 1+ or 2+ adenoma were studied; thus, it is believed that to be effective tumor immunosurveillance systems should be present in early forms of colorectal neoplasia. There were significantly fewer NKT and γδT cells in all polyps from hypercholesterolemic mice than from WT mice (FIGS. 52E-52H). In vivo treatment of hypercholesterolemic mice with NAC for 4 weeks significantly increased the numbers of NKT and γδT cells in all grades of AOM-induced polyps from hypercholesterolemic mice.

Figure 53A:
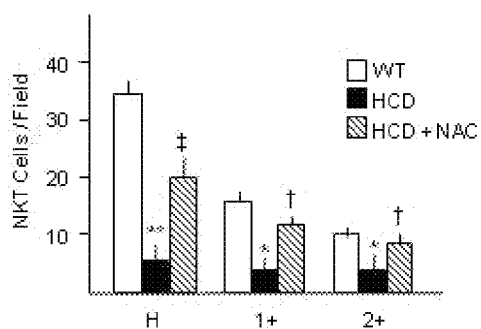
FIGS. 53A-53E. HSCs harvested from WT recipient mice 12 weeks after transplantation with ApoE$^{-/-}$-derived HSCs retain evidence of oxidant stress.
Figure 53A:
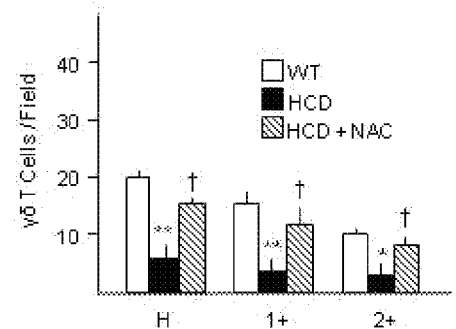
Figure 53A:
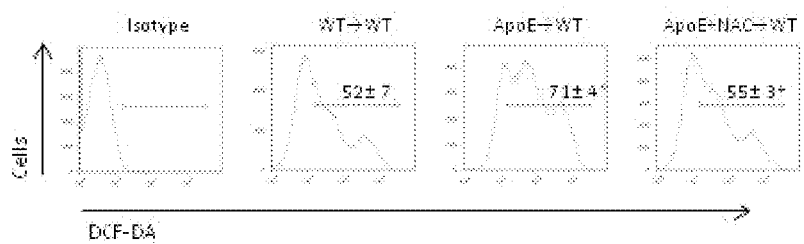

HSCs Harvested from WT Recipient Mice 12 Weeks after Transplantation with ApoE$^{-/-}$-Derived HSCs Retain Evidence of Oxidant Stress:

It was next determined the oxidant status of HSCs transplanted into WT mice. To this end, lethally irradiated WT mice were transplanted with HSCs from WT or ApoE$^{-/-}$ mice, or with HSCs harvested from ApoE$^{-/-}$ mice pretreated with NAC for 4 weeks. Surprisingly, HSCs harvested from WT recipient mice 12 weeks after transplantation with ApoE$^{-/-}$-derived donor cells displayed persistence oxidant stress as evidenced by significantly greater DCF-DA staining than WT mice transplanted with WT donor cells, or with HSCs from NAC-pretreated ApoE$^{-/-}$ donor mice (FIG. 53A). FIGS. 53A-53E show HSCs harvested from WT recipient mice 12 weeks after transplantation with ApoE$^{-/-}$-derived HSCs retain evidence of oxidant stress. (A) The percentage of HSC with DCF-DA staining >isotype was higher in the ApoE$^{-/-}$≥WT transplant group than in the ApoE$^{-/-}$+NAC→WT or the WT→WT transplant groups, indicating persistence of HSC oxidative stress despite 12 weeks in a normal (WT) environment. (B,C) The percentage of HSC and T-cell progenitor cells in total bone marrow cells were higher in the ApoE$^{-/-}$→WT transplant group than in the ApoE$^{-/-}$+NAC→WT or the WT→WT transplant groups. (D,E) The percentage of γδT cells and NKT cells in the thymus and peripheral blood were less in the ApoE$^{-/-}$→WT transplant group than in the ApoE$^{-/-}$+NAC→WT or the WT→WT transplant groups. Numbers in each representative FACS analysis are the m±sd for that group; n=5; *p<0.05 vs. WT→WT group; †p<0.05 for ApoE+NAC→WT vs. Apoe→WT.

Figure 53B:
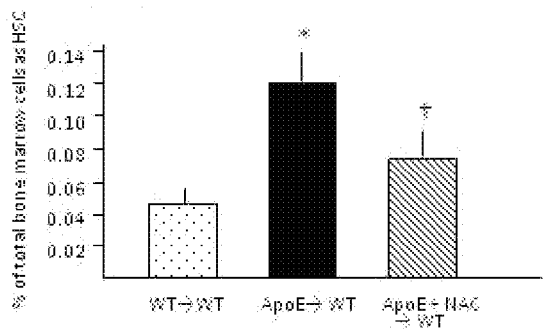
Figure 53C:
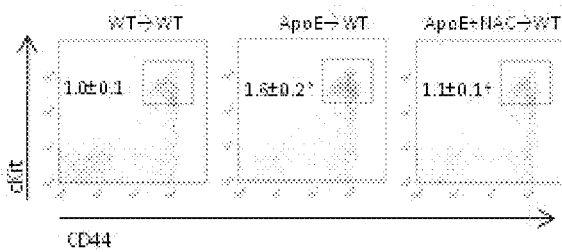
Figure 53D:
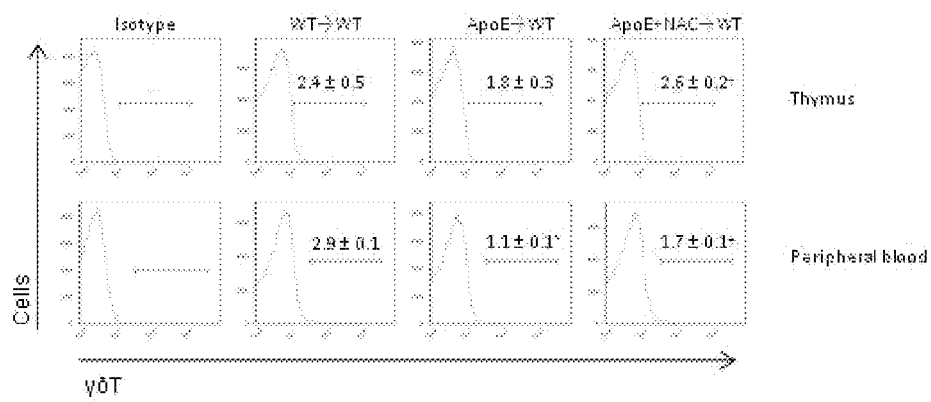
Figure 53E:
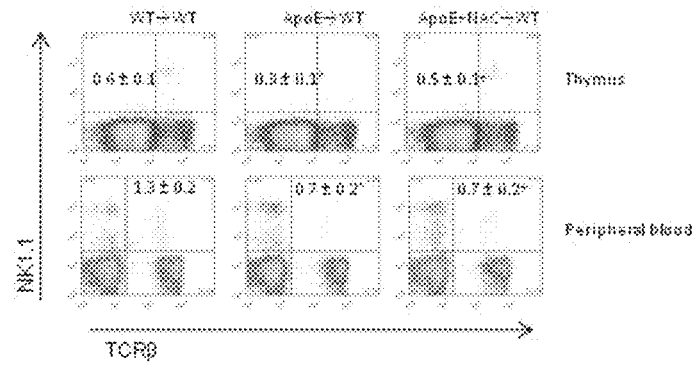

The percentage of total bone marrow cells that manifest the surface phenotype of HSCs, e.g., cKit$^+$Sca-1$^+$CD90.1$^{low}$Lin$^-$ cells was significantly greater in WT recipient mice transplanted with ApoE$^{-/-}$-derived HSCs, as was the number of bone marrow cKit$^+$, CD44$^+$ pro-T cells (FIGS. 53B and 53C). The number of DN1, DN2, and DN3 cells in the thymus, and the number of CD4, CD8, or double positive T cells in the peripheral blood were not different among these study groups. However, the percentage of γδT cells in peripheral blood, as well as the percentages of NKT cells in the thymus and peripheral blood were significantly less in WT recipients transplanted with ApoE$^{-/-}$-derived HSCs than WT mice transplanted with WT HSCs, or HSCs harvested from NAC-pretreated ApoE$^{-/-}$ donor mice (FIGS. 53D and 53E).

Figure 58:
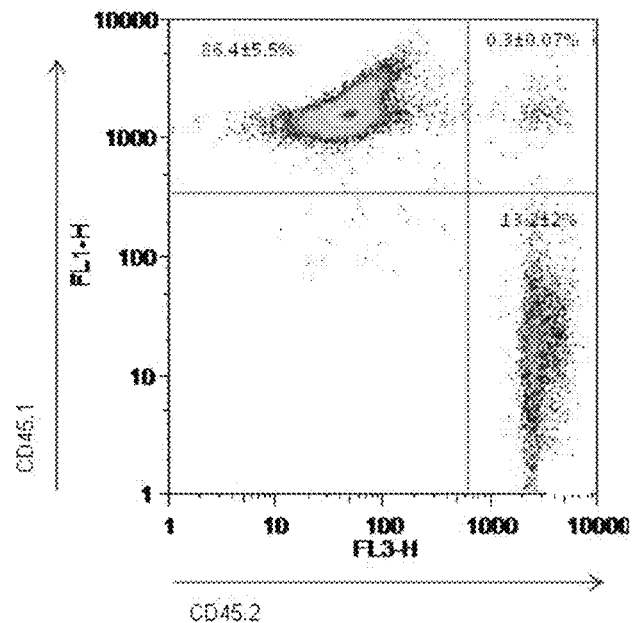
FIG. 58. HSC transplantation into WT recipients led to repopulation of the thymus with daughter cells from the transplanted HSCs.

Chimeric WT Mice Transplanted with ApoE$^{-/-}$ HSCs Show Increased Susceptibility to AOM-Induced Colorectal Neoplasia:

To prove unambiguously that HSC oxidant stress was the principal underlying cause of the higher incidence of colorectal neoplasia and reduced NKT and γδT cell number in hypercholesterolemic mice, chimeric mice were generated by transplanting HSCs from ApoE$^{-/-}$ or WT mice to lethally irradiated WT recipients. Twelve weeks after transplantation of HSCs from WT CD45.1⁺ to congenic WT CD45.2⁺ mice, 86±6% of the total thymocyte population stained for CD45.1⁺, confirming thymocyte repopulation with cells derived from transplanted HSCs (FIG. 58), whereas the serum cholesterol of the recipient mice remained at level seen in WT mice (FIG. 57B). FIG. 58 shows HSC transplantation into WT recipients led to repopulation of the thymus with daughter cells from the transplanted HSCs. After transplant of HSCs from CD45.1 WT donor mice to CD45.2 WT recipient mice, the majority of thymocytes expressed CD45.1. A single FACS dot blot is shown that is representative of 3 replications. WT recipient mice were treated with AOM beginning 12 weeks after transplantation and this treatment was continued for 10 weeks. The incidence and severity of AOM-induced colorectal neoplasia was significantly greater in WT recipient mice receiving ApoE$^{-/-}$ HSCs than in those transplanted with WT HSCs (FIGS. 54A and 54B). FIGS. 54A-54D show chimeric WT mice transplanted with ApoE$^{-/-}$ HSCs show increased susceptibility to AOM-induced colorectal neoplasia. (A) The number of AOM-induced colorectal polyps per mouse was higher in ApoE$^{-/-}$→WT transplant group than in the WT→WT transplant group. Horizontal bars in represent the mean; n=5; *p<0.05 vs WT→WT. (B) The histological severity of these polyps was greater in the ApoE$^{-/-}$→WT transplant group than in the WT→WT transplant groups. The numbers represent the absolute number of polyps for each histological grade within each group. (C,D) There were fewer NKT and γδT cells in AOM-induced colorectal polyps histologically classified as hyperplasia, grade 1 adenoma (1+), or grade 2 adenoma (2+) in the ApoE$^{-/-}$→WT transplant group than in the WT→WT transplant group. m±sd; n=5; *p<0.05, **p<0.01 vs. WT→WT group. Moreover, the number of NKT and γδT cells present in colorectal polyps was significantly lower in recipients transplanted with ApoE$^{-/-}$-derived HSCs than in recipients transplanted with WT HSCs (FIGS. 54C and 54D).

Notch1 Expression in HSCs, Early T Progenitor Cells, and Thymocytes Differs Between Hypercholesterolemic Mice and WT Mice:

The Notch signaling pathways are expressed extensively in the hematopoietic system. Notch signaling dominates the regulation of proliferation, self-renewal, and lineage commitment of HSCs in the bone marrow as well as their downstream differentiation and maturation in the thymus (23-28). Moreover, Notch1 appears to participate in the differentiation of the unique T cell subsets, NKT cells and γδT cells (29-32). In this context, the mechanistic basis between HSC oxidant stress and aberrant lineage specification toward NKT and γδT cells in hypercholesterolemic mice was evaluated by determining Notch expression in HSC, bone marrow T cell progenitors, and immature thymocytes. It was found that Notch1 expression was significantly greater in HSCs and T progenitor cells (cKit⁺,CD44⁺) harvested from ApoE$^{-/-}$ and HCD mice than from WT mice. Notch1 expression was evaluated in HSCs, early T progenitor cells, and thymocytes differs between ApoE$^{-/-}$ and WT mice. Notch1 expression was higher in HSCs and T progenitor cells harvested from ApoE$^{-/-}$ mice than from WT mice. Conversely, Notch1 expression was significantly less in thymic DN2, DN3, DN4, and DP cells harvested from ApoE$^{-/-}$ mice than from WT mice. These differences were significantly reversed by in vivo treatment of ApoE$^{-/-}$ mice with NAC for 4 weeks. The numbers within each box represent the mean percentage of cells that manifest Notch1 staining above the isotype antibody threshold. m±sd; n=8 mice per group; *p<0.05 vs. WT, †p<0.05 for NAC-treated vs. ApoE$^{-/-}$. Notch1 expression also was evaluated in HSCs, early T progenitor cells, and thymocytes differs between HCD and WT mice. Notch1 expression was higher in HSCs and T progenitor cells harvested from HCD mice fed than from WT mice. Conversely, Notch1 expression was less in thymic DN2, DN3, DN4, and DP cells harvested from HCD mice than from WT mice. These differences were significantly reversed by in vivo treatment of HCD mice with NAC for 4 weeks. The numbers within each box represent the mean percentage of cells that manifest Notch1 staining above the isotype antibody threshold. m±sd; n=8 mice per group; *p<0.05 vs. WT, †p<0.05 for NAC-treated vs. HCD.

However, the inverse pattern was observed in DN2 (CD44⁺CD25⁺), DN3 (CD44⁻CD25⁺), and double positive (CD4⁺CD8⁺) thymocytes, wherein Notch1 expression was significantly lower in hypercholesterolemic mice than WT mice. Importantly, all of the differences in Notch1 expression in cells from hypercholesterolemic mice were significantly reversed by in vivo treatment with NAC for 4 weeks, a finding which implicates oxidant stress in the changes in Notch1 expression in these cells. Expression of the other Notch isoforms or the Notch ligands were not different among the three groups of mice (data not shown).

Figure 55A:
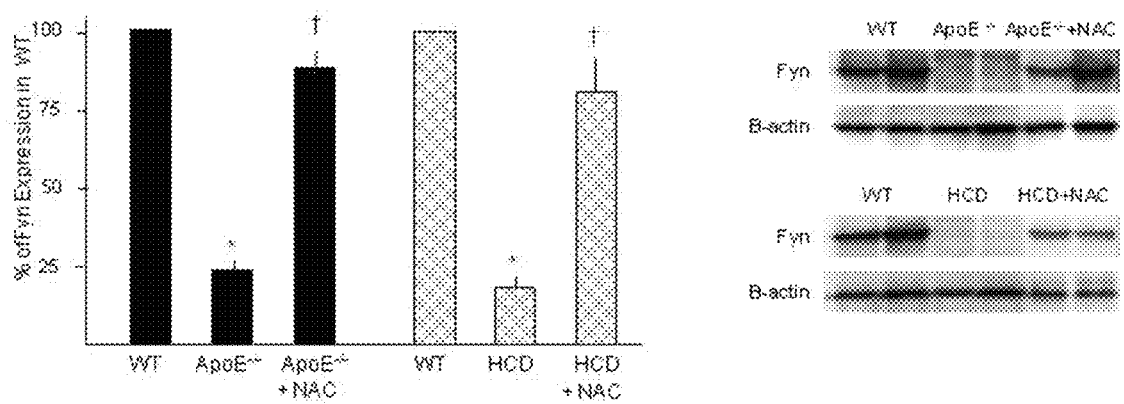
FIGS. 55A-55C. Thymocyte Fyn expression is reduced in hypercholesterolemic mice.
Figure 55B:
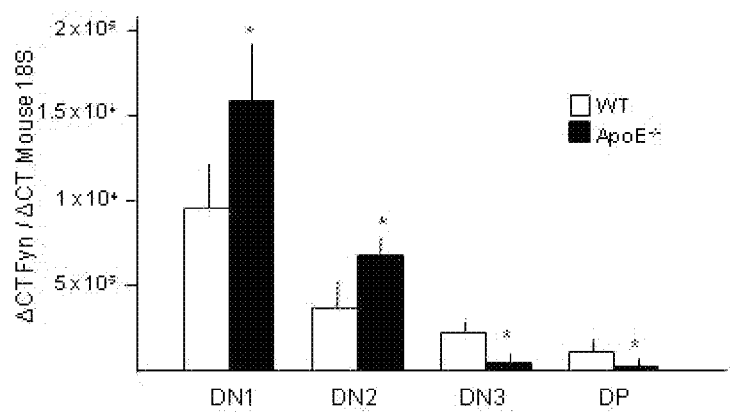
Figure 55C:
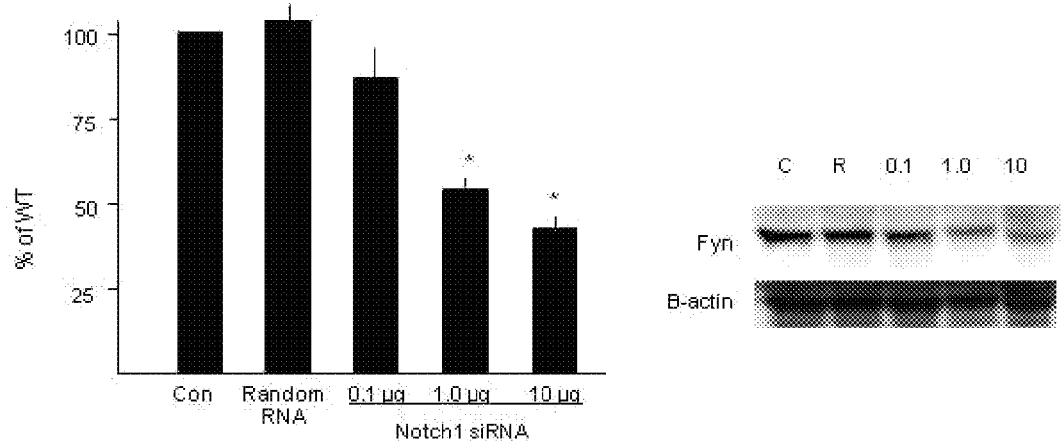
Figure 56:
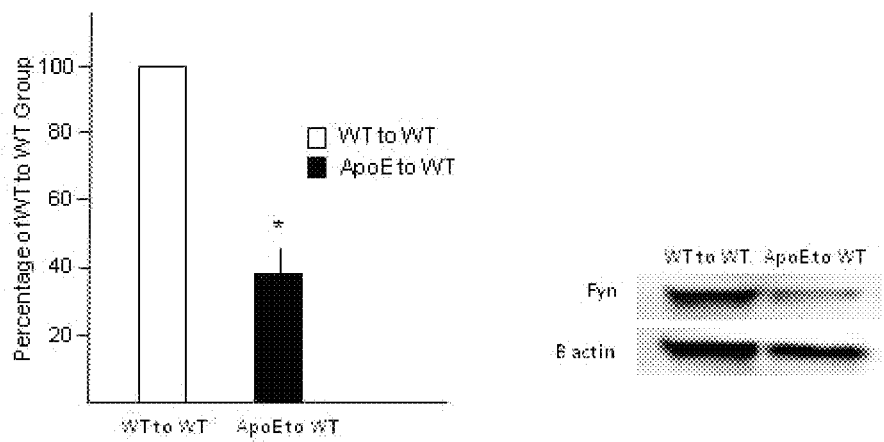
FIG. 56. Fyn expression is reduced in thymocytes harvested from WT recipient mice 12 weeks after transplantation with ApoE$^{-/-}$-derived HSCs.

Fyn Expression in DN3 and DP Thymocytes is Lower in Hypercholesterolemic Mice than in WT Mice:

Fyn, a member of the Src family of tyrosine kinases, is a critical participant in NKT cell development (33,34). Expression of Fyn in lysates from the total thymocyte population was significantly less in ApoE$^{-/-}$ and HCD mice than in WT mice, and was restored in vivo by treatment with NAC (FIG. 55A). FIGS. 55A-55C show Thymocyte Fyn expression is reduced in hypercholesterolemic mice. (A) Fyn expression in the total thymocyte population was less in ApoE$^{-/-}$ and HCD mice than in WT mice, and this effect was reversed in vivo by treatment with NAC. m±sd, †<0.05 vs. ApoE$^{-/-}$ or HCD, n=4-6 mice per group. Representative western blots from 3 mice in each group, all run on the same gel, are shown. (B) Expression of Fyn mRNA was significantly greater in DN1 and DN2 thymocytes from ApoE$^{-/-}$ than from WT mice. However, in DN3 and DN4 thymocytes, Fyn mRNA expression was less in ApoE$^{-/-}$ than in WT mice. m±sd, *p<0.05 vs. WT; n=4 mice per group. (C) siRNA for Notch1 reduced mRNA expression of Fyn in WT thymocytes in vitro, with a threshold observed at 1.0 μg siRNA. m±sd, n=3 mice; *p<0.05 vs. random RNA. A representative western blot showing a single experiment run on the same gel is shown. Fyn mRNA was significantly greater in DN1 and DN2 thymocytes from ApoE$^{-/-}$ mice than from WT mice. However, the inverse was noted in DN3 and double positive thymocytes, wherein Fyn mRNA expression was significantly lower in ApoE$^{-/-}$ mice (FIG. 55B). In in vitro experiments, siRNA knockdown of Notch1 in WT thymocytes caused a significant, dose-dependent reduction in Fyn expression (FIG. 55C). These findings indicate that Notch1 and Fyn expression are linked, and that the reduced NKT expression in hypercholesterolemic mice is due, in part, to the Notch1 dependent reduction of Fyn expression in thymocytes. Finally, Fyn expression was determined in the total thymocyte population from WT recipient mice transplanted with ApoE$^{-/-}$- or WT-derived HSCs. Thymocyte Fyn expression in WT recipients transplanted with ApoE$^{-/-}$-derived HSCs was less than half that observed in WT recipients transplanted with WT-derived HSCs (FIG. 56). FIG. 56 shows Fyn expression is reduced in thymocytes harvested from WT recipient mice 12 weeks after transplantation with ApoE$^{-/-}$-derived HSCs. Fyn expression in thymocytes from the Apoe→WT group was less than in the WT→WT group. m±sd; n=4; *p<0.05 vs. WT→WT group. A western blot showing representative experiments run on a single gel is shown.

Accordingly, in some aspects, the experiments show, for the first time, that hypercholesterolemia induces oxidant stress, impairs differentiation of NKT and γδT cells, and increases susceptibility to experimentally induced colon cancer. Three findings strongly suggest that HSC oxidant stress is a critical basis for the increased vulnerability of hypercholesterolemic mice to experimental colon cancer: first, in vivo pretreatment with the antioxidant NAC significantly reversed HSC oxidant stress, restored NKT and γδT cell differentiation, and reduced susceptibility to AOM-induced neoplasia. Second, the roles of NKT and γδT cells in tumor immunosurveillance are well established [14-19, 35]. Moreover, it was determined that susceptibility to AOM-induced colorectal neoplasia is increased in mice harboring genetic elimination of these unique T cell subsets. Third, WT recipient mice transplanted with HSCs from ApoE$^{-/-}$ mice recapitulated the ApoE$^{-/-}$ phenotype vis-à-vis HSC oxidant stress, aberrant NKT and γδT cell differentiation, and increased susceptibility to experimental colon cancer. The effects of hypercholesterolemia-induced HSC oxidant stress confers a clear and physiologically relevant disadvantage. These findings present a novel pathophysiological paradigm wherein hypercholesterolemia contributes to disease susceptibility via induction of HSC oxidant stress.

The concept of tumor immunosurveillance, first proposed by Erlich [21] and modified by Burnet [22] states that the immune system recognizes and kills nascent tumor cells, as well as reduces the growth rate of tumors in immunocompetent hosts. NKT cells [17,18,35] and γδT cells [14,19], immune cells that bridge the innate and adaptive immune systems [14,15], are critical participants in tumor immunosurveillance. γδT cells that reside in the colon express surface NKG2D receptors that recognize tumor cells that express NKG2 ligands including colon cancer cells [35]. NKT cells, also resident in the colon, are a CD1d-restricted T cell subset which express a biased TCR repertoire that recognizes glycolipid antigens [16]. NKT cells produce IFN-γ and TNF in response to primary stimulation, factors critical in antitumoricidal activity [17,18]. It is clear, however, that the phenomenon of tumor immunosurveillance involves both the innate and adaptive immune systems, e.g., it entails more than NKT and γδT cells. In this context, the finding of reduced NKT and γδT cells in the healthy colon and in colonic polyps from hypercholesterolemic mice does not provide a sufficient basis to conclude that these reductions were the sole reason for the increased susceptibility to experimental colon cancer in these mice. However, the present findings, particularly the transplant data, strongly argue for the importance of HSC oxidant stress in disrupting tumor immunosurveillance in the colon.

The Notch family, especially Notch1, dominates the regulation of T cell lineage commitment of HSCs in bone marrow as well as their downstream differentiation and maturation in the thymus [23-26]. γδT cells arise from DN3 thymocytes, the point of T cell development at which specification to αβ or γδ TCR is initiated [30]. Notch signaling directs T precursor differentiation through the DN2 and DN3 stages of development and has also been implicated in the γδT lineage fate decision and proliferation; thus, although γδT cells can develop in the absence of Notch signaling in p-Tα deficient mice, their numbers increase in the presence of Notch ligand [29,30]. NKT cells, which arise from CD4$^+$CD8$^+$ thymocytes [32], require the Src kinase family member Fyn for development [34,35]. The present findings demonstrate a linkage between Notch1 and Fyn expression in thymocytes, as evidenced by the concomitant reductions in Notch1 and Fyn in these cells, as well as by the effects of Notch1 siRNA knockdown on Fyn expression in thymocytes. In some embodiments, the changes in Notch1 and Fyn expression participate in causing the reduced differentiation of NKT and γδT cells in hypercholesterolemic mice.

A surprising finding was the sustained presence of oxidant stress in HSCs harvested from WT recipient mice 12 weeks after transplantation with ApoE$^{-/-}$-derived HSCs. Hence, the oxidant stress present in the original transplanted HSCs was sustained in the daughter cells arising from subsequent divisions, despite the absence of environmental oxidant stress in the WT recipient. This persistence of HSC oxidant stress might indicate that hypercholesterolemia may affect HSC gene expression, specifically reducing expression of endogenous antioxidant systems such as superoxide dismutase and glutathione peroxidase, reducing the capacity of the HSC to restore redox balance. Importantly, however, HSC oxidant stress, as well as the effects on NKT and γδT cell differentiation that may have resulted from HSC oxidant stress by could be fully reversed by NAC. This finding indicates that the effects of hypercholesterolemia on HSC redox balance are correctable.

According to aspects of the invention, the role of HSC oxidant stress as a critical determinant of these changes was clearly evidenced by their reversal following in vivo NAC treatment of hypercholesterolemic mice, as well as by their duplication in WT recipient mice following transplantation with HSCs derived from ApoE$^{-/-}$ mice.

In summary, the present analysis provides evidence for a novel mechanism whereby hypercholesterolemia may induce significant pathophysiology that is unrelated to its effect on blood vessel homeostasis and atherosclerosis. HSC oxidant stress is clearly present in hypercholesterolemic mice and this effect occurs in mice made hypercholesterolemic by diet or by genetic deficiency of apolipoprotein E. This HSC oxidant stress leads to aberrant differentiation of NKT and γδT cells, and increases susceptibility to experimental colon cancer.

References
1. Chyou P H, Eaker E D. Serum cholesterol concentrations and all-cause mortality in older people. *Age Ageing.* 2000; 29(1):69-74.
2. McMichael A J, Jensen O M, Parkin D M, Zaridze D G. Dietary and endogenous cholesterol and human cancer. *Epidemiol Rev.* 1984; 6:192-216.
3. Notarnicola M, Altomare D F, Correale M, Ruggieri E, D'Attoma B, Mastrosimini A, Guerra V, Caruso M G. Serum lipid profile in colorectal cancer patients with and without synchronous distant metastases. *Oncology.* 2005; 68(4-6):371-374.
4. Suzuki K, Ito Y, Wakai K, Kawado M, Hashimoto S, Toyoshima H, Kojima M, Tokudome S, Hayakawa N, Watanabe Y, Tamakoshi K, Suzuki S, Ozasa K, Tamakoshi A, and Japan Collaborative Cohort Study Group. Serum oxidized low-density lipoprotein levels and risk of colorectal cancer: A case-control study nested in the Japan Collaborative Cohort Study. *Cancer Epidemiol Biomarkers Prev.* 2004; 13:1781-1787.
5. Niho N, Mutoh M, Takahashi M, Tsutsumi K, Sugimura T, Wakabayashi K. Concurrent suppression of hyperlipidemia and intestinal polyp formation by NO-1886, increasing lipoprotein lipase activity in Min mice. *Proc Natl Acad Sci.* 2005; 102(8):970-2974.
6. Niho N, Takahashi M, Kitamura T, Shoji Y, Itoh M, Noda T, Sugimura T, Wakabayashi K. Concomitant suppression of hyperlipidemia and intestinal polyp formation in Apc-deficient mice by peroxisome proliferator-activated receptor ligands. *Cancer Res.* 2003; 63(18):6090-6095.
7. Agarwal B, Rao C V, Bhendwal S, Ramey W R, Shirin H, Reddy B S, Holt P R. Lovastatin augments sulindac-induced apoptosis in colon cancer cells and potentiates chemopreventive effects of sulindac. *Gastroenterology.* 1999; 117(4):838-847.
8. Cruse P, Lewin M, Clark C G. Dietary cholesterol is co-carcinogenic for human colon cancer. *Lancet.* 1979; 1(8119):752-755.
9. De Bont N, Netea M G, Demacker P N, Verschueren I, Kullberg B J, van Dijk K W, van der Meer J W, Stalenhoef A F. Apolipoprotein E knock-out mice are highly susceptible to endotoxemia and *Klebsiella pneumoniae* infection. *J Lipid Res.* 1999; 40(4):680-685.
10. Vonk A G, De Bont N, Netea M G, Demacker P N, van der Meer J W, Stalenhoef A F, Kullberg B J. Apolipoprotein-E-deficient mice exhibit an increased susceptibility to disseminated candidiasis. *Med Mycol.* 2004; 42(4):341-348.
11. Ward J M, Yamamoto R S, Brown C A. Pathology of intestinal neoplasms and other lesions in rats exposed to azoxymethane. *J Natl Cancer Inst.* 1973; 51(3):1029-1039.
12. Vogel R A. Coronary risk factors, endothelial function, and atherosclerosis: a review. *Clin Cardiol.* 1997; 20(5): 426-432.
13. Salvayre R, Auge N, Benoist H, Negre-Salvayre A. Oxidized low-density lipoprotein-induced apoptosis. *Biochem Biophys Acta.* 2002; 1585(2-3):213-221.
14. Girardi M. Immunosurveillance and immunoregulation by γδ T cells. *J Invest Dermatol.* 2006; 126(1):25-31.
15. Taniguchi M, Seino K, Nakayama T. The NKT cell system: bridging innate and acquired immunity. *Nat Immunol.* 2003; 4(12):1165-1165.
16. Swan J, Crowe N Y, Hayakawa, Y, Godfrey D I, Smyth M J. Regulation of antitumour immunity by CD1d-restricted NKT cells. *Immunol Cell Biol.* 2004; 82:323-331.
17. Crowe N Y, Smyth M J, Godfrey D I. A critical role for natural killer T cells in immunosurveillance of methyl-cholanthrene-induced sarcoma. *J Exp Med.* 2002; 196(1): 119-127.
18. Smyth M K, Thia K Y, Street S E, Cretney E, Trapani J A, Taniguchi M, Kawano T, Pelikan S B, Crowe N Y, Godfrey D I. Differential tumor surveillance by natural killer (NK) and NKT cells. *J Exp Med.* 2000; 191(4):661-668.
19. Todaro, M. et al. Efficient killing of human colon cancer stem cells by γδT lymphocytes. *J. Immunol.* 182, 7287-7296 (2009).
20. Swann J B, Smyth M J. Immune surveillance of tumors. *J Clin Invest.* 2007; 117(5):1137-1146.
21. Ehrlich, P. Ueber den jetzigen stand der Karzinomforschung. *Ned. Tijdschr. Geneeskd.* 5, 273-290 (1909).
22. Burnet, F. M. The concept of immunological surveillance. *Prog. Exp. Tumor Res.* 13:1-27 (1970).
23. Radtke F, Wilson A, Mancini S J, MacDonald H R. Notch regulation of lymphocyte development and function. *Nat Immunol.* 2004; 5(3):247-253.
24. Radtke F, Wilson A, Stark G, Bauer M, van Meerwijk J, MacDonald H R, Aguet M. Deficient T cell fate specification in mice with an induced inactivation of Notch1. *Immunity* 1999; 10(5):547-558.
25. Osborne B A, Minter L M. Notch signaling during peripheral T-cell activation and differentiation. *Nat Re. Immunol.* 2007; 7(1):64-75.
26. Wilson A, MacDonald H R, Radtke F. Notch1-deficient common lymphoid precursors adopt a B cell fate in the thymus. *J. Exp. Med.* 2001; 194(7):1003-1012.
27. Lehar, S. M., Dooley, J., Farr, A. G., Bevan, M. J. Notch ligands Delta1 and Jagged1 transmit distinct signals to T-cell precursors. *Blood* 105, 1440-1447 (2005).
28. Schmidt, T., Zúñigaü-Pflücker, J. C. Induction of T cell development from hematopoietic progenitor cells by Delta-like-1 in vitro. Immunity 17, 749-756 (2002).
29. Washburn T, Schweighoffer E, Gridley T, Chang D, Fowlkes B J, Cado D, Robey E. Notch activity influences the αβ versus γδ T cell lineage decision. *Cell* 1997; 88(6):833-843.
30. Rothenberg E. V. Negotiation of the T lineage fate decision by transcription-factor interplay and microenvironmental signals. *Immunity* 26, 690-702 (2007).
31. Ciofani, M., Knowles, G. C., Wiest, D. L., von Boehmer, H., Zúñiga-Pflücker, J. C. Stage-specific and differential notch dependency at the αβ and γδ T lineage bifurcation. *Immunity* 25, 106-116 (2006).
32. Bendelac A, Rivera M N, Park S H, Roark J H. Mouse CD1-specific NK1 T cells: development, specificity, and function. *Annu Rev Immunol.* 1997; 15:535-562.
33. Ebrel G, Lowin-Kropf B, MacDonald H R. Cutting edge: NKT cell development is selectively impaired in Fyn-deficient mice. *J Immunol.* 1999; 163(8):4091-4094.
34. Gadue P, Morton N, Stein P L. The Src family tyrosine kinase Fyn regulates natural killer T cell development. *J Ex. Med.* 1999; 190(8):1189-1195.
35. Bryceson, Y. T., Ljunggren, H-G. Tumor cell recognition by the NK cell activating receptor NKG2D. *Eur. J Immunol.* 38, 2957-2968 (2008).

Example 7

Type 2 Diabetes Causes Oxidative Stress of Hematopoietic Stem Cells (HSCs) that Impairs Wound Healing.

It was hypothesized that increased oxidative stress in the HSC of Type 2 diabetic mice lead to unbalanced HSC differentiation, and decreased monocytes concentration. This can cause impaired wound healing in Type 2 diabetic mice.

Figure 59:
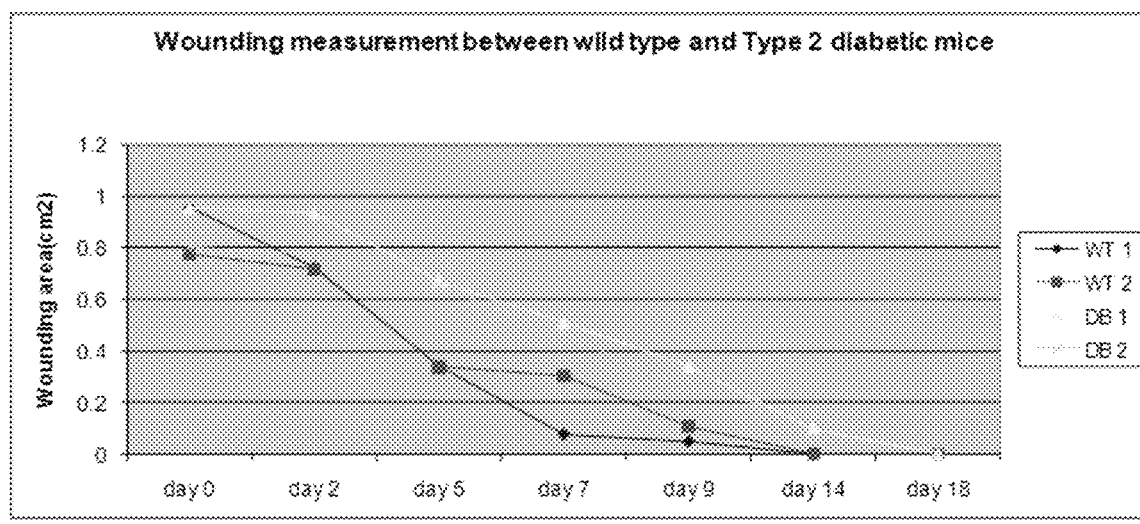
FIG. 59. Wounding measurement between wild type and Type 2 diabetic mice.
Figure 60:
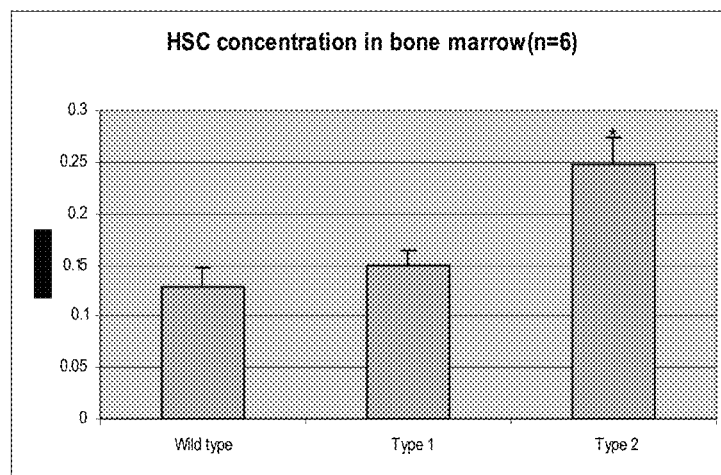
FIG. 60. HSC concentration in bone marrow (n=6) *, P<0.05 vs Wild Type and Type 1.
Figure 61:
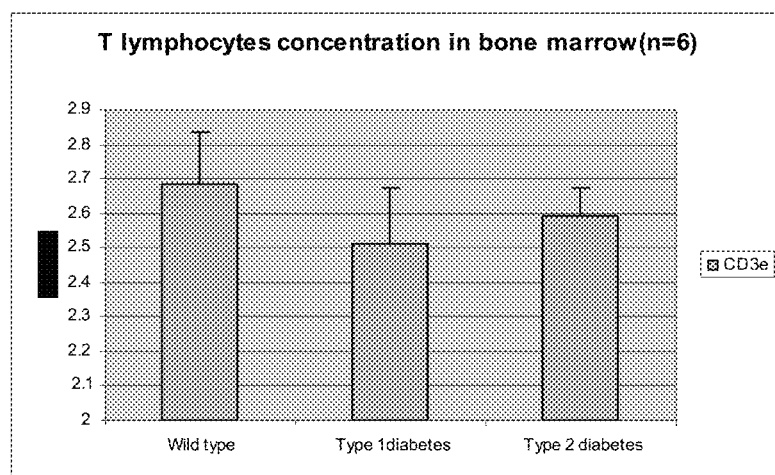
FIG. 61. T lymphocytes concentration in bone marrow (n=6).
Figure 62:
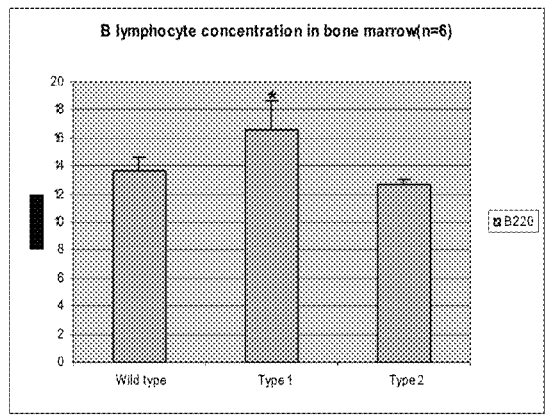
FIG. 62. B Lymphocyte concentration was increased in the bone marrow of Type 1 diabetic mice *, p<0.05 vs Wild Type and Type 2.
Figure 63:
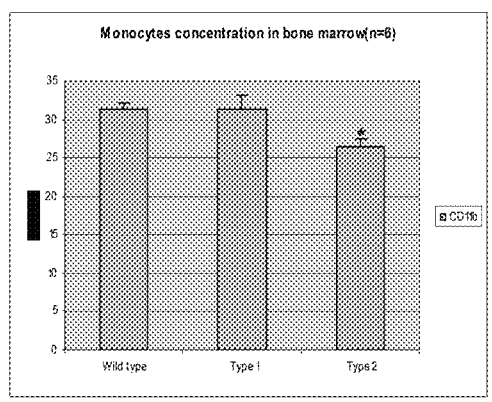
FIG. 63. Monocytes concentration was significantly decreased in the bone marrow of Type 2 diabetic mice *, P<0.05 vs Wild Type and Type 1.
Figure 64:
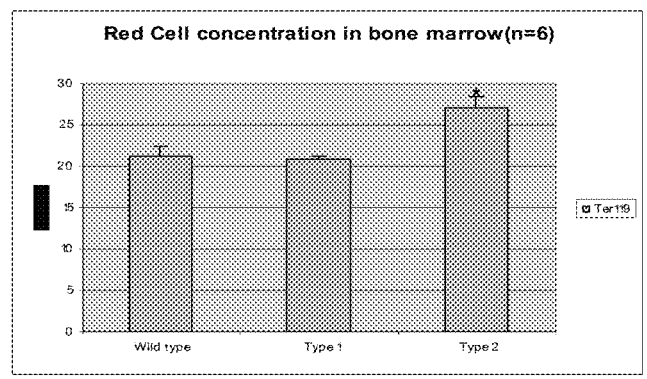
FIG. 64. Red Cell concentration was significantly increased in the bone marrow of Type 2 diabetic mice *, P<0.05 vs Wild Type and Type 1.
Figure 65:
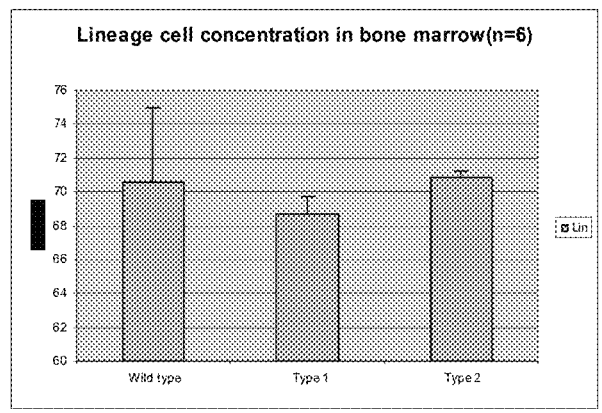
FIG. 65. Lineage cell concentration in bone marrow (n=6).

FIG. 59 shows wounding measurement between wild type and Type 2 diabetic mice. FIG. 60 shows HSC concentration in bone marrow (n=6) *, P<0.05 vs Wild Type and Type 1. FIG. 61 shows T lymphocytes concentration in bone marrow (n=6). FIG. 62 shows that B Lymphocyte concentration was increased in the bone marrow of Type 1 diabetic mice *, p<0.05 vs Wild Type and Type 2. FIG. 63 shows that monocytes concentration was significantly decreased in the bone marrow of Type 2 diabetic mice *, P<0.05 vs Wild Type and Type 1. FIG. 64 shows that Red Cell concentration was significantly increased in the bone marrow of Type 2 diabetic mice *, P<0.05 vs Wild Type and Type 1. FIG. 65 shows Lineage cell concentration in bone marrow (n=6).

In summary, the HSC concentration was increased in Type 2 diabetic mice. Further, in type 2 diabetic mice, monocytes concentration was decreased, but red cells concentration was increased.

Figure 66:
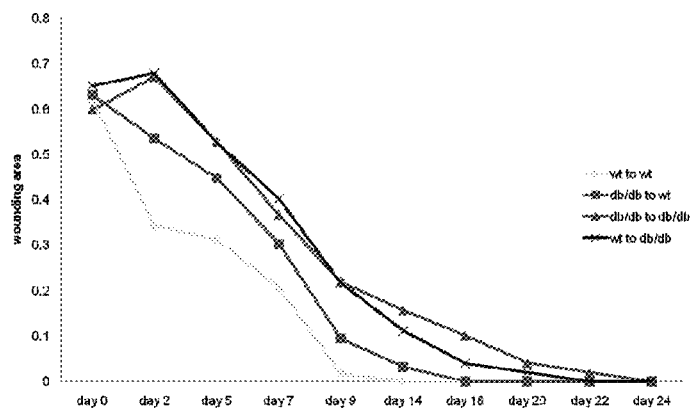
FIG. 66. Wound healing process after HSC transplantation (n=6).

FIG. 66 shows a wound healing process after HSC transplantation (n=6).

This study shows that the impaired wound healing phenotype in a type 2 diabetic mouse can be transferred to a wild type mouse by transplanting the HSCs from the diabetic mouse to the wild type mouse. Moreover, the lineage specification of monocytes is impaired and monocyte number in the peripheral blood of type 2 diabetic mice is abnormal. This indicates that the reduced monocyte number and function accounts for the impaired healing. These findings parallel and support the findings above about the effect of hypercholesterolemia induced oxidative stress of HSC number and function and indicates that a generalizeable model has been identified whereby the effect of oxidative stress on HSC function is oxidant specific.

Example 8

Effect of Triple Therapy on HSC Oxidant Stress in Male Apoe$^{h/h}$Ldlr$^{-/-}$ Mice.

Figure 67:
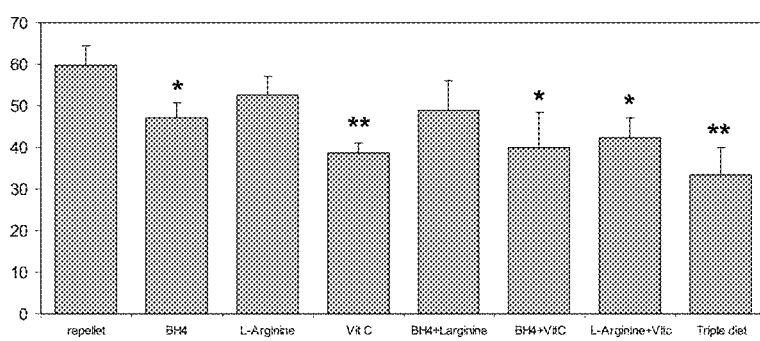
FIG. 67. Oxidative stress in hematopoietic stem cells.
Figure 68:
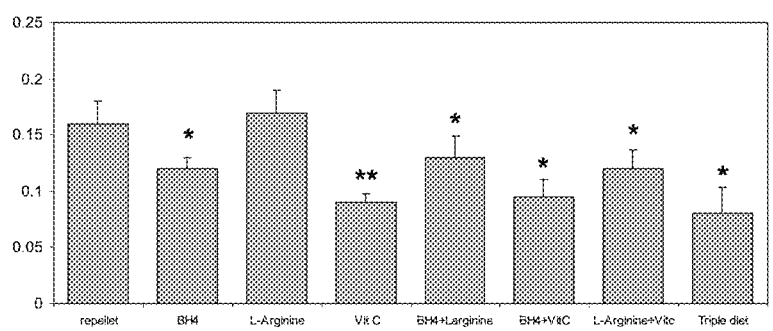
FIG. 68. HSC concentration after different diet in Apoe$^{h/h}$Ldlr$^{-/-}$ mice.

Apoe$^{h/h}$Ldlr$^{-/-}$ mice were fed different diets as indicated and HSC numbers were determined by FACS sorting (n=10 mice). Bone marrow and HSC oxidative stress was analyzed by FACS after DCF staining (FIG. 67, n=10 mice) FIG. 67 shows Oxidative stress in hematopoietic stem cells. FACS analysis (DCF staining). HSC cell lineage change was also assessed by FACS analysis (FIG. 68, n=10 mice).

These results demonstrate that oxidative stress on stem cells is significantly reduced in subjects on the triple therapy diet. Accordingly, triple therapy specifically reverses hypercholesterolemia induced loss of quiescence and increased proliferation of HSC, thereby protecting and/or restoring their repopulation capacity.

All references listed herein, including references listed below, are incorporated herein by reference. In the event of conflict, the disclosure of the present application shall control absent clear error.

It is claimed:

1. A method of reducing oxidative stress in hematopoietic stem cells in a subject who has hypercholesterolemia, the method comprising identifying a subject who has hypercholesterolemia and orally administering to the subject a therapy comprising:
   a. L-arginine,
   b. tetrahydrobiopterin, sepiapterin, or dihydrobiopterin, or any combination thereof, and
   c. ascorbic acid or ascorbate;
   wherein the ratio of (a):(b) is 1-30:1; and
   wherein the ratio of (b):(c) is 1:0.1-15.

2. The method of claim 1, comprising administering:
   a. L-arginine;
   b. tetrahydrobiopterin; and
   c. ascorbic acid or ascorbate.

3. The method of claim 1, comprising administering:
   88.5 mg/kg/day L-arginine;
   10 mg/kg/day tetrahydrobiopterin; and
   88.5 mg/kg/day ascorbic acid or ascorbate.

4. The method of claim 1, wherein the method comprises administering to the subject a pharmaceutical composition, wherein the active ingredients of the composition consist of:
   a. L-arginine,
   b. tetrahydrobiopterin, sepiapterin, or dihydrobiopterin, or any combination thereof, and
   c. ascorbic acid or ascorbate;
   wherein the ratio of (a):(b) is 1-30:1; and
   wherein the ratio of (b):(c) is 1:0.1-15.

5. The method of claim 1, wherein the pharmaceutical composition is formulated as tablets, capsules, powders, granules, or solutions for oral ingestion.

6. The method of claim 1, wherein the pharmaceutical composition comprises one or more excipients selected from the group consisting of: hydroxypropyl methylcellulose; sodium carboxymethyl cellulose; or polyvinylpyrrolidine.

7. The method of claim 1, wherein the treatment increases proliferation of hematopoietic stem cells.

* * * * *